(12) United States Patent
Acton, III et al.

(10) Patent No.: US 9,650,375 B2
(45) Date of Patent: May 16, 2017

(54) INDOLE DERIVATIVES USEFUL AS ANTI-DIABETIC AGENTS

(71) Applicants: Merck Sharp & Dohme Corp., Rahway, NJ (US); John J. Acton, III, Cranford, NJ (US); Rajan Anand, Fanwood, NJ (US); Ashok Arasappan, Bridgewater, NJ (US); Qun Dang, Westfield, NJ (US); Iyassu Sebhat, Jersey City, NJ (US); Zhifa Pu, Shanghai (CN); Takao Suzuki, Shanghai (CN)

(72) Inventors: John J. Acton, III, Cranford, NJ (US); Rajan Anand, Fanwood, NJ (US); Ashok Arasappan, Bridgewater, NJ (US); Qun Dang, Westfield, NJ (US); Iyassu Sebhat, Jersey City, NJ (US); Zhifa Pu, Shanghai (CN); Takao Suzuki, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/769,159

(22) PCT Filed: Mar. 10, 2014

(86) PCT No.: PCT/CN2014/073149
§ 371 (c)(1),
(2) Date: Aug. 20, 2015

(87) PCT Pub. No.: WO2014/139388
PCT Pub. Date: Sep. 18, 2014

(65) Prior Publication Data
US 2016/0002224 A1  Jan. 7, 2016

Related U.S. Application Data

(60) Provisional application No. 61/781,686, filed on Mar. 14, 2013.

(51) Int. Cl.
| | | |
|---|---|---|
| C07D 209/04 | (2006.01) |
| C07D 471/04 | (2006.01) |
| A61K 31/404 | (2006.01) |
| C07D 209/12 | (2006.01) |
| C07D 209/30 | (2006.01) |
| A61K 31/366 | (2006.01) |
| A61K 31/397 | (2006.01) |

(Continued)

(52) U.S. Cl.
CPC .......... *C07D 471/04* (2013.01); *A61K 31/366* (2013.01); *A61K 31/397* (2013.01); *A61K 31/404* (2013.01); *A61K 31/437* (2013.01); *A61K 31/4439* (2013.01); *A61K 31/4545* (2013.01); *A61K 31/496* (2013.01); *A61K 31/4985* (2013.01); *A61K 31/5377* (2013.01);

*A61K 31/541* (2013.01); *C07D 209/08* (2013.01); *C07D 209/12* (2013.01); *C07D 209/18* (2013.01); *C07D 209/30* (2013.01); *C07D 401/04* (2013.01); *C07D 401/06* (2013.01); *C07D 401/10* (2013.01); *C07D 403/04* (2013.01); *C07D 405/04* (2013.01); *C07D 405/06* (2013.01); *C07D 405/10* (2013.01); *C07D 413/04* (2013.01); *C07D 413/10* (2013.01); *C07D 493/04* (2013.01); *C07D 519/00* (2013.01)

(58) Field of Classification Search
CPC .................................................... C07D 209/04
USPC ........................................................ 548/469
See application file for complete search history.

(56) References Cited

U.S. PATENT DOCUMENTS

| 6,312,662 B1 | 11/2001 | Erion et al. |
| 6,489,476 B1 | 12/2002 | Dang et al. |

(Continued)

FOREIGN PATENT DOCUMENTS

| CN | 1368883 A | 9/2002 |
| CN | 1097043 C | 12/2002 |

(Continued)

OTHER PUBLICATIONS

Bergeron, R. et al., Effect of 5-Aminoimidazole-4-Caroboxamide-1-B-D-Ribofuranoside Infusion on In Vivo Glucose and Lipid Metabolism in Lean and Obese Zucker Rats, Diabetes, 2001, p. 1076-1082, vol. 50.

(Continued)

*Primary Examiner* — Niloofar Rahmani
(74) *Attorney, Agent, or Firm* — Baerbel R. Brown; Catherine D. Fitch

(57) ABSTRACT

Novel compounds of the structural formula (I) are activators of AMP-protein kinase and may be useful in the treatment, prevention and suppression of diseases mediated by the AMPK-activated protein kinase. The compounds of the present invention may be useful in the treatment of Type 2 diabetes, hyperglycemia, metabolic syndrome, obesity, hypercholesterolemia, and hypertension.

(I)

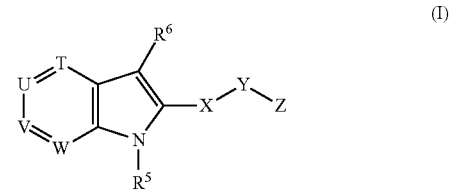

19 Claims, No Drawings

(51) Int. Cl.

| | | |
|---|---|---|
| A61K 31/437 | (2006.01) | |
| A61K 31/4439 | (2006.01) | |
| A61K 31/4545 | (2006.01) | |
| A61K 31/496 | (2006.01) | |
| A61K 31/4985 | (2006.01) | |
| A61K 31/5377 | (2006.01) | |
| A61K 31/541 | (2006.01) | |
| C07D 401/04 | (2006.01) | |
| C07D 401/06 | (2006.01) | |
| C07D 401/10 | (2006.01) | |
| C07D 403/04 | (2006.01) | |
| C07D 405/04 | (2006.01) | |
| C07D 405/06 | (2006.01) | |
| C07D 405/10 | (2006.01) | |
| C07D 413/04 | (2006.01) | |
| C07D 413/10 | (2006.01) | |
| C07D 493/04 | (2006.01) | |
| C07D 209/18 | (2006.01) | |
| C07D 519/00 | (2006.01) | |
| C07D 209/08 | (2006.01) | |

(56) References Cited

U.S. PATENT DOCUMENTS

| | | | |
|---|---|---|---|
| 9,409,905 B2* | 8/2016 | Branstrom | A61K 31/437 |
| 2005/0038068 A1 | 2/2005 | Iyengar et al. | |
| 2005/0148643 A1 | 7/2005 | Rui et al. | |
| 2006/0287356 A1 | 12/2006 | Iyengar et al. | |
| 2007/0015665 A1 | 1/2007 | Potluri et al. | |
| 2007/0032529 A1 | 2/2007 | Takagi et al. | |
| 2011/0071150 A1* | 3/2011 | Alam | C07D 209/18 |
| | | | 514/235.2 |

FOREIGN PATENT DOCUMENTS

| | | |
|---|---|---|
| CN | 101247853 A | 8/2008 |
| DE | 3316095 A1 | 5/1983 |
| EP | 0120403 A2 | 10/1984 |
| EP | 0126030 A2 | 11/1984 |
| EP | 0128862 A2 | 12/1984 |
| EP | 0129506 B1 | 12/1984 |
| EP | 2125718 B1 | 9/2010 |
| JP | 6298731 | 10/1994 |
| WO | WO9307124 A1 | 4/1993 |
| WO | WO9529897 A1 | 11/1995 |
| WO | WO9805327 A1 | 2/1998 |
| WO | WO9839342 A1 | 9/1998 |
| WO | WO9839343 A1 | 9/1998 |
| WO | 9965909 | 12/1999 |
| WO | WO9965908 A1 | 12/1999 |
| WO | WO0003997 A1 | 1/2000 |
| WO | WO0014095 A1 | 3/2000 |
| WO | WO0153272 A1 | 7/2001 |
| WO | WO0153291 A1 | 7/2001 |
| WO | WO0240019 A1 | 5/2002 |
| WO | WO02092575 A1 | 11/2002 |
| WO | WO03018061 A1 | 3/2003 |
| WO | WO2005002520 A2 | 1/2005 |
| WO | WO2005018672 A1 | 3/2005 |
| WO | WO2005020892 A2 | 3/2005 |
| WO | WO2005051298 A2 | 6/2005 |
| WO | WO2005105791 A1 | 11/2005 |
| WO | WO2006061493 A1 | 6/2006 |
| WO | WO2006094209 A2 | 9/2006 |
| WO | WO2007063418 A2 | 6/2007 |
| WO | WO2007081755 A2 | 7/2007 |
| WO | WO2008006432 A1 | 1/2008 |
| WO | WO2009062319 A1 | 5/2009 |
| WO | WO2009100130 A1 | 8/2009 |
| WO | WO2010036613 A1 | 4/2010 |
| WO | WO2010036910 A1 | 4/2010 |
| WO | WO2010047982 A1 | 4/2010 |
| WO | WO2010051176 A1 | 5/2010 |
| WO | WO2010051206 A1 | 5/2010 |
| WO | WO2011123719 A2 | 10/2011 |
| WO | WO2012116145 A1 | 8/2012 |
| WO | WO2013011932 A1 | 2/2013 |
| WO | 2013033258 * | 3/2013 |
| WO | WO2014139388 A1 | 9/2014 |
| WO | WO2012033149 A1 | 3/2015 |

OTHER PUBLICATIONS

Blazquez, C. et al., The AMP-Activated Protein Kinase Is Involved in the Reulation of Ketone Body Production by Astrocytes, Journal of Neurochemistry, 1999, p. 1674-1682, vol. 73.

Buhl. E. S. et al., Long-Term AICAR Administration Reduces Metabolic Disturbances and Lowers Blood Pressure in Rats Displaying Features of the Insulin Resistance Syndrome, Diabetes, 2002, p. 2199-2206, vol. 51.

Butler, A. E. et al., B-Cell Deficit and Increased B-Cell Apoptosis in Humans With Type 2 Diabetes, Diabetes, 2003, p. 102-110, vol. 52.

Carling, D. et al., A common bicyclic protein kinase cascade inactivates the regulatory enzymes of fatty acid and cholesterol biosynthesis, Feb. 1987, p. 217-222, vol. 223, No. 2.

Chen, Z, P. et al., AMP-activated protein kinase phosphorylation of endothelial NO synthase, FEBS Letters, 1999, p. 285-289, vol. 443.

Girdanetto, F. et al., Direct AMP-activated protein kinase activators: a review of evidence from the patent literature, Expert Opin.Ther Patents, 2012, p. 1467-1477, vol. 22, No. 12.

Halseth, A. E. et al., Acute and chronic treatment of ob/ob and db/db mice with AICAR decreases blood glucose concentrations, Biochemical and Biophysical Research Communications, 2002, p. 798-805, vol. 294.

Hardie, D. G. et al., AMP-activated protein kinase: the energy charge hypothesis revisited, BioEssays, 2001, p. 1112-1119, vol. 23.

Kemp, B. E. et al., AMP-activated protein kinase, super metabolic regulator, AMPK 2002—2nd International Meeting on AMP-Activated Protein Kinase, Biochemical Society Transactions, 2003, p. 162-168, vol. 31, Part 1.

Leclerc, I. et al., Hepatocyte Nuclear Factor-4a Involved in Type 1 Maturity-Onset Diabetes of the Young Is a Novel Target of AMP-Activated Protein Kinase, Diabetes, 2001, p. 1515-1521, vol. 50.

Lochhead, P. A. et al., 5-Aminoimidazole-4-Carboxamide Riboside Mimics the Effects of Insulin on the Expression of the 2 Key Gluconeogenic Genes PEPCK and Glucose-6-Phosphatase, Diabetes, 2000, p. 896-903, vol. 49.

Minokoshi, Y. et al., Leptin stimulates fatty-acid oxidation by activating AMP-activated protein kinase, Nature, 2002, p. 339-, vol. 415.

Mu, J. et al., A Role for AMP-Activated Protein Kinase in Contraction- and Hypoxia-Regulated Glucose Transport in Skeletal Muscle, Molecular Cell, 2001, p. 1085-1094, vol. 7.

Muoio, D. M. et al., AMP-activated kinase reciprocally regulates triacylglycerol synthesis and fatty acid oxidation in liver and muscle: evidence that sn-glycerol-3-phosphate acyltransferase is a novel target, Biochem J., 1999, p. 783-791, vol. 338.

Musi, N. et al., Metofrmin Increases AMP-Activated Protein Kinase Activity in Skeletal Muscle of Subjects With Type 2 Diabetes, Diabetes, 2002, p. 2074-2081, vol. 51.

Musi, N. et al., Targeting the AMP-Activated Protein Kinase for the Treatment of Type 2 Diabetes, Current Drug Targets—Immune, Endocrine & Metabolic Disorders, 2002, p. 119-127, vol. 2.

Polonsky, K. S., Dynamics of insulin secretion in obesity and diabetes, International Journal of Obesity, 2000, p. S29-S31, vol. 24, Suppl. 2.

Sakurai, T. et al., The Effect of Tryptophan Administration on Fatty Acid Synthesis in the Liver of the Fasted Normal Rat, Biochimica et Biophysica Acta 1974, p. 275-288, vol. 360.

Song, X. M. et al., 5-Aminoimidazole-4-carboxamide ribonucleoside treatment improve glucose homeostasis in insulin-resistant diabetic (ob/ob) mice, Diabetologia, 2002, p. 56-65, vol. 45.

(56) References Cited

OTHER PUBLICATIONS

Zhou, G. et al., Role of AMP-activated protein kinase in mechanism of metformin action, The Journal of Clinical Investigation, 2001, p. 1167-1174, vol. 108, No. 8.

Zhou, M. et al., UCP-3 expression in skeletal muscle: effects of exercise, hypoxia, and AMP-activated protein kinase, Am. J. Physiol Endocrinol Metab, 2000, p. E622-E629, vol. 279.

Bauman, N. et al., Indole-2-carboxylic acids, a new class of hypoglycemic compounds, Biochemical Pharmacology, 1969, p. 1241-1243, vol. 18, No. 5.

Hardie, D. Grahame, et al., AMP-Activated Protein Kinase: A Target for Drugs both Ancient and Modern, Chemistry & Biology, 2012, p. 1222-1236, vol. 19.

* cited by examiner

INDOLE DERIVATIVES USEFUL AS ANTI-DIABETIC AGENTS

CROSS-REFERENCE TO RELATED APPLICATIONS

This application is a U.S. National Phase application under 35 U.S.C. §371 of PCT Application No. PCT/CN2014/073149, filed on Mar. 10, 2014, which claims priority from and the benefit of U.S. Provisional Application No. 61/781,686; filed Mar. 14, 2013

BACKGROUND OF THE INVENTION

Diabetes is characterized by elevated levels of plasma glucose (hyperglycemia) in the fasting state or after administration of glucose during an oral glucose tolerance test. In type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, Int. J. Obes. Relat. Metab. Disord. 24 Suppl 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., Diabetes 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglutide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobinA1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223:217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et. al., Biochem. J. 338:783 (1999)). Another substrace of AMPK, hepatocyte nuclear factor-4α, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et. al., Biochem. Soc. Transactions 31:162 (2003), Musi, N. and Goodyear, L. J. Current Drug Targets-Immune, Endocrine and Metabolic Disorders 2:119 (2002); Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et. al., Biochem. and Biophys. Res. Comm. 294:798 (2002); and Buhl, E. S. et. al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure should lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); may also be useful to prevent damage from reactive oxygen species (Zhou, M. et. al., Am. J. Physiol. Endocrinol. Metab. 279: E622 (2000)); and may also be useful to improve local circulatory systems (Chen, Z.-P., et. al. AMP-activated protein kinase phosphorylation of endothelial NO synthase. FEBS Letters 443: 285 (1999)).

Compounds that activate AMPK may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that may have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403. AMPK activators are disclosed in WO 08/006432; WO 05/051298; WO 05/020892; US 2007/015665; US 2007/032529; US 2006/287356; and US 2005/038068.

Azabenzimidazole compounds are disclosed in WO 2013/011932; WO 2012/116145; and WO 2012/033149.

AMPK inhibitors are also disclosed in Giordanetto et al., Expert Opin. Ther. Patents (2012) 22(12):1467-1477.

SUMMARY OF THE INVENTION

The present invention is concerned with novel benzimidazole derivatives of structural Formula I:

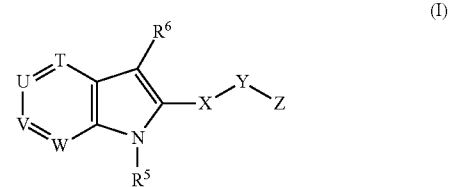

and pharmaceutically acceptable salts thereof. The compounds of structural formula I, and embodiments thereof, are activators of AMP-activated protein kinase (AMPK) and are useful in the treatment, prevention and suppression of diseases, disorders and conditions mediated by activation of AMP-activated protein kinase. The compounds of structural formula I may be useful to treat Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions are responsive to the activation of AMP-activated protein kinase. The present invention is also concerned with treatment of these diseases, disorders and conditions by administering the compounds of the present invention in combination with a therapeutically effective amount of another agent useful to treat the disease, disorder and condition. The invention is further concerned with processes for preparing the compounds of this invention.

DETAILED DESCRIPTION OF THE INVENTION

The present invention is concerned with novel compounds of structural Formula I:

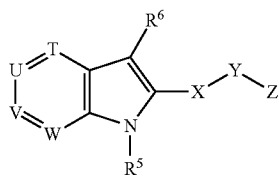

(I)

or a pharmaceutically acceptable salt thereof, wherein:
T is selected from the group consisting of: $CR^3$, N and N-oxide;
U is selected from the group consisting of: $CR^1$, N and N-oxide;
V is selected from the group consisting of: $CR^2$, N and N-oxide;
W is selected from the group consisting of: $CR^4$, N and N-oxide;
X is absent or selected from:
  (1) —$CH_2$—,
  (2) —CHF—,
  (3) —$CF_2$—,
  (4) —S—,
  (5) —S(O)—,
  (6) —S(O)$_2$—,
  (7) —O—,
  (8) —O—$CH_2$—,
  (9) —$CH_2$—O—,
  (10) —$CH_2$—S—,
  (11) —NH—,
  (12) —C(O)—,
  (13) —NHC(O)—,
  (14) —C(O)NH—,
  (15) —$NHSO_2$—,
  (16) —$SO_2NH$—, and
  (17) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl;
Y is selected from:
  (1) —$C_{1-6}$alkyl,
  (2) —$C_{2-6}$alkynyl,
  (3) —CHF—,
  (4) —$CF_2$—,
  (5) $C_{3-10}$cycloalkyl,
  (6) $C_{3-10}$cycloalkenyl,
  (7) $C_{2-10}$cycloheteroalkyl,
  (8) $C_{2-10}$cycloheteroalkenyl,
  (9) aryl,
  (10) heteroaryl, and
  (11)

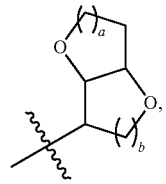

wherein Y is unsubstituted or substituted with 1, 2, 3 or 4 substituents selected from $R^b$;
Z is selected from:
  (1) hydrogen,
  (2) oxo,
  (3) —CN,
  (4) —$CF_3$,
  (5) —$C_{1-6}$alkyl,
  (6) —$(CH_2)_r$-halogen,
  (7) —$(CH_2)_n COC_{1-6}$alkyl,
  (8) —$(CH_2)_n CO_2H$,
  (9) —$(CH_2)_n OCOH$,
  (10) —$(CH_2)_n CO_2R^i$,
  (11) —$(CH_2)_n OCOR^i$,
  (12) —$(CH_2)_n OH$,
  (13) —$(CH_2)_n C(O)N(R^g)_2$,
  (14) —$(CH_2)_n C(O)(CH_2)_n N(R^g)_2$,
  (15) —$(CH_2)_n OC(O)(CH_2)_n N(R^g)_2$,
  (16) —$(CH_2)_n NHC(O)C_{1-6}$alkyl,
  (17) —$(CH_2)_n NHSO_2 R^i$,
  (18) —$(CH_2)_n SO_2 C_{1-6}$alkyl,
  (19) —$(CH_2)_n SO_2 NHR^g$,
  (20) —$(CH_2)_n SO_2 NHC(O)R^i$,
  (21) —$(CH_2)_n SO_2 NHCO_2 R^i$,
  (22) —$(CH_2)_n SO_2 NHCON(R^g)_2$,
  (23) —$(CH_2)_n C(O)NHSO_2 R^i$,
  (24) —$(CH_2)_n NHC(O)N(R^g)_2$,
  (25) —$(CH_2)_n C_{3-10}$cycloalkyl-$CO_2R^e$,
  (26) heteroaryl,
  (27) —$C_{2-10}$cycloheteroalkenyl,
  (28) —$C_{2-10}$cycloheteroalkyl, and
  (29) —$(CH_2)_n P(O)(OR^j)_2$,
wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$;
each $R^1$ and $R^2$ is independently selected from:
  (1) hydrogen,
  (2) halogen,
  (3) CN,
  (4) $CF_3$,
  (5) —$C_{1-6}$alkyl,
  (6) —$C_{2-6}$alkenyl,
  (7) —$C_{2-6}$alkynyl,
  (8) —$(CH_2)_p C_{3-10}$cycloalkyl,
  (9) —$(CH_2)_p C_{3-7}$cycloalkyl-aryl,
  (10) —$(CH_2)_p C_{3-7}$cycloalkyl-heteroaryl,
  (11) —$(CH_2)_p C_{4-10}$cycloalkenyl,
  (12) —$(CH_2)_p C_{4-7}$cycloalkenyl-aryl,
  (13) —$(CH_2)_p C_{4-7}$cycloalkenyl-heteroaryl,
  (14) —$(CH_2)_p C_{2-10}$cycloheteroalkyl,
  (15) —$(CH_2)_p C_{2-10}$cycloheteroalkenyl,
  (16) —$(CH_2)_p$aryl,
  (17) —$(CH_2)_p$aryl-$C_{1-8}$alkyl,

(18) —(CH$_2$)$_p$aryl-C$_{2-8}$alkenyl,
(19) —(CH$_2$)$_p$aryl-C$_{2-8}$alkynyl-C$_{1-8}$alkyl,
(20) —(CH$_2$)$_p$aryl-C$_{2-8}$alkynyl-C$_{3-7}$cycloalkyl,
(21) —(CH$_2$)$_p$aryl-C$_{2-8}$alkynyl-C$_{3-7}$cycloalkenyl,
(22) —(CH$_2$)$_p$aryl-C$_{2-8}$alkynyl-C$_{2-10}$cycloheteroalkyl,
(23) —(CH$_2$)$_p$aryl-C$_{2-8}$alkynyl-C$_{2-10}$cycloheteroalkenyl,
(24) —(CH$_2$)$_p$aryl-C$_{2-8}$alkynyl-aryl,
(25) —(CH$_2$)$_p$aryl-C$_{2-8}$alkynyl-heteroaryl,
(26) —(CH$_2$)$_p$aryl-C$_{3-7}$cycloalkyl,
(27) —(CH$_2$)$_p$aryl-C$_{3-7}$cycloalkenyl,
(28) —(CH$_2$)$_p$aryl-C$_{2-10}$cycloheteroalkyl,
(29) —(CH$_2$)$_p$aryl-C$_{2-10}$cycloheteroalkenyl,
(30) —(CH$_2$)$_p$aryl-aryl,
(31) —(CH$_2$)$_p$aryl-heteroaryl,
(32) —(CH$_2$)$_p$heteroaryl,
(33) —C$_{2-6}$alkenyl-alkyl,
(34) —C$_{2-6}$alkenyl-aryl,
(35) —C$_{2-6}$alkenyl-heteroaryl,
(36) —C$_{2-6}$alkenyl-C$_{3-7}$cycloalkyl,
(37) —C$_{2-6}$alkenyl-C$_{3-7}$cycloalkenyl,
(38) —C$_{2-6}$alkenyl-C$_{2-7}$cycloheteroalkyl,
(39) —C$_{2-6}$alkenyl-C$_{2-7}$cycloheteroalkenyl,
(40) —C$_{2-6}$ alkynyl-(CH$_2$)$_{1-3}$—O-aryl,
(41) —C$_{2-6}$alkynyl-alkyl,
(42) —C$_{2-6}$alkynyl-aryl,
(43) —C$_{2-6}$alkynyl-heteroaryl,
(44) —C$_{2-6}$alkynyl-C$_{3-7}$cycloalkyl,
(45) —C$_{2-6}$alkynyl-C$_{3-7}$cycloalkenyl,
(46) —C$_{2-6}$alkynyl-C$_{2-7}$cycloheteroalkyl,
(47) —C$_{2-6}$alkynyl-C$_{2-7}$cycloheteroalkenyl, and
(48) —C(O)NH—(CH$_2$)$_{0-3}$phenyl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$,
provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl;
R$^3$ and R$^4$ are each absent or independently selected from:
(1) hydrogen,
(2) halogen,
(3) —C$_{1-6}$alkyl,
(4) —C$_{2-6}$alkenyl,
(5) —C$_{2-6}$alkynyl,
(6) —C$_{3-10}$cycloalkyl,
(7) —C$_{3-10}$cycloalkenyl,
(8) aryl,
(9) heteroaryl,
(10) —CN,
(11) —CF$_3$,
(12) —OH,
(13) —OC$_{1-6}$alkyl,
(14) —NH$_2$,
(15) —NHC$_{1-6}$alkyl,
(16) —N(C$_{1-6}$alkyl)$_2$,
(17) —SC$_{1-6}$alkyl,
(18) —SOC$_{1-6}$alkyl,
(19) —SO$_2$C$_{1-6}$alkyl,
(20) —NHSO$_2$C$_{1-6}$alkyl,
(21) —NHC(O)C$_{1-6}$alkyl,
(22) —SO$_2$NHC$_{1-6}$alkyl, and
(23) —C(O)NHC$_{1-6}$alkyl;

R$^5$ is selected from:
(1) hydrogen,
(2) —C$_{1-6}$alkyl,
(3) —CH$_2$CO$_2$H, and
(4) —CH$_2$CO$_2$C$_{1-6}$alkyl;
R$^6$ is selected from:
(1) hydrogen,
(2) —C$_{1-6}$alkyl,
(3) —(CH$_2$)$_m$OC$_{1-6}$alkyl,
(4) halogen,
(5) —(CH$_2$)$_m$CN,
(6) —(CH$_2$)$_m$CF$_3$,
(7) —(CH$_2$)$_m$OCF$_3$,
(8) —(CH$_2$)$_m$CHF$_2$,
(9) —(CH$_2$)$_m$CH$_2$F,
(10) —(CH$_2$)$_m$SO$_2$C$_{1-6}$alkyl,
(11) —(CH$_2$)$_m$CO$_2$H,
(12) —(CH$_2$)$_m$CO$_2$C$_{1-6}$alkyl,
(13) —(CH$_2$)$_m$C(O)H,
(14) —(CH$_2$)$_m$C(O)NH$_2$,
(15) —(CH$_2$)$_m$C$_{3-6}$cycloalkyl,
(16) —(CH$_2$)$_m$C$_{2-7}$cycloheteroalkyl,
(17) —(CH$_2$)$_m$aryl, and
(18) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloheteroalkyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;
each R$^a$ is independently selected from the group consisting of:
(1) —(CH$_2$)$_m$-halogen,
(2) oxo,
(3) —(CH$_2$)$_m$OH,
(4) —(CH$_2$)$_m$N(R$^j$)$_2$,
(5) —(CH$_2$)$_m$NO$_2$,
(6) —(CH$_2$)$_m$CN,
(7) —C$_{1-6}$alkyl,
(8) —(CH$_2$)$_m$CF$_3$,
(9) —(CH$_2$)$_m$OCF$_3$,
(10) —O—(CH$_2$)$_m$—OC$_{1-6}$ alkyl,
(11) —(CH$_2$)$_m$C(O)N(R$^j$)$_2$,
(12) —(CH$_2$)$_m$C(=N—OH)N(R$^j$)$_2$,
(13) —(CH$_2$)$_m$OC$_{1-6}$alkyl,
(14) —(CH$_2$)$_m$O—(CH$_2$)$_m$—C$_{3-7}$cycloalkyl,
(15) —(CH$_2$)$_m$O—(CH$_2$)$_m$—C$_{2-7}$cycloheteroalkyl,
(16) —(CH$_2$)$_m$O—(CH$_2$)$_m$-aryl,
(17) —(CH$_2$)$_m$O—(CH$_2$)$_m$-heteroaryl,
(18) —(CH$_2$)$_m$SC$_{1-6}$alkyl,
(19) —(CH$_2$)$_m$S(O)C$_{1-6}$alkyl,
(20) —(CH$_2$)$_m$SO$_2$C$_{1-6}$alkyl,
(21) —(CH$_2$)$_m$SO$_2$C$_{3-7}$cycloalkyl,
(22) —(CH$_2$)$_m$SO$_2$C$_{2-7}$cycloheteroalkyl,
(23) —(CH$_2$)$_m$SO$_2$-aryl,
(24) —(CH$_2$)$_m$SO$_2$-heteroaryl,
(25) —(CH$_2$)$_m$SO$_2$NHC$_{1-6}$alkyl,
(26) —(CH$_2$)$_m$SO$_2$N(C$_{1-6}$alkyl)$_2$,
(27) —(CH$_2$)$_m$SO$_2$NHC$_{3-7}$cycloalkyl,
(28) —(CH$_2$)$_m$SO$_2$NHC$_{2-7}$cycloheteroalkyl,

(29) —(CH$_2$)$_m$SO$_2$NH-aryl,
(30) —(CH$_2$)$_m$SO$_2$NH-heteroaryl,
(31) —(CH$_2$)$_m$NHSO$_2$—C$_{1-6}$alkyl,
(32) —(CH$_2$)$_m$NHSO$_2$—C$_{3-7}$cycloalkyl,
(33) —(CH$_2$)$_m$NHSO$_2$—C$_{2-7}$cycloheteroalkyl,
(34) —(CH$_2$)$_m$NHSO$_2$-aryl,
(35) —(CH$_2$)$_m$NHSO$_2$NH-heteroaryl,
(36) —(CH$_2$)$_m$N(R$^j$)—C$_{1-6}$alkyl,
(37) —(CH$_2$)$_m$N(R$^j$)—C$_{3-7}$cycloalkyl,
(38) —(CH$_2$)$_m$N(R$^j$)—C$_{2-7}$cycloheteroalkyl,
(39) —(CH$_2$)$_m$N(R$^j$)—C$_{2-7}$cycloheteroalkenyl,
(40) —(CH$_2$)$_m$N(R$^j$)-aryl,
(41) —(CH$_2$)$_m$N(R$^j$)-heteroaryl,
(42) —(CH$_2$)$_m$C(O)R$^f$,
(43) —(CH$_2$)$_m$C(O)N(R$^j$)$_2$,
(44) —(CH$_2$)$_m$N(R$^j$)C(O)N(R$^j$)$_2$,
(45) —(CH$_2$)$_m$CO$_2$H,
(46) —(CH$_2$)$_m$OCOH,
(47) —(CH$_2$)$_m$CO$_2$R$^f$,
(48) —(CH$_2$)$_m$OCOR$^f$,
(49) —(CH$_2$)$_m$C$_{3-7}$cycloalkyl,
(50) —(CH$_2$)$_m$C$_{3-7}$cycloalkenyl,
(51) —(CH$_2$)$_m$C$_{2-6}$cycloheteroalkyl,
(52) —(CH$_2$)$_m$C$_{2-6}$cycloheteroalkenyl,
(53) —(CH$_2$)$_m$aryl, and
(54) —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;

each R$^b$ is independently selected from:
(1) hydrogen,
(2) —C$_{1-6}$alkyl,
(3) —C$_{3-6}$cycloalkyl,
(4) —C$_{3-6}$cycloalkenyl,
(5) —C$_{2-6}$cycloheteroalkyl,
(6) —C$_{2-6}$cycloheteroalkenyl,
(7) aryl,
(8) heteroaryl,
(9) —(CH$_2$)t-halogen,
(10) —(CH$_2$)s-OH,
(11) —(CH$_2$)sNO$_2$,
(12) —(CH$_2$)sNH$_2$,
(13) —(CH$_2$)sNH(C$_{1-6}$alkyl),
(14) —(CH$_2$)sN(C$_{1-6}$alkyl)$_2$,
(15) —(CH$_2$)sOC$_{1-6}$alkyl,
(16) —(CH$_2$)qCO$_2$H,
(17) —(CH$_2$)qCO$_2$C$_{1-6}$alkyl,
(18) —(CH$_2$)sCF$_3$,
(19) —(CH$_2$)sOCF$_3$,
(20) —(CH$_2$)sCHF$_2$,
(21) —(CH$_2$)sCH$_2$F,
(22) —(CH$_2$)sCN,
(23) —(CH$_2$)sSO$_2$C$_{1-6}$alkyl, and
(24) —(CH$_2$)sCON(R$^e$)$_2$, wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens, and wherein two R$^b$ substituents together with the atom to which they are attached may form a C$_{3-6}$cycloalkyl ring or a C$_{2-6}$cycloheteroalkyl ring;

each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each R$^e$, R$^g$ and R$^h$ is independently selected from:
(1) hydrogen,
(2) —C$_{1-6}$alkyl, and
(3) —O—C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^j$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$, wherein each alkyl and cycloalkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$ and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

each a independently selected from 0, 1 or 2;
each b independently selected from 0, 1 or 2;
each n independently selected from 0, 1, 2, 3 or 4;
each m independently selected from 0, 1, 2, 3 or 4;
each p independently selected from 0, 1, 2, or 3;
each q independently selected from 0, 1, 2, 3 or 4;
each r independently selected from 0, 1 or 2;
each s independently selected from 0, 1, 2, 3 or 4; and
each t independently selected from 0, 1, 2, 3 or 4.

In one embodiment of the present invention is concerned with novel compounds of structural Formula I:

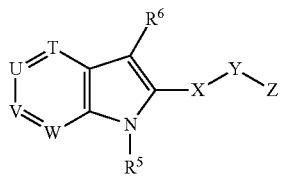
(I)

or a pharmaceutically acceptable salt thereof, wherein:
T is selected from the group consisting of: $CR^3$, N and N-oxide;
U is selected from the group consisting of: $CR^1$, N and N-oxide;
V is selected from the group consisting of: $CR^2$, N and N-oxide;
W is selected from the group consisting of: $CR^4$, N and N-oxide;
X is absent or selected from:
  (1) —$CH_2$—,
  (2) —CHF—,
  (3) —$CF_2$—,
  (4) —S—,
  (5) —O—,
  (6) —O—$CH_2$—,
  (7) —$CH_2$—O—,
  (8) —NH—,
  (9) —C(O)—,
  (10) —NHC(O)—,
  (11) —C(O)NH—,
  (12) —$NHSO_2$—,
  (13) —$SO_2NH$—, and
  (14) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl;
Y is selected from:
  (1) —$C_{1-6}$alkyl,
  (2) —CHF—,
  (3) —$CF_2$—,
  (4) $C_{3-10}$cycloalkyl,
  (5) $C_{3-10}$cycloalkenyl,
  (6) $C_{2-10}$cycloheteroalkyl,
  (7) $C_{2-10}$cycloheteroalkenyl,
  (8) aryl,
  (9) heteroaryl, and
  (10)

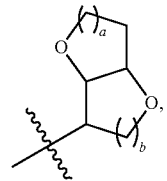

wherein Y is unsubstituted or substituted with 1, 2, 3 or 4 substituents selected from $R^b$;
Z is selected from:
  (1) hydrogen,
  (2) oxo,
  (3) —CN,
  (4) —$CF_3$,
  (5) —$C_{1-6}$alkyl,
  (6) —$(CH_2)_r$-halogen,
  (7) —$(CH_2)_n COC_{1-6}$alkyl,
  (8) —$(CH_2)_n CO_2H$,
  (9) —$(CH_2)_n OCOH$,
  (10) —$(CH_2)_n CO_2R^i$,
  (11) —$(CH_2)_n OCOR^i$,
  (12) —$(CH_2)_n OH$,
  (13) —$(CH_2)_n C(O)N(R^g)_2$,
  (14) —$(CH_2)_n C(O)(CH_2)_n N(R^g)_2$,
  (15) —$(CH_2)_n OC(O)(CH_2)_n N(R^g)_2$,
  (16) —$(CH_2)_n NHC(O)C_{1-6}$alkyl,
  (17) —$(CH_2)_n NHSO_2R^i$,
  (18) —$(CH_2)_n SO_2C_{1-6}$alkyl,
  (19) —$(CH_2)_n SO_2NHR^g$,
  (20) —$(CH_2)_n SO_2NHC(O)R^i$,
  (21) —$(CH_2)_n SO_2NHCO_2R^i$,
  (22) —$(CH_2)_n SO_2NHCON(R^g)_2$,
  (23) —$(CH_2)_n C(O)NHSO_2R^i$,
  (24) —$(CH_2)_n NHC(O)N(R^g)_2$,
  (25) —$(CH_2)_n C_{3-10}$cycloalkyl-$CO_2R^e$,
  (26) heteroaryl,
  (27) —$C_{2-10}$cycloheteroalkenyl, and
  (28) —$C_{2-10}$cycloheteroalkyl,
wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$;
each $R^1$ and $R^2$ is independently selected from:
  (1) hydrogen,
  (2) halogen,
  (3) CN,
  (4) $CF_3$,
  (5) —$C_{1-6}$alkyl,
  (6) —$C_{2-6}$alkenyl,
  (7) —$C_{2-6}$alkynyl,
  (8) —$(CH_2)_p C_{3-10}$cycloalkyl,
  (9) —$(CH_2)_p C_{3-7}$cycloalkyl-aryl,
  (10) —$(CH_2)_p C_{3-7}$cycloalkyl-heteroaryl,
  (11) —$(CH_2)_p C_{4-10}$cycloalkenyl,
  (12) —$(CH_2)_p C_{4-7}$cycloalkenyl-aryl,
  (13) —$(CH_2)_p C_{4-7}$cycloalkenyl-heteroaryl,
  (14) —$(CH_2)_p C_{2-10}$cycloheteroalkyl,
  (15) —$(CH_2)_p C_{2-10}$cycloheteroalkenyl,
  (16) —$(CH_2)_p$aryl,
  (17) —$(CH_2)_p$aryl-$C_{1-8}$alkyl,
  (18) —$(CH_2)_p$aryl-$C_{2-8}$alkenyl,

(19) —(CH$_2$)$_p$aryl-C$_{2-8}$alkynyl-C$_{1-8}$alkyl,
(20) —(CH$_2$)$_p$aryl-C$_{2-8}$alkynyl-C$_{3-7}$cycloalkyl,
(21) —(CH$_2$)$_p$aryl-C$_{2-8}$alkynyl-C$_{3-7}$cycloalkenyl,
(22) —(CH$_2$)$_p$aryl-C$_{2-8}$alkynyl-C$_{2-10}$cycloheteroalkyl,
(23) —(CH$_2$)$_p$aryl-C$_{2-8}$alkynyl-C$_{2-10}$cycloheteroalkenyl,
(24) —(CH$_2$)$_p$aryl-C$_{2-8}$alkynyl-aryl,
(25) —(CH$_2$)$_p$aryl-C$_{2-8}$alkynyl-heteroaryl,
(26) —(CH$_2$)$_p$aryl-C$_{3-7}$cycloalkyl,
(27) —(CH$_2$)$_p$aryl-C$_{2-10}$cycloheteroalkyl,
(28) —(CH$_2$)$_p$aryl-C$_{2-10}$cycloheteroalkenyl,
(29) —(CH$_2$)$_p$aryl-aryl,
(30) —(CH$_2$)$_p$aryl-heteroaryl,
(31) —(CH$_2$)$_p$heteroaryl,
(32) —C$_{2-6}$alkenyl-alkyl,
(33) —C$_{2-6}$alkenyl-aryl,
(34) —C$_{2-6}$alkenyl-heteroaryl,
(35) —C$_{2-6}$alkenyl-C$_{3-7}$cycloalkyl,
(36) —C$_{2-6}$alkenyl-C$_{3-7}$cycloalkenyl,
(37) —C$_{2-6}$alkenyl-C$_{2-7}$cycloheteroalkyl,
(38) —C$_{2-6}$alkenyl-C$_{2-7}$cycloheteroalkenyl,
(39) —C$_{2-6}$ alkynyl-(CH$_2$)$_{1-3}$—O-aryl,
(40) —C$_{2-8}$alkynyl-alkyl,
(41) —C$_{2-8}$alkynyl-aryl,
(42) —C$_{2-8}$alkynyl-heteroaryl,
(43) —C$_{2-8}$alkynyl-C$_{3-7}$cycloalkyl,
(44) —C$_{2-8}$alkynyl-C$_{3-7}$cycloalkenyl,
(45) —C$_{2-8}$alkynyl-C$_{2-7}$cycloheteroalkyl,
(46) —C$_{2-8}$alkynyl-C$_{2-7}$cycloheteroalkenyl, and
(47) —C(O)NH—(CH$_2$)$_{0-3}$phenyl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$,
provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl;
R$^3$ and R$^4$ are each absent or independently selected from:
(1) hydrogen,
(2) halogen,
(3) —C$_{1-6}$alkyl,
(4) —C$_{2-6}$alkenyl,
(5) —C$_{2-6}$alkynyl,
(6) —C$_{3-10}$cycloalkyl,
(7) —C$_{3-10}$cycloalkenyl,
(8) aryl,
(9) heteroaryl,
(10) —CN,
(11) —CF$_3$,
(12) —OH,
(13) —OC$_{1-6}$alkyl,
(14) —NH$_2$,
(15) —NHC$_{1-6}$alkyl,
(16) —N(C$_{1-6}$alkyl)$_2$,
(17) —SC$_{1-6}$alkyl,
(18) —SOC$_{1-6}$alkyl,
(19) —SO$_2$C$_{1-6}$alkyl,
(20) —NHSO$_2$C$_{1-6}$alkyl,
(21) —NHC(O)C$_{1-6}$alkyl,
(22) —SO$_2$NHC$_{1-6}$alkyl, and
(23) —C(O)NHC$_{1-6}$alkyl;

R$^5$ is selected from:
(1) hydrogen,
(2) —C$_{1-6}$alkyl,
(3) —CH$_2$CO$_2$H, and
(4) —CH$_2$CO$_2$C$_{1-6}$alkyl;
R$^6$ is selected from:
(1) hydrogen,
(2) —C$_{1-6}$alkyl,
(3) —(CH$_2$)$_m$OC$_{1-6}$alkyl,
(4) halogen,
(5) —(CH$_2$)$_m$CN,
(6) —(CH$_2$)$_m$CF$_3$,
(7) —(CH$_2$)$_m$OCF$_3$,
(8) —(CH$_2$)$_m$CHF$_2$,
(9) —(CH$_2$)$_m$CH$_2$F,
(10) —(CH$_2$)$_m$SO$_2$C$_{1-6}$alkyl,
(11) —(CH$_2$)$_m$C$_{3-6}$cycloalkyl,
(12) —(CH$_2$)$_m$C$_{2-7}$cycloheteroalkyl,
(13) —(CH$_2$)$_m$aryl, and
(14) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloheteroalkyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;
each R$^a$ is independently selected from the group consisting of:
(1) —(CH$_2$)$_m$-halogen,
(2) oxo,
(3) —(CH$_2$)$_m$OH,
(4) —(CH$_2$)$_m$N(R$^j$)$_2$,
(5) —(CH$_2$)$_m$NO$_2$,
(6) —(CH$_2$)$_m$CN,
(7) —C$_{1-6}$alkyl,
(8) —(CH$_2$)$_m$CF$_3$,
(9) —(CH$_2$)$_m$OCF$_3$,
(10) —O—(CH$_2$)$_m$—OC$_{1-6}$alkyl,
(11) —(CH$_2$)$_m$C(O)N(R$^j$)$_2$,
(12) —(CH$_2$)$_m$C(=N—OH)N(R$^j$)$_2$,
(13) —(CH$_2$)$_m$OC$_{1-6}$alkyl,
(14) —(CH$_2$)$_m$O—(CH$_2$)$_m$—C$_{3-7}$cycloalkyl,
(15) —(CH$_2$)$_m$O—(CH$_2$)$_m$—C$_{2-7}$cycloheteroalkyl,
(16) —(CH$_2$)$_m$O—(CH$_2$)$_m$-aryl,
(17) —(CH$_2$)$_m$O—(CH$_2$)$_m$-heteroaryl,
(18) —(CH$_2$)$_m$SC$_{1-6}$alkyl,
(19) —(CH$_2$)$_m$S(O)C$_{1-6}$alkyl,
(20) —(CH$_2$)$_m$SO$_2$C$_{1-6}$alkyl,
(21) —(CH$_2$)$_m$SO$_2$C$_{3-7}$cycloalkyl,
(22) —(CH$_2$)$_m$SO$_2$C$_{2-7}$cycloheteroalkyl,
(23) —(CH$_2$)$_m$SO$_2$-aryl,
(24) —(CH$_2$)$_m$SO$_2$-heteroaryl,
(25) —(CH$_2$)$_m$SO$_2$NHC$_{1-6}$alkyl,
(26) —(CH$_2$)$_m$SO$_2$N(C$_{1-6}$alkyl)$_2$,
(27) —(CH$_2$)$_m$SO$_2$NHC$_{3-7}$cycloalkyl,
(28) —(CH$_2$)$_m$SO$_2$NHC$_{2-7}$cycloheteroalkyl,
(29) —(CH$_2$)$_m$SO$_2$NH-aryl,
(30) —(CH$_2$)$_m$SO$_2$NH-heteroaryl,
(31) —(CH$_2$)$_m$NHSO$_2$—C$_{1-6}$alkyl,
(32) —(CH$_2$)$_m$NHSO$_2$—C$_{3-7}$cycloalkyl,
(33) —(CH$_2$)$_m$NHSO$_2$—C$_{2-7}$cycloheteroalkyl,
(34) —(CH$_2$)$_m$NHSO$_2$-aryl,

(35) —(CH$_2$)$_m$NHSO$_2$NH-heteroaryl,
(36) —(CH$_2$)$_m$N(R$^j$)—C$_{1-6}$alkyl,
(37) —(CH$_2$)$_m$N(R$^j$)—C$_{3-7}$cycloalkyl,
(38) —(CH$_2$)$_m$N(R$^j$)—C$_{2-7}$cycloheteroalkyl,
(39) —(CH$_2$)$_m$N(R$^j$)—C$_{2-7}$cycloheteroalkenyl,
(40) —(CH$_2$)$_m$N(R$^j$)-aryl,
(41) —(CH$_2$)$_m$N(R$^j$)-heteroaryl,
(42) —(CH$_2$)$_m$C(O)R$^f$,
(43) —(CH$_2$)$_m$C(O)N(R$^j$)$_2$,
(44) —(CH$_2$)$_m$N(R$^j$)C(O)N(R$^j$)$_2$,
(45) —(CH$_2$)$_m$CO$_2$H,
(46) —(CH$_2$)$_m$OCOH,
(47) —(CH$_2$)$_m$CO$_2$R$^f$,
(48) —(CH$_2$)$_m$OCOR$^f$,
(49) —(CH$_2$)$_m$C$_{3-7}$cycloalkyl,
(50) —(CH$_2$)$_m$C$_{3-7}$cycloalkenyl,
(51) —(CH$_2$)$_m$C$_{2-6}$cycloheteroalkyl,
(52) —(CH$_2$)$_m$C$_{2-6}$cycloheteroalkenyl,
(53) —(CH$_2$)$_m$aryl, and
(54) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;
each R$^b$ is independently selected from:
(1) hydrogen,
(2) —C$_{1-6}$alkyl,
(3) —C$_{3-6}$cycloalkyl,
(4) —C$_{3-6}$cycloalkenyl,
(5) —C$_{2-6}$cycloheteroalkyl,
(6) —C$_{2-6}$cycloheteroalkenyl,
(7) aryl,
(8) heteroaryl,
(9) —(CH$_2$)t-halogen,
(10) —(CH$_2$)s-OH,
(11) —(CH$_2$)sNO$_2$,
(12) —(CH$_2$)sNH$_2$,
(13) —(CH$_2$)sNH(C$_{1-6}$alkyl),
(14) —(CH$_2$)sN(C$_{1-6}$alkyl)$_2$,
(15) —(CH$_2$)sOC$_{1-6}$alkyl,
(16) —(CH$_2$)qCO$_2$H,
(17) —(CH$_2$)qCO$_2$C$_{1-6}$alkyl,
(18) —(CH$_2$)sCF$_3$,
(19) —(CH$_2$)sOCF$_3$,
(20) —(CH$_2$)sCHF$_2$,
(21) —(CH$_2$)sCH$_2$F,
(22) —(CH$_2$)sCN,
(23) —(CH$_2$)sSO$_2$C$_{1-6}$alkyl, and
(24) —(CH$_2$)sCON(R$^e$)$_2$,
wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens;
each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;
each R$^e$, R$^g$ and R$^h$ is independently selected from:
(1) hydrogen,
(2) —C$_{1-6}$alkyl, and
(3) —O—C$_{1-6}$alkyl,
wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^j$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$,
wherein each alkyl and cycloalkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl,
wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;
a is 0, 1 or 2;
b is 0, 1 or 2;
n is 0, 1, 2, 3 or 4;
m is 0, 1, 2, 3 or 4;
p is 0, 1, 2, or 3;
q is 0, 1, 2, 3 or 4;

r is 0, 1 or 2;

s is 0, 1, 2, 3 or 4; and t is 0, 1, 2, 3 or 4.

In another embodiment of the present invention, T is selected from the group consisting of: —$CR^3$—, N, and N-oxide. In a class of this embodiment, T is selected from the group consisting of: —$CR^3$—, and N. In another class of this embodiment, T is —$CR^3$—. In another class of this embodiment, T is selected from the group consisting of: N, and N-oxide. In another class of this embodiment, T is N. In another class of this embodiment, T is N-oxide.

In another embodiment of the present invention, U is selected from the group consisting of: —$CR^1$—, N, and N-oxide. In a class of this embodiment, U is selected from the group consisting of: —$CR^1$—, and N. In another class of this embodiment, U is $CR^1$—. In another class of this embodiment, U is selected from the group consisting of: N, and N-oxide. In another class of this embodiment, U is N. In another class of this embodiment, U is selected from the group consisting of: N-oxide.

In another embodiment of the present invention, V is selected from the group consisting of: —$CR^2$—, N, and N-oxide. In a class of this embodiment, V is selected from the group consisting of: —$CR^2$—, and N. In another class of this embodiment, V is —$CR^2$—. In another class of this embodiment, V is selected from the group consisting of: N, and N-oxide. In another class of this embodiment, V is N. In another class of this embodiment, V is N-oxide.

In another embodiment of the present invention, W is selected from the group consisting of: —$CR^4$—, N, and N-oxide. In a class of this embodiment, W is selected from the group consisting of: —$CR^4$—, and N. In another class of this embodiment, W is —$CR^4$—. In another class of this embodiment, W is selected from the group consisting of: N, and N-oxide. In another class of this embodiment, W is N. In another class of this embodiment, W is N-oxide.

In another embodiment of the present invention, T is $CR^3$; U is $CR^1$; V is $CR^2$; and W is $CR^4$.

In another embodiment of the present invention, T is N or N-oxide; U is —$CR^1$—; V is —$CR^2$—; and W is —$CR^4$—. In a class of this embodiment, T is N; U is —$CR^1$—; V is —$CR^2$—; and W is —$CR^4$—. In another class of this embodiment, T is N or N-oxide; U is —$CR^1$—; V is —$CR^2$—, wherein $R^2$ is halogen; and W is —$CR^4$—. In another class of this embodiment, T is N; U is —$CR^1$—; V is —$CR^2$—, wherein $R^2$ is halogen; and W is —$CR^4$—.

In another embodiment of the present invention, T is selected from —$CR^3$— and N; U is —$CR^1$—; V is —$CR^2$—; and W is selected from —$CR^4$— and N. In another embodiment of the present invention, T is —$CR^3$— or N; U is —$CR^1$—; V is —$CR^2$—; and W is —$CR^4$—. In another embodiment of the present invention, T is N; U is —$CR^1$—; V is —$CR^2$—; and W is —$CR^4$—. In another embodiment of the present invention, T is —$CR^3$—; U is —$CR^1$—; V is —$CR^2$—; and W is —$CR^4$— or N. In another embodiment of the present invention, T is selected from —$CR^3$—; U is —$CR^1$—; V is —$CR^2$—; and W is N. In another embodiment of the present invention, T is selected from —$CR^3$— or N; U is —$CR^1$—; V is —$CR^2$—; and W is —$CR^4$—.

In another embodiment of the present invention, one of T and W is N or N-oxide, U is $CR^1$ and V is $CR^2$, provided that if W is N or N-oxide then $R^1$ is selected from hydrogen, halogen, —CN, —$CF_3$, —$C_{1-6}$alkyl, —$C_{2-6}$alkenyl and —$C_{2-6}$alkynyl, and if T is N or N-oxide then $R^2$ is selected from hydrogen, halogen, —CN, —$CF_3$, —$C_{1-6}$alkyl, —$C_{2-6}$alkenyl and —$C_{2-6}$alkynyl.

In another embodiment of the present invention, T is selected from: —$CR^3$—, N and N-oxide; U is —$CR^1$—; V is —$CR^2$—; and W is selected from —$CR^4$—, N and N-oxide.

In another embodiment of the present invention, T is selected from —$CR^3$— and N; U is —$CR^1$—; V is —$CR^2$—; and W is selected from —$CR^4$— and N, provided that one of T and W is N, and further provided that if W is N, then $R^1$ is selected from hydrogen, halogen, —CN, —$CF_3$, —$C_{1-6}$alkyl, —$C_{2-6}$alkenyl and —$C_{2-6}$alkynyl, and if T is N then $R^2$ is selected from hydrogen, halogen, —CN, —$CF_3$, —$C_{1-6}$alkyl, —$C_{2-6}$alkenyl and —$C_{2-6}$alkynyl.

In another embodiment of the present invention, T is selected from —$CR^3$— and N; U is —$CR^1$—; V is —$CR^2$—; and W is —$CR^4$—, provided that if T is N then $R^2$ is selected from hydrogen, halogen, —CN, —$CF_3$, —$C_{1-6}$alkyl, —$C_{2-6}$alkenyl and —$C_{2-6}$alkynyl.

In another embodiment of the present invention, T is selected from —$CR^3$— and N; U is —$CR^1$—; V is —$CR^2$—; and W is selected from —$CR^4$— and N, provided that one of T and W is N, and further provided that if W is N, then $R^1$ is selected from hydrogen and halogen, and if T is N then $R^2$ is selected from hydrogen and halogen.

In another embodiment of the present invention, T is selected from —$CR^3$— and N; U is —$CR^1$—; V is —$CR^2$—; and W is selected from —$CR^4$— and N, provided that one of T and W is N, and further provided that if W is N, then $R^1$ is halogen, and if T is N then $R^2$ is halogen.

In another embodiment of the present invention, T is selected from —$CR^3$— and N; U is —$CR^1$—; V is —$CR^2$—; and W is selected from —$CR^4$— and N, provided that if T is N then $R^2$ is selected from hydrogen and halogen.

In another embodiment of the present invention, T is selected from —$CR^3$— and N; U is —$CR^1$—; V is —$CR^2$—; and W is selected from —$CR^4$— and N, provided that if T is N then $R^2$ is halogen.

In another embodiment of the present invention, one of T and W is N or N-oxide, U is $CR^1$ and V is $CR^2$, provided that if W is N or N-oxide then $R^1$ is halogen, and if T is N or N-oxide then $R^2$ is halogen.

In another embodiment of the present invention, one of T and W is N, U is $CR^1$ and V is $CR^2$, provided that if W is N then $R^1$ is halogen, and if T is N then $R^2$ is chloride.

In another embodiment of the present invention, T is N or N-oxide, U is $CR^1$, V is $CR^2$, and W is $CR^4$. In a subclass of this class, T is N, U is $CR^1$, V is $CR^2$, and W is $CR^4$. In another subclass of this class, T is N, U is $CR^1$, V is $CR^2$, W is $CR^4$, and $R^2$ is halogen. In another subclass of this class, T is N, U is $CR^1$, V is $CR^2$, W is $CR^4$, and $R^2$ is chloride. In another subclass of this class, T is N, U is $CR^1$, V is $CR^2$, W is $CR^4$, $R^2$ is chloride, and $R^4$ is hydrogen.

In another embodiment of the present invention, W is N or N-oxide; U is —$CR^1$—; V is —$CR^2$—; and T is —$CR^3$—. In a class of this embodiment, W is N or N-oxide; U is —$CR^1$—, wherein $R^1$ is halogen; V is —$CR^2$—; and T is —$CR^3$—. In another class of this embodiment, W is N; U is —$CR^1$—, wherein $R^1$ is halogen; V is —$CR^2$—; and T is —$CR^3$—.

In another embodiment of the present invention, W is N or N-oxide, U is $CR^1$, V is $CR^2$, and T is $CR^3$. In a subclass of this class, W is N, U is $CR^1$, V is $CR^2$, and T is $CR^3$. In another subclass of this class, W is N, U is $CR^1$, V is $CR^2$, T is $CR^3$, and $R^1$ is halogen. In another subclass of this class, W is N, U is $CR^1$, V is $CR^2$, T is $CR^3$, and $R^1$ is chloride. In another subclass of this class, W is N, U is $CR^1$, V is $CR^2$, T is $CR^3$, $R^1$ is chloride, and $R^3$ is hydrogen.

In another embodiment of the present invention, X is absent or selected from: —CH$_2$—, —CHF—, —CF$_2$—, —S—, —S(O)—, —S(O)$_2$—, —O—, —O—CH$_2$—, —CH$_2$—O—, —CH$_2$—S—, —NH—, —C(O)—, —NHC(O)—, —C(O)NH—, —NHSO$_2$—, —SO$_2$NH—, and —CO$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, COC$_{1-6}$alkyl, phenyl and —CH$_2$phenyl, and wherein each NH is unsubstituted or substituted with 1 substituent selected from: C$_{1-6}$alkyl, CO$_2$H, CO$_2$C$_{1-6}$alkyl, COC$_{1-6}$alkyl, phenyl and —CH$_2$phenyl.

In another embodiment of the present invention, X is absent or selected from: —CH$_2$—, —CHF—, —CF$_2$—, —S—, —S(O)—, —S(O)$_2$—, —O—, —O—CH$_2$—, —CH$_2$—O—, —CH$_2$—S—, —NH—, —C(O)—, —NHC(O)—, —C(O)NH—, —NHSO$_2$—, —SO$_2$NH—, and —CO$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl.

In another embodiment of the present invention, X is absent or selected from: —CH$_2$—, —S—, —S(O)—, —S(O)$_2$—, —O—, —O—CH$_2$—, —CH$_2$—O—, —CH$_2$—S—, —NH—, —C(O)—, and —C(O)NH—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl.

In another embodiment of the present invention, X is absent or selected from: —CH$_2$—, —S—, —S(O)—, —S(O)$_2$—, —O—, —O—CH$_2$—, —CH$_2$—O—, —CH$_2$—S—, —NH—, —C(O)—, —C(O)NH—, wherein each CH$_2$ is unsubstituted or substituted with 1 or 2 substituents selected from: C$_{1-6}$alkyl, and wherein each NH is unsubstituted or substituted with 1 substituent selected from: C$_{1-6}$alkyl.

In another embodiment of the present invention, X is absent or selected from: —CH$_2$—, —S—, —S(O)—, —S(O)$_2$—, —O—, —O—CH$_2$—, —CH$_2$—O—, —CH$_2$—S—, —N(CH$_3$)—, —C(O)—, and —C(O)NH—.

In another embodiment of the present invention, X is absent.

In another embodiment of the present invention, X is selected from: —CH$_2$—, —CHF—, —CF$_2$—, —S—, —O—, —O—CH$_2$—, —CH$_2$—O—, —NH—, —C(O)—, —NHC(O)—, —C(O)NH—, —NHSO$_2$—, —SO$_2$NH—, and —CO$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl. In a class of this embodiment of the present invention, X is selected from: —CH$_2$—, —CHF—, —CF$_2$—, —S—, —O—, —O—CH$_2$—, —CH$_2$—O—, and —NH—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl. In another class of this embodiment, X is selected from: —CH$_2$—, and —CH$_2$—O—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl. In another class of this embodiment, X is selected from: —CH$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl. In another class of this embodiment, X is —CH$_2$—O—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl.

In another embodiment of the present invention, X is selected from: —CH$_2$—, —CHF—, —CF$_2$—, —S—, —O—, —O—CH$_2$—, —CH$_2$—O—, —NH—, —C(O)—, —NHC(O)—, —C(O)NH—, —NHSO$_2$—, —SO$_2$NH—, and —CO$_2$—. In a class of this embodiment of the present invention, X is selected from: —CH$_2$—, —CHF—, —CF$_2$—, —S—, —O—, —O—CH$_2$—, —CH$_2$—O—, and —NH—. In a class of this embodiment, X is selected from: —CH$_2$—, and —CH$_2$—O—. In another class of this embodiment, X is —CH$_2$—. In another class of this embodiment, X is —CH$_2$—O—.

In another embodiment of the present invention, Y is selected from: —C$_{1-6}$alkyl, —C$_{2-6}$alkynyl, —CHF—, —CF$_2$—, C$_{3-10}$cycloalkyl, C$_{3-10}$cycloalkenyl, C$_{2-10}$cycloheteroalkyl, C$_{2-10}$cycloheteroalkenyl, aryl, heteroaryl, and

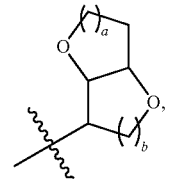

wherein Y is unsubstituted or substituted with 1, 2, 3 or 4 substituents selected from R$^b$.

In another embodiment of the present invention, Y is selected from: —C$_{1-6}$alkyl, —C$_{2-6}$alkynyl, C$_{3-10}$cycloalkyl, C$_{2-10}$cycloheteroalkyl, aryl, heteroaryl, and

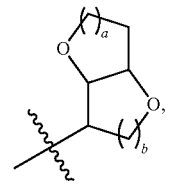

wherein Y is unsubstituted or substituted with 1, 2, 3 or 4 substituents selected from R$^b$.

In another embodiment of the present invention, Y is selected from: —C$_{1-3}$alkyl, —C$_2$alkynyl, cyclohexyl, tetrahydropyran, tetrahydrofuran, piperidine, phenyl, thiophene, and

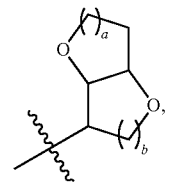

wherein a is 1, and b is 1, and wherein Y is unsubstituted or substituted with 1, 2, 3 or 4 substituents selected from $R^b$.

In another embodiment of the present invention, Y is selected from: —$C_{1-6}$alkyl, —CHF—, —$CF_2$—, —$C_{3-10}$cycloalkyl, —$C_{3-10}$cycloalkenyl, —$C_{2-10}$cycloheteroalkyl, $C_{2-10}$cycloheteroalkenyl, aryl, heteroaryl, and

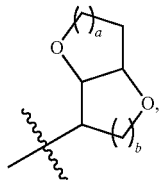

wherein Y is unsubstituted or substituted with 1, 2, 3 or 4 substituents selected from $R^b$.

In another embodiment of the present invention, Y is selected from: —$C_{1-6}$alkyl, —CHF—, —$CF_2$—, $C_{3-10}$cycloalkyl, $C_{3-10}$cycloalkenyl, $C_{2-10}$cycloheteroalkyl, $C_{2-10}$cycloheteroalkenyl, aryl, and heteroaryl, wherein Y is unsubstituted or substituted with 1, 2, 3 or 4 substituents selected from $R^b$.

In another embodiment of the present invention, Y is selected from: $C_{1-6}$alkyl, $C_{3-10}$cycloalkyl, $C_{2-10}$cycloheteroalkyl, and aryl, wherein Y is unsubstituted or substituted with 1, 2, 3 or 4 substituents selected from $R^b$. In a class of this embodiment, Y is selected from: —$(CH_2)_2$, —$(CH_2)_3$, cyclohexyl, tetrahydropyran, piperidine, and phenyl, wherein Y is unsubstituted or substituted with 1, 2, 3 or 4 substituents selected from $R^b$.

In another embodiment of the present invention, Y is selected from: $C_{1-6}$alkyl, $C_{3-10}$cycloalkyl, and aryl, wherein Y is unsubstituted or substituted with 1, 2, 3 or 4 substituents selected from $R^b$. In a class of this embodiment, Y is selected from: —$(CH_2)_2$, —$(CH_2)_3$, cyclohexyl, and phenyl, wherein Y is unsubstituted or substituted with 1, 2, 3 or 4 substituents selected from $R^b$.

In another embodiment of the present invention, Y is selected from:

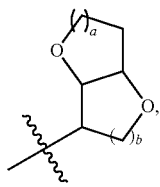

wherein Y is unsubstituted or substituted with 1, 2, 3 or 4 substituents selected from $R^b$.

In another embodiment of the present invention, Z is selected from: hydrogen, oxo, —CN, —$CF_3$, —$C_{1-6}$alkyl, —$(CH_2)_t$-halogen, —$(CH_2)_nCOC_{1-6}$alkyl, —$(CH_2)_nCO_2H$, —$(CH_2)_nOCOH$, —$(CH_2)_nCO_2R^i$, —$(CH_2)_nOCOR^i$, —$(CH_2)_nOH$, —$(CH_2)_nC(O)N(R^g)_2$, —$(CH_2)_nC(O)(CH_2)_nN(R^g)_2$, —$(CH_2)_nOC(O)(CH_2)_nN(R^g)_2$, —$(CH_2)_nNHC(O)C_{1-6}$alkyl, —$(CH_2)_nNHSO_2R^i$, —$(CH_2)_nSO_2C_{1-6}$alkyl, —$(CH_2)_nSO_2NHR^g$, —$(CH_2)_nSO_2NHC(O)R^i$, —$(CH_2)_nSO_2NHCO_2R^i$, —$(CH_2)_nSO_2NHCON(R^g)_2$, —$(CH_2)_nC(O)NHSO_2R^i$, —$(CH_2)_nNHC(O)N(R^g)_2$, —$(CH_2)_nC_{3-10}$cycloalkyl-$CO_2R^e$, heteroaryl, —$C_{2-10}$cycloheteroalkenyl, —$C_{2-10}$cycloheteroalkyl, and —$(CH_2)_nP(O)(OR^j)_2$, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$.

In another embodiment of the present invention, Z is selected from: hydrogen, oxo, —$(CH_2)_nCO_2H$, —$(CH_2)_nCO_2R^i$, —$(CH_2)_nOCOR^i$, —$(CH_2)_nOH$, and —$(CH_2)_nP(OR^j)_2$, wherein each $CH_2$ is unsubstituted or substituted with 1 or 2 substituents selected from $C_{1-6}$alkyl, —OH and —$NH_2$.

In another embodiment of the present invention, Z is selected from: hydrogen, oxo, —$CO_2H$, —$CH_2CO_2H$, —$CH_2CO_2CH_2CH_3$, —$OC(O)CH(CH_3)_2$, —OH, —$CH_2OH$—$P(O)(OH)_2$, —$(CH_2)_nP(O)(OCH_2CH_3)_2$, and —$(CH_2)_nP(O)(OH)(OCH_2CH_3)$.

In another embodiment of the present invention, Z is selected from: hydrogen, oxo, —CN, —$CF_3$, —$C_{1-6}$alkyl, —$(CH_2)_t$-halogen, —$(CH_2)_nCOC_{1-6}$alkyl, —$(CH_2)_nCO_2H$, —$(CH_2)_nOCOH$, —$(CH_2)_nCO_2R^i$, —$(CH_2)_nOCOR^i$, —$(CH_2)_nOH$, —$(CH_2)_nC(O)N(R^g)_2$, —$(CH_2)_nC(O)(CH_2)_nN(R^g)_2$, —$(CH_2)_nOC(O)(CH_2)_nN(R^g)_2$, —$(CH_2)_nNHC(O)C_{1-6}$alkyl, —$(CH_2)_nNHSO_2R^i$, —$(CH_2)_nSO_2C_{1-6}$alkyl, —$(CH_2)_nSO_2NHR^g$, —$(CH_2)_nSO_2NHC(O)R^i$, —$(CH_2)_nSO_2NHCO_2R^i$, —$(CH_2)_nSO_2NHCON(R^g)_2$, —$(CH_2)_nC(O)NHSO_2R^i$, and —$(CH_2)_nNHC(O)N(R^g)_2$, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl is unsubstituted or substituted with 1, 2, 3 or 4 substituents selected from $R^c$.

In another embodiment of the present invention, Z is selected from: hydrogen, oxo, —CN, —$CF_3$, —$C_{1-6}$alkyl, —$(CH_2)_t$-halogen, —$(CH_2)_nCOC_{1-6}$alkyl, —$(CH_2)_nCO_2H$, —$(CH_2)_nOCOH$, —$(CH_2)_nCO_2R^i$, —$(CH_2)_nOCOR^i$, and —$(CH_2)_nOH$, wherein each $CH_2$ is unsubstituted or substituted with 1 or 2 substituents selected from $C_{1-6}$alkyl, —OH and —$NH_2$, and wherein each alkyl is unsubstituted or substituted with 1, 2, 3 or 4 substituents selected from $R^c$.

In another embodiment of the present invention, Z is selected from: hydrogen, —$(CH_2)_nCO_2H$, and —$(CH_2)_nOH$, wherein each $CH_2$ is unsubstituted or substituted with 1 or 2 substituents selected from $C_{1-6}$alkyl, —OH and —$NH_2$. In a class of this embodiment, Z is selected from: hydrogen, —$CO_2H$, —OH, and —$CH_2OH$, wherein each $CH_2$ is unsubstituted or substituted with 1 or 2 substituents selected from $C_{1-6}$alkyl, —OH and —$NH_2$. In another class of this embodiment, Z is selected from: hydrogen, —$CO_2H$, —OH, and —$CH_2OH$.

In another embodiment of the present invention, Z is selected from: —$(CH_2)_nCO_2H$, and —$(CH_2)_nOH$, wherein each $CH_2$ is unsubstituted or substituted with 1 or 2 substituents selected from $C_{1-6}$alkyl, —OH and —$NH_2$. In a class of this embodiment, Z is selected from: —$CO_2H$, —OH, and —$CH_2OH$, wherein each $CH_2$ is unsubstituted or substituted with 1 or 2 substituents selected from $C_{1-6}$alkyl, —OH and —$NH_2$. In another class of this embodiment, Z is selected from: —$CO_2H$, —OH, and —$CH_2OH$.

In another embodiment of the present invention, Z is hydrogen.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —$C(O)NH$—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, aryl, aryl-$C_{3-7}$cycloalkyl, aryl-$C_{3-7}$cycloalkenyl, aryl-$C_{2-10}$cycloheteroalkyl, aryl-$C_{2-10}$cycloheteroalkenyl, aryl-aryl, aryl-heteroaryl, heteroaryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, and —$C_{2-6}$alkynyl-$C_{2-7}$cycloheteroalkenyl, wherein each alkyl, alkenyl, alkynyl, cycloalkyl, cycloalkenyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl.

In another embodiment of the present invention, each $R^1$ and $R^2$ is independently selected from: hydrogen, halogen, aryl, aryl-$C_{3-7}$cycloalkyl, aryl-$C_{3-7}$cycloalkenyl, aryl-$C_{2-10}$cycloheteroalkyl, aryl-aryl, aryl-heteroaryl, heteroaryl, and —$C_{2-6}$alkynyl-aryl, wherein each alkynyl, cycloalkyl, cycloalkenyl, cycloheteroalkyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, and halogen.

In another embodiment of the present invention, each $R^1$ and $R^2$ is independently selected from: hydrogen, halogen, benzodioxole, phenyl-cyclopropyl, phenyl-cyclohexene, phenyl-azetidine, phenyl-pyrrolidine, phenyl-piperidine, phenyl-piperazine, phenyl-morpholine, phenyl-thiomorpholine, biphenyl, indole, —$C_2$alkynyl-phenyl, phenyl, phenyl-oxazole, phenyl-pyridine, phenyl-furan, phenyl-oxadiazole, pyridine, benzofuran, pyrrolo[2,3-b]pyridine, pyrazole, and benzisoxazole, wherein each alkynyl, cycloalkyl, cycloalkenyl, cycloheteroalkyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, and halogen.

In another embodiment of the present invention, $R^1$ and $R^2$ are independently selected from: hydrogen, and halogen. In a class of this embodiment, $R^1$ and $R^2$ are independently selected from: hydrogen, F and Cl.

In another embodiment of the present invention, $R^1$ is selected from: hydrogen, and halogen. In a class of this embodiment, $R^1$ is selected from: hydrogen, F and Cl. In another class of this embodiment, $R^1$ is hydrogen. In another class of this embodiment, $R^1$ is halogen. In another class of this embodiment, $R^1$ is selected from F and Cl.

In another embodiment of the present invention, $R^2$ is selected from: hydrogen, and halogen. In a class of this embodiment, $R^2$ is selected from: hydrogen, F and Cl. In another class of this embodiment, $R^2$ is hydrogen. In another class of this embodiment, $R^2$ is halogen. In another class of this embodiment, $R^2$ is selected from F and Cl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{4-10}$cycloalkenyl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{3-7}$cycloalkyl, —$(CH_2)_p$aryl-$C_{2-10}$cycloheteroalkyl, —$(CH_2)_p$ aryl-$C_{2-10}$cycloheteroalkenyl, —$(CH_2)_p$aryl-aryl, —$(CH_2)_p$aryl-heteroaryl, —$(CH_2)_p$heteroaryl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$jalkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —$C(O)NH$—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, one of $R^1$ and $R^2$ is halogen. In a subclass of this class, one of $R^1$ and $R^2$ is Br, F, or Cl. In another subclass of this class, one of $R^1$ and $R^2$ is Cl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —(CH$_2$)$_p$aryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-aryl, —(CH$_2$)$_p$aryl-heteroaryl, and —(CH$_2$)$_p$heteroaryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkyl, alkenyl, alkynyl, cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl. In a class of this embodiment, one of R$^1$ and R$^2$ is halogen. In a subclass of this class, one of R$^1$ and R$^2$ is Br, F, or Cl. In another subclass of this class, one of R$^1$ and R$^2$ is Cl.

In another embodiment of the present invention, each R$^1$ and R$^2$ is independently selected from: hydrogen, halogen, —(CH$_2$)$_p$aryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-aryl, —(CH$_2$)$_p$aryl-heteroaryl, and —(CH$_2$)$_p$heteroaryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, and halogen. In a class of this embodiment, one of R$^1$ and R$^2$ is halogen. In a subclass of this class, one of R$^1$ and R$^2$ is Br, F or Cl. In another subclass of this class, one of R$^1$ and R$^2$ is Cl.

In another embodiment of the present invention, each R$^1$ and R$^2$ is independently selected from: halogen, —(CH$_2$)$_p$aryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-aryl, —(CH$_2$)$_p$aryl-heteroaryl, and —(CH$_2$)$_p$heteroaryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and N(C$_{1-6}$alkyl)$_2$, and wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen. In a class of this embodiment, one of R$^1$ and R$^2$ is Br, F, or Cl. In a subclass of this class, one of R$^1$ and R$^2$ is Cl.

In another embodiment of the present invention, each R$^1$ and R$^2$ is independently selected from: halogen, aryl, aryl-C$_{3-7}$cycloalkyl, aryl-C$_{2-10}$cycloheteroalkyl, aryl-aryl, aryl-heteroaryl, and heteroaryl, wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen. In a class of this embodiment, one of R$^1$ and R$^2$ is Br, F, or Cl. In a subclass of this class, one of R$^1$ and R$^2$ is Cl. In another class of this embodiment, each R$^1$ and R$^2$ is independently selected from: halogen, phenyl, phenyl-cyclopropyl, phenyl-pyrrolidine, phenyl piperidine, phenyl-piperazine, biphenyl, phenyl-oxazole, phenyl-pyridine, phenyl-furan, phenyl-oxadiazole, pyridine, indole, benzofuran, benzodioxole, pyrrolo[2,3-b]pyridine, pyrazole, and benzisoxazole, wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen. In a subclass of this class, one of R$^1$ and R$^2$ is Br, F, or Cl. In another subclass of this class, one of R$^1$ and R$^2$ is Cl. In another class of this embodiment, R$^1$ is independently selected from: aryl, aryl-C$_{3-7}$cycloalkyl, aryl-C$_{2-10}$cycloheteroalkyl, aryl-aryl, aryl-heteroaryl, and heteroaryl, wherein each cycloalkyl, cycloheteroalkyl, aryl and heteroaryl is unsubstituted or substituted with 1, 2, 3 or 4 substituents independently selected from R$^a$, and R$^2$ is halogen. In a subclass of this class, R$^2$ is Br, F, or Cl. In another subclass of this class, R$^2$ is Cl. In a subclass of this class, R$^1$ is independently selected from: aryl, aryl-C$_{3-7}$cycloalkyl, aryl-C$_{2-10}$cycloheteroalkyl, aryl-aryl, aryl-heteroaryl, and heteroaryl, wherein cycloalkyl, cycloheteroalkyl, aryl and heteroaryl is unsubstituted or substituted with 1, 2, 3 or 4 substituents independently selected from R$^a$. In another subclass of this class, R$^2$ is halogen. In another subclass of this class, R$^2$ is Br, F, or Cl. In another subclass of this class, R$^2$ is Cl.

In another class of this embodiment, R$^1$ is independently selected from: phenyl, phenyl-cyclopropyl, phenyl-pyrrolidine, phenyl piperidine, phenyl-piperazine, biphenyl, phenyl-oxazole, phenyl-pyridine, phenyl-furan, phenyl-oxadiazole, pyridine, indole, benzofuran, benzodioxole, pyrrolo[2,3-b]pyridine, pyrazole, and benzisoxazole, wherein each cycloalkyl, cycloheteroalkyl, aryl and heteroaryl is unsubstituted or substituted with 1, 2, 3 or 4 substituents independently selected from R$^a$, and R$^2$ is halogen. In a subclass of this class, R$^2$ is Br, F, or Cl. In another subclass of this class, R$^2$ is Cl.

In another class of this embodiment, R$^1$ is independently selected from: phenyl, phenyl-cyclopropyl, phenyl-pyrrolidine, phenyl piperidine, phenyl-piperazine, biphenyl, phenyl-oxazole, phenyl-pyridine, phenyl-furan, phenyl-oxadiazole, pyridine, indole, benzofuran, benzodioxole, pyrrolo[2,3-b]pyridine, pyrazole, and benzisoxazole, wherein each cycloalkyl, cycloheteroalkyl, aryl and heteroaryl is unsubstituted or substituted with 1, 2, 3 or 4 substituents independently selected from R$^a$. In another class of this embodiment, R$^2$ is halogen. In a subclass of this class, R$^2$ is Br, F, or Cl. In another subclass of this class, R$^2$ is Cl.

In another embodiment of the present invention, each R$^1$ and R$^2$ is independently selected from: halogen, aryl, aryl-C$_{3-7}$cycloalkyl, aryl-C$_{2-10}$cycloheteroalkyl, aryl-aryl, and aryl-heteroaryl, wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen. In a class of this embodiment, one of R$^1$ and R$^2$ is Br, F, or Cl. In a subclass of this class, one of R$^1$ and R$^2$ is Cl. In another class of this embodiment, each R$^1$ and R$^2$ is independently selected from: halogen, phenyl, phenyl-cyclopropyl, phenyl-pyrrolidine, biphenyl, and phenyl-pyridine, wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen. In a subclass of this class, one of R$^1$ and R$^2$ is Br, F, or Cl. In another subclass of this class, one of R$^1$ and R$^2$ is Cl. In another class of this embodiment, R$^1$ is independently selected from: aryl, aryl-C$_{3-7}$cycloalkyl, aryl-C$_{2-10}$cycloheteroalkyl, aryl-aryl, and aryl-heteroaryl, wherein each cycloalkyl, cycloheteroalkyl, aryl and heteroaryl is unsubstituted or substituted with 1, 2, 3 or 4 substituents independently selected from R$^a$, and R$^2$ is halogen. In a subclass of this class, R$^2$ is Br, F, or Cl. In another subclass of this class, R$^2$ is Cl.

In another class of this embodiment of the present invention, R$^1$ is independently selected from: aryl, aryl-C$_{3-7}$cycloalkyl, aryl-C$_{2-10}$cycloheteroalkyl, aryl-aryl, and aryl-heteroaryl, wherein each cycloalkyl, cycloheteroalkyl, aryl and heteroaryl is unsubstituted or substituted with 1, 2, 3 or 4 substituents independently selected from $R^a$.

In another class of this embodiment, $R^1$ is independently selected from: phenyl, phenyl-cyclopropyl, phenyl-pyrrolidine, biphenyl, and phenyl-pyridine, wherein each cycloalkyl, cycloheteroalkyl, aryl and heteroaryl is unsubstituted or substituted with 1, 2, 3 or 4 substituents independently selected from $R^a$; and $R^2$ is halogen. In a subclass of this class, $R^2$ is Br, F, or Cl. In another subclass of this class, $R^2$ is Cl. In a subclass of this class, $R^1$ is independently selected from: phenyl, phenyl-cyclopropyl, phenyl-pyrrolidine, biphenyl, and phenyl-pyridine, wherein each cycloalkyl, cycloheteroalkyl, aryl and heteroaryl is unsubstituted or substituted with 1, 2, 3 or 4 substituents independently selected from $R^a$.

In another class of this embodiment, $R^2$ is halogen. In a subclass of this class, $R^2$ is Br, F, or Cl. In another subclass of this class, $R^2$ is Cl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_p$aryl-$C_{2-10}$cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, $C_{1-6}$alkyl, —$OC_{1-6}$alkyl, —$NHC_{1-6}$alkyl, and $N(C_{1-6}$alkyl$)_2$, and wherein each alkyl, alkenyl, alkynyl, cycloheteroalkyl, and aryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, one of $R^1$ and $R^2$ is halogen. In a subclass of this class of this embodiment, one of $R^1$ and $R^2$ is selected from Br, F, and Cl. In another subclass of this class of this embodiment, one of $R^1$ and $R^2$ is Cl.

In a class of this embodiment, each $R^2$ is independently selected from: —$(CH_2)_p$aryl-$C_{2-10}$ cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloheteroalkyl, and aryl is unsubstituted or substituted with 1, 2, 3 or 4 substituents independently selected from $R^a$, and $R^1$ is selected from the group consisting of: hydrogen, halogen, —CN, —$CF_3$, —$C_{1-6}$alkyl, —$C_{2-6}$alkenyl and —$C_{2-6}$alkynyl. In a subclass of this class, $R^1$ is halogen. In another subclass of this class, $R^1$ is selected from Br, F, and Cl. In another subclass of this class, $R^1$ is Cl.

In another class of this embodiment, $R^2$ is independently selected from: phenyl-pyrrolidine, and biphenyl, wherein each cycloheteroalkyl, and aryl is unsubstituted or substituted with 1, 2, 3 or 4 substituents independently selected from $R^a$, and $R^1$ is selected from the group consisting of: hydrogen, halogen, —CN, —$CF_3$, —$C_{1-6}$alkyl, —$C_{2-6}$alkenyl and —$C_{2-6}$alkynyl. In a subclass of this class, $R^1$ is halogen. In another subclass of this class, $R^1$ is selected from Br, F, and Cl. In another subclass of this class, $R^1$ is Cl.

In another embodiment of the present invention, each $R^1$ and $R^2$ is independently selected from: hydrogen, halogen, —$(CH_2)_p$aryl-$C_{2-10}$cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloheteroalkyl, and aryl is unsubstituted or substituted with 1, 2, 3 or 4 substituents independently selected from $R^a$, provided that at least one of and only one of $R^1$ and $R^2$ is selected from: hydrogen and halogen. In a class of this embodiment, one of $R^1$ and $R^2$ is selected from hydrogen, Br, F, and Cl. In another subclass of this class, one of $R^1$ and $R^2$ is Cl.

In another class of this embodiment, $R^2$ is independently selected from: —$(CH_2)_p$aryl-$C_{2-10}$ cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloheteroalkyl, and aryl is unsubstituted or substituted with 1, 2, 3 or 4 substituents independently selected from $R^a$, and $R^1$ is selected from the group consisting of: hydrogen and halogen. In a subclass of this class, $R^1$ is selected from hydrogen, Br, F, and Cl. In another subclass of this class, $R^1$ is Cl.

In another embodiment of the present invention, each $R^1$ and $R^2$ is independently selected from: halogen, —$(CH_2)_p$aryl-$C_{2-10}$cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and $N(C_{1-6}$alkyl$)_2$, and wherein each cycloheteroalkyl, and aryl is unsubstituted or substituted with 1, 2, 3 or 4 substituents independently selected from $R^a$, provided that at least one of and only one of $R^1$ and $R^2$ is halogen. In a class of this embodiment, one of $R^1$ and $R^2$ is Br, F, or Cl. In a subclass of this class, one of $R^1$ and $R^2$ is Cl. In another class of this embodiment, $R^2$ is independently selected from: —$(CH_2)_p$aryl-$C_{2-10}$cycloheteroalkyl, and —$(CH_2)_p$aryl-aryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and $N(C_{1-6}$alkyl$)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, and $R^1$ is halogen. In a subclass of this class, $R^1$ is Br, F, or Cl. In another subclass of this class, $R^1$ is Cl.

In another embodiment of the present invention, each $R^1$ and $R^2$ is independently selected from: halogen, aryl-$C_{2-10}$cycloheteroalkyl, and aryl-aryl, wherein each cycloheteroalkyl, and aryl is unsubstituted or substituted with 1, 2, 3 or 4 substituents independently selected from $R^a$, provided that at least one of and only one of $R^1$ and $R^2$ is halogen. In a class of this embodiment, one of $R^1$ and $R^2$ is Br, F, or Cl. In another class of this embodiment, one of $R^1$ and $R^2$ is Cl. In a class of this embodiment, each $R^1$ and $R^2$ is independently selected from: Cl, phenyl-pyrrolidine, and biphenyl, wherein each cycloheteroalkyl, and aryl is unsubstituted or substituted with 1, 2, 3 or 4 substituents independently selected from $R^a$, provided that at least one of and only one of $R^1$ and $R^2$ is halogen. In a subclass of this class, one of $R^1$ and $R^2$ is Br, F, or Cl. In another subclass of this class, one of $R^1$ and $R^2$ is Cl. In another class of this embodiment, $R^2$ is independently selected from: phenyl-pyrrolidine, and biphenyl, wherein each cycloheteroalkyl and aryl is unsubstituted or substituted with 1, 2, 3 or 4 substituents independently selected from $R^a$, and $R^1$ is Cl. In another class of this embodiment, $R^2$ is independently selected from: phenyl-pyrrolidine, and biphenyl, wherein each cycloheteroalkyl, and aryl is unsubstituted or substituted with 1, 2, 3 or 4 substituents independently selected from $R^a$.

In another class of this embodiment, $R^1$ is Br, F, or Cl. In another class of this embodiment, $R^1$ is Cl.

In another embodiment of the present invention, $R^3$ and $R^4$ are each absent or independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, $R^3$ and $R^4$ are each absent or independently selected from: hydrogen, halogen, —$C_{1-6}$alkyl, —CN, —$CF_3$, —OH, —$OC_{1-6}$alkyl, —$NH_2$, —$NHC_{1-6}$alkyl, —$N(C_{1-6}alkyl)_2$, and —$SC_{1-6}$alkyl. In another class of this embodiment, $R^3$ and $R^4$ are each absent or independently selected from: hydrogen, halogen, and —$C_{1-6}$alkyl.

In another embodiment of the present invention, $R^3$ and $R^4$ are each absent or hydrogen. In a class of this embodiment, $R^3$ and $R^4$ are absent. In another class of this embodiment, $R^3$ and $R^4$ are hydrogen.

In another embodiment of the present invention, each $R^3$ is absent or independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl.

In another embodiment of the present invention, each $R^3$ is absent or independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, each $R^3$ is absent or independently selected from: hydrogen, halogen, —$C_{1-6}$alkyl, —CN, —$CF_3$, —OH, —$OC_{1-6}$alkyl, —$NH_2$, —$NHC_{1-6}$alkyl, —$N(C_{1-6}alkyl)_2$, and —$SC_{1-6}$alkyl. In another class of this embodiment, each $R^3$ is absent or independently selected from: hydrogen, halogen, and —$C_{1-6}$alkyl.

In another embodiment of the present invention, $R^3$ and $R^4$ are each absent or hydrogen.

In another embodiment of the present invention, $R^3$ and $R^4$ are each absent or hydrogen; and $R^5$ is hydrogen.

In another embodiment of the present invention, $R^3$ is absent or hydrogen. In a class of this embodiment, $R^3$ is hydrogen. In another class of this embodiment of the present invention, $R^3$ is absent.

In another embodiment of the present invention, each $R^4$ is absent or independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl.

In another embodiment of the present invention, each $R^4$ is absent or independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, each $R^4$ is absent or independently selected from: hydrogen, halogen, —$C_{1-6}$alkyl, —CN, —$CF_3$, —OH, —$OC_{1-6}$alkyl, —$NH_2$, —$NHC_{1-6}$alkyl, —$N(C_{1-6}alkyl)_2$, and —$SC_{1-6}$alkyl. In another class of this embodiment, each $R^4$ is absent or independently selected from: hydrogen, halogen, and —$C_{1-6}$alkyl.

In another embodiment of the present invention, $R^4$ is absent or hydrogen. In a class of this embodiment, $R^4$ is hydrogen. In another class of this embodiment of the present invention, $R^4$ is absent.

In another embodiment of the present invention, $R^5$ is selected from: hydrogen, —$C_{1-6}$alkyl, —$CH_2CO_2H$, and —$CH_2CO_2C_{1-6}$alkyl. In a class of this embodiment, $R^5$ is selected from: hydrogen, and —$C_{1-6}$alkyl. In another class of this embodiment, $R^5$ is hydrogen.

In another embodiment of the present invention, $R^6$ is selected from: hydrogen, —$C_{1-6}$alkyl, —$(CH_2)_mOC_{1-6}$alkyl, halogen, —$(CH_2)_mCN$, —$(CH_2)_mCF_3$, —$(CH_2)_mOCF_3$, —$(CH_2)_mCHF_2$, —$(CH_2)_mCH_2F$, and —$(CH_2)_mSO_2C_{1-6}$alkyl, wherein each $CH_2$ is unsubstituted or substituted with 1 or 2 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein each alkyl is unsubstituted or substituted with 1, 2, 3 or 4 substituents selected from: oxo, —$(CH_2)_{0-5}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, $R^6$ is selected from: hydrogen, —$C_{1-6}$alkyl, —$(CH_2)_mOC_{1-6}$alkyl, halogen, —$(CH_2)_mCN$, —$(CH_2)_mCF_3$, —$(CH_2)_mOCF_3$, —$(CH_2)_mCHF_2$, —$(CH_2)_mCH_2F$, —$(CH_2)_mSO_2C_{1-6}$alkyl, —$(CH_2)_mCO_2H$, —$(CH_2)_mCO_2C_{1-6}$alkyl, —$(CH_2)_mC(O)H$, —$(CH_2)_mC(O)NH_2$, —$(CH_2)_mC_{3-6}$cycloalkyl, —$(CH_2)_mC_{2-7}$cycloheteroalkyl, —$(CH_2)_m$aryl, and —$(CH_2)_m$heteroaryl, wherein each $CH_2$ is unsubstituted or substituted with 1 or 2 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloheteroalkyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$SO_2C_{1-6}$alkyl, —$C_{3-7}$cycloalkyl, phenyl, $CH_2$phenyl, heteroaryl and $CH_2$heteroaryl.

In another embodiment of the present invention, $R^6$ is selected from: hydrogen, —$C_{1-6}$alkyl, —$OC_{1-6}$alkyl, halogen, CN, $CF_3$, $OCF_3$, $CHF_2$, $CH_2F$, $SO_2C_{1-6}$alkyl, $CO_2H$, $CO_2C_{1-6}$alkyl, $C(O)H$, $C(O)NH_2$, $C_{3-6}$cycloalkyl, $C_{2-7}$cycloheteroalkyl, aryl, and heteroaryl, wherein alkyl, cycloalkyl, cycloheteroalkyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, $R^6$ is selected from: hydrogen, —$C_{1-6}$alkyl, —$OC_{1-6}$alkyl, halogen, CN, $CF_3$, $CO_2H$, $CO_2C_{1-6}$alkyl, $C(O)H$, $C(O)NH_2$, $C_{3-6}$cycloalkyl, $C_{3-6}$cycloheteroalkyl, aryl, and heteroaryl, wherein alkyl, cycloalkyl, cycloheteroalkyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, $R^6$ is selected from: hydrogen, $—C_{1-6}$alkyl, halogen, CN, $CF_3$, $—CO_2H$, $—C(O)H$, $—C(O)NH_2$, $—C_{3-6}$cycloalkyl, and aryl, wherein alkyl, cycloalkyl, and aryl are unsubstituted or substituted with 1, 2, 3 or 4 substituents selected from: oxo, $—(CH_2)_{0-5}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, $—CO_2C_{1-6}$alkyl, and $—SO_2C_{1-6}$alkyl.

In another embodiment of the present invention, $R^6$ is selected from: hydrogen, $—C_{1-6}$alkyl, halogen, CN, $CF_3$, $—CO_2H$, $—C(O)H$, $—C(O)NH_2$, $—C_{3-6}$cycloalkyl, and aryl.

In another embodiment of the present invention, $R^6$ is selected from: hydrogen, $—CH_3$, F, CN, $CF_3$, $—CO_2H$, $—C(O)H$, $—C(O)NH_2$, cyclopropyl, and phenyl.

In another embodiment of the present invention, $R^6$ is selected from: hydrogen, $—C_{1-6}$alkyl, halogen, $—(CH_2)_mCN$, $—(CH_2)_mCF_3$, $—(CH_2)_mOCF_3$, and $—(CH_2)_mSO_2C_{1-6}$alkyl, wherein each $CH_2$ is unsubstituted or substituted with 1 or 2 substituents selected from: $—(CH_2)_{0-1}OH$, halogen, $—CO_2H$, $—CO_2C_{1-6}$alkyl, $—C_{3-7}$cycloalkyl, wherein each alkyl is unsubstituted or substituted with 1, 2, 3 or 4 substituents selected from: $—(CH_2)_{0-3}OH$, -halogen, $CO_2H$, and $—CO_2C_{1-6}$alkyl. In a class of this embodiment, $R^6$ is selected from: hydrogen, $—C_{1-6}$alkyl, halogen, CN, $CF_3$, $OCF_3$, and $SO_2C_{1-6}$alkyl, wherein each alkyl is unsubstituted or substituted with 1, 2, 3 or 4 substituents selected from: $—(CH_2)_{0-3}OH$, -halogen, $CO_2H$, and $—CO_2C_{1-6}$alkyl.

In another embodiment of the present invention, $R^6$ is selected from: hydrogen, $—C_{1-6}$alkyl, and halogen, wherein each alkyl is unsubstituted or substituted with 1, 2, 3 or 4 substituents selected from: $—(CH_2)_{0-3}OH$, -halogen, $CO_2H$, and $—CO_2C_{1-6}$alkyl. In a class of this embodiment, $R^6$ is selected from: hydrogen, $C_{1-6}$alkyl, F, Cl and Br. In another class of this embodiment, $R^6$ is hydrogen, $C_{1-6}$alkyl or F.

In another embodiment of the present invention, $R^6$ is selected from: hydrogen, and halogen, wherein each alkyl is unsubstituted or substituted with 1, 2, 3 or 4 substituents selected from: $—(CH_2)_{0-3}OH$, -halogen, $CO_2H$, and $—CO_2C_{1-6}$alkyl. In a class of this embodiment, $R^6$ is selected from: hydrogen, F, Cl and Br. In another class of this embodiment, $R^6$ is hydrogen or F. In a class of this embodiment of the present invention, $R^6$ is hydrogen. In another class of this embodiment of the present invention, $R^6$ is halogen. In a class of this embodiment, $R^6$ is selected from: F, Cl and Br. In another class of this embodiment, $R^6$ is F.

In another embodiment of the present invention, each $R^a$ is independently selected from the group consisting of: $—(CH_2)_m$-halogen, oxo, $—(CH_2)_mOH$, $—(CH_2)_mN(R^j)_2$, $—(CH_2)_mNO_2$, $—(CH_2)_mCN$, $—C_{1-6}$alkyl, $—(CH_2)_mCF_3$, $—(CH_2)_mOCF_3$, $—(CH_2)_mOC_{1-6}$ alkyl, $—(CH_2)_mSO_2C_{1-6}$alkyl, $—(CH_2)_mOCOR^f$, $—(CH_2)_mC_{3-7}$cycloalkyl, $—(CH_2)_mC_{2-6}$cycloheteroalkyl, $—(CH_2)_m$aryl, $—(CH_2)_m$heteroaryl, $—(CH_2)_mO—(CH_2)_m$-aryl, $—(CH_2)_mSO_2N(C_{1-6}$alkyl$)_2$, $—(CH_2)_mC(O)R^f$, $—(CH_2)_mC(O)N(R^j)_2$, and $—(CH_2)_mCO_2R^f$, wherein each $CH_2$ is unsubstituted or substituted with 1 or 2 substituents selected from: oxo, $—(CH_2)_{0-3}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, and $—CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, $—(CH_2)_{0-5}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, $—CO_2C_{1-6}$alkyl, and $—SO_2C_{1-6}$alkyl.

In another embodiment of the present invention, each $R^a$ is independently selected from the group consisting of: oxo, $—(CH_2)_mOH$, $—C_{1-6}$alkyl, $—OC_{1-6}$alkyl, $—(CH_2)_mSO_2C_{1-6}$alkyl, $—OCOR^f$, heteroaryl, halogen, $—O—(CH_2)_m$-aryl, $—SO_2N(C_{1-6}$alkyl$)_2$, $—C(O)R^f$, $—C(O)N(R^j)_2$, $—CO_2R^f$, $C_{3-7}$cycloalkyl, and $C_{2-6}$cycloheteroalkyl, wherein each $CH_2$ is unsubstituted or substituted with 1 or 2 substituents selected from: oxo, $—(CH_2)_{0-3}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, and $—CO_2C_{1-6}$alkyl, and wherein alkyl, cycloalkyl, cycloheteroalkyl, aryl and heteroaryl are unsubstituted or substituted with 1, 2, 3 or 4 substituents selected from: oxo, $—(CH_2)_{0-5}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, $—CO_2C_{1-6}$alkyl, and $—SO_2C_{1-6}$alkyl.

In another embodiment of the present invention, each $R^a$ is independently selected from the group consisting of: oxo, $—OH$, $—CH_2OH$, $—CH(CH_3)OH$, $—CH_3$, $—OCH(CH_3)CH_2OH$, $—SO_2CH_3$, $—CH_2SO_2CH_3$, $—OC(O)CH(CH_3)_2$, triazole, F, $—(CH_2)_3OH$, $—OCH_2CH_3$, $—OCH(CH_3)_2$, $—O—CH_2$-phenyl, $—SO_2N(CH_3)_2$, $—C(O)$-pyrrolidine, $—C(O)NHCH_3$, $—C(O)NH$-cyclopropyl, $—CO_2C(CH_3)_3$, cyclopropyl, and pyrrolidine, wherein each $CH_2$ is unsubstituted or substituted with 1 or 2 substituents selected from: oxo, $—(CH_2)_{0-3}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, and $—CO_2C_{1-6}$alkyl, and wherein alkyl and heteroaryl are unsubstituted or substituted with 1, 2, 3 or 4 substituents selected from: oxo, $—(CH_2)_{0-5}OH$, $—CN$, $—NH_2$, $—NH(C_{1-6}$alkyl), $—N(C_{1-6}$alkyl$)_2$, $—C_{1-6}$alkyl, $—OC_{1-6}$alkyl, halogen, $—CH_2F$, $—CHF_2$, $—CF_3$, $—CO_2H$, $—CO_2C_{1-6}$alkyl, and $—SO_2C_{1-6}$alkyl.

In another embodiment of the present invention, each $R^a$ is independently selected from the group consisting of: oxo, $—OH$, $—CH_2OH$, $—CH(CH_3)OH$, $—CH_3$, $—OC(O)CH(CH_3)_2$, $—OCH(CH_3)CH_2OH$, $—SO_2CH_3$, $—CH_2SO_2CH_3$, triazole, F, $—(CH_2)_3OH$, $—OCH_2CH_3$, $—OCH(CH_3)_2$, $—O—CH_2$-phenyl, $—SO_2N(CH_3)_2$, $—C(O)$-pyrrolidine, $—C(O)NHCH_3$, $—C(O)NH$-cyclopropyl, $—CO_2C(CH_3)_3$, cyclopropyl-$CH_2OH$, and pyrrolidine, wherein each $CH_2$ is unsubstituted or substituted with 1 or 2 substituents selected from: oxo, $—(CH_2)_{0-3}OH$ and $—C_{1-6}$alkyl, $—OC_{1-6}$alkyl, and halogen, and wherein alkyl and heteroaryl are unsubstituted or substituted with 1, 2, 3 or 4 substituents selected from: oxo, $—(CH_2)_{0-5}OH$, $—C_{1-6}$alkyl, $—OC_{1-6}$alkyl, and halogen.

In another embodiment of the present invention, each $R^a$ is independently selected from the group consisting of: $—(CH_2)_m$-halogen, oxo, $—(CH_2)_mOH$, $—(CH_2)_mN(R^j)_2$, $—(CH_2)_mNO_2$, $—(CH_2)_mCN$, $—C_{1-6}$alkyl, $—(CH_2)_mCF_3$, $—(CH_2)_mOCF_3$, $—O—(CH_2)_m—OC_{1-6}$ alkyl, $—(CH_2)_mC(O)N(R^j)_2$, $—(CH_2)_mC(=N—OH)N(R^j)_2$, $—(CH_2)_mOC_{1-6}$alkyl, $—(CH_2)_mO—(CH_2)_m—C_{3-7}$cycloalkyl, $—(CH_2)_mO—(CH_2)_m—C_{2-7}$cycloheteroalkyl, $—(CH_2)_mO—(CH_2)_m$-aryl, $—(CH_2)_mO—(CH_2)_m$-heteroaryl, $—(CH_2)_mSC_{1-6}$alkyl, $—(CH_2)_mS(O)C_{1-6}$alkyl, $—(CH_2)_mSO_2C_{1-6}$alkyl, $—(CH_2)_mSO_2C_{3-7}$cycloalkyl, $—(CH_2)_mSO_2C_{2-7}$cycloheteroalkyl, $—(CH_2)_mSO_2$-aryl, $—(CH_2)_mSO_2$-heteroaryl, $—(CH_2)_mSO_2NHC_{1-6}$alkyl, $—(CH_2)_mSO_2N(C_{1-6}$alkyl$)_2$, $—(CH_2)_mSO_2NHC_{3-7}$cycloalkyl, $—(CH_2)_mSO_2NHC_{2-7}$cycloheteroalkyl, —$(CH_2)_m SO_2NH$-aryl, —$(CH_2)_m SO_2NH$-heteroaryl, —$(CH_2)_m NHSO_2$—$C_{1-6}$alkyl, —$(CH_2)_m NHSO_2$—$C_{3-7}$cycloalkyl, —$(CH_2)_m NHSO_2$—$C_{2-7}$cycloheteroalkyl, —$(CH_2)_m NHSO_2$-aryl, —$(CH_2)_m NHSO_2$-heteroaryl, —$(CH_2)_m N(R^j)$—$C_{1-6}$alkyl, —$(CH_2)_m N(R^j)$—$C_{3-7}$cycloalkyl, —$(CH_2)_m N(R^j)$—$C_{2-7}$cycloheteroalkyl, —$(CH_2)_m N(R^j)$—$C_{2-7}$cycloheteroalkenyl, —$(CH_2)_m N(R^j)$-aryl, —$(CH_2)_m N(R^j)$-heteroaryl, —$(CH_2)_m C(O)R^f$, —$(CH_2)_m C(O)N(R^j)_2$, —$(CH_2)_m N(R^j)C(O)N(R^j)_2$, —$(CH_2)_m CO_2H$, —$(CH_2)_m OCOH$, —$(CH_2)_m CO_2R^f$, —$(CH_2)_m OCOR^f$, —$(CH_2)_m C_{3-7}$cycloalkyl, —$(CH_2)_m C_{3-7}$cycloalkenyl, —$(CH_2)_m C_{2-6}$cycloheteroalkyl —$(CH_2)_m C_{2-6}$cycloheteroalkenyl, —$(CH_2)_m$aryl, and —$(CH_2)_m$heteroaryl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, each $R^a$ is independently selected from the group consisting of: —$(CH_2)_m$-halogen, oxo, —$(CH_2)_m OH$, —$(CH_2)_m N(R^j)_2$, —$(CH_2)_m NO_2$, —$(CH_2)_m CN$, —$C_{1-6}$alkyl, —$(CH_2)_m CF_3$, —$(CH_2)_m OCF_3$, —O—$(CH_2)_m$—$OC_{1-6}$ alkyl, —$(CH_2)_m C(O)N(R^j)_2$, —$(CH_2)_m C(=N$—$OH)N(R^j)_2$, —$(CH_2)_m OC_{1-6}$alkyl, —$(CH_2)_m O$—$(CH_2)_m$—$C_{3-7}$cycloalkyl, —$(CH_2)_m O$—$(CH_2)_m$—$C_{2-7}$cycloheteroalkyl, —$(CH_2)_m O$—$(CH_2)_m$-aryl, —$(CH_2)_m O$—$(CH_2)_m$-heteroaryl, —$(CH_2)_m SO_2C_{1-6}$alkyl, —$(CH_2)_m SO_2NHC_{1-6}$alkyl, —$(CH_2)_m SO_2N(C_{1-6}$alkyl)$_2$, —$(CH_2)_m C(O)R^f$, —$(CH_2)_m C(O)N(R^j)_2$, —$(CH_2)_m N(R^j)C(O)N(R^j)_2$, —$(CH_2)_m CO_2H$, —$(CH_2)_m OCOH$, —$(CH_2)_m CO_2R^f$, —$(CH_2)_m OCOR^f$, —$(CH_2)_m C_{3-7}$cycloalkyl, —$(CH_2)_m C_{3-7}$cycloalkenyl, —$(CH_2)_m C_{2-6}$cycloheteroalkyl, —$(CH_2)_m C_{2-6}$cycloheteroalkenyl, —$(CH_2)_m$aryl, and —$(CH_2)_m$heteroaryl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, each $R^a$ is independently selected from the group consisting of: halogen, oxo, —$(CH_2)_m OH$, —$N(R^j)_2$, —$NO_2$, —CN, —$C_{1-6}$alkyl, —$CF_3$, —$OCF_3$, —O—$(CH_2)_m$—$OC_{1-6}$ alkyl, —$C(O)N(R^j)_2$, —$OC_{1-6}$alkyl, —O—$(CH_2)_m$—$C_{3-7}$cycloalkyl, —O—$(CH_2)_m$—$C_{2-7}$cycloheteroalkyl, —O—$(CH_2)_m$-aryl, —O—$(CH_2)_m$-heteroaryl, —$SO_2C_{1-6}$alkyl, —$SO_2NHC_{1-6}$alkyl, —$SO_2N(C_{1-6}$alkyl)$_2$, —$C(O)R^f$, —$C(O)N(R^j)_2$, —$N(R^j)C(O)N(R^j)_2$, —$CO_2H$, —OCOH, —$CO_2R^f$, —$OCOR^f$, $C_{3-7}$cycloalkyl, $C_{3-7}$cycloalkenyl, $C_{2-6}$cycloheteroalkyl, $C_{2-6}$cycloheteroalkenyl, aryl, and heteroaryl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl.

In another embodiment of the present invention, each $R^a$ is independently selected from the group consisting of: —$(CH_2)_m$-halogen, —$(CH_2)_m OH$, —$C_{1-6}$alkyl, —$(CH_2)_m OC_{1-6}$alkyl, —$(CH_2)_m O$—$(CH_2)_m$-aryl, —$(CH_2)_m SO_2C_{1-6}$alkyl, —$(CH_2)_m SO_2N(C_{1-6}$alkyl)$_2$, —$(CH_2)_m C(O)R^f$, —$(CH_2)_m C(O)N(R^j)_2$, —$(CH_2)_m CO_2R^f$, —$(CH_2)_m C_{3-7}$cycloalkyl, and —$(CH_2)_m C_{2-6}$cycloheteroalkyl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$SO_2C_{1-6}$alkyl. In a class of this embodiment, each $R^a$ is independently selected from the group consisting of: —$(CH_2)_m$-halogen, —$(CH_2)_m OH$, —$C_{1-6}$alkyl, —$(CH_2)_m OC_{1-6}$alkyl, —$(CH_2)_m O$—$(CH_2)_m$-aryl, —$(CH_2)_m SO_2C_{1-6}$alkyl, —$(CH_2)_m SO_2N(C_{1-6}$alkyl)$_2$, —$(CH_2)_m C(O)R^f$, —$(CH_2)_m C(O)N(R^j)_2$, —$(CH_2)_m CO_2R^f$, —$(CH_2)_m C_{3-7}$cycloalkyl, and —$(CH_2)_m C_{2-6}$cycloheteroalkyl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl. In another class of this embodiment, each $R^a$ is independently selected from the group consisting of: halogen, —$(CH_2)_m OH$, —$C_{1-6}$alkyl, —$OC_{1-6}$alkyl, —O—$(CH_2)_m$-aryl, —$SO_2C_{1-6}$alkyl, —$SO_2N(C_{1-6}$alkyl)$_2$, —$C(O)R^f$, —$C(O)N(R^j)_2$, —$CO_2R^f$, $C_{3-7}$cycloalkyl, and $C_{2-6}$cycloheteroalkyl, wherein each $CH_2$ is unsubstituted or substituted with 1 or 2 substituents selected from: oxo, —$(CH_2)_{0-3}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}OH$, —CN, —$NH_2$, —$NH(C_{1-6}$alkyl), —$N(C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl. In another class of this embodiment, each $R^a$ is independently selected from the group consisting of: F, —OH, —$CH_2OH$, —$(CH_2)_3OH$, —$CH_3$, —$OCH_2CH_3$, —$OCH(CH_3)_2$, —O—$CH_2$-phenyl, —$SO_2CH_3$, —$SO_2N(CH_3)_2$, —C(O)-pyrrolidine, —$C(O)NHCH_3$, —C(O)NH-cyclopropyl, —$CO_2C(CH_3)_3$, cyclopropyl, and pyrrolidine, wherein each $CH_2$ is unsubstituted or substituted with 1 or 2 substituents selected from: oxo, —$(CH_2)_{0-3}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, —$CO_2C_{1-6}$alkyl, —$SO_2C_{1-6}$alkyl. In another class of this embodiment, each $R^a$ is independently selected from the group consisting of: F, —OH, —$CH_2$OH, —$(CH_2)_3$OH, —$CH_3$, —$OCH_2CH_3$, —$OCH(CH_3)_2$, —O—$CH_2$-phenyl, —$SO_2CH_3$, —$SO_2N(CH_3)_2$, —C(O)-pyrrolidine, —C(O)$NHCH_3$, —C(O)NH-cyclopropyl, —$CO_2C(CH_3)_3$, cyclopropyl-$CH_2$OH, and pyrrolidine.

In another embodiment of the present invention, each $R^a$ is independently selected from the group consisting of: —$(CH_2)_m$-halogen, —$(CH_2)_m$OH, —$(CH_2)_mOC_{1-6}$alkyl, and —$(CH_2)_mSO_2C_{1-6}$alkyl, wherein each $CH_2$ is unsubstituted or substituted with 1 or 2 substituents selected from: oxo, —$(CH_2)_{0-3}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, and —$CO_2C_{1-6}$alkyl, and wherein alkyl is unsubstituted or substituted with 1, 2, 3 or 4 substituents selected from: oxo, —$(CH_2)_{0-5}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, —$CO_2C_{1-6}$alkyl, —$SO_2C_{1-6}$alkyl. In a class of this embodiment, each $R^a$ is independently selected from the group consisting of: halogen, —$(CH_2)_m$OH, —O$C_{1-6}$alkyl, and —$SO_2C_{1-6}$alkyl, wherein each $CH_2$ is unsubstituted or substituted with 1 or 2 substituents selected from: oxo, —$(CH_2)_{0-3}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, and —$CO_2C_{1-6}$alkyl, and wherein alkyl is unsubstituted or substituted with 1, 2, 3 or 4 substituents selected from: oxo, —$(CH_2)_{0-5}$OH, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2$F, —$CHF_2$, —$CF_3$, —$CO_2$H, —$CO_2C_{1-6}$alkyl, —$SO_2C_{1-6}$alkyl. In another class of this embodiment, each $R^a$ is independently selected from the group consisting of: halogen, —$(CH_2)_m$OH, —O$C_{1-6}$alkyl, and —$SO_2C_{1-6}$alkyl. In another class of this embodiment, each $R^a$ is independently selected from the group consisting of: F, —$CH_2$OH, —$OCH_2CH_3$ and —$SO_2CH_3$.

In another embodiment of the present invention, each $R^b$ is independently selected from: hydrogen, —$C_{1-6}$alkyl, —$(CH_2)$t-halogen, —$(CH_2)$s-OH, —$(CH_2)$s$NO_2$, —$(CH_2)$s$NH_2$, —$(CH_2)$sNH($C_{1-6}$alkyl), —$(CH_2)$sN($C_{1-6}$alkyl)$_2$, —$(CH_2)$sO$C_{1-6}$alkyl, —$(CH_2)$q$CO_2$H, —$(CH_2)$q$CO_2C_{1-6}$alkyl, —$(CH_2)$s$CF_3$, —$(CH_2)$sO$CF_3$, —$(CH_2)$s$CHF_2$, —$(CH_2)$s$CH_2$F, —$(CH_2)$sCN, —$(CH_2)$s$SO_2C_{1-6}$alkyl, and —$(CH_2)$sCON($R^e$)$_2$, wherein each $CH_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens, and wherein two $R^b$ substituents together with the atom to which they are attached may form a $C_{3-6}$cycloalkyl ring or a $C_{2-6}$cycloheteroalkyl ring.

In another embodiment of the present invention, each $R^b$ is independently selected from: —$C_{1-6}$alkyl, —$(CH_2)$s-OH, —$(CH_2)$sO$C_{1-6}$alkyl, and —$(CH_2)$t-halogen, wherein each $CH_2$ is unsubstituted or substituted with 1 or 2 halogens, and wherein each alkyl is unsubstituted or substituted with 1, 2 or 3 halogens, and wherein two $R^b$ substituents together with the atom to which they are attached may form a $C_{3-6}$cycloalkyl ring or a $C_{2-6}$cycloheteroalkyl ring.

In another embodiment of the present invention, each $R^b$ is independently selected from: —$C_{1-6}$alkyl, OH, —O$C_{1-6}$alkyl, and halogen, wherein each $CH_2$ is unsubstituted or substituted with 1 or 2 halogens, and wherein each alkyl is unsubstituted or substituted with 1, 2 or 3 halogens, and wherein two $R^b$ substituents together with the atom to which they are attached may form a $C_{3-6}$cycloalkyl ring or a $C_{2-6}$cycloheteroalkyl ring.

In another embodiment of the present invention, each $R^b$ is independently selected from: —$CH_3$, OH, —$OCH_3$, Cl, Br, and F, wherein two $R^b$ substituents together with the atom to which they are attached may form a $C_3$cycloalkyl ring or a $C_2$cycloheteroalkyl ring.

In another embodiment of the present invention, each $R^b$ is independently selected from: —$CH_3$, OH, —$OCH_3$, Cl, Br, and F.

In another embodiment of the present invention, each $R^b$ is independently selected from: hydrogen, —$C_{1-6}$alkyl, —$(CH_2)$t-halogen, —$(CH_2)$s-OH, —$(CH_2)$s$NO_2$, —$(CH_2)$s$NH_2$, —$(CH_2)$sNH($C_{1-6}$alkyl), —$(CH_2)$sN($C_{1-6}$alkyl)$_2$, —$(CH_2)$sO$C_{1-6}$alkyl, —$(CH_2)$q$CO_2$H, —$(CH_2)$q$CO_2C_{1-6}$alkyl, —$(CH_2)$s$CF_3$, —$(CH_2)$sO$CF_3$, —$(CH_2)$s$CHF_2$, —$(CH_2)$s$CH_2$F, —$(CH_2)$sCN, —$(CH_2)$s$SO_2C_{1-6}$alkyl, and —$(CH_2)$sCON($R^e$)$_2$, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, -halogen, —OH, —$NO_2$, —$NH_2$, —NH($C_{1-6}$alkyl), —N($C_{1-6}$alkyl)$_2$, —O$C_{1-6}$alkyl, —$CO_2$H, —$CO_2C_{1-6}$alkyl, —$CF_3$, —$OCF_3$, —$CHF_2$, —$CH_2$F, —CN, —$SO_2C_{1-6}$alkyl, and —CON($R^e$)$_2$, wherein each alkyl is unsubstituted or substituted with 1, 2 or 3 halogens.

In another embodiment of the present invention, each $R^b$ is independently selected from: hydrogen, —$C_{1-6}$alkyl, —$(CH_2)$t-halogen, and —$(CH_2)$s-OH, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, and —$(CH_2)$t-halogen, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, and halogen, wherein each alkyl is unsubstituted or substituted with 1, 2 or 3 halogens.

In another embodiment of the present invention, each $R^b$ is independently selected from: —$C_{1-6}$alkyl, and —$(CH_2)$t-halogen, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: —$C_{1-6}$alkyl, and halogen, wherein each alkyl is unsubstituted or substituted with 1, 2 or 3 halogens. In subclass of this class, each $R^b$ is independently selected from: —$CH_3$, Cl, Br, and F. In another subclass of this class, each $R^b$ is independently selected from: —$CH_3$, and F. In another class of this embodiment, each $R^b$ is independently selected from: —$C_{1-6}$alkyl, wherein each alkyl is unsubstituted or substituted with 1, 2 or 3 halogens. In a subclass of this class, each $R^b$ is —$CH_3$. In another class of this embodiment, each $R^b$ is independently selected from: —$(CH_2)$t-halogen, wherein each $CH_2$ is unsubstituted or substituted with 1 or 2 halogens, and wherein each alkyl is unsubstituted or substituted with 1, 2 or 3 halogens. In a subclass of this class, each $R^b$ is halogen. In another subclass of this class, each $R^b$ is independently selected from: Cl, Br, and F. In another subclass of this class, each $R^b$ is F.

In another embodiment of the present invention, each $R^c$ and $R^d$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$OCH_2$aryl, —$(CH_2)_rSC_{1-6}$alkyl, —$(CH_2)_rC(O)R^f$, —$(CH_2)_rC(O)N(R^e)_2$, —$(CH_2)_rCO_2H$, —$(CH_2)_rCO_2R^f$, —$(CH_2)_rC_{3-7}$cycloalkyl, —$(CH_2)_rC_{2-6}$cycloheteroalkyl, —$(CH_2)_r$aryl, and —$(CH_2)_r$heteroaryl, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl. In a class of this embodiment, each $R^c$ and $R^d$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$(CH_2)_rSC_{1-6}$alkyl, —$(CH_2)_rC(O)R^f$, —$(CH_2)_rC(O)N(R^e)_2$, —$(CH_2)_rCO_2H$, and —$(CH_2)_rCO_2R^f$, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^c$ and $R^d$ is independently selected from: halogen, oxo, —OH, —$N(R^e)_2$, —CN, —$C_{1-6}$alkyl, —$CF_3$, and —$C_{1-6}$alkyl-OH, wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^c$ and $R^d$ is independently selected from: halogen, and —$C_{1-6}$alkyl, wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In another class of this embodiment, each $R^c$ and $R^d$ is —$C_{1-6}$alkyl.

In another embodiment of the present invention, each $R^c$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$OCH_2$aryl, —$(CH_2)_rSC_{1-6}$alkyl, —$(CH_2)_rC(O)R^f$, —$(CH_2)_rC(O)N(R^e)_2$, —$(CH_2)_rCO_2H$, —$(CH_2)_rCO_2R^f$, —$(CH_2)_rC_{3-7}$cycloalkyl, —$(CH_2)_rC_{2-6}$cycloheteroalkyl, —$(CH_2)_r$aryl, and —$(CH_2)_r$heteroaryl, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl. In a class of this embodiment, each $R^c$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$(CH_2)_rSC_{1-6}$alkyl, —$(CH_2)_rC(O)R^f$, —$(CH_2)_rC(O)N(R^e)_2$, —$(CH_2)_rCO_2H$, and —$(CH_2)_rCO_2R^f$, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^c$ is independently selected from: halogen, oxo, —OH, —$N(R^e)_2$, —CN, —$C_{1-6}$alkyl, —$CF_3$, and —$C_{1-6}$alkyl-OH, wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^c$ is independently selected from: halogen, and —$C_{1-6}$alkyl, wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In another class of this embodiment, each $R^c$ is —$C_{1-6}$alkyl. In another class of this embodiment, $R^c$ is —$CH_3$.

In another embodiment of the present invention, each $R^d$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$OCH_2$aryl, —$(CH_2)_rSC_{1-6}$alkyl, —$(CH_2)_rC(O)R^f$, —$(CH_2)_rC(O)N(R^e)_2$, —$(CH_2)_rCO_2H$, —$(CH_2)_rCO_2R^f$, —$(CH_2)_rC_{3-7}$cycloalkyl, —$(CH_2)_rC_{2-6}$cycloheteroalkyl, —$(CH_2)_r$aryl, and —$(CH_2)_r$heteroaryl, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl. In a class of this embodiment, each $R^d$ is independently selected from: halogen, oxo, —$(CH_2)_rOH$, —$(CH_2)_rN(R^e)_2$, —$(CH_2)_rCN$, —$C_{1-6}$alkyl, —$CF_3$, —$C_{1-6}$alkyl-OH, —$OCH_2OC_{1-6}$alkyl, —$(CH_2)_rOC_{1-6}$alkyl, —$(CH_2)_rSC_{1-6}$alkyl, —$(CH_2)_rC(O)R^f$, —$(CH_2)_rC(O)N(R^e)_2$, —$(CH_2)_rCO_2H$, and —$(CH_2)_rCO_2R^f$, wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^d$ is independently selected from: halogen, oxo, —OH, —$N(R^e)_2$, —CN, —$C_{1-6}$alkyl, —$CF_3$, and —$C_{1-6}$alkyl-OH, wherein each alkyl is are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —CHF$_2$, —CF$_3$, —CO$_2$H, and —CO$_2$C$_{1-6}$alkyl. In a class of this embodiment, each R$^d$ is independently selected from: halogen, and —C$_{1-6}$alkyl, wherein each alkyl is are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In another class of this embodiment, each R$^d$ is —C$_{1-6}$alkyl.

In another embodiment of the present invention, each R$^e$, R$^g$ and R$^h$ is independently selected from: hydrogen, —C$_{1-6}$alkyl, and —O—C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$, R$^g$ and R$^h$ is independently selected from: hydrogen, and —C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$, R$^g$ and R$^h$ is independently selected from: hydrogen, and —C$_{1-6}$alkyl.

In another embodiment of the present invention, each R$^e$, R$^g$ and R$^h$ is hydrogen.

In another embodiment of the present invention, each R$^e$, R$^g$ and R$^h$ is —C$_{1-6}$alkyl.

In another embodiment of the present invention, each R$^e$ is independently selected from: hydrogen, —C$_{1-6}$alkyl, and —O—C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$ is independently selected from: hydrogen, and —C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^e$ is independently selected from: hydrogen, and —C$_{1-6}$alkyl.

In another embodiment of the present invention, each R$^e$ is hydrogen.

In another embodiment of the present invention, each R$^e$ is —C$_{1-6}$alkyl.

In another embodiment of the present invention, each R$^g$ is independently selected from: hydrogen, —C$_{1-6}$alkyl, and —O—C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^g$ is independently selected from: hydrogen, and —C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^g$ is independently selected from: hydrogen, and —C$_{1-6}$alkyl.

In another embodiment of the present invention, each R$^g$ is hydrogen.

In another embodiment of the present invention, each R$^g$ is —C$_{1-6}$alkyl.

In another embodiment of the present invention, each R$^h$ is independently selected from: hydrogen, —C$_{1-6}$alkyl, and —O—C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^h$ is independently selected from: hydrogen, and —C$_{1-6}$alkyl, wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$.

In another embodiment of the present invention, each R$^h$ is independently selected from: hydrogen, and —C$_{1-6}$alkyl.

In another embodiment of the present invention, each R$^h$ is hydrogen.

In another embodiment of the present invention, each R$^h$ is —C$_{1-6}$alkyl.

In another embodiment of the present invention, each R$^j$ is independently selected from: hydrogen, C$_{1-6}$alkyl, C$_{3-6}$cycloalkyl, —C(O)R$^i$, and —SO$_2$R$^i$.

In another embodiment of the present invention, each R$^j$ is independently selected from: hydrogen, C$_{1-6}$alkyl, and C$_{3-6}$cycloalkyl, wherein each alkyl and cycloalkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^j$ is independently selected from: hydrogen, —CH$_3$, and -cyclopropyl, wherein each alkyl and cyclopropyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In another class of this embodiment, each R$^j$ is independently selected from: hydrogen, —CH$_3$, —CH$_2$CH$_3$, and -cyclopropyl, wherein each alkyl and cyclopropyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In another class of this embodiment, each R$^j$ is independently selected from: hydrogen, —CH$_3$, —CH$_2$CH$_3$, and -cyclopropyl, wherein each alkyl and cyclopropyl.

In another embodiment of the present invention, each R$^j$ is independently selected from: hydrogen, C$_{1-6}$alkyl, and C$_{3-6}$cycloalkyl. In a class of this embodiment, each R$^j$ is independently selected from: hydrogen, —CH$_3$, and -cyclopropyl.

In another embodiment of the present invention, each R$^f$ and R$^i$ is independently selected from: C$_{1-6}$alkyl, C$_{4-7}$cycloalkyl, C$_{4-7}$cycloalkenyl, C$_{3-7}$cycloheteroalkyl, C$_{3-7}$cyclohetero-alkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl.

In a class of this embodiment, each R$^f$ and R$^i$ is independently selected from: C$_{1-6}$alkyl, C$_{4-7}$cycloalkyl, C$_{4-7}$cycloalkenyl, C$_{3-7}$cycloheteroalkyl, C$_{3-7}$cycloheteroalkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl.

In another embodiment of the present invention, each R$^f$ and R$^i$ is independently selected from: C$_{1-6}$alkyl, and C$_{3-7}$cycloheteroalkyl, wherein each alkyl and cycloheteroalkyl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF₃, —CO₂H, —CO₂C₁₋₆alkyl, —C₃₋₇cycloalkyl, and heteroaryl. In a class of this embodiment, each $R^f$ and $R^i$ is independently selected from: C₁₋₆alkyl, and C₃₋₇cycloheteroalkyl, wherein each alkyl and cycloheteroalkyl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^f$ and $R^i$ is independently selected from: —C(CH₃)₃, and pyrrolidine, wherein each alkyl and pyrrolidine is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^f$ and $R^i$ is independently selected from: —C(CH₃)₃, and pyrrolidine.

In another embodiment of the present invention, each $R^f$ and $R^i$ is independently selected from: —C(CH₃)₃, —CH₂CH₃, —CH(CH₃)₂, and pyrrolidine.

In another embodiment of the present invention, each $R^f$ is independently selected from: C₁₋₆alkyl, C₄₋₇cycloalkyl, C₄₋₇cycloalkenyl, C₃₋₇cycloheteroalkyl, C₃₋₇cycloheteroalkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, —CO₂C₁₋₆alkyl, —C₃₋₇cycloalkyl, and heteroaryl.

In a class of this embodiment, each $R^f$ is independently selected from: C₁₋₆alkyl, C₄₋₇cycloalkyl, C₄₋₇cycloalkenyl, C₃₋₇cycloheteroalkyl, C₃₋₇cycloheteroalkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl.

In another embodiment of the present invention, each $R^f$ is independently selected from: C₁₋₆alkyl, and C₃₋₇cycloheteroalkyl, wherein each alkyl and cycloheteroalkyl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, —CO₂C₁₋₆alkyl, —C₃₋₇cycloalkyl, and heteroaryl. In a class of this embodiment, each $R^f$ is independently selected from: C₁₋₆alkyl, and C₃₋₇cycloheteroalkyl, wherein each alkyl and cycloheteroalkyl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^f$ is independently selected from: —C(CH₃)₃, and pyrrolidine, wherein each alkyl and pyrrolidine is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^f$ is independently selected from: —C(CH₃)₃, and pyrrolidine. In another class of this embodiment, each $R^f$ is independently selected from: —C(CH₃)₃, —CH(CH₃)₂, and pyrrolidine.

In another embodiment of the present invention, each $R^i$ is independently selected from: C₁₋₆alkyl, C₄₋₇cycloalkyl, C₄₋₇cycloalkenyl, C₃₋₇cycloheteroalkyl, C₃₋₇cycloheteroalkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, —CO₂C₁₋₆alkyl, —C₃₋₇cycloalkyl, and heteroaryl.

In a class of this embodiment, each $R^i$ is independently selected from: C₁₋₆alkyl, C₄₋₇cycloalkyl, C₄₋₇cycloalkenyl, C₃₋₇cycloheteroalkyl, C₃₋₇cycloheteroalkenyl, aryl, and heteroaryl, wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl.

In another embodiment of the present invention, each $R^i$ is independently selected from: C₁₋₆alkyl, and C₃₋₇cycloheteroalkyl, wherein each alkyl and cycloheteroalkyl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, —CO₂C₁₋₆alkyl, —C₃₋₇cycloalkyl, and heteroaryl. In a class of this embodiment, each $R^i$ is independently selected from: C₁₋₆alkyl, and C₃₋₇cycloheteroalkyl, wherein each alkyl and cycloheteroalkyl is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^i$ is independently selected from: —C(CH₃)₃, and pyrrolidine, wherein each alkyl and pyrrolidine is unsubstituted or substituted with 1, 2, 3 or 4 substituents selected from: oxo, —OH, —CN, —NH₂, —C₁₋₆alkyl, —OC₁₋₆alkyl, halogen, —CH₂F, —CHF₂, —CF₃, —CO₂H, and —CO₂C₁₋₆alkyl. In another class of this embodiment, each $R^i$ is independently selected from: —C(CH₃)₃, and pyrrolidine. In another class of this embodiment, each $R^i$ is independently selected from: —C(CH₃)₃, —CH₂CH₃, —CH(CH₃)₂, and pyrrolidine.

In another embodiment of the present invention, a is 0, 1 or 2. In a class of this embodiment, a is 0 or 1. In another class of this embodiment, a is 1 or 2. In another class of this embodiment, a is 0. In another class of this embodiment, a is 1. In another class of this embodiment, a is 2.

In another embodiment of the present invention, b is 0, 1 or 2. In a class of this embodiment, b is 0 or 1. In another class of this embodiment, b is 1 or 2. In another class of this embodiment, b is 0. In another class of this embodiment, b is 1. In another class of this embodiment, b is 2.

In another embodiment of the present invention, n is 0, 1, 2, 3 or 4. In a class of this embodiment, n is 1, 2, 3 or 4. In another class class of this embodiment, n is 1, 2 or 3. In another class of this embodiment, n is 0, 1, 2 or 3. In another class of this embodiment, n is 0, 1 or 2. In another class of this embodiment, n is 1 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, m is 0, 1, 2, 3 or 4. In a class of this embodiment, m is 1, 2, 3 or 4. In another class of this embodiment, m is 1, 2 or 3. In another class of this embodiment, m is 0, 1, 2 or 3. In another class of this embodiment, m is 0, 1 or 2. In another class of this embodiment, m is 1 or 2. In another class of this embodiment, m is 0. In another class of this embodiment, m is 1. In another class of this embodiment, m is 2. In another class of this embodiment, m is 3. In another class of this embodiment, m is 4.

In another embodiment of the present invention, p is 0, 1, 2 or 3. In a class of this embodiment, p is 1, 2 or 3. In another class of this embodiment, p is 0, 1 or 2. In another class of this embodiment, p is 1 or 2. In another class of this embodiment, p is 0 or 2. In another class of this embodiment, p is 0. In another class of this embodiment, p is 1. In another class of this embodiment, p is 2. In another class of this embodiment, p is 3.

In another embodiment of the present invention, q is 0, 1, 2, 3 or 4. In a class of this embodiment, q is 1, 2, 3 or 4. In another class of this embodiment, q is 1, 2 or 3. In another class of this embodiment, q is 0, 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2. In another class of this embodiment, q is 3. In another class of this embodiment, q is 4.

In another embodiment of the present invention, r is 0, 1 or 2. In a class of this embodiment, r is 0 or 1. In another class of this embodiment, r is 1 or 2. In another class of this embodiment, r is 0. In another class of this embodiment, r is 1. In another class of this embodiment, r is 2.

In another embodiment of the present invention, s is 0, 1, 2, 3 or 4. In a class of this embodiment, s is 1, 2, 3 or 4. In another class of this embodiment, s is 1, 2 or 3. In another class of this embodiment, s is 0, 1, 2 or 3. In another class of this embodiment, s is 0, 1 or 2. In another class of this embodiment, s is 1 or 2. In another class of this embodiment, s is 0. In another class of this embodiment, s is 1. In another class of this embodiment, s is 2. In another class of this embodiment, s is 3. In another class of this embodiment, s is 4.

In another embodiment of the present invention, t is 0, 1, 2, 3 or 4. In a class of this embodiment, t is 1, 2, 3 or 4. In another class of this embodiment, t is 1, 2 or 3. In another class of this embodiment, t is 0, 1, 2 or 3. In another class of this embodiment, t is 0, 1 or 2. In another class of this embodiment, t is 1 or 2. In another class of this embodiment, t is 0. In another class of this embodiment, t is 1. In another class of this embodiment, t is 2. In another class of this embodiment, t is 3. In another class of this embodiment, t is 4.

Another embodiment of the present invention relates to compounds of structural formula I wherein:
T is selected from —$CR^3$— and N;
U is —$CR^1$—;
V is —$CR^2$—; and
W is selected from —$CR^4$— and N,
provided that one of T and W is N, and further provided that if W is N, then $R^1$ is selected from hydrogen, halogen, —CN, —$CF_3$, —$C_{1-6}$alkyl, —$C_{2-6}$alkenyl and —$C_{2-6}$alkynyl, and if T is N then $R^2$ is selected from hydrogen, halogen, —CN, —$CF_3$, —$C_{1-6}$alkyl, —$C_{2-6}$alkenyl and —$C_{2-6}$alkynyl;
X is absent or selected from:
 (1) —$CH_2$—,
 (2) —S—,
 (3) —S(O)—,
 (4) —$S(O)_2$—,
 (5) —O—,
 (6) —O—$CH_2$—,
 (7) —$CH_2$—O—,
 (8) —$CH_2$—S—,
 (9) —NH—,
 (10) —C(O)—, and
 (11) —C(O)NH—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, and $COC_{1-6}$alkyl, and wherein each NH is unsubstituted or substituted with 1 substituent selected from: $C_{1-6}$alkyl, $CO_2H$, $CO_2C_{1-6}$alkyl, and $COC_{1-6}$alkyl;
Y is selected from:
 (1) —$C_{1-6}$alkyl,
 (2) —$C_{2-6}$alkynyl,
 (3) $C_{3-10}$cycloalkyl,
 (4) $C_{2-10}$cycloheteroalkyl,
 (5) aryl,
 (6) heteroaryl, and
 (7)

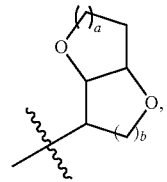

wherein Y is unsubstituted or substituted with 1, 2, 3 or 4 substituents selected from $R^b$;
Z is selected from:
 (1) hydrogen,
 (2) oxo,
 (3) —$(CH_2)_n CO_2 H$,
 (4) —$(CH_2)_n CO_2 R^i$,
 (5) —$(CH_2)_n OCOR^i$,
 (6) —$(CH_2)_n OH$, and
 (7) —$(CH_2)_n P(O)(OR^j)_2$,
wherein each $CH_2$ is unsubstituted or substituted with 1 or 2 substituents selected from $C_{1-6}$alkyl, —OH and —$NH_2$;
$R^1$ and $R^2$ are independently selected from:
 (1) hydrogen,
 (2) halogen,
 (3) aryl,
 (4) aryl-$C_{3-7}$cycloalkyl,
 (5) aryl-$C_{3-7}$cycloalkenyl,
 (6) aryl-$C_{2-10}$cycloheteroalkyl,
 (7) aryl-aryl,
 (8) aryl-heteroaryl,
 (9) heteroaryl, and
 (10) —$C_{2-6}$alkynyl-aryl,
wherein each alkynyl, cycloalkyl, cycloalkenyl, cycloheteroalkyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, and halogen;
$R^3$ is hydrogen or absent;
$R^4$ is hydrogen or absent;
$R^5$ is hydrogen, and
$R^6$ is selected from:
 (1) hydrogen,
 (2) —$C_{1-6}$alkyl,
 (3) halogen,
 (4) CN,
 (5) $CF_3$,
 (6) —$CO_2 H$,
 (7) —C(O)H, (8) —C(O)NH$_2$,
(9) —C$_{3-6}$cycloalkyl, and
(10) aryl,
wherein alkyl, cycloalkyl, and aryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, and —SO$_2$C$_{1-6}$alkyl; and
each n independently selected from 0, 1, 2, 3 or 4;
or a pharmaceutically acceptable salt thereof.

Another embodiment of the present invention relates to compounds of structural formula I wherein:
T is selected from —CR$^3$— and N;
U is —CR$^1$—;
V is —CR$^2$—; and
W is selected from —CR$^4$— and N,
provided that one of T and W is N, and further provided that if W is N, then R$^1$ is selected from hydrogen and halogen, and if T is N then R$^2$ is selected from hydrogen and halogen;
X is absent or selected from:
 (1) —CH$_2$—,
 (2) —S—,
 (3) —S(O)—,
 (4) —S(O)$_2$—,
 (5) —O—,
 (6) —O—CH$_2$—,
 (7) —CH$_2$—O—,
 (8) —CH$_2$—S—,
 (9) —N(CH$_3$)—,
 (10) —C(O)—, and
 (11) —C(O)NH—;
Y is selected from:
 (1) —C$_{1-3}$alkyl,
 (2) —C$_2$alkynyl,
 (3) cyclohexyl,
 (4) tetrahydropyran,
 (5) tetrahydrofuran,
 (6) piperidine,
 (7) phenyl,
 (8) thiophene, and
 (9)

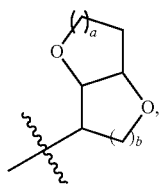

wherein a is 1, and b is 1, and
wherein Y is unsubstituted or substituted with 1, 2, 3 or 4 substituents selected from R$^b$;
Z is selected from:
 (1) hydrogen,
 (2) oxo,
 (3) —CO$_2$H,
 (4) —CH$_2$CO$_2$H,
 (5) —CH$_2$CO$_2$CH$_2$CH$_3$,
 (6) —OC(O)CH(CH$_3$)$_2$,
 (7) —OH,
 (8) —CH$_2$OH
 (9) —P(O)(OH)$_2$,
 (10) —(CH$_2$)$_n$P(O)(OCH$_2$CH$_3$)$_2$, and
 (11) —(CH$_2$)$_n$P(O)(OH)(OCH$_2$CH$_3$);
R$^1$ and R$^2$ are independently selected from:
 (1) hydrogen,
 (2) halogen,
 (3) benzodioxole,
 (4) phenyl-cyclopropyl,
 (5) phenyl-cyclohexene,
 (6) phenyl-azetidine,
 (7) phenyl-pyrrolidine,
 (8) phenyl-piperidine,
 (9) phenyl-piperazine,
 (10) phenyl-morpholine,
 (11) phenyl-thiomorpholine,
 (12) biphenyl,
 (13) indole,
 (14) —C$_2$alkynyl-phenyl,
 (15) phenyl,
 (16) phenyl-oxazole,
 (17) phenyl-pyridine,
 (18) phenyl-furan,
 (19) phenyl-oxadiazole,
 (20) pyridine,
 (21) benzofuran,
 (22) pyrrolo[2,3-b]pyridine,
 (23) pyrazole, and
 (24) benzisoxazole,
wherein each alkynyl, cycloalkyl, cycloalkenyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, and halogen;
R$^3$ is hydrogen or absent;
R$^4$ is hydrogen or absent;
R$^5$ is hydrogen, and
R$^6$ is selected from:
 (1) hydrogen,
 (2) —CH$_3$,
 (3) F
 (4) CN,
 (5) CF$_3$,
 (6) —CO$_2$H,
 (7) —C(O)H,
 (8) —C(O)NH$_2$,
 (9) cyclopropyl, and
 (10) phenyl; and
each n independently selected from 0, 1, 2, 3 or 4;
or a pharmaceutically acceptable salt thereof.

Another embodiment of the present invention relates to compounds of structural formula I wherein:
T is —CR$^3$—, N or N-oxide;
U is —CR$^1$—;
V is —CR$^2$—;
W is —CR$^4$—;
X is selected from:
 (1) —CH$_2$—, and
 (2) —CH$_2$—O—;
Y is selected from:
 (1) C$_{1-6}$alkyl,
 (2) C$_{3-10}$cycloalkyl,
 (3) C$_{2-10}$cycloheteroalkyl, and
 (4) aryl,
wherein Y is unsubstituted or substituted with 1, 2, 3 or 4 substituents selected from R$^b$;

Z is selected from:
(1) hydrogen,
(2) —(CH$_2$)$_n$CO$_2$H, and
(3) —(CH$_2$)$_n$OH,
wherein each CH$_2$ is unsubstituted or substituted with 1 or 2 substituents selected from C$_{1-6}$alkyl, —OH and —NH$_2$;
each R$^1$ and R$^2$ is independently selected from:
(1) halogen,
(2) aryl,
(3) aryl-C$_{3-7}$cycloalkyl,
(4) aryl-C$_{2-10}$cycloheteroalkyl,
(5) aryl-aryl,
(6) aryl-heteroaryl, and
(7) heteroaryl,
wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen;
R$^3$ is hydrogen or absent;
R$^4$ is hydrogen;
R$^5$ is hydrogen, and
R$^6$ is hydrogen or halogen;
or a pharmaceutically acceptable salt thereof.

Another embodiment of the present invention relates to compounds of structural formula I wherein:
T is —CR$^3$—, N or N-oxide;
U is —CR$^1$—;
V is —CR$^2$—;
W is —CR$^4$—;
X is selected from:
(1) —CH$_2$—, and
(2) —CH$_2$—O—;
Y is selected from:
(1) C$_{1-6}$alkyl,
(2) C$_{3-10}$cycloalkyl,
(3) C$_{2-10}$cycloheteroalkyl, and
(4) aryl,
wherein Y is unsubstituted or substituted with 1, 2, 3 or 4 substituents selected from R$^b$;
Z is selected from:
(1) hydrogen,
(2) —(CH$_2$)$_n$CO$_2$H, and
(3) —(CH$_2$)$_n$OH,
wherein each CH$_2$ is unsubstituted or substituted with 1 or 2 substituents selected from C$_{1-6}$alkyl, —OH and —NH$_2$;
each R$^1$ and R$^2$ is independently selected from:
(1) halogen,
(2) phenyl,
(3) phenyl-cyclopropyl,
(4) phenyl-pyrrolidine,
(5) phenyl piperidine,
(6) phenyl-piperazine,
(7) biphenyl,
(8) phenyl-oxazole,
(9) phenyl-pyridine,
(10) phenyl-furan,
(11) phenyl-oxadiazole,
(12) pyridine,
(13) indole,
(14) benzofuran,
(15) benzodioxole,
(16) pyrrolo[2,3-b]pyridine,
(17) pyrazole, and
(18) benzisoxazole,
wherein each cycloalkyl, cycloheteroalkyl, aryl and heteroaryl is unsubstituted or substituted with 1, 2, 3 or 4 substituents independently selected from R$^a$, provided that at least one of and only one of R$^1$ and R$^2$ is halogen;
R$^3$ is hydrogen or absent;
R$^4$ is hydrogen;
R$^5$ is hydrogen, and
R$^6$ is hydrogen or halogen;
or a pharmaceutically acceptable salt thereof.

Another embodiment of the present invention relates to compounds of structural formula I wherein:
T is —CR$^3$— or N;
U is —CR$^1$—;
V is —CR$^2$—;
W is —CR$^4$—;
X is —CH$_2$—;
Y is selected from:
(1) C$_{1-6}$alkyl,
(2) —C$_{3-10}$cycloalkyl, and
(3) aryl,
wherein Y is unsubstituted or substituted with 1, 2, 3 or 4 substituents selected from R$^b$;
Z is selected from:
(1) —(CH$_2$)$_n$CO$_2$H, and
(2) —(CH$_2$)$_n$OH,
wherein each CH$_2$ is unsubstituted or substituted with 1 or 2 substituents selected from C$_{1-6}$alkyl, —OH and —NH$_2$;
R$^1$ is independently selected from:
(1) aryl,
(2) aryl-C$_{3-7}$cycloalkyl,
(3) aryl-C$_{2-10}$cycloheteroalkyl,
(4) aryl-aryl, and
(5) aryl-heteroaryl,
wherein each cycloalkyl, cycloheteroalkyl, aryl and heteroaryl is unsubstituted or substituted with 1, 2, 3 or 4 substituents independently selected from R$^a$;
R$^2$ is halogen;
R$^3$ is hydrogen or absent;
R$^4$ is hydrogen;
R$^5$ is hydrogen, and
R$^6$ is hydrogen;
or a pharmaceutically acceptable salt thereof.

Another embodiment of the present invention relates to compounds of structural formula I wherein:
T is —CR$^3$— or N;
U is —CR$^1$—;
V is —CR$^2$—;
W is —CR$^4$—;
X is —CH$_2$—;
Y is selected from:
(1) C$_{1-6}$alkyl,
(2) C$_{3-10}$cycloalkyl, and
(3) aryl,
wherein Y is unsubstituted or substituted with 1, 2, 3 or 4 substituents selected from R$^b$;
Z is selected from:
(1) —(CH$_2$)$_n$CO$_2$H, and
(2) (CH$_2$)$_n$OH,
wherein each CH$_2$ is unsubstituted or substituted with 1 or 2 substituents selected from C$_{1-6}$alkyl, —OH and —NH$_2$;
R$^1$ is independently selected from:
(1) phenyl,
(2) phenyl-cyclopropyl,
(3) phenyl-pyrrolidine,
(4) biphenyl, and
(5) phenyl-pyridine,
wherein each cycloalkyl, cycloheteroalkyl, aryl and heteroaryl is unsubstituted or substituted with 1, 2, 3 or 4 substituents independently selected from R$^a$;

$R^2$ is halogen;
$R^3$ is hydrogen or absent;
$R^4$ is hydrogen;
$R^5$ is hydrogen, and
$R^6$ is hydrogen;
or a pharmaceutically acceptable salt thereof.

In another embodiment of the present invention, the invention relates to compounds of structural formula Ia:

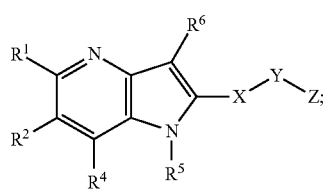

(Ia)

or a pharmaceutically acceptable salt thereof.

In another embodiment of the present invention, the invention relates to compounds of structural formula Ib:

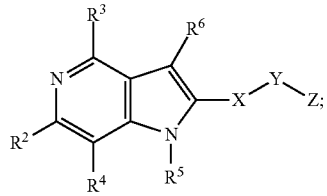

(Ib)

or a pharmaceutically acceptable salt thereof.

In another embodiment of the present invention, the invention relates to compounds of structural formula Ic:

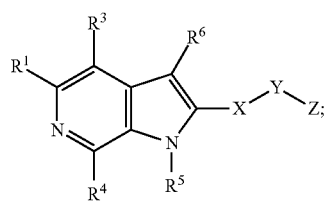

(Ic)

or a pharmaceutically acceptable salt thereof.

In another embodiment of the present invention, the invention relates to compounds of structural formula Id:

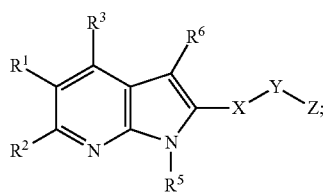

(Id)

or a pharmaceutically acceptable salt thereof.

The compound of structural formula I, includes the compounds of structural formulas Ia, Ib, Ic and Id, and pharmaceutically acceptable salts, hydrates and solvates thereof.

Illustrative, but non-limiting, examples of the compounds of the present invention that are useful as activators of AMP-protein kinase are the following compounds:

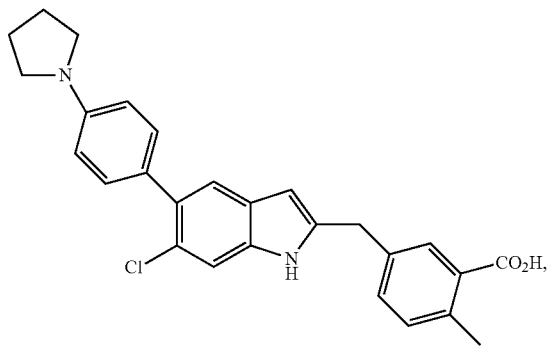

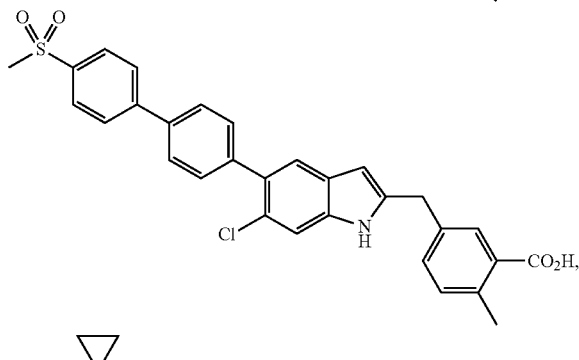

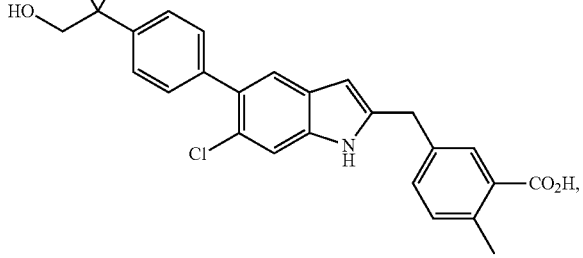

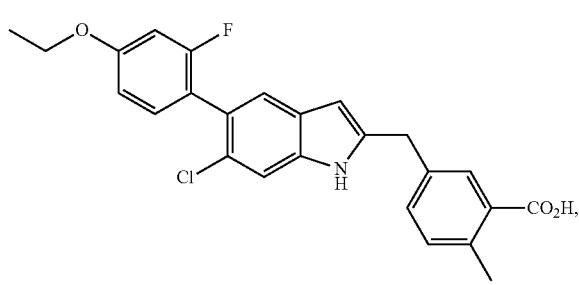

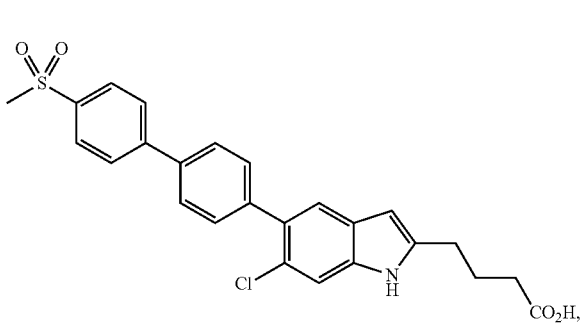

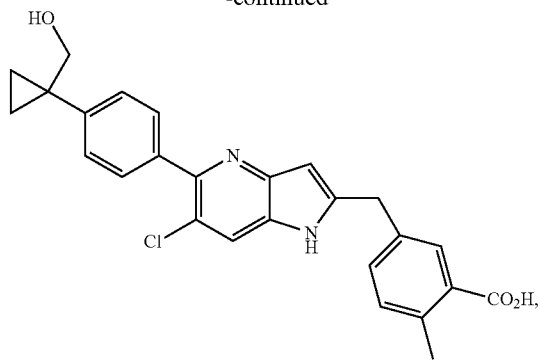

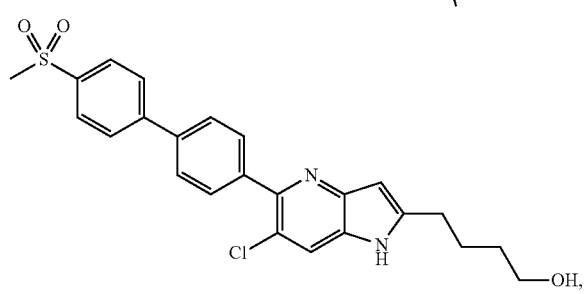

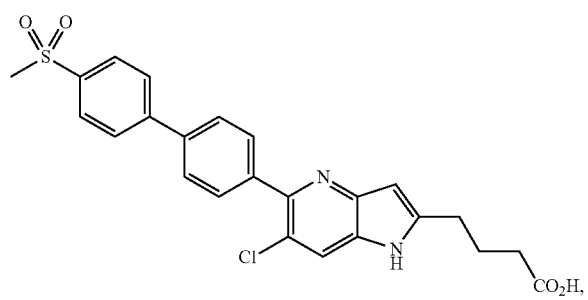

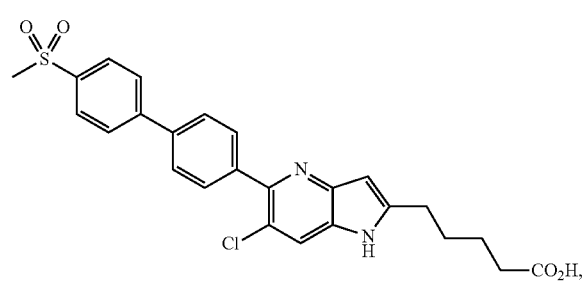

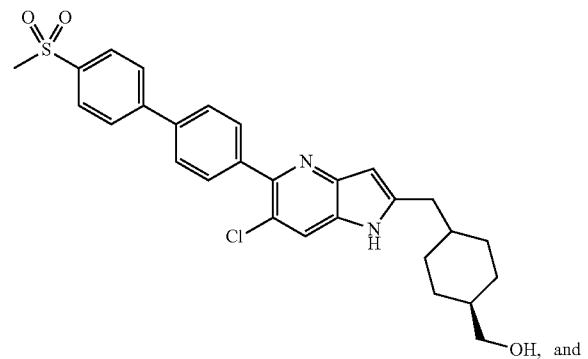

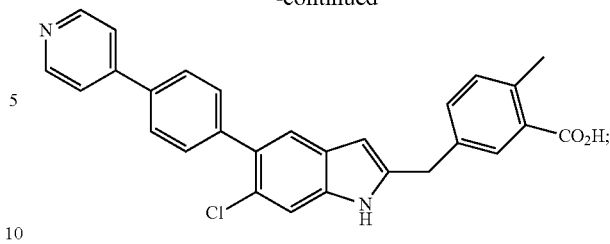

or a pharmaceutically acceptable salts thereof.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. In one embodiment, $C_{2-8}$alkynyl means a carbon chain with 2 to 8 carbons that contains one carbon-carbon triple bond. Examples of alkynyl include ethynyl, propargyl, 3-methyl-1-pentynyl, 2-heptynyl and the like. In one embodiment of the present invention, alkynyl is ethynyl. In another embodiment, alkynyl is propargyl.

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl. In another embodiment of the present invention, cycloalkyl is cyclopropyl. In another embodiment of the present invention, cycloalkyl is cyclohexyl.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. In one embodiment, $C_{2-10}$cycloheteroalkyl means non-aromatic, mono- or bicyclic or bridged saturated carbocyclic rings, having from 2 to 10 carbon atoms and containing, 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from piperidine, pyrrolidine, oxazolidine, 1,3-oxazolidine-2,4-dione, thiazolidine, 1,3-thiazolidine-2,4-dione, imidazolidine, and hydantoin, and the like. In another embodiment of the present invention cycloheteroalkyl is selected from: morpholine, pyrrolidine, piperazine, and piperidine. In another embodiment of the present invention, cycloalkyl is selected from: tetrahydropyran, pyrrolidine, piperazine and piperidine. In another embodiment of the present invention, cycloheteroalkyl is selected from: tetrahydropyran and piperidine. In another embodiment of the present invention, cycloheteroalkyl is selected from: pyrrolidine, piperazine and piperidine. In another embodiment of the present invention, cycloheteroalkyl is pyrrolidine.

In another embodiment of the present invention, cycloheteroalkyl is dianhydro-mannitol. In another embodiment of the present invention, cycloheteroalkyl is 1,4:3,6-dianhydro-mannitol. In another embodiment of the present invention, cycloheteroalkyl is 1,4:3,6-dianhydro-D-mannitol. In another embodiment of the present invention, cycloheteroalkyl is hexahydrofuro[3,2-b]furan. In a class of this embodiment, cycloheteroalkyl is 2,3,3a,5,6,6a-hexahydrofuro[3,2-b]furan.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

In another embodiment of the present invention, cycloheteroalkenyl is dihydropyrrolo[3,4-c]pyrazole. In a class of this embodiment, cycloheteroalkenyl is 4,6-dihydropyrrolo[3,4-c]pyrazole.

In another embodiment of the present invention, cycloheteroalkenyl is dihydroimidazole or tetrahydropyrimidine. In a class of this embodiment, cycloheteroalkenyl is 2,5 dihydro-1H-imidazole or 1,4,5,6-tetrahydropyrimidine. In another class of this embodiment, cycloheteroalkenyl is dihydroimidazole. In another class of this embodiment, cycloheteroalkenyl is 2,5 dihydro-1H-imidazole. In another class of this embodiment, cycloheteroalkenyl is tetrahydropyrimidine. In another class of this embodiment, cycloheteroalkenyl is 1,4,5,6-tetrahydropyrimidine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 2-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as acycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, benzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4 dihydropyrido[3,2-b][1,4]oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole. In another class of this embodiment, heteroaryl is indole. In another embodiment of the present invention, heteroaryl is triazole. In another class of this embodiment, heteroaryl is benzodioxole.

In another embodiment, heteroaryl is selected from: furan, oxazole, pyridine, oxadiazole, indole, benzofuran, benzodioxole, azaindole, pyrazole, and benzisoxazole.

In another embodiment, heteroaryl is selected from: furan, oxazole, pyridine, and oxadiazole.

In another embodiment, heteroaryl is selected from: indole, benzofuran, benzodioxole, azaindole, pyrazole, and benzisoxazole.

"Halogen" includes fluorine, chlorine, bromine and iodine. In one embodiment of the present invention, halogen is selected from fluorine, chlorine, and bromine. In another embodiment of the present invention, halogen is selected from fluorine, and chlorine. In another embodiment of the present invention, halogen is fluorine. In another embodiment of the present invention, halogen is chlorine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$alkyl substituent is equivalent to:

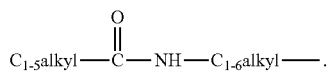

For example, a $—(CH_2)_mOCOR^f$ substituent is equivalent to $—(CH_2)_mOC(O)R^f$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, trifluoroacetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are activators of the AMP-activated protein kinase. The methods of treatment of this invention comprise a method of activating AMPK-activated protein kinase and treating AMPK-activated protein kinase mediated diseases by administering to a patient in need of such treatment a non-toxic therapeutically effective amount of a compound of this invention that activates AMPK-activated protein kinase.

AMP-activated protein kinase (AMPK) is a heterotrimeric enzyme composed of a catalytic α subunit and regulatory β and γ subunits. There are two genes encoding isoforms of both the α and β subunits (α1, α2, β1 and β2) and three genes encoding isoforms of the γ subunit (γ1, γ2 and γ3) leading to 12 possible heterotrimeric combinations. The α2 isoform is predominately found in skeletal and cardiac muscle AMPK; both the α1 and α2 isoforms are found in hepatic AMPK; while in pancreatic islet β-cells the α1 isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention may be efficacious in the treatment and prevention of diseases, disorders and conditions that are responsive to the activation of AMP-activated protein kinase, including but not limited to: type 2 diabetes, insulin resistance, hyperglycemia, obesity, hyperinsulinemia, glucose intolerance, atherosclerosis, Metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds may also be useful for the treatment of cancer, hypoxia and glucocorticoid-induced apoptosis. The compounds may also be useful for the treatment of sarcopenia by treating or preventing the loss of skeletal muscle mass, including but not limited to a loss of skeletal muscle mass due to aging.

One or more of the following diseases may be treated by the administration of a therapeutically effective amount of a compound of Formula I, or a pharmaceutically acceptable salt thereof, to a patient in need of treatment or prevention of: (1) non-insulin dependent diabetes mellitus (Type 2 diabetes); (2) hyperglycemia; (3) Metabolic Syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; (11) atherosclerosis, (12) hypertension, (13) sarcopenia, (14) high circulating free fatty acids (FFAs), (15) non-alcoholic steatohepatitis (NASH), (16) non-alcoholic fatty liver disease (NAFLD), (17) Type 1 diabetes, (18) heart attack, (19) cardiomyopathy, and (20) heart failure.

One embodiment of the potential uses of the compounds is directed to the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; and (6) hypertension.

In another embodiment of the potential uses of the compounds is directed to the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; (6) hypertension; and (7) cancer.

In another embodiment of the potential uses of the compounds is directed to the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; (6) hypertension; (7) low HDL; (8) high LDL; (9) high triglycerides; (10) atherosclerosis; (11) sarcopenia; and (12) cancer.

The compounds of structural Formula I may also be used for manufacturing a medicament for potential use in the treatment of one or more of the above diseases.

The compounds may also be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in: a) reducing the risks of adverse sequelae associated with metabolic syndrome, b) reducing the risk of developing atherosclerosis, c) delaying the onset of atherosclerosis, and/or d) reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or may be useful in delaying or preventing a patient with Type 2 diabetes from needing insulin therapy.

Other possible outcomes of treatment with the compounds of the present invention may be, but are not limited to: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in LDL; 10) a decrease in plasma triglycerides; 11) a decrease in free fatty acids; 12) a decrease in hepatic glucose output; 13) an improvement in insulin action; 14) a decrease in blood pressure; 15) an improvement in insulin sensitivity; 16) a suppression of hepatic glucose output; 17) an inhibition of de novo lipogenesis; 18) stimulation of muscle glucose uptake; 19) modulation of insulin secretion by pancreatic β cells; 20) a decrease in body weight; 21) an increase in skeletal muscle mass; 22) a prevention in the loss of skeletal muscle mass.

The compounds may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides a potential method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example anacetrapib, torcetrapib, and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The present invention also relates to potential methods and medicaments for the treatment, control, or prevention of Type 2 diabetes by administering the compounds and pharmaceutical compositions of the present invention. The present invention also relates to potential methods and medicaments for the treatment, control, or prevention of Type 2 diabetes by administering the compounds of the present invention in combination with a therapeutically effective amount of another agent known to be useful to treat the condition. The present invention also relates to potential methods and medicaments for the treatment, control, or prevention of diabetes related disorders by administering the compounds and pharmaceutical compositions of the present invention alone, or in combination. The present invention also relates to potential methods and medicaments for the treatment and prevention of diabetes in pre-diabetic subject by administering the compounds and pharmaceutical compositions of the present invention alone, or in combination.

The present invention also relates to potential methods and medicaments for the treatment, control, or prevention of obesity by administering the compounds and pharmaceutical compositions of the present invention, alone or in combination with a therapeutically effective amount of another agent known to be useful to treat the condition. The present invention also relates to potential methods and medicaments for the treatment, control, or prevention of obesity related disorders by administering the compounds and pharmaceutical compositions of the present invention alone, or in combination. The present invention also relates to potential methods and medicaments for the treatment and prevention of obesity in overweight subject by administering the compounds and pharmaceutical compositions of the present invention alone, or in combination. The compounds may also be useful for the treatment of obesity related disorders, and eating disorders associated with excessive food intake, and complications associated therewith, including left ventricular hypertrophy, as well as treating or preventing obesity in other mammalian species, including canines and felines.

The present invention also relates to potential methods and medicaments for the treatment, control, or prevention of hyperglycemia by administering the compounds and pharmaceutical compositions of the present invention, alone or in combination with a therapeutically effective amount of another agent known to be useful to treat the condition.

The present invention also relates to potential methods and medicaments for the treatment, control, or prevention of insulin resistance by administering the compounds and pharmaceutical compositions of the present invention, alone or in combination with a therapeutically effective amount of another agent known to be useful to treat the condition.

The present invention also relates to potential methods and medicaments for the treatment, control, or prevention of lipid disorders by administering the compounds and pharmaceutical compositions of the present invention, alone or in combination with a therapeutically effective amount of another agent known to be useful to treat the condition. The present invention also relates to potential methods and medicaments for the treatment, control, or prevention of dyslipidemia related disorders and lipid disorder-related disorders by administering the compounds and pharmaceutical compositions of the present invention alone, or in combination.

The present invention also relates to potential methods and medicaments for the treatment, control, or prevention of atherosclerosis by administering the compounds and pharmaceutical compositions of the present invention, alone or in combination with a therapeutically effective amount of another agent known to be useful to treat the condition.

The present invention also relates to potential methods and medicaments for the treatment, control, or prevention of hypertension by administering the compounds and pharmaceutical compositions of the present invention, alone or in combination with a therapeutically effective amount of another agent known to be useful to treat the condition. The present invention also relates to potential methods and medicaments for the treatment and prevention of hypertension in pre-hypertensive subject by administering the compounds and pharmaceutical compositions of the present invention alone, or in combination.

The present invention also relates to potential methods and medicaments for the treatment, control, or prevention of Metabolic Syndrome by administering the compounds and pharmaceutical compositions of the present invention, alone or in combination with a therapeutically effective amount of another agent known to be useful to treat the condition.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity. The compositions are especially effective for treating Type 2 diabetes. The compositions of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

Left ventricular hypertrophy (LVH) is identified based on left ventricular mass index (LVMI) and relative wall thickness (RWT). Left ventricular mass index is defined as left ventricular mass in grams divided by body surface area in meters$^2$. Relative wall thickness is defined as 2× posterior wall thickness/left ventricular end diastolic diameter. Normal LVMI values are typically 85 and normal RWT approximately 0.36. A male subject with LVH has a LVMI greater than 131 g/m$^2$; a female subject with LVH has a LVMI greater than 100 g/m$^2$. A subject with an elevated LVMI value is a male subject with a LVMI between 85 g/m$^2$ and 131 g/m$^2$, or a female subject with a LVMI between 85 g/m$^2$ and 100 g/m$^2$.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 43.5 |
| Benzalkonium chloride | 1.0 | Magnesium Stearate | 2.5 |
| Water for injection to a total volume of 1 mL | | | 500 |

| Capsule | mg/capsule | Aerosol | Per canister |
|---|---|---|---|
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| | 600 | Dichlorodifluoromethane, NF | 12.15 g |

Compounds of Formula I may be used in combination with other drugs that are used in the treatment/prevention/suppression or amelioration of the diseases, disorders or conditions for which compounds of Formula I may be useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dylipidemic agents, and anti-hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief.

In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the potential treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-$NH_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphate inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]-isothiazole-3-ol 1-oxide, 5-(4-((3-(2,6-dimethyl-4-(3-(methylsulfonyl)propoxy)-phenyl)phenyl)-methoxy)phenyl)iso, 5-(4-((3-(2-methyl-6-(3-hydroxypropoxyl)pyridine-3-yl)-2-methylphenyl) methoxy)phenyl)isothiazole-3-ol 1-oxide, and 5-[4-[[3-[4-(3-aminopropoxy)-2,6-dimethylphenyl]phenyl] methoxy]phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche), ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X—Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AteroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH$_2$R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512, 565, 5,391,571, 5,602,151, 4,405,644, 4,189,438, and 4,242, 453, and the like; (41) fatty acid transporter inhibitors; (42) dicarboxylate transporter inhibitors; (43) glucose transporter inhibitors; and (44) phosphate transporter inhibitors; (45)

anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, topiramate, naltrexone, bupriopion, phentermine, and losartan, losartan with hydrochlorothiazide.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of structural formula I of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N. Y., 1991. CBZ and BOC are commonly used protecting groups in organic synthesis, and their removal conditions are known to those skilled in the art. All temperatures are degrees Celsius unless otherwise noted. Mass spectra (MS) were measured by electron-spray ion-mass spectroscopy.

Abbreviations used in the description of the preparation of the compounds of the present invention: ACN is acetonitrile; AcO is acetoxy; AcOH is acetic acid; $Ac_2O$ is acetic anhydride; Ar is aryl; aq is aqueous; Boc is tert-butoxycarbonyl; $Boc_2$ is di-tert-butoxycarbonyl; n-BuLi is n-butyl lithium; t-Bu is tert-butyl; C is carbon; cat is catalytic; con and conc. is concentrated; $Cu(OAc)_2$ is Copper (II) acetate; CV is column volume(s); $Cy_2NMe$ is N-cyclohexyl-N-methylcyclohexanamine; DAST is (diethylamino)sulfur trifluoride; DBU is 1,8-diazabicyclo-[5.4.0]undec-7-ene; DIBAL-H is di-isobutyl aluminum hydride; DCM is dichloromethane; DIPEA or DIEA is diisopropylethyl amine; DMA is dimethyl acetal; DMAc is N,N-dimethylacetamide;

DMAP is dimethylaminopyridine; DME is 1,2-dimethoxyethane; DMF is dimethyl formamide; DMP is Dess-Martin Periodinane; DMSO is dimethyl sulfoxide; dppf DCM complex is 1,1'-bis(diphenyl-phosphino)ferrocene dichloromethane complex; DTBPF-PdCl$_2$ is [1,1'-Bis(di-tert-butylphosphino)ferrocene]dichloropalladium(II); Et is ethyl; Et$_2$O is diethyl ether; EA and EtOAc is ethyl acetate; EtOH is ethanol; dppf is 1,1'-Bis(diphenyl-phosphino)ferrocene; EtOH is ethanol; Et$_3$N is triethyl amine; h and hr is hour(s); HMDS is hexamethyldisilazane; HPLC is high pressure liquid chromatography; ISCO R$_f$ is the R$^f$ determined via medium pressure liquid chromatography using aTeledyne ISCO RediSep® column; isomannide is 1,4:3,6-Di-anhydro-mannitol; KOAc is potassium acetate; L is liter; LC/MS and LC-MS is liquid chromatography/mass spectroscopy; KOTMS is potassium trimethylsilanolate; LAH is lithium aluminum hydride; LDA is lithium diisopropylamide: M is molar; ml and mL is milliliter; Me is methyl; MeCN is acetonitrile; MeI is methyl iodide; MeMgBr is methyl magnesium bromide; MeOH is methanol; MgBr is magnesium bromide; min is minutes; mmol is millimole(s); m-CPBA is meta chloro per benzoic acid; MTBE is tert-butyl methyl ether; MS is mass spectrum; MW is microwave; N is normal; NaCN is sodium cyanide; NaOAc is sodium acetate; NBS is N-bromo succinamide; NIS is N-iodo succinamide; NMP is 1-methylpyrrolidin-2-one; OTBS is tert-butyldimethylsilyloxy; TBS is tert-butyldimethylsilyl; Pd(OAc)$_2$ is palladium (II) acetate; P(OEt)$_3$ is triethylphosphite; Pd(PPh$_3$)$_2$Cl$_2$ is Bis(triphenylphosphine) palladium(II) dichloride; PE is petroleum ether; PPh$_3$ is triphenyl phosphine; iPrOH is isopropanol; PhSiH is phenyl silane; Prep TLC or Pre TLC Preparative Thin Layer Chromatography; Prep HPLC or Pre HPLC or p-HPLC-Preparative High Pressure Liquid Chromatography; wt % is weight percent; psi is pounds per square inch; RT, r.t. and rt is room temperature; Rt is retention time; Rochelles' Salt is potassium sodium tartrate; SEM is 2-(trimethylsilyl)-ethoxymethyl; SEMCl is 2-(trimethylsilyl)-ethoxymethyl chloride; Select-Fluor is 1-Chloromethyl-4-fluoro-1,4-diazoniabicyclo{2.2.2}octane bis(tetrafluoroborate); TEA is triethylamine; TBAD is di-tert-butyl azodicarboxylate; TBAF is tetrabutyl ammonium fluoride; TBDMS-Cl is tert-butyldimethylsilyl chloride; TBSCl is tert-butyldimethylsilyl chloride; TMS is trimethylsilyl; TMSBr is trimethylsilyl bromide; tol is toluene; TFA is trifluoro acetic acid; TFAA is trifluoro acetic anhydride; and THF is tetrahydrofuran.

Microwave (MW) reactions were performed with a single mode operating Biotage Emrys Optimizer in sealed reaction vials at the indicated fixed temperature held constant for the designated reaction time. The medium pressure liquid chromatography (MPLC) purifications were performed with Biotage normal-phase columns pre-packed with 35-60 micron silica gel unless otherwise noted. The LC-MS system contained an Applied Biosystems API150EX MS operating in a positive ion mode receiving 0.1 mL/min flowrate with a Shimadzu UV detector receiving 0.1 mL/min flowrate. Unless specified, the LC conditions were solvent A=0.05% TFA in acetonitrile; solvent B=0.05% TFA in water; flowrate=2.5 mL/min; column: Waters Xterra MS C18, 20×2.1 mm; 3.5 micron particle size, gradient program (4 minute run): min (% B) 0 (95), 1.6 (5), 2.6 (5), 2.7 (95), 3.0 (95). Unless specified, the $^1$H NMRs were obtained in CDCl$_3$ at 500 MHz and spectra were recorded in units δ with CHCl$_3$ (δ 7.260) as the reference line internal standard.

Solvents, reagents, and intermediates that are commercially available were used as received. Reagents and intermediates that were not commercially available were prepared in the manner as described below. $^1$H NMR spectra were measured on either a Varian VNMR System 400 or Bruker Avance 400 spectrometer at 400 MHz and are reported as ppm downfield from Me$_4$Si with number of protons, multiplicities, and coupling constants in Hertz indicated parenthetically. Where LC/MS data are presented, analyses were performed using an Agilent 6110A MSD or an Applied Shimadzu 2020MSD. The parent ion is given. Purification were conducted with reverse phase HPLC (Phenomenex Gemini C18 (250*21.2 mm*5 μm) or Phenomenex Synergi C18 (250*50 mm*10 μm) column, elution of acetonitrile/water from 100% acetonitrile to 0% acetonitrile.) or silica gel column chromatography (SAN PONT, ZXC II).

The following reaction schemes illustrate methods which may be employed for the synthesis of the compounds of structural formula I described in this invention. All substituents are as defined above unless indicated otherwise. Several strategies based upon synthetic transformations known in the literature of organic synthesis may be employed for the preparation of the title compounds of general formula I.

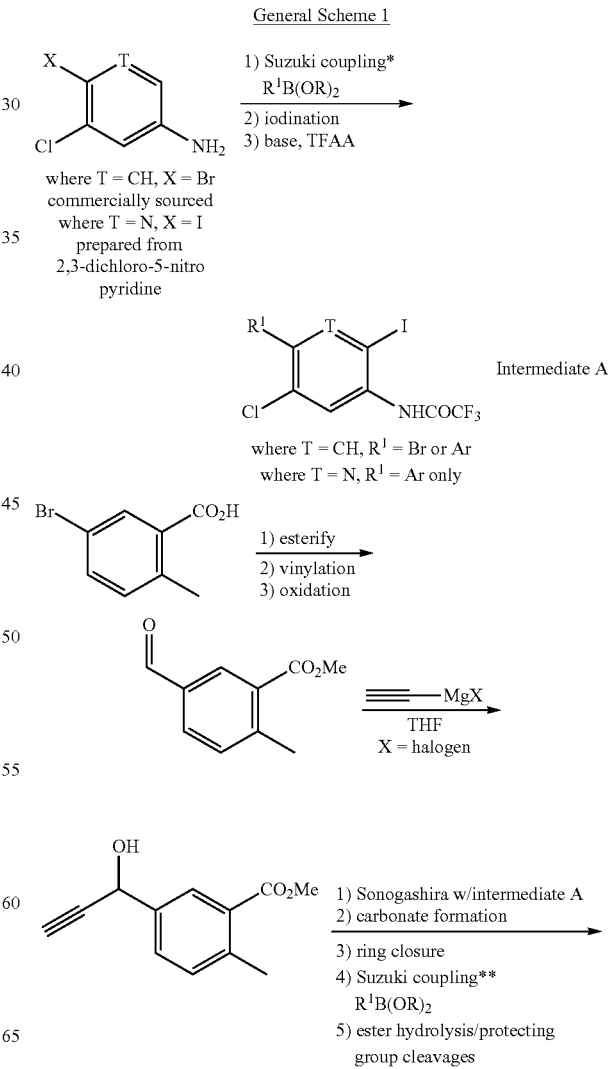

-continued

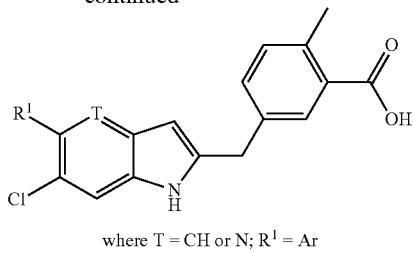

where T = CH or N; R¹ = Ar

General Scheme 1 shows a general protocol for the preparation of the compounds of the present invention. An appropriately substituted phenyl (T=CH) or pyridyl (T=N) derivative is subjected to Suzuki conditions using either a boronate (R is alkyl) or boronic acid (R is H), followed by iodination and amino group protection to provide intermediate A. * Alternatively, for compounds in which T=CH and R¹=Br, a Suzuki reaction may be done later in the sequence after ring closure. Separately, 3-Bromobenzoic acid derivative is subjected to esterification, vinylation under palladium catalyzed conditions, followed by oxidative conditions to provide the aldehyde derivative. Conversion to the alkyne derivative is accomplished via treatment of the aldehyde derivative with ethynyl magnesium halide. The resulting alkyne derivative and intermediate A are coupled together under Sonogashira conditions. Activation of the resultant alcohol via carbonate formation, followed by ring closure provides the corresponding indole and azaindole compounds. For compounds with protecting groups, ester hydrolysis and protecting group cleavage provides the compounds of the present invention. **For indole derivatives in which T=CH and R¹=Br, a Suzuki reaction may be used to install the required R¹ aryl moiety after ring closure.

General Scheme 2

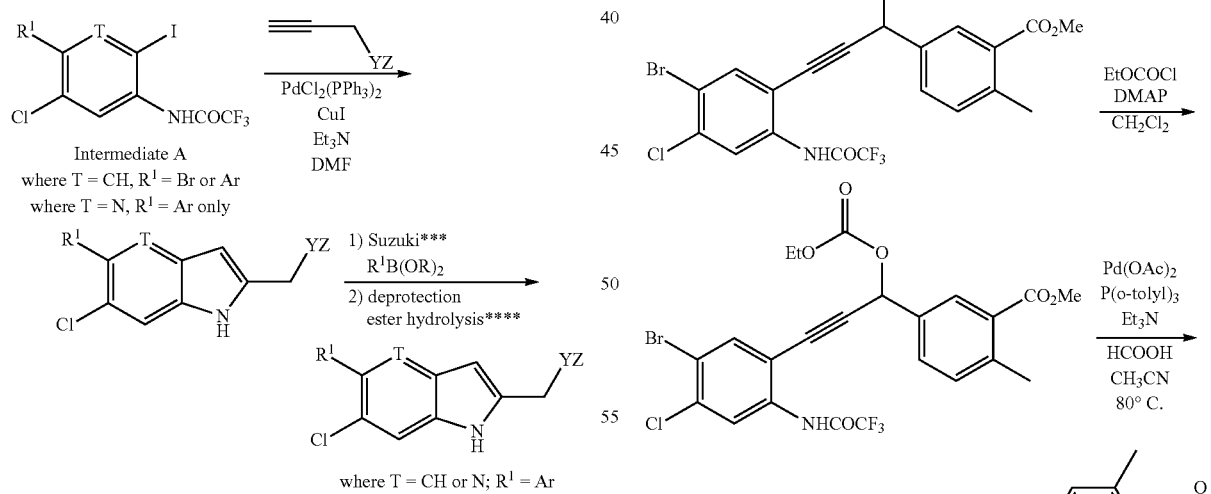

where T = CH or N; R¹ = Ar

Another general protocol for preparation of the compounds of the present invention is shown in General Scheme 2. Intermediate A is coupled with appropriately substituted alkyne under Sonogashira-like conditions to give the compounds of the present invention. *For indole derivatives in which R¹ is Br, a Suzuki reaction may be used to install the required aryl moiety at R¹ after reaction with the substituted alkyne. **Ester hydrolysis or deprotection of the compounds with protecting groups on the YZ moiety gives the compounds of the present invention.

SCHEME 1

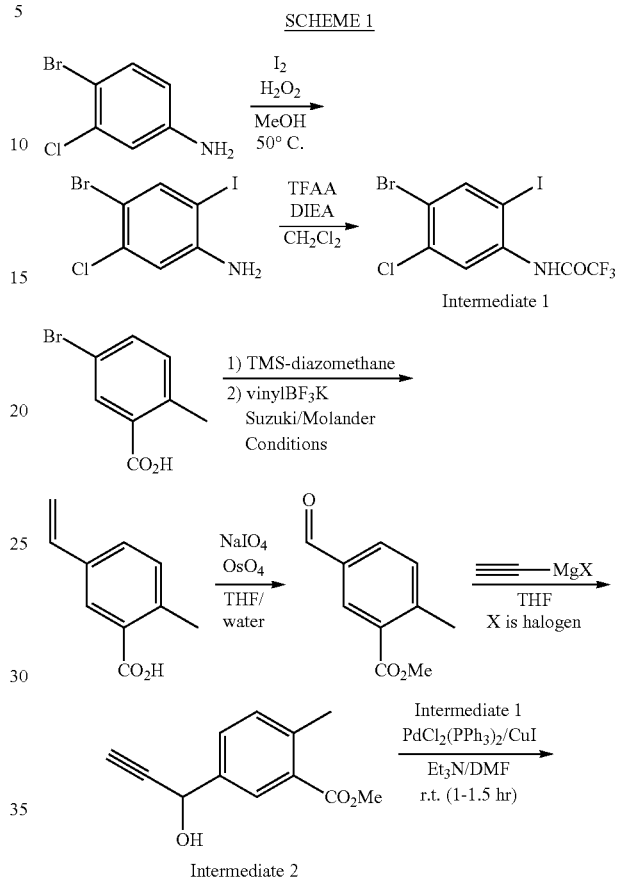

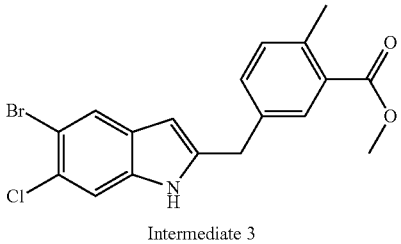

Intermediate 3

Intermediate 1

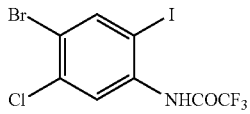

N-(4-bromo-5-chloro-2-iodophenyl)-2,2,2-trifluoro-acetamide

Step A: 4-bromo-5-chloro-2-iodoaniline

A solution of 3-chloro-4-bromoaniline (6.19 g, 30 mmol) in methanol (375 ml) was treated with portionwise additions of iodine (7.99 g, 31.5 mmol) over about 5 minutes, followed by the dropwise addition of 30% hydrogen peroxide (22.98 ml, 225 mmol) over about 5 minutes. The reaction was heated to 50° C. overnight. Then approximately 500 mL of saturated aqueous $Na_2S_2O_3$ was added to the reaction dropwise, followed by 500 mL of ethyl acetate. The mixture was separated, and the aqueous layer was extracted a second time with 250 mL of ethyl acetate. The combined organic layers were washed with saturated aqueous $Na_2S_2O_3$, and brine, and then dried over sodium sulfate, filtered and evaporated under high vacuum overnight. Purification of the crude product on a Biotage 65i silica gel column with linear gradient elution of 5-20% ethyl acetate in hexanes over 4.5 liters provided the title compound as the major isolate and the regioisomeric 3-chloro-4-bromo-2-iodoaniline as the minor product. NMR δ (ppm) ($CDCl_3$): 7.81 (s, 1H), 6.83 (s, 1H), 4.17 (br s, 2H).

Step B: N-(4-bromo-5-chloro-2-iodophenyl)-2,2,2-trifluoroacetamide

4-Bromo-5-chloro-2-iodoaniline (5.65 g, 17.00 mmol) was dissolved in $CH_2Cl_2$ (85 ml) and cooled to 0° C. Then N,N-diisopropylethylamine (5.2 ml, 29.7 mmol) was added, followed by trifluoroacetic anhydride (3.2 ml, 22.95 mmol). The reaction was stirred for about 2 hours, then diluted with $CH_2Cl_2$, and washed twice with aqueous $NH_4Cl$, once with aqueous $NaHCO_3$ and once with brine. The organic layer was dried over $Na_2SO_4$, filtered and the filtrate was evaporated by rotary evaporation to give the crude title compound, which was used without further purification. NMR δ (ppm) ($CDCl_3$): 8.42 (s, 1H), 8.21 (br s, 1H), 8.08 (s, 1H).

Intermediate 2

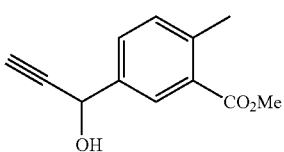

Methyl 5-(1-hydroxyprop-2-yn-1-yl)-2-methylbenzoate

Step A: methyl 5-bromo-2-methylbenzoate

2-Methyl-5-bromobenzoic acid (2.89 g, 13.44 mmol) was dissolved in toluene (44 ml) and methanol (22 ml). After cooling to 0° C., trimethylsilyl diazomethane (10.8 ml, 21.6 mmol) was slowly added and the reaction was stirred overnight. Upon completion, the volatiles were evaporated and the crude product was dried under high vacuum overnight. The resulting crude product was used without further purification. NMR δ (ppm) ($CDCl_3$): 8.03 (d, 1H), 7.50 (dd, 1H), 7.11 (d, 1H), 3.89 (s, 3H), 2.56 (s, 3H).

Step B: methyl 2-methyl-5-vinylbenzoate

Methyl 5-bromo-2-methylbenzoate (2.99 g, 13.05 mmol) was dissolved in 2-propanol (64 mL). Then potassium vinyltrifluoroborate (2.448 g, 18.27 mmol) and water (16 ml) were added. The reaction mixture was stirred until the reagents were completely dissolved, then triethylamine (5.5 ml, 39.2 mmol) and $PdCl_2(dppf)$ (0.239 g, 0.326 mmol) were added. The reaction was stirred at 100° C. for 75 minutes, followed by the addition of water. The reaction mixture was then extracted with ethyl acetate. The organic layer was separated, washed with brine, dried over sodium sulfate, filtered and evaporated. The crude product was purified on a Biotage 40M silica gel column, eluting with a gradient of 10-50% dichloromethane in hexanes to give the title compound. NMR δ (ppm) ($CDCl_3$): 7.94 (d, 1H), 7.44 (dd, 1H), 7.20 (d, 1H), 6.70 (dd, 1H), 5.76 (d, 1H), 5.26 (d, 1H), 3.90 (s, 3H), 2.58 (s, 3H).

Step C: methyl 5-formyl-2-methylbenzoate

Methyl 2-methyl-5-vinylbenzoate (2.13 g, 12.09 mmol) was dissolved in THF (60 ml). Then 2.5% osmium tetroxide in t-butanol (9.5 ml, 0.755 mmol) was added, followed by water (20 ml). The reaction stirred 15 minutes, then sodium periodate (5.43 g, 25.4 mmol) was added portionwise. Once the reaction was complete, it was quenched with aqueous sodium bicarbonate and extracted with ethyl acetate. The organic layer was separated, and washed with water followed by aqueous NaCl. The organic was dried over sodium sulfate, filtered and evaporated. The crude product was dried under high vacuum overnight. The crude product was purified on a Biotage 40M silica gel column, eluting with a gradient of 10-35% ethyl acetate in hexanes to give the title compound. NMR δ (ppm) ($CDCl_3$): 10.01 (s, 1H), 8.41 (d, 1H), 7.92 (dd, 1H), 7.42 (d, 1H), 3.94 (s, 3H), 2.70 (s, 3H).

Step D: methyl 5-(1-hydroxyprop-2-yn-1-yl)-2-methylbenzoate

Methyl 5-formyl-2-methylbenzoate (1.76 g, 9.88 mmol) was dissolved in THF (20 ml) under nitrogen. The solution was cooled to 0° C., then 0.5 M ethynylmagnesium bromide (21.7 ml, 10.85 mmol) was added dropwise. The solution was stirred for 30 minutes at 0° C., then warmed to room temperature for an additional 30 minutes. Once complete, the reaction was quenched by adding excess saturated aqueous $NH_4Cl$. After 5-10 minutes of stirring, the mixture was partitioned between ethyl acetate and water. The organic layer was separated, washed with brine, dried over sodium sulfate, filtered and evaporated. The crude product was purified on a Biotage 40M silica gel column, eluting with a gradient of 20-50% ethyl acetate in hexanes to give the title compound. NMR δ (ppm) ($CDCl_3$): 8.08 (d, 1H), 7.59 (dd, 1H), 7.28 (d, 1H), 5.47 (d, 1H), 3.91 (s, 3H), 2.68 (d, 1H), 2.60 (s, 3H), 2.30 (d, 1H).

Intermediate 3

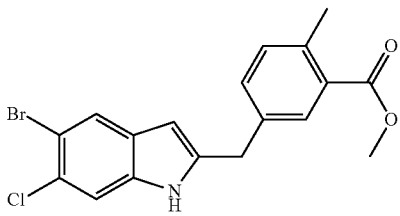 [SMILES: COC(=O)c1cc(Cc2cc3cc(Br)c(Cl)cc3[nH]2)ccc1C]

Methyl 5-((5-bromo-6-chloro-1H-indol-2-yl)methyl)-2-methylbenzoate

Step A: methyl 5-(3-(5-bromo-4-chloro-2-(2,2,2-trifluoroacetamido)phenyl)-1-hydroxyprop-2-yn-1-yl)-2-methylbenzoate Intermediate 1 (3.02 g, 7.05 mmol), copper(I) iodide (0.067 g, 0.353 mmol) and bis(triphenylphosphine)palladium(II) chloride (0.099 g, 0.141 mmol) were added to an oven-dried flask flushed with nitrogen. Then DMF (11 mL) was added, followed by Et$_3$N (9.8 mL) to form the catalyst mixture. Intermediate 2 (1.73 g, 8.46 mmol) was placed in a flask, which was flushed with nitrogen, and Et$_3$N (10.0 mL) was added to form the alkyne solution. The alkyne solution was added dropwise to the stirring catalyst mixture. Then additional DMF (2 mL) was added to the reaction mixture. After 2 hours of stirring at room temperature, the reaction was quenched with aqueous NH$_4$Cl, and partitioned between water and ethyl acetate. Washed the organic again with aqueous NH$_4$Cl, and then dried over sodium sulfate, filtered and evaporated. The crude product was purified on a Biotage 40M silica gel column, eluting with a gradient of 10-40% ethyl acetate in heptane to give the title compound. NMR δ (ppm) (CDCl$_3$): 8.54 (br s, 1H), 8.52 (s, 1H), 8.08 (d, 1H), 7.74 (s, 1H), 7.58 (dd, 1H), 7.32 (d, 1H), 5.76 (d, 1H), 3.91 (s, 3H), 2.63 (s, 3H), 2.43 (d, 1H).

Step B: methyl 5-(3-(5-bromo-4-chloro-2-(2,2,2-trifluoroacetamido)phenyl)-1-((ethoxycarbonyl)oxy)prop-2-yn-1-yl)-2-methylbenzoate Methyl 5-(3-(5-bromo-4-chloro-2-(2,2,2-trifluoroacetamido)phenyl)-1-hydroxyprop-2-yn-1-yl)-2-methylbenzoate (2.09 g, 4.14 mmol) and DMAP (0.809 g, 6.63 mmol) were dissolved in CH$_2$Cl$_2$ (21 ml) and stirred at −20° C. for 10 minutes. Then ethyl chloroformate (0.557 ml, 5.80 mmol) was added and the reaction allowed to stir until the reaction was complete. Once complete the reaction was directly purified on a Biotage 40S silica gel column, eluting with a gradient of 10-25% ethyl acetate in hexanes to give the title compound. NMR δ (ppm) (CDCl$_3$): 8.57 (br s, 1H), 8.55 (s, 1H), 8.09 (d, 1H), 7.74 (s, 1H), 7.58 (dd, 1H), 7.33 (d, 1H), 6.45 (s, 1H), 4.26 (q, 2H), 3.91 (s, 3H), 2.63 (s, 3H), 1.33 (t, 3H).

Step C: methyl 5-((5-bromo-6-chloro-1H-indol-2-yl)methyl)-2-methylbenzoate

Palladium(II) acetate (11.23 mg, 0.050 mmol) and tri-O-tolylphosphine (30.4 mg, 0.100 mmol) were added to a nitrogen blanketed flask, which was evacuated and charged with nitrogen. Acetonitrile (1 mL) was then added to the catalyst/ligand mixture. In a separate flask, methyl 5-(3-(5-bromo-4-chloro-2-(2,2,2-trifluoro-acetamido)-phenyl)-1-((ethoxycarbonyl)oxy)prop-2-yn-1-yl)-2-methylbenzoate (288 mg, 0.5 mmol) was dissolved in acetonitrile (4 mL) and the reaction flask was evacuated and charged with nitrogen. Then Et$_3$N (209 μl, 1.500 mmol) was added to form the alkyne suspension. Then the alkyne suspension was added to the stirring catalyst mixture, followed by formic acid (38.4 μl, 1.000 mmol). The resulting reaction mixture was stirred at 40° C. for 1 hour 45 minutes, then removed from heat and quenched with aqueous NH$_4$Cl. The reaction mixture was then extracted with ethyl acetate. The organic layer was washed with brine, dried over sodium sulfate, filtered and evaporated. The crude product was purified on a Biotage 25S silica gel column, eluting with a gradient of 10-40% ethyl acetate in hexanes to give the title compound. NMR δ (ppm) (CDCl$_3$): 7.81 (br s, 1H), 7.78 (s, 1H), 7.76 (s, 1H), 7.36 (s, 1H), 7.25 (dd, 1H), 7.21 (d, 1H), 6.23 (s, 1H), 4.09 (s, 2H), 3.88 (s, 3H), 2.57 (s, 3H).

Intermediate 4

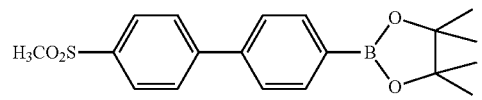

4,4,5,5-tetramethyl-2-(4'-(methylsulfonyl)-[1,1'-biphenyl]-4-yl)-1,3,2-dioxaborolane 4-Bromophenyl methyl sulfone (3.5 g, 14.89 mmol), 1,4-diphenylboronic acid, bis(pinacol) ester (14.74 g, 44.7 mmol) and silver carbonate (4.52 g, 16.38 mmol) were added to an oven dried 250 ml round bottom flask, which was then evacuated and charged with nitrogen. Then THF (100 ml) was added, followed by tetrakis(triphenylphosphine)palladium (0) (0.860 g, 0.744 mmol). The flask was evacuated and charged with nitrogen. Then the reaction was heated to 70° C. overnight, and stirred at room temperature for an additional 24 hours. Then the reaction mixture was filtered through Celite™ and the filtrate was evaporated. The crude product was purified on a Biotage 65i silica gel column, eluting with a gradient of 10-50% ethyl acetate in hexanes to give the title compound. NMR δ (ppm) (CDCl$_3$): 8.01 (d, 2H), 7.92 (d, 2H), 7.79 (s, 2H), 7.61 (d, 2H), 3.09 (s, 3H), 1.37 (s, 12H).

SCHEME 2

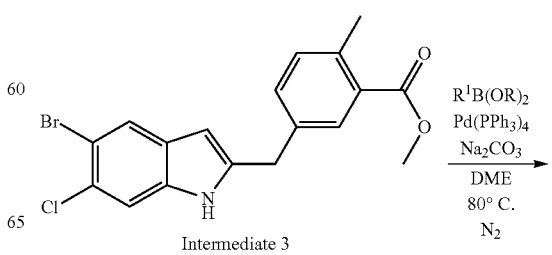

Intermediate 3

87
-continued

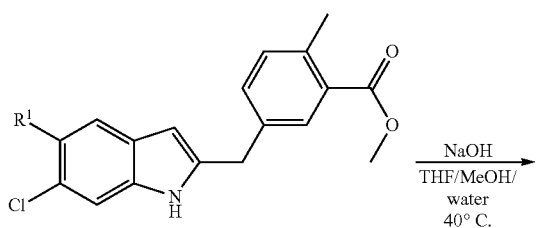

Examples 1 through 8

Example 1

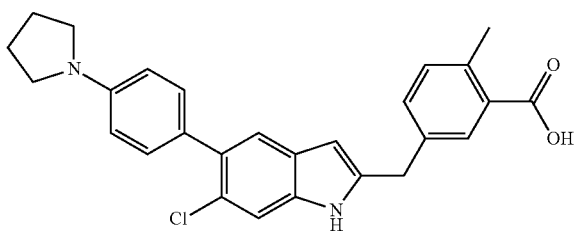 [SMILES: Cc1ccc(Cc2cc3cc(-c4ccc(N5CCCC5)cc4)c(Cl)cc3[nH]2)cc1C(=O)O]

88

5-((6-chloro-5-(4-(pyrrolidin-1-yl)phenyl)-1H-indol-2-yl)methyl)-2-methylbenzoic acid Step A: methyl 5-((6-chloro-5-(4-(pyrrolidin-1-yl)phenyl)-1H-indol-2-yl)methyl)-2-methylbenzoate Methyl 5-((5-bromo-6-chloro-1H-indol-2-yl)methyl)-2-methylbenzoate (95 mg, 0.242 mmol), 1-[4-(4,4,5,5-tetramethyl-1,3,2-dioxaborolan-2-yl)phenyl]pyrrolidine (72.7 mg, 0.266 mmol) and Pd(Ph$_3$P)$_4$ (7.0 mg, 6.05 µmol) were mixed in a microwave vial, which was evacuated and charged with nitrogen. Then DME (1.9 mL) and 2N Na$_2$CO$_3$ (272 µl, 0.544 mmol) were added. The reaction was stirred at 80° C. in an oil bath for 3.5 hours. Then additional Pd(PPh$_3$)$_4$ (7 mg) was added and the reaction was stirred overnight. The reaction mixture was then partitioned between ethyl acetate and water. The aqueous layer was separated and extracted again with ethyl acetate. The organic layers were combined, and washed with brine, dried over sodium sulfate, filtered and evaporated. The crude product was purified on a Biotage 25S silica gel column, eluting with a gradient of 40-90% dichloromethane in hexanes to give the title compound. LC-MS: calculated for C$_{28}$H$_{27}$ClN$_2$O$_2$ 458.18, observed m/e: 459.31 (M+H)$^+$ (Rt 2.45/4 min).

Step B: 5-((6-chloro-5-(4-(pyrrolidin-1-yl)phenyl)-1H-indol-2-yl)methyl)-2-methylbenzoic acid Methyl 5-((6-chloro-5-(4-(pyrrolidin-1-yl)phenyl)-1H-indol-2-yl)methyl)-2-methylbenzoate (35 mg, 0.076 mmol) was dissolved in THF (750 µl), methanol (150 µl), and water (75 µl). Then 5N NaOH (76 µl, 0.381 mmol) was added and the reaction was stirred at 40° C. for 16 hours. Once the reaction was complete, it was diluted with water and 1N HCl (381 µl), and then extracted twice with ethyl acetate. The combined organic layers were dried over sodium sulfate, filtered and evaporated. The crude product was purified on MS directed HPLC on a C18 column eluting with a linear gradient of CH$_3$CN in water (0.1% formic acid) to give the title compound. NMR δ (ppm) (CDCl$_3$): 7.94 (d, 1H), 7.79 (br s, 1H), 7.46 (s, 1H), 7.33 (m, 4H), 7.23 (d, 1H), 6.79 (d, 1H), 6.29 (s, 1H), 4.13 (s, 2H), 3.34 (m, 4H), 2.62 (s, 3H), 2.02 (m, 4H). LC-MS: calculated for C$_{27}$H$_{25}$ClN$_2$O$_2$ 444.16, observed m/e: 445.24 (M+H)$^+$ (Rt 2.16/4 min).

TABLE 1

Compounds prepared according to the methods described in Example 1.

| Example Number | Structure | HPLC-mass spectrum m/e |
|---|---|---|
| 2 | 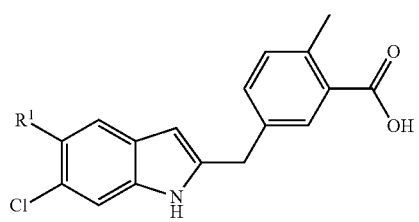 | 452.26 |

TABLE 1-continued

Compounds prepared according to the methods described in Example 1.

| Example Number | Structure | HPLC-mass spectrum m/e |
|---|---|---|
| 3 | 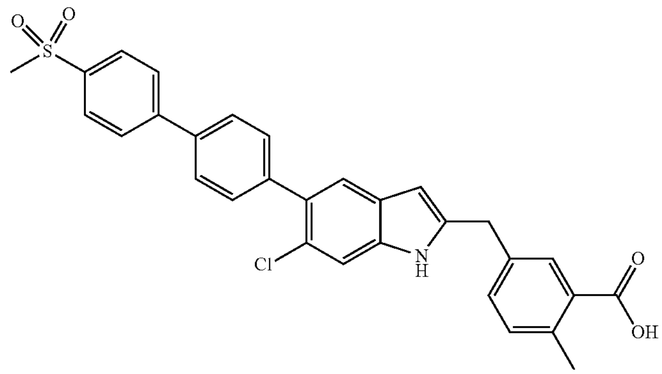 [SMILES: Cc1ccc(Cc2cc3cc(-c4ccc(-c5ccc(S(C)(=O)=O)cc5)cc4)c(Cl)cc3[nH]2)cc1C(=O)O] | 530.11 |
| 4 | 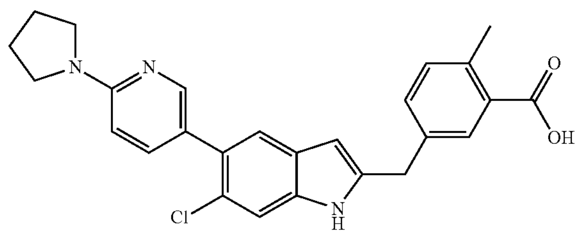 [SMILES: Cc1ccc(Cc2cc3cc(-c4ccc(N5CCCC5)nc4)c(Cl)cc3[nH]2)cc1C(=O)O] | 446.18 |

Example 5

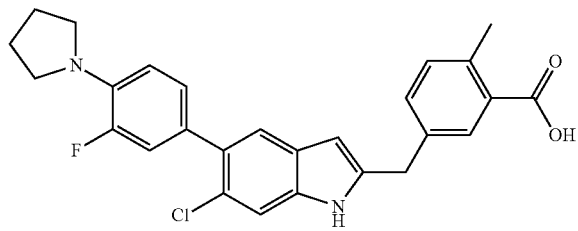 [SMILES: Cc1ccc(Cc2cc3cc(-c4ccc(N5CCCC5)c(F)c4)c(Cl)cc3[nH]2)cc1C(=O)O]

5-((6-chloro-5-(3-fluoro-4-(pyrrolidin-1-yl)phenyl)-1H-indol-2-yl)methyl)-2-methylbenzoic acid Methyl 5-((6-chloro-5-(4-(pyrrolidin-1-yl)phenyl)-1H-indol-2-yl)methyl)-2-methylbenzoate (48 mg, 0.105 mmol) was dissolved in CH$_2$Cl$_2$ (3000 µl). Then Selectfluor™ (38.3 mg, 0.108 mmol) was added and the reaction was stirred at room temperature for 4 days. More CH$_2$Cl$_2$ was added to the reaction as needed to keep the reaction volume at about 3 mL. Then the reaction was partitioned between water and CH$_2$Cl$_2$, and the organic layer was separated, washed with water (2×) and brine. The organic layer was dried over sodium sulfate, filtered and evaporated. The crude product was dissolved in THF (1.5 mL) and MeOH (0.5 mL). Then NaOH (0.105 mL, 2.5N) was added, and the mixture was stirred overnight at room temperature. The reaction was then heated to 40° C. for another 24 hours, and quenched by the addition of 1N HCl (0.263 mL). The reaction mixture was partitioned between water and ethyl acetate. The organic was separated, washed with brine, dried over sodium sulfate, filtered and evaporated. The crude product was purified by preparative HPLC (C18 column), eluting with 35-100% CH$_3$CN/H$_2$O (0.1% formic acid) over 4 injections. Two compounds were isolated after lyophilization of the requisite fractions. The less polar of the two products is the title compound, while the more polar of the two products is the des-fluoro compound also prepared in Example 1. NMR δ (ppm) (CDCl$_3$): 7.93 (d, 1H), 7.80 (br s, 1H), 7.45 (s, 1H), 7.34 (s, 1H), 7.32 (dd, 1H), 7.23 (d, 1H), 7.11 (m, 2H), 6.71 (t, 1H), 6.29 (s, 1H), 4.13 (s, 2H), 3.44 (m, 4H), 2.62 (s, 3H), 1.96 (m, 4H). LC-MS: calculated for C$_{27}$H$_{24}$ClFN$_2$O$_2$ 462.15, observed m/e: 463.5 (M+H)$^+$ (Rt 1.29/2 min).

Example 6

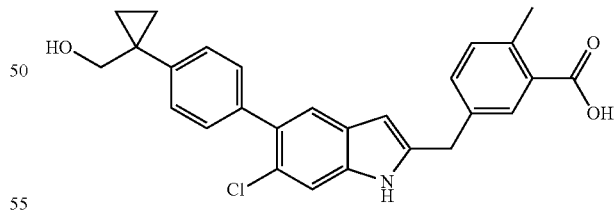

5-((6-chloro-5-(4-(1-(hydroxymethyl)cyclopropyl)phenyl)-1H-indol-2-yl)methyl)-2-methylbenzoic acid Step A: 5-((5-bromo-6-chloro-1H-indol-2-yl)methyl)-2-methylbenzoic acid Methyl 5-((5-bromo-6-chloro-1H-indol-2-yl)methyl)-2-methylbenzoate (39.3 mg, 0.1 mmol, Intermediate 3) was dissolved in methanol (450 µl) and THF (450 µl). Then 5N NaOH (100 µl, 0.500 mmol) was added, followed by water (100 µl). The reaction was heated to 40° C. and stirred for 2 hours. Once the reaction was complete it was cooled to room temperature and the reaction was neutralized with the addition of 1N HCl (0.5 mL). Then ethyl acetate and water were added, and the resulting layers were separated. The organic layer was dried over sodium sulfate, filtered and evaporated. The crude product was used in the next step without further purification. LC-MS: calculated for $C_{17}H_{13}BrClNO_2$ 376.98/378.98, observed m/e: 378.4/380.4 $(M+H)^+$ (Rt 1.22/2 min).

Step B: 5-((5-(4-(1-(acetoxymethyl)cyclopropyl)phenyl)-6-chloro-1H-indol-2-yl)methyl)-2-methylbenzoic acid 5-((5-Bromo-6-chloro-1H-indol-2-yl)methyl)-2-methylbenzoic acid (37.9 mg, 0.1 mmol) and (1-(4-(4,4,5,5-tetramethyl-1,3,2-dioxaborolan-2-yl)phenyl)cyclopropyl) methyl acetate (39.5 mg, 0.125 mmol) were mixed in a vial, which was evacuated and charged with nitrogen. Then THF (0.425 ml) was added to prepare the indole solution. A second vial containing palladium(II) acetate (1.1 mg, 5.00 µmol), 2-dicyclohexylphosphino-2',6'-dimethoxybiphenyl (4.1 mg, 10.00 µmol) and tribasic potassium phosphate (63.7 mg, 0.300 mmol) was also evacuated and charged with nitrogen to prepare the catalyst mixture. Then the indole solution was added to the catalyst mixture. The resulting reaction mixture was stirred at 60° C. in an oil bath, followed by the addition of water (0.075 ml) shortly after the start of the reaction. After 3 hours, the reaction was cooled and partitioned between water and ethyl acetate. Then brine was added to the aqueous layer and the aqueous layer was extracted with ethyl acetate again. The combined ethyl acetate layers was dried over sodium sulfate, filtered and evaporated. The crude product was purified on C18 reverse phase column, eluting with a gradient of 40-100% $CH_3CN$ in water (0.05% TFA) to give the title compound mixed with a small amount of the bromoindole starting material. This product mixture was used as is without further purification in the next step. LC-MS: calculated for $C_{29}H_{26}ClNO_4$ 487.16, observed m/e: 488.5 $(M+H)^+$ (Rt 1.30/2 min).

Step C: 5-((6-chloro-5-(4-(1-(hydroxymethyl)cyclopropyl)phenyl)-1H-indol-2-yl)methyl)-2-methylbenzoic acid 5-((5-(4-(1-(Acetoxymethyl)cyclopropyl)phenyl)-6-chloro-1H-indol-2-yl)methyl)-2-methylbenzoic acid (10 mg, 0.020 mmol) was dissolved in methanol (205 µl). Then 1N potassium carbonate (102 µl, 0.102 mmol) was added and the reaction was stirred at room temperature for 90 minutes. When the reaction was complete, the reaction was neutralized with 1N HCl (102 µL, 0.102 mmole), diluted with water and extracted with ethyl acetate (2×). The combined organic layers were dried over sodium sulfate, filtered and evaporated. The crude product was purified by preparative C18 reverse phase HPLC, eluting with a gradient of $CH_3CN$ in water (0.05% TFA) to give the title compound after lyophilization of the product containing fractions. NMR δ (ppm) ($CD_3OD$): 7.83 (s, 1H), 7.35 (m, 7H), 7.22 (d, 1H), 6.17 (s, 1H), 4.10 (s, 2H), 3.67 (s, 2H), 2.54 (s, 3H), 0.87 (m, 4H). LC-MS: calculated for $C_{27}H_{24}ClNO_3$ 445.14, observed m/e: 446.12 $(M+H)^+$ (Rt 2.12/4 min).

Intermediate 5

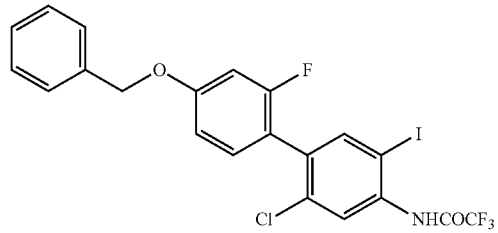

N-(4'-(benzyloxy)-2-chloro-2'-fluoro-5-iodo-[1,1'-biphenyl]-4-yl)-2,2,2-trifluoroacetamide Step A: 4'-(benzyloxy)-2-chloro-2'-fluoro-[1,1'-biphenyl]-4-amine 4-Bromo-3-chloroaniline (0.651 g, 3.15 mmol), 4-benzyloxy-2-fluorophenylboronic acid (0.966 g, 3.93 mmol) and $PdCl_2(dppf)$ (0.115 g, 0.158 mmol) were placed under a nitrogen atmosphere and dissolved in DME (16 ml). Then 2M $Na_2CO_3$ (3.55 ml, 7.09 mmol) was added and the reaction was heated to 60° C. and stirred overnight. Then the reaction was cooled to room temperature, diluted with ethyl acetate, and washed with water. The layers were separated, and the organic layer was washed again with a mixture of aqueous $NaHCO_3$ and NaCl, followed by aqueous NaCl. The organic layer was dried over sodium sulfate, filtered and evaporated. The crude product was purified on a Biotage 40S silica gel column, eluting with a gradient of 15-50% ethyl acetate in hexanes to give the title compound. Some mixed fractions were re-purified on a Biotage 40S silica gel column, eluting with 23-28% ethyl acetate/hexanes to give additional title compound. NMR δ (ppm) ($CDCl_3$): 7.47 (d, 2H), 7.39 (t, 2H), 7.34 (m, 1H), 7.19 (dd, 1H), 7.08 (m, 2H), 7.02 (t, 1H), 6.78 (d, 1H), 6.60 (dd, 1H), 5.18 (s, 2H), 3.76 (s, 2H).

Step B: 4'-(benzyloxy)-2-chloro-2'-fluoro-5-iodo-[1,1'-biphenyl]-4-amine

N-(4'-(Benzyloxy)-2-chloro-2'-fluoro-[1,1'-biphenyl]-4-yl)-2,2,2-trifluoroacetamide (328 mg, 1.0 mmol) was dissolved in methanol (12.5 mL). Iodine (254 mg, 1.000 mmol) was added, followed by the dropwise addition of 30% hydrogen peroxide (751 µl, 7.35 mmol). The reaction was stirred at room temperature overnight, then quenched with aqueous sodium thiosulfate and extracted with ethyl acetate. The organic layer was separated, washed with aqueous sodium thiosulfate, followed by brine, and then dried over sodium sulfate, filtered and evaporated. The crude product was purified on a Biotage 40S silica gel column, eluting with a gradient of 5-30% ethyl acetate in hexanes to give the title compound. NMR δ (ppm) ($CDCl_3$): 7.57 (s, 1H), 7.46 (d, 2H), 7.40 (t, 2H), 7.34 (m, 1H), 7.16 (dd, 1H), 7.03 (m, 2H), 6.82 (s, 1H), 5.18 (s, 2H), 4.18 (s, 2H).

Step C: N-(4'-(benzyloxy)-2-chloro-2'-fluoro-5-iodo-[1,1'-biphenyl]-4-yl)-2,2,2-trifluoro acetamide 4'-(Benzyloxy)-2-chloro-2'-fluoro-5-iodo-[1,1'-biphenyl]-4-amine (293 mg, 0.646 mmol) was dissolved in $CH_2Cl_2$ (3.2 mL) and cooled to 0° C. DIEA (169 µl, 0.969 mmol) was added, followed by trifluoroacetic anhydride (96 µl, 0.678 mmol). The reaction was stirred for about 2 hours, then additional DIEA (50 µl) and trifluoroacetic anhydride (25 µl) were added to push the reaction to completion. The reaction mixture was purified directly on a Biotage 25S silica gel column, eluting with a gradient of 10-40% ethyl acetate in hexanes to give the title compound. NMR δ (ppm) (CDCl$_3$): 8.39 (s, 1H), 8.27 (br s, 1H), 7.78 (s, 1H), 7.47 (d, 2H), 7.41 (t, 2H), 7.35 (m, 1H), 7.20 (dd, 1H), 7.06 (m, 2H), 5.20 (s, 2H).

Intermediate 6

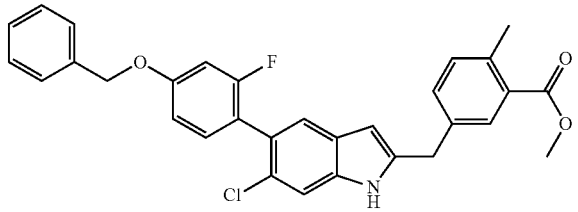 [SMILES: COC(=O)c1cc(Cc2cc3cc(-c4ccc(OCc5ccccc5)cc4F)c(Cl)cc3[nH]2)ccc1C]

Methyl 5-((5-(4-(benzyloxy)-2-fluorophenyl)-6-chloro-1H-indol-2-yl)methyl)-2-methylbenzoate Step A: methyl 5-(3-(4'-(benzyloxy)-6-chloro-2'-fluoro-4-(2,2,2-trifluoroacetamido)-[1,1'-biphenyl]-3-yl)-1-hydroxyprop-2-yn-1-yl)-2-methylbenzoate Intermediate 5 (350 mg, 0.637 mmol), copper(I) iodide (6.1 mg, 0.032 mmol) and bis(triphenylphosphine)-palladium(II) chloride (8.9 mg, 0.013 mmol) were flushed with nitrogen. Then Et$_3$N (0.9 mL) was added to prepare the catalyst mixture. Intermediate 2 (156 mg, 0.764 mmol) was flushed with nitrogen, and then dissolved in Et$_3$N (0.9 mL) to prepare the alkyn-ol solution. The alkyn-ol solution was added dropwise to the stirring catalyst mixture, followed by DMF (1 mL). After stirring for 2 hours, the reaction was quenched with aqueous NH$_4$Cl and extracted with ethyl acetate. The organic layer was separated, washed with aqueous NH$_4$Cl, followed by brine, dried over sodium sulfate, filtered and evaporated. The crude product was purified on a Biotage 12M silica gel column, eluting with a gradient of 0-15% ethyl acetate in toluene to give the title compound. LC-MS: calculated for C$_{33}$H$_{24}$ClF$_4$NO$_5$ 625.13, observed m/e: 624.3 (M–H)$^-$ (Rt 1.26/2 min).

Step B: methyl 5-(3-(4'-(benzyloxy)-6-chloro-2'-fluoro-4-(2,2,2-trifluoroacetamido)-[1,1'-biphenyl]-3-yl)-1-((ethoxycarbonyl)oxy)prop-2-yn-1-yl)-2-methylbenzoate Methyl 5-(3-(4'-(benzyloxy)-6-chloro-2'-fluoro-4-(2,2,2-trifluoroacetamido)-[1,1'-biphenyl]-3-yl)-1-hydroxyprop-2-yn-1-yl)-2-methylbenzoate (275 mg, 0.439 mmol) and DMAP (86 mg, 0.703 mmol) were dissolved in CH$_2$Cl$_2$ (2.2 mL) and stirred at –20° C. for 10 minutes. Then ethyl chloroformate (59.1 µl, 0.615 mmol) was added and the reaction was stirred between –20° C. and 0° C. for 2-3 hours. Then the reaction was diluted with ethyl acetate. The organic layer was separated, washed twice with 1N HCl and once with brine, and then dried over sodium sulfate, filtered and evaporated. The crude product was purified on a Biotage 12M silica gel column, eluting with a gradient of 10-30% ethyl acetate in hexanes to give the title compound. NMR δ (ppm) (CDCl$_3$): 8.62 (br s, 1H), 8.53 (s, 1H), 8.10 (d, 1H), 7.60 (dd, 1H), 7.48-7.28 (m, 6H), 7.18 (dd, 1H), 7.07 (m, 2H), 6.46 (s, 1H), 5.19 (s, 2H), 4.26 (q, 2H), 3.89 (s, 3H), 2.63 (s 3H), 1.33 (t, 3H).

Step C: methyl 5-((5-(4-(benzyloxy)-2-fluorophenyl)-6-chloro-1H-indol-2-yl)methyl)-2-methylbenzoate Methyl 5-(3-(4'-(benzyloxy)-6-chloro-2'-fluoro-4-(2,2,2-trifluoroacetamido)-[1,1'-biphenyl]-3-yl)-1-((ethoxycarbonyl)oxy)prop-2-yn-1-yl)-2-methylbenzoate (250 mg, 0.358 mmol) was dissolved in acetonitrile (3.6 mL) and added to a 2-5 mL microwave vial. The vessel was flushed with nitrogen, then Pd(Ph$_3$P)$_4$ (20.7 mg, 0.018 mmol), Et$_3$N (150 µl, 1.074 mmol) and formic acid (27.5 µl, 0.716 mmol) were added. The reaction was heated to 80° C. in a microwave for 30 minutes, and then diluted with ethyl acetate. The reaction mixture was washed with aqueous NH$_4$Cl and brine, dried over sodium sulfate, filtered and evaporated. The crude product was purified on a Biotage 12M silica gel column, eluting with a gradient of 0-6% ethyl acetate in toluene to give the title compound. LC-MS: calculated for C$_{31}$H$_{25}$ClFNO$_3$ 513.15, observed m/e: 512.4 (M–H)$^-$ (Rt 1.32/2 min).

Example 7

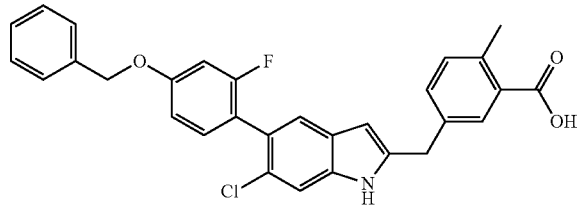 [SMILES: Cc1ccc(Cc2cc3cc(-c4ccc(OCc5ccccc5)cc4F)c(Cl)cc3[nH]2)cc1C(=O)O]

5-((5-(4-(benzyloxy)-2-fluorophenyl)-6-chloro-1H-indol-2-yl)methyl)-2-methylbenzoic acid Methyl 5-((5-(4-(benzyloxy)-2-fluorophenyl)-6-chloro-1H-indol-2-yl)methyl)-2-methylbenzoate (Intermediate 6, 10 mg, 0.019 mmol) was dissolved in MeOH (185 µL) and THF (185 µL). Added 5N NaOH (10.00 µL, 0.050 mmol) and water (10 µL). Stirred at 50° C. An additional 15 µL of 5N NaOH was added in portions over the next 5 hours to push reaction to completion. LC/MS at 7 hours shows reaction essentially complete. Diluted with water and ethyl acetate. Partitioned; neutralized aqueous with 125 microliters of 1N HCl and extracted with ethyl acetate. The organics were washed with dilute aqueous HCl, dried over sodium sulfate, filtered and evaporated. The resulting crude was purified on a preparative C18 column by MS-directed HPLC, eluting with a gradient of CH$_3$CN in water (0.05% TFA) to give the title compound after lyophilization of the product containing fractions. NMR δ (ppm) (CDCl$_3$): 7.95 (s, 1H), 7.83 (br s, 1H), 7.48 (d, 2H), 7.44 (s, 1H), 7.40 (t, 2H), 7.33 (m, 2H), 7.24 (m, 2H), 7.11 (d, 1H), 7.03 (t, 1H), 6.30 (s, 1H), 5.19 (s, 2H), 4.13 (s, 2H), 2.63 (s, 3H). LC-MS: calculated for C$_{30}$H$_{23}$ClFNO$_3$ 499.14, observed m/e: 498.51 (M–H)$^-$ (Rt 1.20/2 min).

Example 8

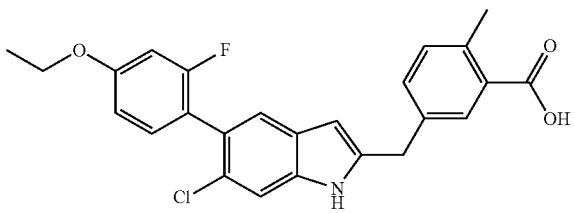 [SMILES: CCOc1ccc(-c2cc3cc(Cc4ccc(C)c(C(=O)O)c4)[nH]c3cc2Cl)c(F)c1]

5-((6-chloro-5-(4-ethoxy-2-fluorophenyl)-1H-indol-2-yl)methyl)-2-methylbenzoic acid Step A: methyl 5-((6-chloro-5-(2-fluoro-4-hydroxyphenyl)-1H-indol-2-yl)methyl)-2-methylbenzoate Intermediate 6 (60 mg, 0.117 mmol) was transferred to a vial and dissolved in ethyl acetate (900 μL), MeOH (300 μL), and THF (300 μL). 1,4-cyclohexadiene (110 μL, 1.167 mmol) was added, followed by the addition of 10% Pd—C (5 mg, 4.67 μmol). Additional portions of Pd—C (12 mg) and 1,4-cyclohexadiene were added and the reaction heated to 60° C. for 4 hours. The reaction temperature was stirred at 55° C. overnight, and then worked up by filtering the reaction through Celite™ and concentrating the filtrate. The crude product was purified on a Biotage 25S silica gel column, eluting with a gradient of 20-50% ethyl acetate in hexanes to give the title compound. LC-MS: calculated for $C_{24}H_{19}ClFNO_3$ 423.10, observed m/e: 422.3 (M−H)⁻ (Rt 1.08/2 min).

Step B: methyl 5-((6-chloro-5-(4-ethoxy-2-fluorophenyl)-1H-indol-2-yl)methyl)-2-methylbenzoate Methyl 5-((6-chloro-5-(2-fluoro-4-hydroxyphenyl)-1H-indol-2-yl)methyl)-2-methylbenzoate (21.4 mg, 0.050 mmol) was dissolved in N,N-dimethylformamide (252 μl). Then powdered potassium carbonate (14 mg, 0.101 mmol) and iodoethane (4.9 μl, 0.061 mmol) were added. After 4 hours, the reaction was diluted with water and extracted with ethyl acetate. The organic layer was separated, washed with water (2×), dried over sodium sulfate, filtered and evaporated to give the title compound, which was used in the next step without further purification. LC-MS: calculated for $C_{26}H_{23}ClFNO_3$ 451.14, observed m/e: 452.22 (M+H)⁺ (Rt 2.65/4 min).

Step C: 5-((6-chloro-5-(4-ethoxy-2-fluorophenyl)-1H-indol-2-yl)methyl)-2-methylbenzoic acid Methyl 5-((6-chloro-5-(4-ethoxy-2-fluorophenyl)-1H-indol-2-yl)methyl)-2-methylbenzoate (19.3 mg, 0.043 mmol) was dissolved in THF (500 μl) and MeOH (192 μl). Then 5N NaOH (42.7 μl, 0.214 mmol) and water (42.7 μl) were added. The reaction stirred at room temperature for 16 hours and at 40° C. for an additional 4 hours. The reaction mixture was then neutralized with 1N HCl (214 μl), and partitioned between water and ethyl acetate. The organic layer was separated, dried over sodium sulfate, filtered and evaporated to give the crude product. The crude product was purified by preparative C18 HPLC, eluting with a gradient of CH₃CN in water (0.05% TFA) to give the title compound after lyophilization of the product containing fractions. NMR δ (ppm) (CDCl₃): 7.95 (d, 1H), 7.83 (br s, 1H), 7.44 (s, 1H), 7.35 (s, 1H), 7.33 (dd, 1H), 7.24 (d, 1H), 7.21 (dd, 1H), 7.13 (d, 1H), 6.99 (t, 1H), 6.30 (s, 1H), 4.14 (m, 4H), 2.63 (s, 3H), 1.48 (t, 3H). LC-MS: calculated for $C_{25}H_{21}ClFNO_3$ 437.12, observed m/e: 438.21 (M+H)⁺ (Rt 2.45/4 min).

Example 9

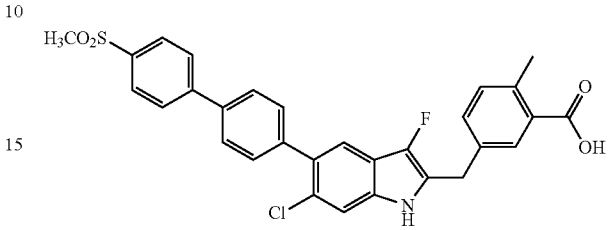

5-((6-chloro-3-fluoro-5-(4'-(methylsulfonyl)-[1,1'-biphenyl]-4-yl)-1H-indol-2-yl)methyl)-2-methylbenzoic acid Step A: methyl 5-((6-chloro-3-fluoro-5-(4'-(methylsulfonyl)-[1,1'-biphenyl]-4-yl)-1H-indol-2-yl)methyl)-2-methylbenzoate Methyl 5-((6-chloro-5-(4'-(methylsulfonyl)-[1,1'-biphenyl]-4-yl)-1H-indol-2-yl)methyl)-2-methylbenzoate (the methyl ester precursor of Example 3, 54.4 mg, 0.10 mmol) was dissolved in DMSO (500 μl) and acetonitrile (500 μl). Then Selectfluor™ (37.2 mg, 0.105 mmol) was added incrementally and the reaction was stirred for 18 hours. Then the reaction was quenched with water and extracted with ethyl acetate. The organic layer was separated, dried over sodium sulfate, filtered and evaporated. The crude product was purified by preparative reverse phase chromatography (C18), eluting with 60-100% CH₃CN/water (0.05% TFA) to give the title compound. LC-MS: calculated for $C_{31}H_{25}ClFNO_4S$ 561.12, observed m/e: 562.24 (M+H)⁺ (Rt 2.69/4 min).

Step B: 5-((6-chloro-3-fluoro-5-(4'-(methylsulfonyl)-[1,1'-biphenyl]-4-yl)-1H-indol-2-yl)methyl)-2-methylbenzoic acid Methyl 5-((6-chloro-3-fluoro-5-(4'-(methylsulfonyl)-[1,1'-biphenyl]-4-yl)-1H-indol-2-yl)methyl)-2-methylbenzoate (10.5 mg, 0.019 mmol) was suspended in THF (112 μl), MeOH (56.0 μl), 5N NaOH (18.7 μl, 0.093 mmol) and water (18.7 μl). The reaction was stirred at room temperature for 6 hours, and then heated to 45° C. for 75 minutes. The reaction was then diluted with water and neutralized with 1N HCl (93 μL). The quenched reaction was extracted twice with ethyl acetate. The combined organics were dried over sodium sulfate, filtered and evaporated. The crude product was purified by preparative reverse phase chromatography (C18), eluting with 40-100% CH₃CN/water (0.05% TFA) to give the title compound. NMR δ (ppm) (CD₃OD): 10.46 (s, 1H), 8.04 (d, 2H), 7.96 (d, 2H), 7.83 (d, 1H), 7.77 (d, 2H), 7.58 (d, 2H), 7.47 (s, 1H), 7.39 (d, 1H), 7.32 (dd, 1H), 7.22 (d, 1H), 4.12 (s, 2H), 3.16 (s, 3H), 2.54 (s, 3H). LC-MS: calculated for $C_{30}H_{23}ClFNO_4S$ 547.10, observed m/e: 548.47 (M+H)⁺ (Rt 2.45/4 min).

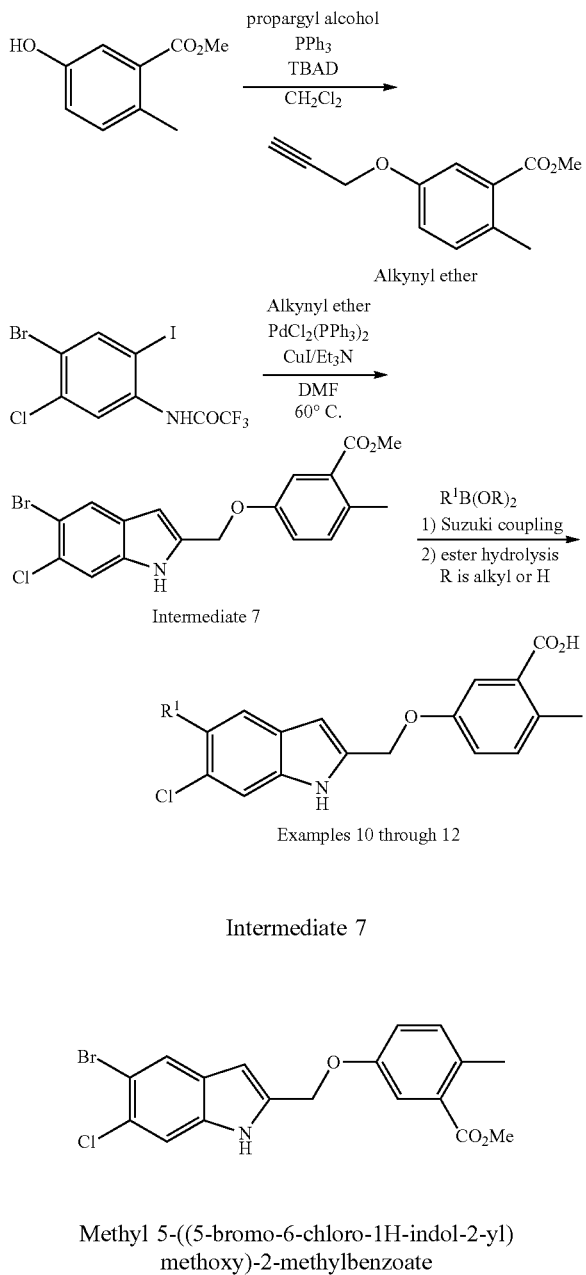

Intermediate 7

Methyl 5-((5-bromo-6-chloro-1H-indol-2-yl)methoxy)-2-methylbenzoate

Step A: methyl 2-methyl-5-(prop-2-yn-1-yloxy)benzoate

Methyl 5-hydroxy-2-methylbenzoate (665 mg, 4.0 mmol) and propargyl alcohol (358 µl, 6.00 mmol) were dissovled in CH$_2$Cl$_2$ (20 mL). The reaction was cooled to 0° C., then triphenylphosphine (1.31 g, 5.00 mmol) and di-tert-butyl azodicarboxylate (1.15 g, 5.00 mmol) were added. The reaction was allowed to warm to room temperature and stirred for 36 hours. The reaction was then diluted with CH$_2$Cl$_2$ and washed with 0.5N HCl (2×), aqueous saturated NaHCO$_3$ and brine. The organic layer was separated, dried over sodium sulfate, filtered and evaporated. The crude product was purified on a Biotage 40S silica gel column, eluting with a gradient of 10-40% ethyl acetate in hexanes to give the title compound. NMR δ (ppm) (CDCl$_3$): 7.52 (d, 1H), 7.17 (d, 1H), 7.04 (dd, 1H), 4.70 (d, 2H), 3.89 (s, 3H), 2.53 (s and m, 4H).

Step B: methyl 5-((5-bromo-6-chloro-1H-indol-2-yl)methoxy)-2-methylbenzoate

Intermediate 1 (514 mg, 1.2 mmol) and methyl 2-methyl-5-(prop-2-yn-1-yloxy)benzoate (343 mg, 1.680 mmol) were dissolved in DMF (6 mL). Then copper(I) iodide (22.9 mg, 0.120 mmol), bis(triphenylphosphine)-palladium(II) chloride (42.1 mg, 0.060 mmol) and Et$_3$N (836 µl, 6.00 mmol) were added. The reaction was stirred at 60° C. for 3 hours, then quenched with saturated NH$_4$Cl followed by dilution with water and extraction with ethyl acetate. The organic layer was separated, washed with aqueous NH$_4$Cl and brine, dried over sodium sulfate, filtered and evaporated. The crude product was purified on a Biotage 25S silica gel column, eluting with a gradient of 10-40% ethyl acetate in hexanes to give the title compound mixed with small impurities. Recrystallization from hexanes/ethyl acetate and filtration of the suspension and collection of the solid provided the title compound as an off white solid. NMR δ (ppm) (CDCl$_3$): 8.40 (br s, 1H), 7.84 (s, 1H), 7.55 (d, 1H), 7.49 (s, 1H), 7.16 (d, 1H), 7.03 (dd, 1H), 6.46 (s, 1H), 5.21 (s, 2H), 3.89 (s, 3H), 2.52 (s, 3H).

Example 10

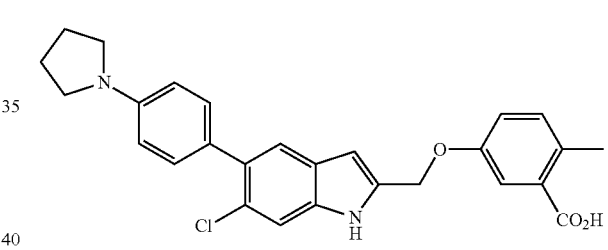

5-((6-chloro-5-(4-(pyrrolidin-1-yl)phenyl)-1H-indol-2-yl)methoxy-2-methylbenzoic acid Step A: methyl 5-((6-chloro-5-(4-(pyrrolidin-1-yl)phenyl)-1H-indol-2-yl)methoxy)-2-methylbenzoate Intermediate 7 (98 mg, 0.240 mmol) and 1-[4-(4,4,5,5-tetramethyl-1,3,2-dioxaborolan-2-yl)phenyl]pyrrolidine (79 mg, 0.288 mmol) were dissolved in DME (1.2 mL), and the reaction vessel was evacuated and charged with nitrogen. Then Pd(Ph$_3$P)$_4$ (13.9 mg, 0.012 mmol) and 2N aqueous Na$_2$CO$_3$ (264 µl, 0.528 mmol) were added. The reaction was stirred at 80° C. for 4 hours, then additional Pd(PPh$_3$)$_4$ (13.8 mg) was added and the reaction was stirred at 90° C. for 2 hours. Once the reaction was complete it was cooled to room temperature and partitioned between water and ethyl acetate. The organic layer was separated, washed with water, and brine, dried over sodium sulfate, filtered and evaporated. The crude product was purified on a Biotage 25S silica gel column, eluting with a gradient of 40-90% dichloromethane in hexanes to give the title compound. NMR δ (ppm) (CDCl$_3$): 8.31 (br s, 1H), 7.57 (d, 1H), 7.52 (s, 1H), 7.45 (s, 1H), 7.34 (d, 2H), 7.16 (d, 1H), 7.04 (dd, 1H), 6.62 (d, 2H), 6.51 (s, 1H), 5.22 (s, 2H), 3.90 (s, 3H), 3.34 (m, 4H), 2.52 (s, 3H), 2.02 (m, 4H).

Step B: 5-((6-chloro-5-(4-(pyrrolidin-1-yl)phenyl)-1H-indol-2-yl)methoxy)-2-methylbenzoic acid Methyl 5-((6-chloro-5-(4-(pyrrolidin-1-yl)phenyl)-1H-indol-2-yl)methoxy)-2-methylbenzoate (46 mg, 0.097 mmol) was suspended in THF (900 μl) and MeOH (450 μl). Then 5N NaOH (97 μl, 0.484 mmol) was added, followed by water (100 μl). Then the reaction was heated to 40° C. and stirred until the reaction was complete. The reaction was neutralized with 1N HCl (0.485 mL), and partitioned between water and ethyl acetate. The organic layer was separated, dried over sodium sulfate, filtered and evaporated. The crude product was purified by preparative reverse phase chromatography (C18), eluting with 30-90% $CH_3CN$/water (0.05% TFA) to give the title compound. NMR δ (ppm) (DMSO-d6): 11.39 (s, 1H), 7.44 (m, 3H), 7.20 (d, 3H), 7.16 (dd, 1H), 6.58 (d, 2H), 6.50 (s, 1H), 5.23 (s, 2H), 3.25 (m, 4H), 2.42 (s, 3H), 1.96 (t, 4H). LC-MS: calculated for $C_{27}H_{25}ClN_2O_3$ 460.16, observed m/e: 461.16 $(M+H)^+$ (Rt 2.16/4 min).

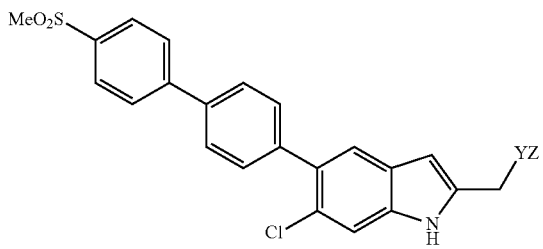

Examples 13 through 17

TABLE 2

Compounds prepared according to the methods described in Example 10.

| Example Number | Structure | HPLC-mass spectrum m/e |
|---|---|---|
| 11 | ![structure] | 462.3 |
| 12 | ![structure] | 546.3 |

SCHEME 4

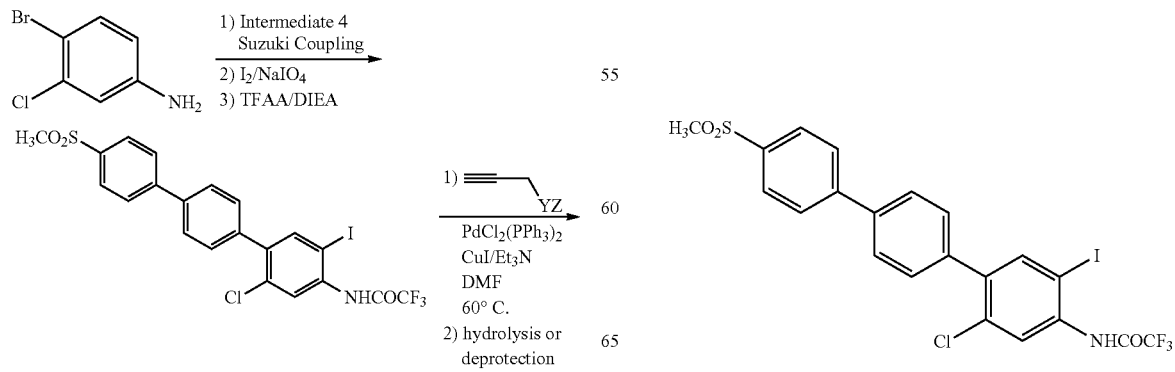

Intermediate 8

N-(2-chloro-5-iodo-4"-(methylsulfonyl)-[1,1':4',1"-terphenyl]-4-yl)-2,2,2-trifluoroacetamide Step A: 2-chloro-4"-(methylsulfonyl)-[1,1':4',1"-terphenyl]-4-amine 3-Chloro-4-bromoaniline (0.400 g, 1.937 mmol), Intermediate 4 (0.826 g, 2.306 mmol) and Pd(Ph$_3$P)$_4$ (0.112 g, 0.097 mmol) were blanketed in nitrogen, and then dissolved in DME (13 ml) and 2N Na$_2$CO$_3$ (2.1 ml, 4.26 mmol). The reaction was stirred at 80° C. for 72 hours, then cooled to room temperature, and partitioned between water and ethyl acetate. The organic layer was separated, washed with water, then brine, dried over sodium sulfate, filtered and evaporated. The crude product was purified on a Biotage 40S silica gel column, eluting with a gradient of 30-100% ethyl acetate in hexanes to give the title compound. NMR δ (ppm) (CDCl$_3$): 8.02 (d, 2H), 7.82 (d, 2H), 7.65 (m, 2H), 7.55 (d, 2H), 7.17 (d, 1H), 6.83 (d, 1H), 6.65 (dd, 1H), 3.81 (s, 2H) 3.11 (s, 3H).

Step B: 2-chloro-5-iodo-4"-(methylsulfonyl)-[1,1':4', 1"-terphenyl]-4-amine

2-Chloro-4"-(methylsulfonyl)-[1,1':4',1"-terphenyl]-4-amine (615 mg, 1.719 mmol) was dissolved in DMF (3.4 mL). Then iodine (436 mg, 1.719 mmol) and sodium periodate (368 mg, 1.719 mmol) were added. The reaction was stirred at 60° C. for 2 hours, and removed from heat. Then aqueous sodium metabisulfite was added to the reaction, followed by ethyl acetate. The mixture was stirred for 20 minutes, then the organic layer was separated. The organic layer was washed with aqueous sodium metabisulfite, and then with water, followed by brine. The organic layer was dried over sodium sulfate, filtered and evaporated. The crude product was purified on a Biotage 40S silica gel column, eluting with a gradient of 20-60% ethyl acetate in hexanes to give the title compound as the major product isolated. NMR (major) δ (ppm) (CDCl$_3$): 8.02 (d, 2H), 7.81 (d, 2H), 7.65 (m, 3H), 7.52 (d, 2H), 6.87 (s, 1H), 4.24 (s, 2H) 3.12 (s, 3H). NMR (minor) δ (ppm) (CDCl$_3$): 8.02 (d, 2H), 7.81 (d, 2H), 7.65 (m, 2H), 7.49 (d, 2H), 7.14 (d, J=8.2 Hz, 1H), 6.73 (d, J=8.3 Hz, 1H), 4.43 (br s, 2H) 3.11 (s, 3H).

Step C: N-(2-chloro-5-iodo-4"-(methylsulfonyl)-[1, 1':4',1"-terphenyl]-4-yl)-2,2,2-trifluoro acetamide 2-Chloro-5-iodo-4"-(methylsulfonyl)-[1,1':4',1"-terphenyl]-4-amine (392 mg, 0.810 mmol) was dissolved in CH$_2$Cl$_2$ (4 mL) and cooled to 0° C. Then DIEA (248 μl, 1.418 mmol) was added, followed by trifluoroacetic anhydride (155 μl, 1.094 mmol). The reaction was stirred for about 2 hours. The crude product was purified on a Biotage 40S silica gel column, eluting with a gradient of 20-75% ethyl acetate in hexanes to give the title compound. NMR δ (ppm) (CDCl$_3$): 8.45 (s, 1H), 8.31 (br s, 1H), 8.04 (d, 2H), 7.87 (s, 1H), 7.82 (d, 2H), 7.70 (d, 2H), 7.55 (d, 2H), 3.12 (s, 3H).

Example 13

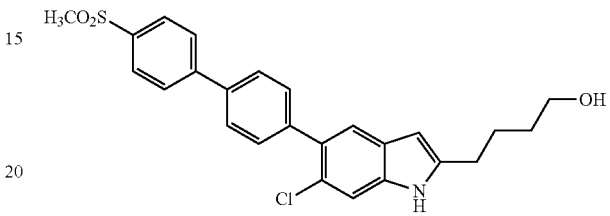

4-(6-chloro-5-(4'-(methylsulfonyl)-[1,1'-biphenyl]-4-yl)-1H-indol-2-yl)butan-1-ol Intermediate 8 (58.0 mg, 0.1 mmol), copper(I) iodide (1.9 mg, 10.00 μmol), and bis(triphenylphosphine)palladium(II) chloride (3.5 mg, 5.00 μmol) were placed in a flask, which was evacuated and charged with nitrogen. Then DMF (0.4 mL) and Et$_3$N (69.7 μl, 0.500 mmol) were added. Then 5-hexyn-1-ol (14.7 mg, 0.150 mmol) was dissolved in DMF (0.1 mL) and the resulting solution was added dropwise to the reaction. The reaction was stirred at room temperature for 45 minutes, and then heated to 60° C. for 1 hour and 80° C. for an additional hour. Then the reaction was quenched with saturated aqueous NH$_4$Cl, and extracted with ethyl acetate. The organic layer was separated and washed with water (2×) and with brine (1×), dried over sodium sulfate, filtered and evaporated. The crude product was purified on a Biotage 25S silica gel column, eluting with a gradient of 30-100% ethyl acetate in hexanes to give the title compound. NMR δ (ppm) (CDCl$_3$): 8.12 (br s, 1H), 8.03 (d, 2H), 7.84 (d, 2H), 7.68 (d, 2H), 7.61 (d, 2H), 7.50 (s, 1H), 7.44 (s, 1H), 6.27 (s, 1H), 3.73 (m, 2H), 3.11 (s, 3H), 2.84 (t, 2H), 2.31 (t, 1H), 1.85 (m, 2H), 1.58 (m, 2H). LC-MS: calculated for C$_{25}$H$_{24}$ClNO$_3$S 453.12, observed m/e: 454.18 (M+H)$^+$ (Rt 2.19/4 min).

TABLE 3

Compounds prepared according to the methods described in Example 13.

| Example Number | Structure | HPLC-mass spectrum m/e |
|---|---|---|
| 14 | H$_3$CO$_2$S—⟨biphenyl-indole-propanol with Cl⟩ | 440.08 |

TABLE 3-continued

Compounds prepared according to the methods described in Example 13.

| Example Number | Structure | HPLC-mass spectrum m/e |
|---|---|---|
| 15* | (5-(4'-(methylsulfonyl)-[1,1'-biphenyl]-4-yl)-6-chloro-1H-indol-2-yl)propanoic acid structure | 468.08 |
| 16* | (5-(4'-(methylsulfonyl)-[1,1'-biphenyl]-4-yl)-6-chloro-1H-indol-2-yl)butanoic acid structure | 482.08 |

*This compound was prepared in 2 steps:
1) the indole formation with the requisite alkynyl ester (see Example 12 for a representative synthetic method), and
2) the ester hydrolysis step (see Example 9 step B for a representative synthetic method).

Intermediate 9

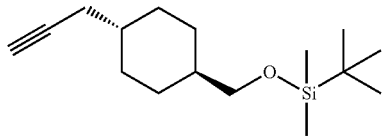 [SMILES: C#CC[C@H]1CC[C@H](CO[Si](C)(C)C(C)(C)C)CC1]

tert-Butyldimethyl(((trans)-4-(prop-2-yn-1-yl)cyclohexyl)methoxy)silane

Step A: trans-4-(((tert-butyldimethylsilyl)oxy)methyl)cyclohexyl)methanol

To a solution of trans-1,4-cyclohexanedimethanol (3.46 g, 24.0 mmol) in DMF (40 ml) was added tert-butyldimethylsilyl chloride (3.01 g, 20 mmol) and imidazole (3.27 g, 48.0 mmol). The reaction was allowed to stir overnight. The reaction was then partitioned between ether and brine. The organic layer was separated, washed with brine, dried over sodium sulfate, filtered and evaporated. The crude product was purified on a Biotage 40M silica gel column, eluting with a gradient of 10-50% ethyl acetate in hexanes to give the title compound. NMR δ (ppm) (CDCl$_3$): 3.46 (d, 2H), 3.40 (d, 2H), 1.81 (m, 4H), 1.42 (m, 2H), 1.26 (s, 1H), 0.94 (m, 4H), 0.89 (s, 9H), 0.03 (s, 6H).

Step B: trans-4-(((tert-butyldimethylsilyl)oxy)methyl)cyclohexyl)methyl 4-methylbenzene-sulfonate trans-4-(((tert-Butyldimethylsilyl)oxy)methyl)cyclohexyl)methanol (2.99 g, 11.57 mmol) was dissolved in CH$_2$Cl$_2$ (29 mL). Then p-toluenesulfonyl chloride (2.87 g, 15.04 mmol) and pyridine (2.81 ml, 34.7 mmol) were added. The reaction was stirred overnight, and then the solvent was evaporated. The resulting crude residue was reconstituted by adding diethyl ether (50 mL) and filtered through a sintered glass funnel. The resulting solid was washed with ether (2×) and the filtrate was evaporated. The resulting residue was purified on a Biotage 40M silica gel column, eluting with a gradient of 35-100% dichloromethane in hexanes to give the title compound. NMR δ (ppm) (CDCl$_3$): 7.78 (d, 2H), 7.34 (d, 2H), 3.82 (d, 2H), 3.37 (d, 2H), 2.45 (s, 3H), 1.75 (br t, 4H), 1.61 (m, 1H), 1.37 (m, 1H), 0.88 (s and m, 13H), 0.02 (s, 6H).

Step C: tert-butyldimethyl(((trans)-4-(prop-2-yn-1-yl)cyclohexyl)methoxy)silane To trans-4-(((tert-butyldimethylsilyl)oxy)methyl)cyclohexyl)methyl 4-methylbenzene-sulfonate (1.238 g, 3.00 mmol) in an oven dried flask was added fresh, anhydrous DMSO (15 ml) and freshly pulverized lithium acetylide ethylenediamine complex (0.829 g, 9.00 mmol) as a single portion. The reaction stirred at room temperature for 2 hours. The reaction was then quenched cautiously with the dropwise addition of 31 ml of water, by keeping the temperature <35° C. by placing the reaction vessel in a water bath containing some ice. Once addition of water was complete, ethyl acetate was added and the reaction was stirred vigorously for 10 minutes. The layers were separated and the aqueous layer was extracted with ethyl acetate (2×). The combined organic layers were washed with brine, dried over sodium sulfate, filtered and evaporated. The crude product was purified on a 100 gram silica gel column, eluting with a gradient of 0-50% ethyl acetate in hexanes to give the title compound as a mixture. A second 25 gram silica gel column was run, eluting with 25% dichloromethane in hexanes to give pure title compound. NMR δ (ppm) (CDCl$_3$): 3.40 (d, 2H), 2.09 (dd, 2H), 1.96 (m, 1H), 1.82 (dd, 4H), 1.42 (m, 2H), 0.98 (m, 4H), 0.89 (s, 9H), 0.03 (s, 6H).

Example 17

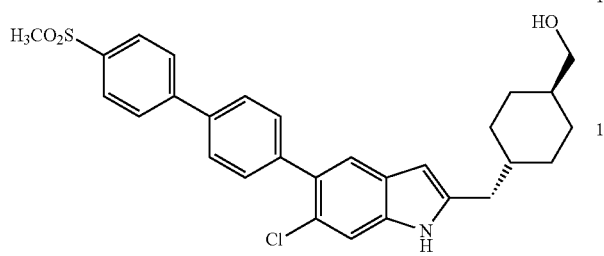

((trans)-4-((6-chloro-5-(4'-(methylsulfonyl)-[1,1'-biphenyl]-4-yl)-1H-indol-2-yl)methyl)cyclohexyl)methanol Step A: 2-(((trans)-4-(((tert-butyldimethylsilyl)oxy)methyl)cyclohexyl)methyl)-6-chloro-5-(4'-(methylsulfonyl)-[1,1'-biphenyl]-4-yl)-1H-indole Intermediate 8 (145 mg, 0.25 mmol), copper (I) iodide (4.8 mg, 0.025 mmol) and bis(triphenylphosphine)palladium (II) chloride (10.5 mg, 0.015 mmol) were added to a 1 dram vial, which was then evacuated and charged with nitrogen. Then DMF (0.75 mL) and Et$_3$N (174 µl, 1.250 mmol) were added to prepare the catalyst mixture. Separately, intermediate 9 (100 mg, 0.375 mmol) was dissolved in DMF (0.50 mL), and this solution was added dropwise to the stirring catalyst mixture. The resulting reaction was heated to 60° C. for 4 hours. The reaction was quenched by pouring into aqueous NH$_4$Cl followed by extraction with ethyl acetate. The organic layer was separated, washed with NH$_4$Cl, then with brine, dried over sodium sulfate, filtered and evaporated. The crude product was purified on a RediSep 40 gram silica gel column, eluting with a gradient of 10-50% ethyl acetate in hexanes to give the title compound. LC-MS: calculated for C$_{35}$H$_{44}$ClNO$_3$SSi 621.25, observed m/e: 622.3 (M+H)$^+$ (Rt 3.29/4 min).

Step B: ((trans)-4-((6-chloro-5-(4'-(methylsulfonyl)-[1,1'-biphenyl]-4-yl)-1H-indol-2-yl)methyl)cyclohexyl)methanol A solution of 2-(((trans)-4-(((tert-butyldimethylsilyl)oxy)methyl)cyclohexyl)methyl)-6-chloro-5-(4'-(methylsulfonyl)-[1,1'-biphenyl]-4-yl)-1H-indole (63.5 mg, 0.102 mmol) in THF (510 µl) was treated with 1 M tetrabutylammonium fluoride (102 µl, 0.102 mmol). The reaction was stirred under nitrogen atmosphere overnight, and then diluted with water and extracted twice with dichloromethane. The combined organic layers were washed with water, then with brine, dried over sodium sulfate, filtered and evaporated. The crude product was purified on a Biotage SNAP 10 gram silica gel column, eluting with a gradient of 20-100% ethyl acetate in hexanes to give the title compound. NMR δ (ppm) (CDCl$_3$): 8.03 (d, 2H), 7.90 (br s, 1H), 7.84 (d, 2H), 7.68 (d, 2H), 7.61 (d, 2H), 7.50 (s, 1H), 7.44 (s, 1H), 6.25 (s, 1H), 3.46 (t, 2H), 3.11 (s, 3H), 2.67 (d, 2H), 1.84 (br t, 4H), 1.63 (m, 1H), 1.47 (m, 1H), 1.25 (m, 1H), 1.11-0.91 (m, 4H). LC-MS: calculated for C$_{29}$H$_{30}$ClNO$_3$S 507.16, observed m/e: 508.22 (M+H)$^+$ (Rt 2.42/4 min).

SCHEME 5

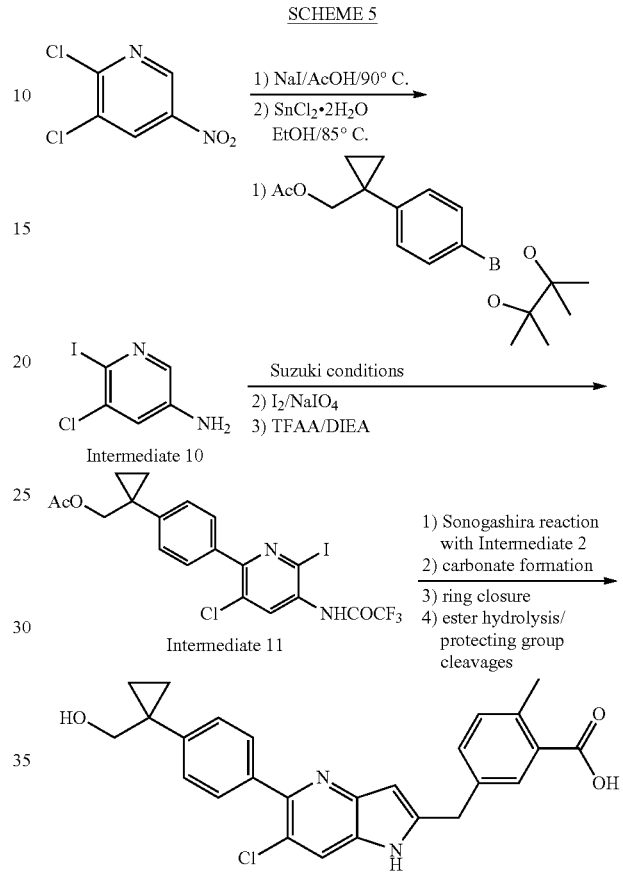

Example 18

Intermediate 10

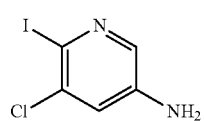

3-chloro-2-iodo-5-aminopyridine

Step A: 3-chloro-2-iodo-5-nitropyridine 2,3-Dichloro-5-nitropyridine (2.892 g, 14.99 mmol) and sodium iodide (11.23 g, 74.9 mmol) were dissolved in acetic acid (15 mL). The reaction was heated to 90° C. for 4 hours, then diluted with water and filtered. The resulting solid was dried on the filter for a few minutes, and then transferred to a flask and dried in vacuo over the weekend to give the title compound, which was used in the next step without further purification. NMR δ (ppm) (CDCl$_3$): 9.07 (d, 2H), 8.40 (d, 2H).

Step B: 3-chloro-2-iodo-5-aminopyridine

3-Chloro-2-iodo-5-nitropyridine (1.42 g, 5.0 mmol) and tin (II) chloride dihydrate (5.64 g, 25.00 mmol) were heated to 85° C. in ethanol (25 mL) for 3 hours. Then the reaction was partitioned between 1N NaOH and ethyl acetate. The organic layer was separated, washed with 1N NaOH, then with brine, dried over sodium sulfate, filtered and evaporated to give the title compound. NMR δ (ppm) (CDCl$_3$): 7.80 (d, 2H), 7.03 (d, 2H), 3.22 (br s, 2H). LC-MS: calculated for C$_5$H$_4$ClIN$_2$ 253.91, observed m/e: 255.2 (M+H)$^+$ (Rt 0.84/2 min).

Intermediate 11

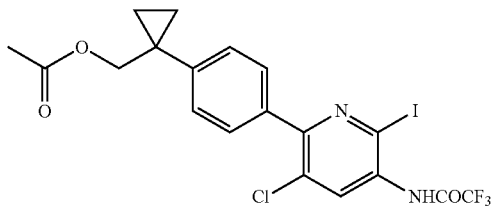

(1-(4-(3-chloro-6-iodo-5-(2,2,2-trifluoroacetamido) pyridin-2-yl)phenyl)cyclopropyl)methyl acetate

Step A: (1-(4-(5-amino-3-chloropyridin-2-yl)phenyl) cyclopropyl)methyl acetate (1-(4-(4,4,5,5-Tetramethyl-1,3,2-dioxaborolan-2-yl)phenyl)cyclopropyl)methyl acetate, Intermediate 10 (254 mg, 1.0 mmol), potassium phosphate tribasic (637 mg, 3.00 mmol) and PdCl$_2$(dppf) (36.6 mg, 0.050 mmol) were added to a reaction vessel, which was then evacuated and charged with nitrogen three times. Then 1,4-dioxane (5 mL) was added and the reaction was heated to 80° C. overnight. Then additional PdCl$_2$(dppf) (77 mg) was added in portions over the next 3 days. After 96 hours, the reaction was cooled to room temperature, and then partitioned between water and ethyl acetate. The layers were separated and the aqueous layer was extracted with ethyl acetate. The organic layers were combined, and washed with water, followed by brine, then dried over sodium sulfate, filtered and evaporated. The crude product was purified on a Biotage 25S silica gel column, eluting with a gradient of 25-75% ethyl acetate in hexanes to give the title compound plus an impurity. The impure title compound was then re-purified on a Biotage 25S silica gel column, eluting with 10-25% ethyl acetate in dichloromethane to give the purified title compound. NMR δ (ppm) (CDCl$_3$): 8.06 (d, 1H), 7.62 (d, 2H), 7.36 (d, 2H), 7.09 (d, 1H), 4.19 (s, 2H), 3.80 (br s, 2H), 2.03 (s, 3H), 0.96 (q, 4H).

Step B: (1-(4-(5-amino-3-chloro-6-iodopyridin-2-yl) phenyl)cyclopropyl)methyl acetate (1-(4-(5-Amino-3-chloropyridin-2-yl)phenyl)cyclopropyl)methyl acetate (96 mg, 0.303 mmol) was dissolved in DMF (600 μl) and transferred to a screw cap vial. Then iodine (77 mg, 0.303 mmol) and sodium periodate (64.8 mg, 0.303 mmol) were added, and the reaction was stirred at 60° C. for 7 hours. The reaction was then quenched with aqueous sodium thiosulfate and extracted twice with ethyl acetate. The organic layer was separated and washed with sodium thiosulfate solution followed by sodium bisulfite/metabisulfite solution. The organic layer was then washed with brine, dried over sodium sulfate, filtered and evaporated. The crude product was purified on a Biotage 25S silica gel column, eluting with a gradient of 10-40% ethyl acetate in hexanes to give the title compound. NMR δ (ppm) (CDCl$_3$): 7.62 (d, 2H), 7.36 (d, 2H), 7.01 (s, 1H), 4.19 (s, 4H), 2.04 (s, 3H), 0.96 (d, 4H).

Step C: (1-(4-(3-chloro-6-iodo-5-(2,2,2-trifluoroacetamido)pyridin-2-yl)phenyl)cyclopropyl) methyl acetate (1-(4-(5-Amino-3-chloro-6-iodopyridin-2-yl)phenyl)cyclopropyl)methyl acetate (92 mg, 0.208 mmol) was dissolved in CH$_2$Cl$_2$ (1 mL) and cooled to 0° C. Then DIEA (63.5 μl, 0.364 mmol) was added, followed by trifluoroacetic anhydride (39.6 μl, 0.281 mmol). The reaction was stirred for 2 hours. The crude reaction mixture was then purified directly on a Biotage 25S silica gel column, eluting with a gradient of 10-40% ethyl acetate in hexanes to give the title compound. NMR δ (ppm) (CDCl$_3$): 8.62 (s, 1H), 8.37 (br s, 1H), 7.70 (d, 2H), 7.41 (d, 2H), 4.21 (s, 2H), 2.04 (s, 3H), 1.00 (s, 4H).

Example 18

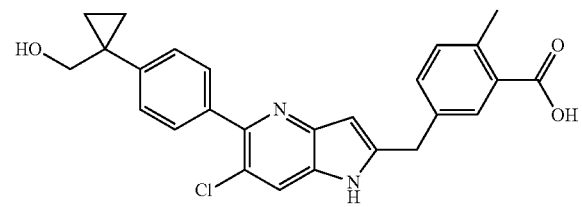

5-((6-chloro-5-(4-(1-(hydroxymethyl)cyclopropyl) phenyl)-1H-pyrrolo[3,2-b]pyridin-2-yl)methyl)-2-methylbenzoic acid

Step A: methyl 5-(3-(6-(4-(1-(acetoxymethyl)cyclopropyl)phenyl)-5-chloro-3-(2,2,2-trifluoroacetamido) pyridin-2-yl)-1-hydroxyprop-2-yn-1-yl)-2-methylbenzoate Intermediate 11 (85 mg, 0.158 mmol), copper (I) iodide (1.5 mg, 7.89 μmol) and bis(triphenylphosphine) palladium (II) chloride (2.2 mg, 3.16 μmol) were added to an oven-dried flask flushed with nitrogen. Then DMF (0.25 mL) was added, followed by Et$_3$N (0.25 mL) to prepare the catalyst mixture. Intermediate 2 (38.7 mg, 0.189 mmol) was also flushed with nitrogen, and Et$_3$N (0.25 mL) and DMF (0.15 mL) were added to prepare the alkyne solution. Then the alkyne solution was added dropwise to the stirring catalyst mixture. After 2 hours the reaction was quenched with aqueous NH$_4$Cl, and the reaction mixture was partitioned between water and ethyl acetate. The organic layer was separated, and washed with aqueous NH$_4$Cl, dried over sodium sulfate, filtered and evaporated. The crude product was purified on a Biotage 25S silica gel column, eluting with a gradient of 15-50% ethyl acetate in hexanes to give the title compound. LC-MS: calculated for $C_{31}H_{26}ClIF_3N_2O_6$ 614.14, observed m/e: 615.6 (M+H)⁺ (Rt 1.42/2 min).

Step B: methyl 5-(3-(6-(4-(1-(acetoxymethyl)cyclopropyl)phenyl)-5-chloro-3-(2,2,2-trifluoroacetamido)pyridin-2-yl)-1-((ethoxycarbonyl)oxy)prop-2-yn-1-yl)-2-methylbenzoate Methyl 5-(3-(6-(4-(1-(acetoxymethyl)cyclopropyl)phenyl)-5-chloro-3-(2,2,2-trifluoroacetamido)pyridin-2-yl)-1-hydroxyprop-2-yn-1-yl)-2-methylbenzoate (35 mg, 0.057 mmol) was dissolved in $CH_2Cl_2$ (285 μl) and cooled to −20° C. Then DMAP (11.1 mg, 0.091 mmol) and ethyl chloroformate (7.7 μl, 0.080 mmol) were added. The reaction was stirred for about 3 hours, then it was directly purified on a Biotage 12M silica gel column, eluting with a gradient of 15-40% ethyl acetate in hexanes to give the title compound. NMR δ (ppm) (CDCl₃): 8.86 (s, 1H), 8.69 (br s, 1H), 8.10 (d, 1H), 7.63 (m, 3H), 7.39 (d, 2H), 7.30 (d, 1H), 6.47 (s, 1H), 4.26 (q, 2H), 4.19 (s, 2H), 3.89 (s, 3H), 2.62 (s, 3H), 2.03 (s, 3H), 1.33 (t, 3H), 0.98 (s, 4H).

Step C: methyl 5-((5-(4-(1-(acetoxymethyl)cyclopropyl)phenyl)-6-chloro-1H-pyrrolo[3,2-b]pyridin-2-yl)methyl)-2-methylbenzoate Methyl 5-(3-(6-(4-(1-(acetoxymethyl)cyclopropyl)phenyl)-5-chloro-3-(2,2,2-trifluoroacetamido)pyridin-2-yl)-1-((ethoxycarbonyl)oxy)prop-2-yn-1-yl)-2-methylbenzoate (28 mg, 0.041 mmol) was dissolved in acetonitrile (400 μl). Then reaction was flushed with nitrogen, then Pd(Ph₃P)₄ (2.4 mg, 2.038 μmol), Et₃N (17.0 μl, 0.122 mmol) and formic acid (3.1 μl, 0.082 mmol) were added. The reaction was heated to 40° C. for 120 minutes, and to 60° C. for 16 hours. Then the reaction was worked up by diluting with ethyl acetate and washing once with aqueous NH₄Cl and once with brine. The organic layer was separated, dried over sodium sulfate, filtered and evaporated. The crude product was purified on a Biotage 25M silica gel column, eluting with a gradient of 15-30% ethyl acetate in hexanes to give the title compound along with impurities, which was used as is in the subsequent reaction. LC-MS: calculated for $C_{29}H_{27}ClN_2O_4$ 502.17, observed m/e: 503.24 (M+H)⁺ (Rt 1.94/4 min).

Step D: 5-((6-chloro-5-(4-(1-(hydroxymethyl)cyclopropyl)phenyl)-1H-pyrrolo[3,2-b]pyridin-2-yl)methyl)-2-methylbenzoic acid Methyl 5-((5-(4-(1-(acetoxymethyl)cyclopropyl)phenyl)-6-chloro-1H-pyrrolo[3,2-b]pyridin-2-yl)methyl)-2-methylbenzoate (5.2 mg, 10.34 μmol) was dissolved in MeOH (100 μl). Then NaOH (2.5M, 20.7 μl, 0.052 mmol) was added, followed by THF (100 μl). The reaction was heated to 40° C. overnight, then quenched with 1N HCl (0.052 mL), and partitioned between ethyl acetate and water. The organic layer was separated, dried over sodium sulfate, filtered and evaporated. The resulting crude product was purified by C18 preparative HPLC, eluting with a gradient of 25-100% $CH_3CN$/water (0.05% TFA) to give the title compound. NMR δ (ppm) (CD₃OD): 7.86 (s, 1H), 7.85 (br s, 1H), 7.49 (m, 4H), 7.36 (d, 1H), 7.24 (d, 1H), 6.38 (s, 1H), 4.19 (s, 2H), 3.69 (s, 2H), 2.55 (s, 3H), 0.80 (m, 4H). LC-MS: calculated for $C_{26}H_{23}ClN_2O_3$ 446.14, observed m/e: 447.18 (M+H)⁺ (Rt 1.60/4 min).

SCHEME 6

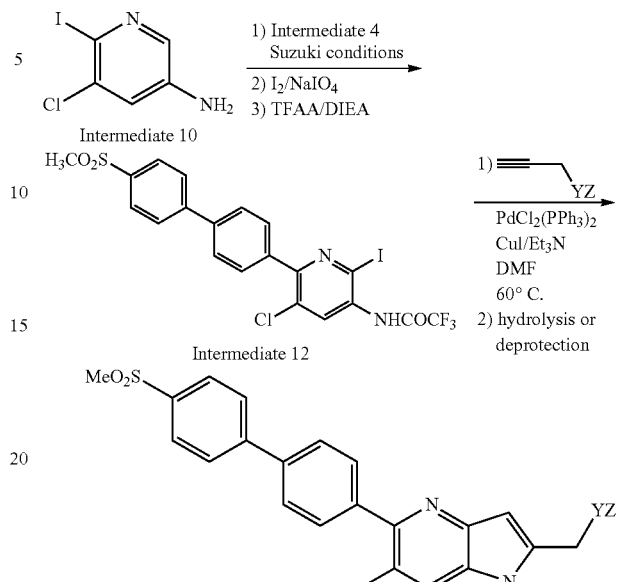

Intermediate 12

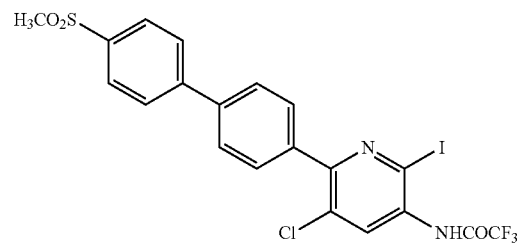

N-(5-chloro-2-iodo-6-(4'-(methylsulfonyl)-[1,1'-biphenyl]-4-yl)pyridin-3-yl)-2,2,2-trifluoroacetamide Step A: 5-chloro-6-(4'-(methylsulfonyl)-[1,1'-biphenyl]-4-yl)pyridin-3-amine Intermediate 4 (645 mg, 1.800 mmol), intermediate 10 (382 mg, 1.5 mmol) and PdCl₂(dppf) (110 mg, 0.150 mmol) were added to the reaction vessel, which was then evacuated and charged three times with nitrogen. Then 1,4-dioxane (7.5 ml) was added, followed by 3M LiOH (1.5 ml, 4.50 mmol) and the reaction was heated to 80° C. After 1 hour the reaction was cooled to room temperature, diluted with ethyl acetate and washed with aqueous citric acid, and then with brine. The organic layer was separated, dried over sodium sulfate, filtered and evaporated. The crude product was dissolved in acetone and added to a size 40 silica gel column insert, which was then dried under vacuum. The insert was added to a 40S Biotage silica gel column and eluted with a gradient of 50-100% ethyl acetate in hexanes to give the title compound. LC-MS: calculated for $C_{18}H_{15}ClN_2O_2S$ 358.05 observed m/e: 359.09 (M+H)⁺ (Rt 1.52/4 min).

Step B: 5-chloro-2-iodo-6-(4'-(methylsulfonyl)-[1,1'-biphenyl]-4-yl)pyridin-3-amine 5-Chloro-6-(4'-(methylsulfonyl)-[1,1'-biphenyl]-4-yl)pyridin-3-amine (392 mg, 1.092 mmol) was dissolved in DMF (2.2 mL). Iodine (277 mg, 1.092 mmol) and sodium periodate (234 mg, 1.092 mmol) were added and the reaction was stirred at 60° C. for 3 hours. The reaction was poured into aqueous sodium metabisulfite and extracted with ethyl acetate. The organic layer was separated and washed again with sodium metabisulfite, then with brine, dried over sodium sulfate, filtered and evaporated. The crude product was purified on a Biotage 25S silica gel column, eluting with a gradient of 15-75% ethyl acetate in hexanes to give the title compound. LC-MS: calculated for $C_{18}H_{14}ClIN_2O_2S$ 483.95, observed m/e: 484.93 (M+H)$^+$ (Rt 2.07/4 min).

Step C: N-(5-chloro-2-iodo-6-(4'-(methylsulfonyl)-[1,1'-biphenyl]-4-yl)pyridin-3-yl)-2,2,2-trifluoroacetamide 5-Chloro-2-iodo-6-(4'-(methylsulfonyl)-[1,1'-biphenyl]-4-yl)pyridin-3-amine (179.3 mg, 0.370 mmol) was dissolved in $CH_2Cl_2$ (1.9 mL) and cooled to 0° C. DIEA (113 µl, 0.647 mmol) was added, followed by trifluoroacetic anhydride (70.5 µl, 0.499 mmol). The reaction was stirred for about 2 hours, after which the reaction was directly purified on a Biotage 25S silica gel column, eluting with a gradient of 25-70% ethyl acetate in hexanes to give the title compound. LC-MS: calculated for $C_{20}H_{13}ClF_3IN_2O_3S$ 579.93, observed m/e: 581.09 (M+H)$^+$ (Rt 2.19/4 min).

Intermediate 13

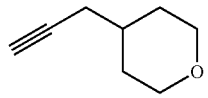

4-(prop-2-yn-1-yl)tetrahydro-2H-pyran

Step A: 4-(3,3-dibromoallyl)tetrahydro-2H-pyran

Triphenylphosphine (7.92 g, 30.2 mmol) was dissolved in 60 mL of $CH_2Cl_2$ and cooled to 0° C. under nitrogen. Then carbon tetrabromide (5.00 g, 15.09 mmol) was added, and the reaction was stirred for about 5 minutes. Then a solution of tetrahydropyran-4-yl acetaldehyde (0.967 g, 7.54 mmol) in 20 mL of $CH_2Cl_2$ was added dropwise. The reaction was stirred for 2 hours, and then evaporated to about ⅕ volume. The resulting solid was filtered off, and the solid was rinsed with a minimal amount of $CH_2Cl_2$. The crude product was purified on a Biotage 40M silica gel column, eluting with methylene chloride to give the title compound. NMR δ (ppm) ($CDCl_3$): 6.41 (t, 1H), 3.96 (dd, 2H), 3.37 (t, 2H), 2.07 (m, 2H), 1.66 (m, 1H), 1.61 (d, 2H), 1.37 (m, 2H).

Step B: 4-(prop-2-yn-1-yl)tetrahydro-2H-pyran 4-(3,3-Dibromoallyl)tetrahydro-2H-pyran (0.500 g, 1.761 mmol) was added to an oven dried flask, then dissolved in anhydrous THF (13 mL). The reaction mixture was cooled to −78° C. in a dry ice/acetone bath, then evacuated and charged three times with nitrogen gas. Then BuLi (1.75 ml, 4.40 mmol, 2.5M) in hexanes was added dropwise over about 3 minutes, and the reaction stirred for 2 hours. Aqueous sodium bicarbonate was added and the reaction was removed from the cooling bath. The reaction mixture was extracted with ethyl acetate. The organic layer was separated, washed with water and brine, dried over sodium sulfate, filtered and evaporated. The crude product was used as is without purification. NMR δ (ppm) ($CDCl_3$): 3.97 (dd, 2H), 3.38 (t, 2H), 2.15 (m, 2H), 1.98 (m, 1H), 1.72 (m, 2H), 1.39 (m, 2H), 0.90 (m, 1H).

Example 19

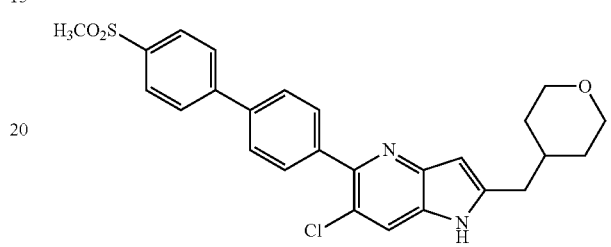

6-chloro-5-(4'-(methylsulfonyl)-[1,1'-biphenyl]-4-yl)-2-((tetrahydro-2H-pyran-4-yl)methyl)-1H-pyrrolo[3,2-b]pyridine Intermediate 12 (58.1 mg, 0.1 mmol), copper (I) iodide (1.9 mg, 10.00 µmol) and bis(triphenylphosphine)palladium (II) chloride (3.5 mg, 5.00 µmol) were added to a 1 dram vial, which was then evacuated and charged with nitrogen. Then DMF (0.35 mL) and added $Et_3N$ (69.7 µl, 0.500 mmol) were added to prepare the catalyst mixture. Separately intermediate 13 (18.6 mg, 0.150 mmol) was dissolved in DMF (0.15 mL), and the resulting solution was added dropwise to the stirring catalyst mixture. The reaction was heated to 60° C. for 2 hours, and then cooled to room temperature and quenched with aqueous $NH_4Cl$. The reaction mixture was diluted with water and ethyl acetate, and saturated aqueous $NaHCO_3$ was added to the aqueous layer. The aqueous layer was extracted twice with ethyl acetate. The combined organic layers were washed with water, then dried over sodium sulfate, filtered and evaporated. The crude product was purified on a Biotage 12M silica gel column, eluting with a gradient of 50-100% ethyl acetate in hexanes to give the title compound. NMR δ (ppm) ($CDCl_3$): 8.06 (br s, 1H), 8.03 (d, 2H), 7.84 (m, 4H), 7.71 (s and d, 3H), 6.50 (s, 1H), 3.98 (dd, 2H), 3.38 (m, 2H), 3.11 (s, 3H), 2.76 (d, 2H), 1.93 (m, 1H) 1.66 (br d, 2H), 1.42 (m, 2H). LC-MS: calculated for $C_{26}H_{25}ClN_2O_3S$ 480.13, observed m/e: 481.17 (M+H)$^+$ (Rt 1.67/4 min).

TABLE 4

Compounds prepared according to the methods described in Example 19.

| Example Number | Structure | HPLC-mass spectrum m/e |
|---|---|---|
| 20 | H₃CO₂S-biphenyl-[6-chloro-pyrrolo[3,2-b]pyridin-2-yl]-(CH₂)₃OH | 441.1 |
| 21 | H₃CO₂S-biphenyl-[6-chloro-pyrrolo[3,2-b]pyridin-2-yl]-(CH₂)₄OH | 455.2 |
| 22* | MeSO₂-biphenyl-[6-chloro-pyrrolo[3,2-b]pyridin-2-yl]-(CH₂)₃CO₂H | 469.1 |
| 23* | MeSO₂-biphenyl-[6-chloro-pyrrolo[3,2-b]pyridin-2-yl]-(CH₂)₄CO₂H | 483.1 |

*This compound was prepared in 2 steps:
1) the indole formation with the requisite alkynyl ester (see Example 12 for a representative synthetic method), and
2) the ester hydrolysis step (see Example 9 step B for a representative synthetic method).

Example 24

((trans)-4-((6-chloro-5-(4'-(methylsulfonyl)-[1,1'-biphenyl]-4-yl)-1H-pyrrolo[3,2-b]pyridin-2-yl)methyl)cyclohexyl)methanol

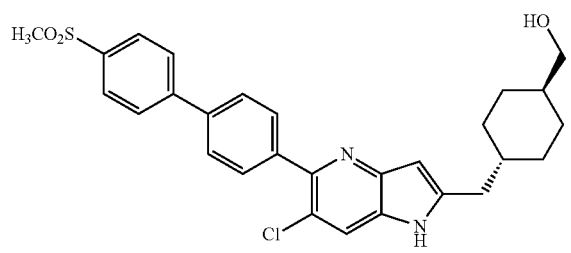

The title compound was prepared according to the two step procedure of Example 16 using Intermediate 12 and Intermediate 9. NMR δ (ppm) (CDCl₃): 8.03 (d, 2H), 7.98 (br s, 1H), 7.84 (m, 4H), 7.70 (m, 3H), 6.48 (s, 1H), 3.46 (t, 2H), 3.11 (s, 3H), 2.71 (d, 2H), 1.84 (br t, 4H), 1.64 (br, 1H), 1.47 (br, 1H), 1.14-0.90 (m, 4H). LC-MS: calculated for $C_{28}H_{29}ClN_2O_3S$ 508.16, observed m/e: 509.19 (M+H)⁺ (Rt 1.73/4 min).

Example 25

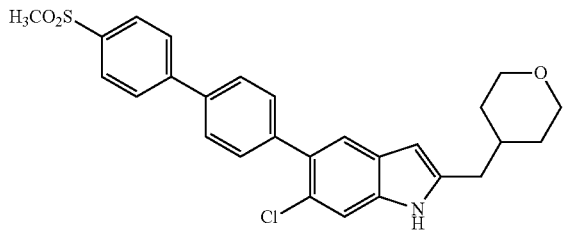

6-chloro-5-(4'-(methylsulfonyl)-[1,1'-biphenyl]-4-yl)-2-((tetrahydro-2H-pyran-4-yl)methyl)-1H-indole The title compound was prepared according to the procedure of Example 19 using Intermediate 8 and Intermediate 13. NMR δ (ppm) (CDCl$_3$): 8.03 (d, 2H), 7.93 (br s, 1H), 7.84 (d, 2H), 7.68 (d, 2H), 7.60 (d, 2H), 7.51 (s, 1H), 7.45 (s, 1H), 6.26 (s, 1H), 3.98 (dd, 2H), 3.38 (m, 2H), 3.11 (s, 3H), 2.71 (d, 2H), 1.93 (m, 1H) 1.66 (br d, 2H), 1.42 (m, 2H). LC-MS: calculated for $C_{27}H_{26}ClNO_3S$ 479.13, observed m/e: 480.11 (M+H)$^+$ (Rt 2.39/4 min).

Example 26

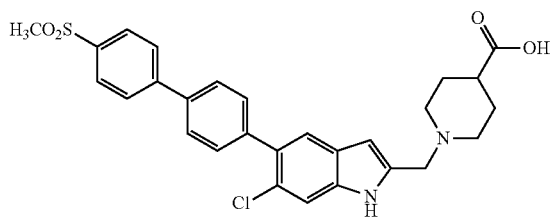

1-((6-chloro-5-(4'-(methylsulfonyl)-[1,1'-biphenyl]-4-yl)-1H-indol-2-yl)methyl)piperidine-4-carboxylic acid

Step A: ethyl 1-(prop-2-yn-1-yl)piperidine-4-carboxylate

Ethyl isonipectoate (1.541 ml, 10 mmol) was dissolved in acetone (20 ml). Solid potassium carbonate (3.46 g, 25.00 mmol) was added, followed by the dropwise addition of 80% propargyl bromide (1.225 ml, 11.00 mmol) in toluene. The reaction was stirred at room temperature for 48 hours, then the potassium carbonate was filtered off, and the filtrate was evaporated to give the crude product, which was used without further purification. NMR δ (ppm) (CDCl$_3$): 4.12 (q, 2H), 3.30 (d, 2H), 2.85 (m, 2H), 2.16 (m, 4H), 1.92 (m, 2H), 1.77 (m, 2H), 1.34 (t, 3H).

Step B: ethyl 1-((6-chloro-5-(4'-(methylsulfonyl)-[1,1'-biphenyl]-4-yl)-1H-indol-2-yl)methyl)piperidine-4-carboxylate Intermediate 8 (87 mg, 0.15 mmol), copper(I) iodide (2.86 mg, 0.015 mmol), and bis(triphenylphosphine)palladium(II) chloride (5.26 mg, 7.50 μmol) were dissolved in 0.75 mL of DMF, followed by the addition of triethylamine (0.105 ml, 0.750 mmol). Then ethyl 1-(prop-2-yn-1-yl)piperidine-4-carboxylate (29.3 mg, 0.150 mmol) was dissolved in 0.15 mL of DMF and added dropwise to the reaction mixture. The reaction was stirred at 60° C. for 2.5 hours, then aqueous NH$_4$Cl was added and the mixture was extracted with ethyl acetate. The organic layer was separated, washed with aqueous NH$_4$Cl, and brine, then dried over sodium sulfate, filtered and evaporated. The resulting crude product was purified on a Biotage 25S silica gel column, eluting with 50-100% EtOAc/hexanes to give the title compound as a tan solid. LC-MS: calculated for $C_{30}H_{31}ClN_2O_4S$ 550.17, observed m/e: 551.27 (M+H)$^+$ (Rt 1.87/4 min).

Step C: 1-((6-chloro-5-(4'-(methylsulfonyl)-[1,1'-biphenyl]-4-yl)-1H-indol-2-yl)methyl)piperidine-4-carboxylic acid Ethyl 1-((6-chloro-5-(4'-(methylsulfonyl)-[1,1'-biphenyl]-4-yl)-1H-indol-2-yl)methyl)piperidine-4-carboxylate (39 mg, 0.071 mmol) was dissolved in THF (425 μl) and MeOH (212 μl). Then 5N NaOH (70.8 μl, 0.354 mmol) and water (70.8 μl) were added. An additional 0.425 mL of THF was added, and the reaction was heated to 40° C. Once complete, the reaction was neutralized with 1N HCl (0.355 mL), and partitioned between ethyl acetate and water. The aqueous was extracted with dichloromethane; followed by saturation of the aqueous layer with NaCl and extraction with THF. A solid was suspended in the organic layers. The organic layers were combined and filtered. The solid recovered in the filtration was the title compound. LC-MS: calculated for $C_{28}H_{27}ClN_2O_4S$ 522.14, observed m/e: 523.02 (M+H)$^+$ (Rt 1.75/4 min).

SCHEME 7

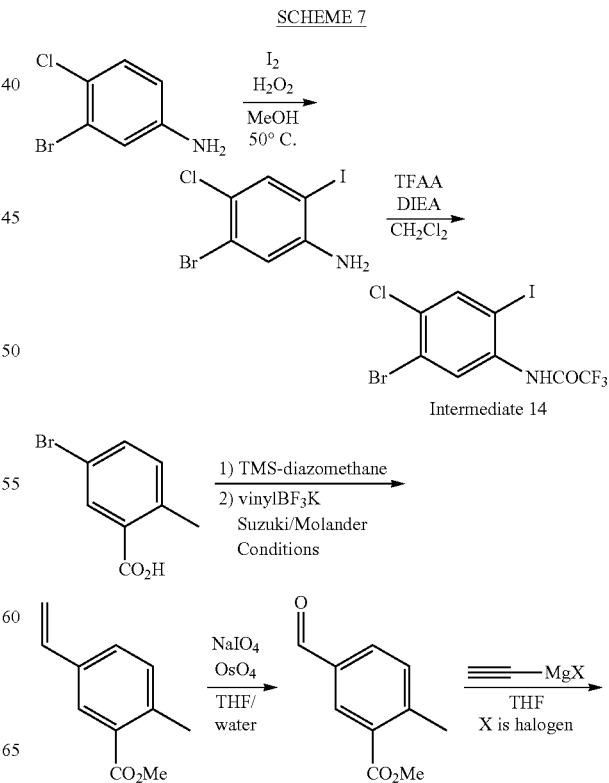

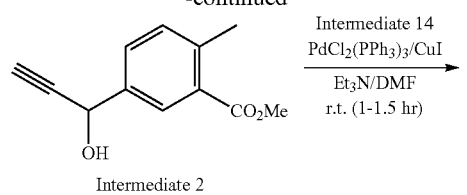

Intermediate 2

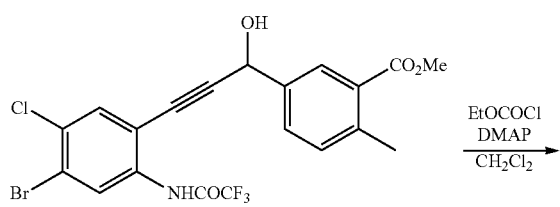

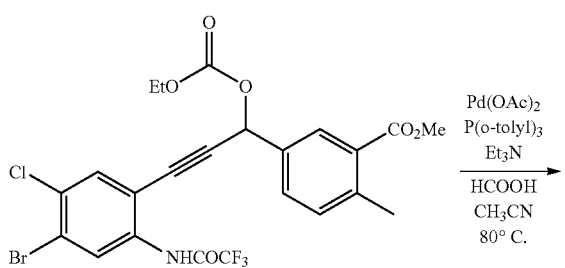

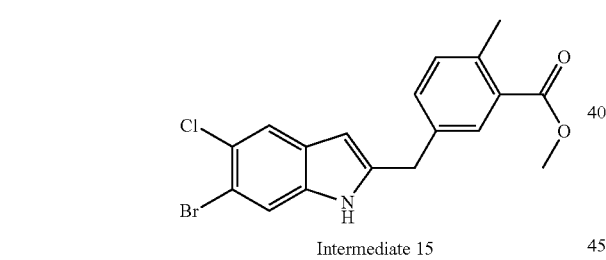

Intermediate 14

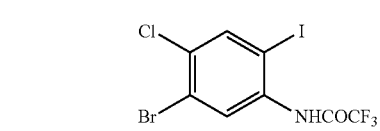

N-(5-bromo-4-chloro-2-iodophenyl)-2,2,2-trifluoro-acetamide

The title compound was prepared according to the 2 step procedure of Intermediate 1 starting with 3-Bromo-4-chloroaniline. NMR δ (ppm) (CDCl₃): 8.53 (s, 1H), 8.21 (br s, 1H), 7.91 (s, 1H).

Intermediate 15

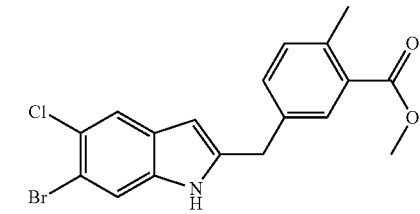

methyl 5-((6-bromo-5-chloro-1H-indol-2-yl)methyl)-2-methylbenzoate

The title compound was prepared according to the three step procedure of Intermediate 3 from Intermediate 14 and Intermediate 2. NMR δ (ppm) (CDCl₃): 7.79 (br s, s, 2H), 7.61 (s, 1H), 7.50 (s, 1H), 7.25 (d, 1H), 7.21 (d, 1H), 6.23 (s, 1H), 4.09 (s, 2H), 3.88 (s, 3H), 2.58 (s, 3H).

SCHEME 8

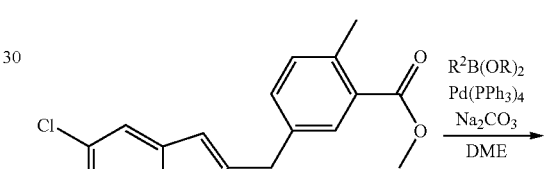

Intermediate 15

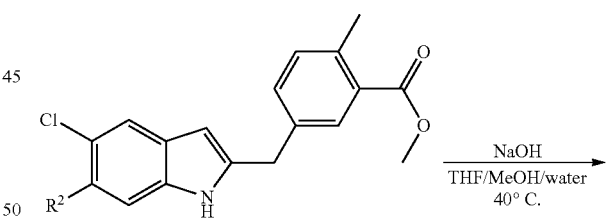

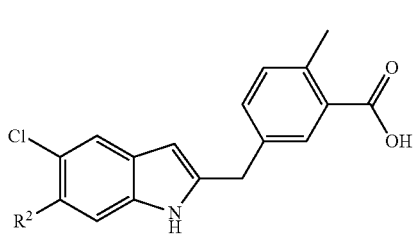

Examples 27 and 28

Example 27

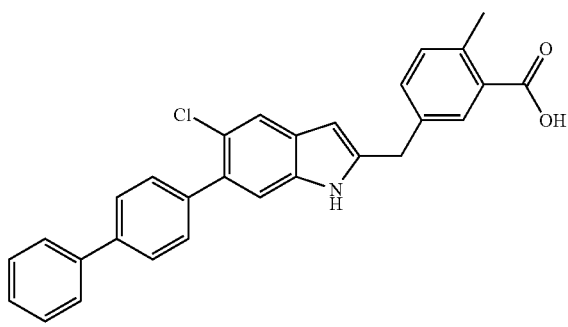 [SMILES: Cc1ccc(Cc2cc3cc(Cl)c(-c4ccc(-c5ccccc5)cc4)cc3[nH]2)cc1C(=O)O]

5-((6-([1,1'-biphenyl]-4-yl)-5-chloro-1H-indol-2-yl)methyl)-2-methylbenzoic acid The title compound was prepared according to the two step procedure of Example 1 starting from biphenylboronic acid and Intermediate 15. NMR δ (ppm) (CDCl₃): 7.97 (d, 1H), 7.86 (br s, 1H), 7.65 (m, 4H), 7.54 (d, 2H), 7.45 (t, 2H), 7.35 (m, 2H), 7.21 (m, 2H), 6.23 (s, 1H), 4.15 (s, 2H), 2.64 (s, 3H). LC-MS: calculated for C₂₉H₂₂ClNO₂ 451.13, observed m/e: 452.23 (M+H)⁺ (Rt 2.63/4 min).

Example 28

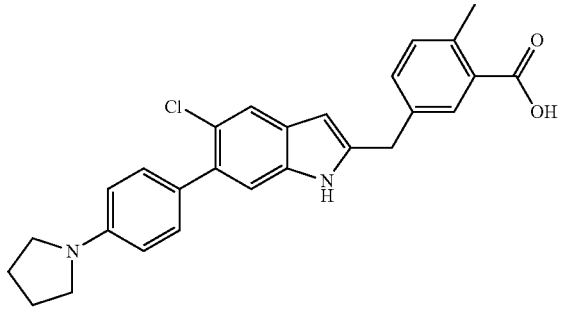 [SMILES: Cc1ccc(Cc2cc3cc(Cl)c(-c4ccc(N5CCCC5)cc4)cc3[nH]2)cc1C(=O)O]

5-((5-chloro-6-(4-(pyrrolidin-1-yl)phenyl)-1H-indol-2-yl)methyl)-2-methylbenzoic acid The title compound was prepared according to the two step procedure of Example 1 starting from 1-[4-(4,4,5,5-tetramethyl-1,3,2-dioxaborolan-2-yl)phenyl]pyrrolidine and Intermediate 15. NMR δ (ppm) (CDCl₃): 7.92 (s, 1H), 7.81 (br s, 1H), 7.60 (s, 1H), 7.39 (d, 2H), 7.23 (d, 1H), 7.18 (s, 1H), 6.83 (d, 2H), 6.27 (s, 1H), 4.13 (s, 2H), 3.44 (m, 4H), 2.61 (s, 3H), 2.08 (m, 4H). LC-MS: calculated for C₂₇H₂₅ClN₂O₂ 444.16, observed m/e: 445.27 (M+H)⁺ (Rt 2.26/4 min).

Example 29

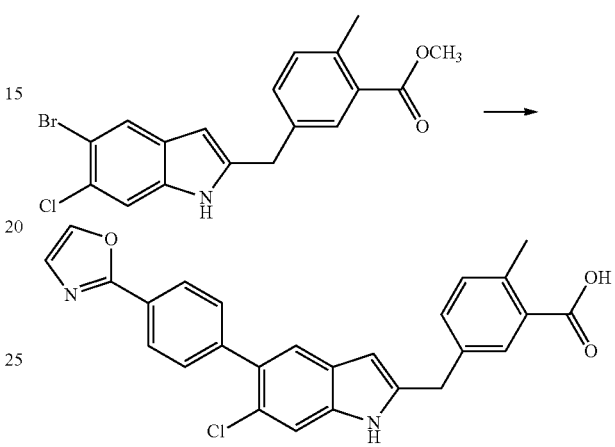

5-({6-chloro-5-[4-(1,3-oxazol-2-yl)phenyl]-1H-indol-2-yl}methyl)-2-methylbenzoic acid To a solution of Intermediate 3 (methyl 5-((5-bromo-6-chloro-1H-indol-2-yl)methyl)-2-methylbenzoate, 40 mg, 0.102 mmol) in THF (1 ml) in a microwave vial was added LiOH (0.102 ml, 0.204 mmol), Pd(Ph₃P)₄ (11.77 mg, 10.19 μmol) and 2-(4-(4,4,5,5-tetramethyl-1,3,2-dioxaborolan-2-yl)phenyl)oxazole (40.5 mg, 0.204 mmol). The reaction was heated to 130° C. for 1 h and then cooled to 21° C. Then an aliquot of LiOH (0.2 ml, 0.400 mmol) was added to the reaction, and the reaction was warmed to 40° C. for 2 h. The reaction was then quenched with citric acid (10% w/v, 1 mL) and extracted with EtOAc (2×2 mL). The combined organic layers were concentrated in vacuo and the resulting residue was purified via HPLC to afford the title compound as an amorphous white solid. (Waters Sunfire C18, 5 u, 19×100 mm, 25 mL/min, 8 min run time, 10% Water to 60% with MeCN modified with 0.1% formic acid).

TABLE 5

Compounds prepared according to the procedure described in Example 29.

| Example number | Structure | IUPAC Name | Exact Mass [M + H]+ |
|---|---|---|---|
| 29 | 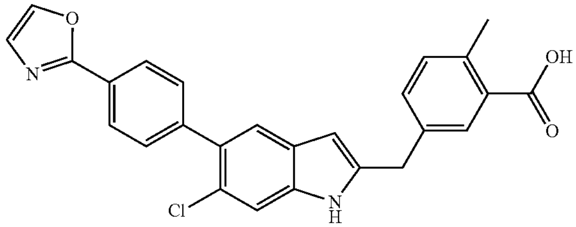 [SMILES: Cc1ccc(Cc2cc3cc(-c4ccc(-c5ncco5)cc4)c(Cl)cc3[nH]2)cc1C(=O)O] | 5-({6-chloro-5-[4-(1,3-oxazol-2-yl)phenyl]-1H-indol-2-yl}methyl)-2-methylbenzoic acid | 443 |

TABLE 5-continued

Compounds prepared according to the procedure described in Example 29.

| Example number | Structure | IUPAC Name | Exact Mass [M + H]+ |
| --- | --- | --- | --- |
| 30 | 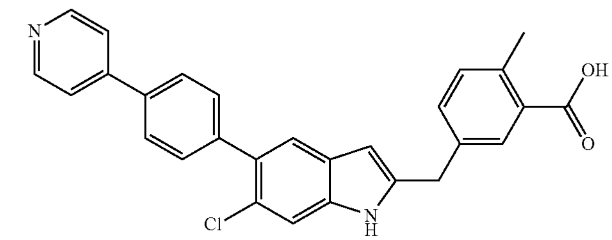 [SMILES: Cc1ccc(Cc2cc3cc(-c4ccc(-c5ccncc5)cc4)c(Cl)cc3[nH]2)cc1C(=O)O] | 5-{[6-chloro-5-(4-pyridin-4-ylphenyl)-1H-indol-2-yl]methyl}-2-methylbenzoic acid | 453 |
| 31 | 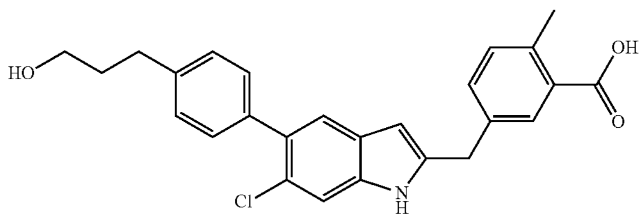 [SMILES: Cc1ccc(Cc2cc3cc(-c4ccc(CCCO)cc4)c(Cl)cc3[nH]2)cc1C(=O)O] | 5-({6-chloro-5-[4-(3-hydroxypropyl)phenyl]-1H-indol-2-yl}methyl)-2-methylbenzoic acid | 434 |
| 32 | 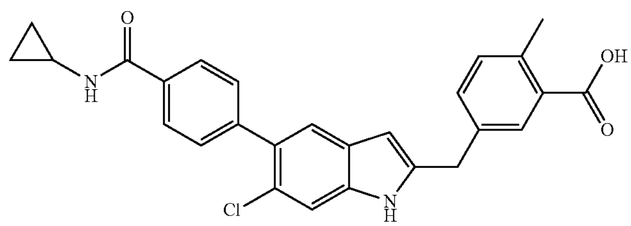 [SMILES: Cc1ccc(Cc2cc3cc(-c4ccc(C(=O)NC5CC5)cc4)c(Cl)cc3[nH]2)cc1C(=O)O] | 5-({6-chloro-5-[4-(cyclopropylcarbamoyl)phenyl]-1H-indol-2-yl}methyl)-2-methylbenzoic acid | 459 |
| 33 | 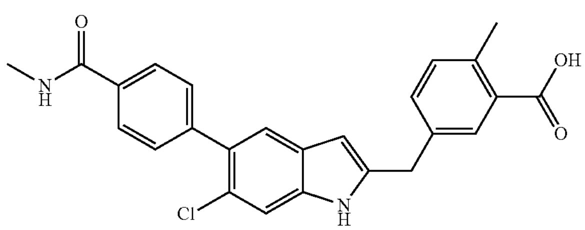 [SMILES: CNC(=O)c1ccc(-c2cc3cc(Cc4ccc(C)c(C(=O)O)c4)[nH]c3cc2Cl)cc1] | 5-({6-chloro-5-[4-(methylcarbamoyl)phenyl]-1H-indol-2-yl}methyl)-2-methylbenzoic acid | 433 |
| 34 | 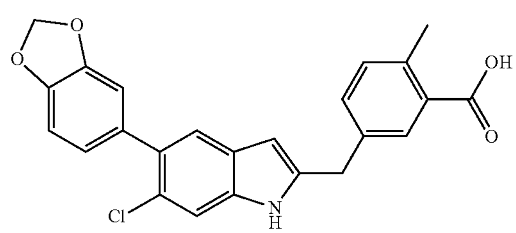 [SMILES: Cc1ccc(Cc2cc3cc(-c4ccc5c(c4)OCO5)c(Cl)cc3[nH]2)cc1C(=O)O] | 5-{[5-(1,3-benzodioxol-5-yl)-6-chloro-1H-indol-2-yl]methyl}-2-methylbenzoic acid | 420 |
| 35 | 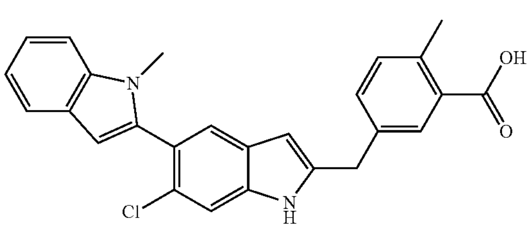 [SMILES: Cc1ccc(Cc2cc3cc(-c4cc5ccccc5n4C)c(Cl)cc3[nH]2)cc1C(=O)O] | 5-[(6'-chloro-1-methyl-1H,1'H-2,5'-biindol-2'-yl)methyl]-2-methylbenzoic acid | 429 |

TABLE 5-continued

Compounds prepared according to the procedure described in Example 29.

| Example number | Structure | IUPAC Name | Exact Mass [M + H]+ |
|---|---|---|---|
| 36 | 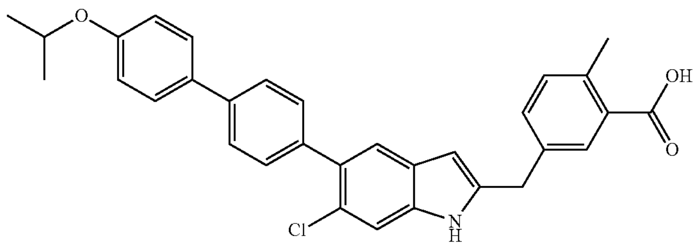 [SMILES: Cc1ccc(Cc2cc3cc(-c4ccc(-c5ccc(OC(C)C)cc5)cc4)c(Cl)cc3[nH]2)cc1C(=O)O] | 5-({6-chloro-5-[4'-(1-methylethoxy)biphenyl-4-yl]-1H-indol-2-yl}methyl)-2-methylbenzoic acid | 510 |
| 37 | 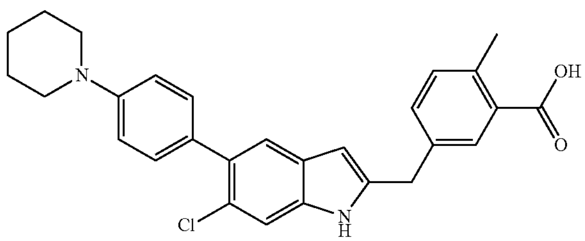 [SMILES: Cc1ccc(Cc2cc3cc(-c4ccc(N5CCCCC5)cc4)c(Cl)cc3[nH]2)cc1C(=O)O] | 5-{[6-chloro-5-(4-piperidin-1-ylphenyl)-1H-indol-2-yl]methyl}-2-methylbenzoic acid | 459 |
| 38 | 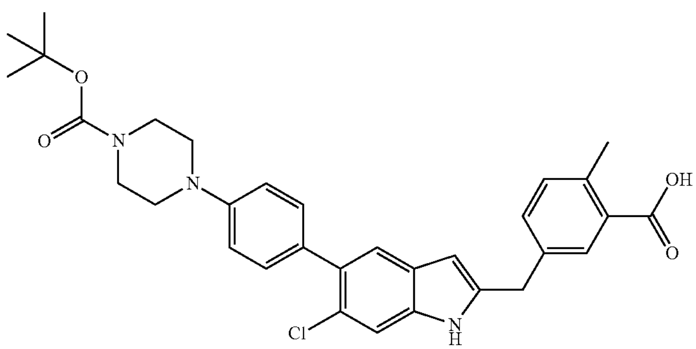 [SMILES: Cc1ccc(Cc2cc3cc(-c4ccc(N5CCN(C(=O)OC(C)(C)C)CC5)cc4)c(Cl)cc3[nH]2)cc1C(=O)O] | 5-[(5-{4-[4-(tert-butoxycarbonyl)piperazin-1-yl]phenyl}-6-chloro-1H-indol-2-yl)methyl]-2-methylbenzoic acid | 560 |
| 39 | 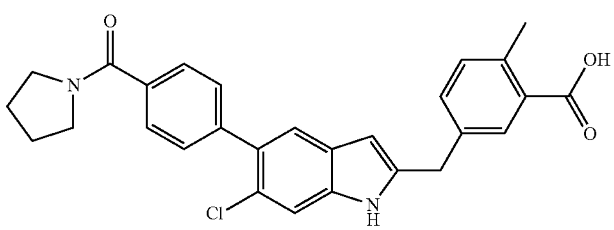 [SMILES: Cc1ccc(Cc2cc3cc(-c4ccc(C(=O)N5CCCC5)cc4)c(Cl)cc3[nH]2)cc1C(=O)O] | 5-({6-chloro-5-[4-(pyrrolidin-1-ylcarbonyl)phenyl]-1H-indol-2-yl}methyl)-2-methylbenzoic acid | 473 |
| 40 | 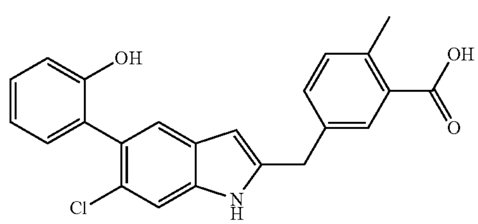 [SMILES: Cc1ccc(Cc2cc3cc(-c4ccccc4O)c(Cl)cc3[nH]2)cc1C(=O)O] | 5-{[6-chloro-5-(2-hydroxyphenyl)-1H-indol-2-yl]methyl}-2-methylbenzoic acid | 392 |
| 41 | 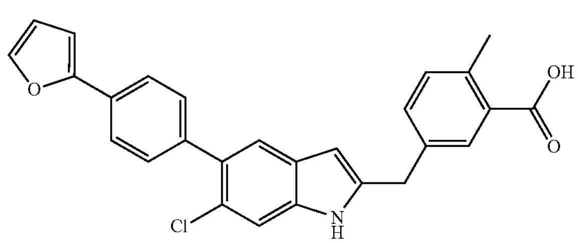 [SMILES: Cc1ccc(Cc2cc3cc(-c4ccc(-c5ccco5)cc4)c(Cl)cc3[nH]2)cc1C(=O)O] | 5-{[6-chloro-5-(4-furan-2-ylphenyl)-1H-indol-2-yl]methyl}-2-methylbenzoic acid | 442 |

TABLE 5-continued

Compounds prepared according to the procedure described in Example 29.

| Example number | Structure | IUPAC Name | Exact Mass [M + H]+ |
|---|---|---|---|
| 42 | 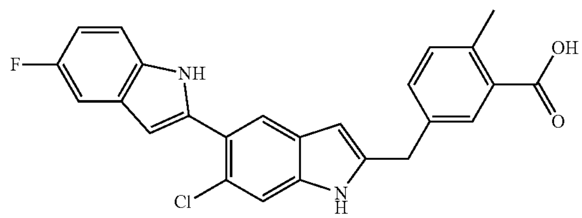 [SMILES: Cc1ccc(Cc2cc3cc(-c4cc5cc(F)ccc5[nH]4)c(Cl)cc3[nH]2)cc1C(=O)O] | 5-[(6'-chloro-5-fluoro-1H,1'H-2,5'-biindol-2'-yl)methyl]-2-methylbenzoic acid | 433 |
| 43 | 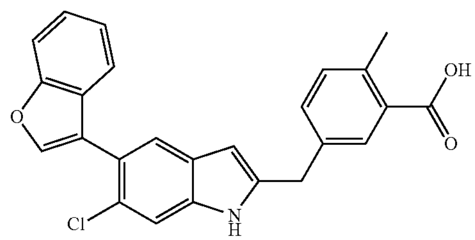 [SMILES: Cc1ccc(Cc2cc3cc(-c4coc5ccccc45)c(Cl)cc3[nH]2)cc1C(=O)O] | 5-{[5-(1-benzofuran-3-yl)-6-chloro-1H-indol-2-yl]methyl}-2-methylbenzoic acid | 416 |
| 44 | 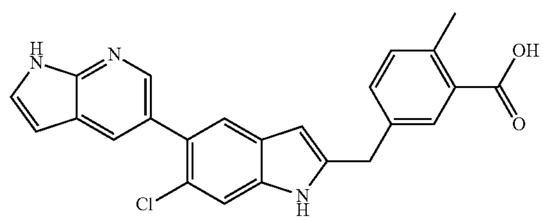 [SMILES: Cc1ccc(Cc2cc3cc(-c4cnc5[nH]ccc5c4)c(Cl)cc3[nH]2)cc1C(=O)O] | 5-{[6-chloro-5-(1H-pyrrolo[2,3-b]pyridin-5-yl)-1H-indol-2-yl]methyl}-2-methylbenzoic acid | 416 |
| 45 | 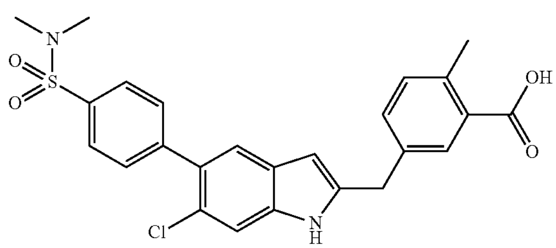 [SMILES: Cc1ccc(Cc2cc3cc(-c4ccc(S(=O)(=O)N(C)C)cc4)c(Cl)cc3[nH]2)cc1C(=O)O] | 5-({6-chloro-5-[4-(dimethylsulfamoyl)phenyl]-1H-indol-2-yl}methyl)-2-methylbenzoic acid | 483 |
| 46 | 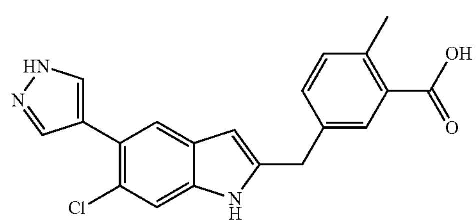 [SMILES: Cc1ccc(Cc2cc3cc(-c4cn[nH]c4)c(Cl)cc3[nH]2)cc1C(=O)O] | 5-{[6-chloro-5-(1H-pyrazol-4-yl)-1H-indol-2-yl]methyl}-2-methylbenzoic acid | 366 |
| 47 | 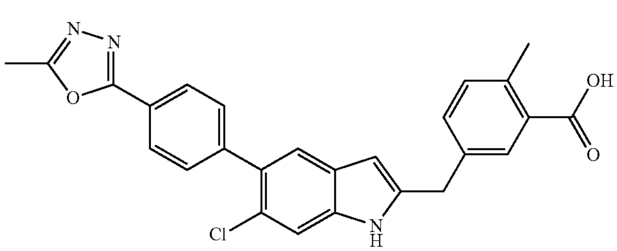 [SMILES: Cc1nnc(-c2ccc(-c3cc4cc(Cc5ccc(C)c(C(=O)O)c5)[nH]c4cc3Cl)cc2)o1] | 5-({6-chloro-5-[4-(5-methyl-1,3,4-oxadiazol-2-yl)phenyl]-1H-indol-2-yl}methyl)-2-methylbenzoic acid | 458 |

| Example number | Structure | IUPAC Name | Exact Mass [M + H]+ |
|---|---|---|---|
| 48 | 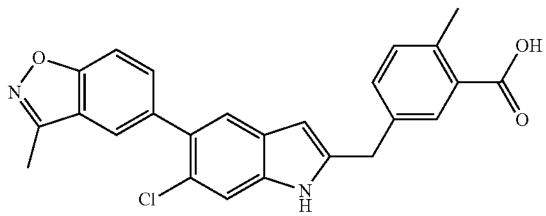 [SMILES: Cc1ccc(Cc2cc3cc(-c4ccc5onc(C)c5c4)c(Cl)cc3[nH]2)cc1C(=O)O] | 5-{[6-chloro-5-(3-methyl-1,2-benzisoxazol-5-yl)-1H-indol-2-yl]methyl}-2-methylbenzoic acid | 431 |

Intermediate 16 tert-butyldimethyl(((3R,3aS,6R,6aR)-6-(prop-2-yn-1-yloxy)hexahydrofuro[3,2-b]furan-3-yl)oxy)silane To a solution of (3R,3aR,6R,6aS)-6-((tert-butyldimethylsilyl)oxy)-hexahydrofuro[3,2-b]furan-3-ol (2.0 g, 7.7 mmol) in DMF (20 mL) was added NaH (369 mg, 9.2 mmol) at 0° C. The mixture was stirred at 0° C. for 30 min, then 3-bromoprop-1-yne (1.1 mg, 9.2 mmol) was added. The mixture was stirred at room temperature for 1 h, then quenched with saturated aqueous NH₄Cl (10 mL) and extracted with ethyl acetate. The combined organic layers were washed with brine, dried over anhydrous Na₂SO₄, filtered and evaporated. The resulting residue was purified by silica gel column chromatography (petroleum ether (PE):EtOAc=20:1~5:1) to afford the title compound. NMR δ (ppm) (CDCl₃): 4.53 (m, 1H), 4.40 (m, 1H), 4.34 (m, 3H), 4.07 (t, 1H), 3.88 (t, 1H), 3.67 (m, 2H), 2.46 (t, 1H), 0.9 (s, 9H), 0.98 (d, 6H).

Intermediate 17

2-((((3R,3aR,6R,6aS)-6-((tert-butyldimethylsilyl)oxy)hexahydrofuro[3,2-b]furan-3-yl)oxy)methyl)-5-chloro-1H-pyrrolo[3,2-b]pyridine To a solution of tert-butyldimethyl(((3R,3aS,6R,6aR)-6-(prop-2-yn-1-yloxy)hexahydrofuro[3,2-b]furan-3-yl)oxy)silane (235 mg, 0.79 mmol) in 1,2-dichloroethane (3 mL) were added 6-chloro-2-iodopyridin-3-amine (200 mg, 0.79 mmol) and Cu(OAc)₂ (14 mg, 0.079 mmol). The mixture was heated to 150° C. under microwave (MW) and stirred for 30 min. Then the mixture was filtered and concentrated under reduced pressure to give a residue, which was purified by silica gel column chromatography (PE:EtOAc=10:1~3:1) to give the title compound. NMR δ (ppm) (CDCl₃): 9.30 (brs, 1H), 7.48 (d, 1H), 6.98 (d, 1H), 6.41 (s, 1H), 4.75 (q, 2H), 4.32 (m, 2H), 4.22 (m, 1H), 4.03 (m, 1H), 3.85 (m, 2H), 3.63 (m, 2H), 0.80 (s, 9H), 0.00 (d, 6H).

Intermediate 18

5-bromo-2-((((3R,3aR,6R,6aS)-6-((tert-butyldimethylsilyl)oxy)hexahydrofuro[3,2-b]furan-3-yl)oxy)methyl)-6-chloro-1H-pyrrolo[3,2-b]pyridine Step A: 6-bromo-2-(3-(((3R,3aR,6R,6aS)-6-((tert-butyldimethylsilyl)oxy)hexa-hydrofuro[3,2-b]furan-3-yl)oxy)prop-1-yn-1-yl)-5-chloropyridin-3-amine To a solution of 2,6-dibromo-5-chloropyridin-3-amine (1.0 g, 3.5 mmol) in N,N-dimethylformamide (10 mL) were added tert-butyldimethyl(((3R,3aS,6R,6aR)-6-(prop-2-yn-1-yloxy)hexa-hydrofuro[3,2-b]furan-3-yl)oxy)silane (1.3 mg, 4.2 mmol), Pd(PPh₃)₂Cl₂ (245 mg, 0.35 mmol), CuI (67 mg, 0.35 mmol) and Et₃N (530 mg, 5.2 mmol). The mixture was heated to 80° C. under MW and stirred for 30 min. Then the mixture was filtered and concentrated under reduced pressure. The resulting residue was purified by silica gel column chromatography (PE:EtOAc=10:1~3:1) to afford the title compound. NMR δ (ppm) (CDCl₃): 7.05 (s, 1H), 4.52 (m, 1H), 4.50 (m, 1H), 4.45 (m, 1H), 4.20 (m, 1H), 4.31 (m, 1H), 3.66 (m, 1H), 3.64 (M, 2H), 3.62 (m, 1H), 3.55 (m, 1H), 2.50 (m, 2H), 0.80 (s, 9H), 0.00 (d, 6H).

Step B: tert-butyl (6-bromo-2-(3-(((3R,3aR,6R,6aS)-6-((tert-butyldimethylsilyl)oxy)-hexahydrofuro[3,2-b]furan-3-yl)oxy)prop-1-yn-1-yl)-5-chloropyridin-3-yl)carbamate To a mixture of 6-bromo-2-(3-(((3R,3aR,6R,6aS)-6-((tert-butyldimethylsilyl)oxy)hexa-hydrofuro[3,2-b]furan-3-yl)oxy)prop-1-yn-1-yl)-5-chloropyridin-3-amine (800 mg, 1.6 mmol) in dichloromethane (20 mL) were added Et$_3$N (241 mg, 2.4 mmol) and N,N-dimethylpyridin-4-amine (19 mg, 0.16 mmol), followed by di-tert-butyl dicarbonate (416 mg, 1.9 mmol). The mixture was stirred at room temperature for 4 h, then washed with brine, dried over anhydrous Na$_2$SO$_4$, filtered and concentrated under reduced pressure. The resulting residue was purified by silica gel column chromatography (PE:EtOAc=30:1~5:1) to afford the title compound. LC-MS: calculated for C$_{25}$H$_{36}$BrClN$_2$O$_6$Si 602.12, observed m/e: 603.2/605.2 (M+H)$^+$ (Rt 1.87/2 min).

Step C: 5-bromo-2-((((3R,3aR,6R,6aS)-6-((tert-butyldimethylsilyl)oxy)hexahydrofuro-[3,2-b]furan-3-yl)oxy)methyl)-6-chloro-1H-pyrrolo[3,2-b]pyridine A mixture of tert-butyl (6-bromo-2-(3-(((3R,3aR,6R,6aS)-6-((tert-butyldimethylsilyl)oxy)hexahydrofuro-[3,2-b]furan-3-yl)oxy)prop-1-yn-1-yl)-5-chloropyridin-3-yl)carbamate (300 mg, 0.50 mmol) and DBU (151 mg, 1.0 mmol) in methanol (10 mL) was heated to 90° C. under MW and stirred for 30 min. The mixture was concentrated under reduced pressure, and the resulting residue was purified by silica gel column chromatography (PE:EtOAc=10:1~1:1) to afford the title compound.

Intermediate 19

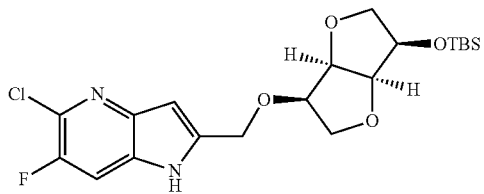 [SMILES: CC(C)(C)[Si](C)(C)O[C@@H]1CO[C@H]2[C@@H]1OC[C@H]2OCc1cc2nc(Cl)c(F)cc2[nH]1]

2-((((3R,3aR,6R,6aS)-6-((tert-butyldimethylsilyl)oxy)hexahydrofuro[3,2-b]furan-3-yl)oxy)methyl)-5-chloro-6-fluoro-1H-pyrrolo[3,2-b]pyridine

Step A: tert-butyl (2-(3-(((3R,3aR,6R,6aS)-6-((tert-butyldimethylsilyl)oxy)-hexahydrofuro[3,2-b]furan-3-yl)oxy)prop-1-yn-1-yl)-6-chloro-5-fluoropyridin-3-yl)carbamate To a solution of tert-butyl (2,6-dichloro-5-fluoropyridin-3-yl)carbamate (1.0 g, 3.6 mmol) in N,N-dimethylacetamide (10 mL) were added tert-butyldimethyl-(((3R,3aS,6R,6aR)-6-(prop-2-yn-1-yloxy)hexahydrofuro[3,2-b]furan-3-yl)oxy) silane (1.3 g, 4.3 mmol), DTBPF.PdCl$_2$ (242 mg, 0.36 mmol) and N-cyclohexyl-N-methylcyclohexanamine (1.0 g, 5.3 mmol). The mixture was heated to 60° C. under MW and stirred for 30 min. Then the mixture was filtered and concentrated under reduced pressure, and the resulting residue was purified by silica gel column chromatography (PE:EtOAc=10:1~3:1) to afford the title compound.

Step B: 2-((((3R,3aR,6R,6aS)-6-((tert-butyldimethylsilyl)oxy)hexahydrofuro[3,2-b]furan-3-yl)oxy)methyl)-5-chloro-6-fluoro-1H-pyrrolo[3,2-b]pyridine A mixture of tert-butyl (2-(3-(((3R,3aR,6R,6aS)-6-((tert-butyldimethylsilyl)oxy)hexahydrofuro[3,2-b]furan-3-yl)oxy)prop-1-yn-1-yl)-6-chloro-5-fluoropyridin-3-yl)carbamate (400 mg, 0.74 mmol) and DBU (224 mg, 1.5 mmol) in methanol (10 mL) was heated to 90° C. under MW and stirred for 30 min. Then the mixture was filtered and concentrated under reduced pressure, and the resulting residue was purified by silica gel column chromatography (PE:EtOAc=10:1~1:1) to afford the title compound. LC-MS: calculated for C$_{20}$H$_{28}$ClFN$_2$O$_4$Si 442.15, observed m/e: 443.0 (M+H)$^+$ (Rt 1.36/2 min).

Intermediate 20

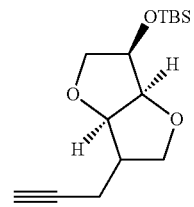 [SMILES: C#CCC1CO[C@H]2[C@@H]1OC[C@H]2O[Si](C)(C)C(C)(C)C]

tert-butyldimethyl(((3R,3aS,6aR)-6-(prop-2-yn-1-yl)hexahydrofuro[3,2-b]furan-3-yl)oxy)silane

Step A: ethyl 2-((3aR,6R,6aS)-6-((tert-butyldimethylsilyl)oxy)hexahydrofuro[3,2-b]furan-3-yl)acetate To a solution of ethyl 2-((3aR,6R,6aR)-6-hydroxyhexahydro-furo[3,2-b]furan-3-yl)acetate (20.0 g, 93 mmol) in DMF (100 mL) were added imidazole (9.4 g, 139 mmol) and tert-butylchlorodimethylsilane (16.7 g, 111 mmol). The mixture was heated to 40° C. and stirred for 4 h. Then the mixture was diluted with EtOAc (1 L), it was washed with brine, dried over anhydrous Na$_2$SO$_4$, filtered and concentrated to give the crude product, which was purified by silica gel column chromatography (PE:EtOAc=20:1~50:1) to afford the title compound. NMR δ (ppm) (CDCl$_3$): 4.43 (m, 1H), 4.31 (m, 1H), 4.18 (m, 1H), 4.01 (m, 3H), 3.67 (m, 1H), 3.42 (m, 2H), 2.51 (m, 2H), 2.33 (m, 1H), 1.15 (t, 3H), 0.80 (s, 9H), 0.00 d, 6H).

Step B: 2-((3aR,6R,6aS)-6-((tert-butyldimethylsilyl)oxy)hexahydrofuro[3,2-b]furan-3-yl)ethanol Aluminum(III) lithium hydride (5.1 g, 133 mmol) was carefully added to a solution of ethyl 2-((3aR,6R,6aS)-6-((tert-butyldimethylsilyl)oxy)hexahydrofuro[3,2-b]furan-3-yl)acetate (22.0 g, 67 mmol) in anhydrous THF (200 mL) at 0° C. The mixture was stirred at the room temperature for 2 h, then cooled to 0° C. Water (5 mL), 15% NaOH aq. (5 mL) and H$_2$O (15 mL) were added to the reaction and the mixture was stirred for 30 min at room temperature. Then anhydrous MgSO$_4$ (30 g) was added, and the mixture was filtered, and the filtrate was concentrated to afford the title compound, which was used in the next step without further purification.

NMR δ (ppm) (CDCl₃): 4.40 (m, 1H), 4.31 (m, 1H), 4.22 (m, 1H), 3.94 (m, 1H), 3.65 (m, 4H), 3.42 (m, 2H), 2.21 (br, 1H), 1.78 (m, 1H), 1.69 (m, 1H), 1.52 (m, 2H), 0.80 (s, 9H), 0.00 (d, 6H).

Step C: 2-((3aR,6R,6aS)-6-((tert-butyldimethylsilyl)oxy)hexahydrofuro[3,2-b]furan-3-yl)acetaldehyde DMSO (19.5 g, 250 mmol) was added dropwise to a solution of (COCl)₂ (15.8 g, 125 mmol) in anhydrous DCM (200 mL) at −78° C. The mixture was stirred at −78° C. for 30 min, then a solution of 2-((3aR,6R,6aS)-6-((tert-butyldimethylsilyl)-oxy)hexahydrofuro[3,2-b]furan-3-yl)ethanol (18.0 g, 62 mmol) in DCM (50 mL) was added slowly, and the reaction mixture was stirred at −78° C. for 1 h. Then Et₃N (50.5 g, 499 mmol) was added dropwise, and the reaction mixture was stirred at −30° C. for 1 h. The mixture was then washed with brine, dried over Na₂SO₄ and concentrated to afford the title compound, which was used in the next step without further purification. NMR δ (ppm) (CDCl₃): 9.63 (s, 1H), 4.37 (m, 1H), 4.31 (m, 1H), 4.22 (m, 1H), 3.88 (m, 1H), 3.61 (m, 1H), 2.66 (m, 1H), 0.80 (s, 9H), 0.00 (d, 6H).

Step D: 2-((3aR,6R,6aS)-6-((tert-butyldimethylsilyl)oxy)hexahydrofuro[3,2-b]furan-3-yl)ethanol To a solution of PPh₃ (42.1 g, 161 mmol) in anhydrous DCM (500 mL) was added CBr₄ (26.6 g, 80 mmol) at 0° C., and the mixture was stirred at 0° C. for 30 min. Then 2-((3aR,6R,6aS)-6-((tert-butyldimethylsilyl)oxy)hexahydrofuro[3,2-b]furan-3-yl)-acetaldehyde (11.5 g, 40 mmol) was added, and the reaction was stirred at room temperature for 2 h. The reaction mixture was then washed with brine, dried over Na₂SO₄ and evaporated. The resulting residue was purified by silica gel column chromatography (PE:EtOAc=20:1~5:1) to afford the title compound. NMR δ (ppm) (CDCl₃): 6.37 (t, 1H), 4.33 (m, 2H), 4.17 (m, 1H), 3.93 (m, 1H), 3.68 (m, 1H), 3.41 (m, 2H), 2.20 (m, 2H), 0.80 (s, 9H), 0.00 d, 6H).

Step E: tert-butyldimethyl(((3R,3aS,6aR)-6-(prop-2-yn-1-yl)hexahydrofuro[3,2-b]furan-3-yl)oxy)silane To a solution of 2-((3aR,6R,6aS)-6-((tert-butyldimethylsilyl)oxy)-hexahydrofuro[3,2-b]furan-3-yl)ethanol (8.5 g, 19 mmol) in EtOAc (5 mL) was added n-BuLi (16.9 mL, 42 mmol, 2.5 M in hexane) at −78° C. and the reaction mixture was stirred at −78° C. for 1 h. The mixture was then quenched with saturated aqueous NH₄Cl, and extracted with EtOAc. The combined organic layers were washed with brine, dried over anhydrous Na₂SO₄, filtered and evaporated. The resulting residue was purified by silica gel column chromatography (PE:EtOAc=20:1~5:1) to afford the title compound. NMR δ (ppm) (CDCl₃): 4.40 (m, 1H), 4.32 (m, 1H), 4.19 (m, 1H), 3.97 (m, 1H), 3.71 (m, 1H), 3.46 (m, 2H), 2.35 (m, 2H), 2.23 (m, 1H), 1.84 (m, 1H), 0.80 (s, 9H), 0.00 (d, 6H).

Intermediate 21

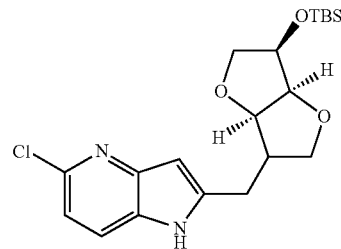 [SMILES: CC(C)(C)[Si](C)(C)O[C@@H]1CO[C@@H]2C(Cc3cc4nc(Cl)ccc4[nH]3)CO[C@@H]21]

tert-butyldimethyl(((3R,3aS,6aR)-6-(prop-2-yn-1-yl)hexahydrofuro[3,2-b]furan-3-yl)oxy)silane To a solution of tert-butyldimethyl(((3R,3aS,6aR)-6-(prop-2-yn-1-yl)hexahydrofuro[3,2-b]furan-3-yl)oxy)silane (555 mg, 2.0 mmol, Intermediate 20) in 1,2-dichloroethane (10 mL) were added 6-chloro-2-iodopyridin-3-amine (500 mg, 2.0 mmol) and Cu(OAc)₂ (36 mg, 0.20 mmol). The mixture was heated to 150° C. under MW and stirred for 30 min. Then the mixture was filtered and concentrated under reduced pressure to give a residue, which was purified by silica gel column chromatography (PE:EtOAc=20:1~3:1) to afford the title compound. NMR δ (ppm) (CDCl₃): 8.93 (brs, 1H), 7.41 (d, 1H), 6.92 (d, 1H), 6.29 (s, 1H), 4.34 (m, 1H), 4.30 (m, 1H), 4.23 (m, 1H), 3.97 (m, 1H), 3.78 (m, 1H), 3.65 (m, 1H), 3.51 (m, 1H), 2.84 (m, 2H), 2.39 (m, 1H), 0.80 (s, 9H), 0.01 (d, 6H).

Intermediate 22

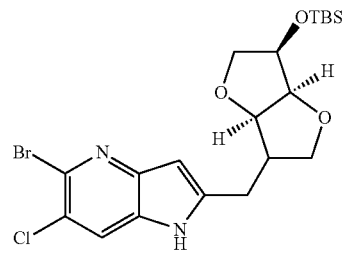

5-bromo-2-(((3aR,6R,6aS)-6-((tert-butyldimethylsilyl)oxy)hexahydrofuro[3,2-b]furan-3-yl)methyl)-6-chloro-1H-pyrrolo[3,2-b]pyridine Step A: 6-bromo-2-(3-((3aR,6R,6aS)-6-((tert-butyldimethylsilyl)oxy)hexahydrofuro[3,2-b]furan-3-yl)prop-1-yn-1-yl)-5-chloropyridin-3-amine To a solution of 2,6-dibromo-5-chloropyridin-3-amine (500 mg, 1.7 mmol) in THF (10 mL) were added tert-butyldimethyl(((3R,3aS,6aR)-6-(prop-2-yn-1-yl)hexahydrofuro[3,2-b]furan-3-yl)oxy)silane (591 mg, 2.1 mmol), Pd(PPh₃)₂Cl₂ (123 mg, 0.17 mmol), CuI (33 mg, 0.17 mmol) and triethylamine (265 mg, 2.6 mmol). Then the mixture was stirred at room temperature for 2 h, filtered and concentrated under reduced pressure. The resulting residue was purified by silica gel column chromatography (PE:EtOAc=20:1~5:1) to afford the title compound. NMR δ

(ppm) (CDCl₃): 6.96 (s, 1H), 4.45 (m, 1H), 4.33 (m, 1H), 4.26 (m, 2H), 4.23 (m, 1H), 3.99 (m, 1H), 3.68 (m, 1H), 3.50 (M, 2H), 3.38 (m, 1H), 2.65 (m, 1H), 2.50 (m, 2H), 0.80 (s, 9H), 0.00 (d, 6H).

Step B: tert-butyl (6-bromo-2-(3-((3aR,6R,6aS)-6-((tert-butyldimethylsilyl)oxy)hexahydrofuro[3,2-b]furan-3-yl)prop-1-yn-1-yl)-5-chloropyridin-3-yl) carbamate To a solution of 6-bromo-2-(3-((3aR,6R,6aS)-6-((tert-butyldimethyl-silyl)oxy)hexahydrofuro[3,2-b]furan-3-yl)prop-1-yn-1-yl)-5-chloropyridin-3-amine (500 mg, 1.0 mmol) in dichloromethane (20 mL) were added Et₃N (156 mg, 1.5 mmol) and N,N-dimethylpyridin-4-amine (13 mg, 0.10 mmol), followed by di-tert-butyl dicarbonate (268 mg, 1.2 mmol). The mixture was stirred at room temperature for 4 h, then washed with brine, dried over anhydrous Na₂SO₄, filtered and concentrated under reduced pressure. The resulting residue was purified by silica gel column chromatography (PE:EtOAc=20:1~5:1) to afford the title compound.

Step C: 5-bromo-2-(((3aR,6R,6aS)-6-((tert-butyldimethylsilyl)oxy)hexahydrofuro[3,2-b]furan-3-yl)methyl)-6-chloro-1H-pyrrolo[3,2-b]pyridine The mixture of tert-butyl (6-bromo-2-(3-((3aR,6R,6aS)-6-((tert-butyldimethylsilyl)oxy)hexahydrofuro[3,2-b]furan-3-yl)prop-1-yn-1-yl)-5-chloropyridin-3-yl)carbamate (500 mg, 0.85 mmol) and DBU (259 mg, 1.7 mmol) in methanol (10 mL) was heated to 65° C. under MW and stirred for 30 min. The mixture was then concentrated under reduced pressure and the resulting residue was purified by silica gel column chromatography (PE:EtOAc=10:1~1:1) to afford the title compound.

Intermediate 23

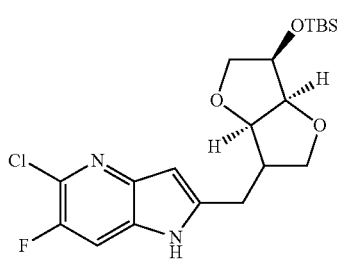 [SMILES: CC(C)(C)[Si](C)(C)O[C@@H]1CO[C@@H]2C(Cc3cc4nc(Cl)c(F)cc4[nH]3)CO[C@@H]21]

2-(((3aR,6R,6aS)-6-((tert-butyldimethylsilyl)oxy) hexahydrofuro[3,2-b]furan-3-yl)methyl)-5-chloro-6-fluoro-1H-pyrrolo[3,2-b]pyridine Step A: tert-butyl (2-(3-((3aR,6R,6aS)-6-((tert-butyldimethylsilyl)oxy)hexa-hydrofuro[3,2-b]furan-3-yl)prop-1-yn-1-yl)-6-chloro-5-fluoropyridin-3-yl) carbamate To a solution of tert-butyl (2,6-dichloro-5-fluoropyridin-3-yl)carbamate (500 mg, 1.8 mmol) in N,N-dimethylacetamide (10 mL) were added tert-butyldimethyl(((3R,3aS,6aR)-6-(prop-2-yn-1-yl)hexa-hydrofuro[3,2-b]furan-3-yl)oxy)silane (603 mg, 2.1 mmol), DTBPF.PdCl₂ (121 mg, 0.18 mmol), CuI (54 mg, 0.28 mmol) and N-cyclohexyl-N-methylcyclohexanamine (521 mg, 2.7 mmol). The mixture was heated to 90° C. under MW and stirred for 30 min. Then the mixture was filtered and concentrated under reduced pressure. The resulting residue was purified by silica gel column chromatography (PE:EtOAc=10:1~3:1) to afford the title compound.

Step B: 2-(((3aR,6R,6aS)-6-((tert-butyldimethylsilyl)oxy)hexahydrofuro[3,2-b]furan-3-yl)methyl)-5-chloro-6-fluoro-1H-pyrrolo[3,2-b]pyridine A mixture of tert-butyl (2-(3-((3aR,6R,6aS)-6-((tert-butyldimethylsilyl)oxy)hexahydrofuro[3,2-b]furan-3-yl)prop-1-yn-1-yl)-6-chloro-5-fluoropyridin-3-yl)carbamate (400 mg, 0.76 mmol) and DBU (231 mg, 1.5 mmol) in methanol (10 mL) was heated to 90° C. under MW and stirred for 30 min. Then the mixture was concentrated under reduced pressure and the resulting residue was purified by silica gel column chromatography (PE:EtOAc=10:1~1:1) to afford the title compound. LC-MS: calculated for $C_{20}H_{28}ClFN_2O_3Si$ 426.15, observed m/e: 427.2 (M+H)⁺ (Rt 1.52/2 min).

SCHEME 9

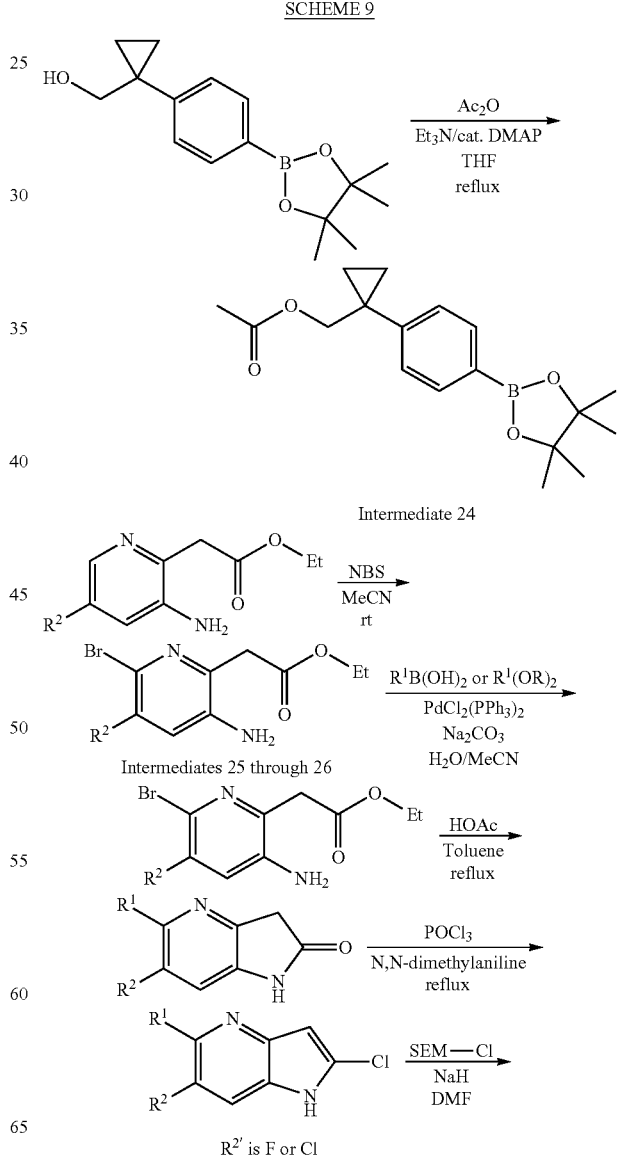

Intermediate 24

R² is F or Cl

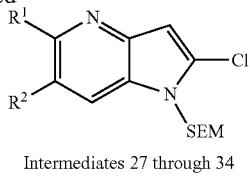

Intermediates 27 through 34

Intermediate 24

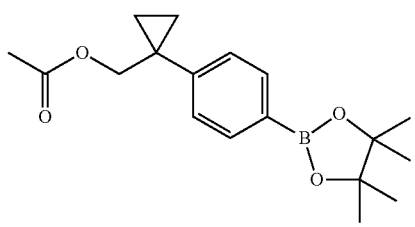 [SMILES: CC(=O)OCC1(c2ccc(B3OC(C)(C)C(C)(C)O3)cc2)CC1]

(1-(4-(4,4,5,5-tetramethyl-1,3,2-dioxaborolan-2-yl)phenyl)cyclopropyl)methyl acetate A mixture of (1-(4-(4,4,5,5-tetramethyl-1,3,2-dioxaborolan-2-yl)phenyl)cyclopropyl)-methanol (16 g, 0.088 mol), Ac$_2$O (26.5 g, 0.26 mol), TEA (35.5 g, 0.352 mol) and DMAP (2.14 g, 0.0176 mol) in THF (160 ml) was stirred at 80° C. for 16 h. Then the reaction was concentrated and the crude product was purified via silica gel (PE:EA=50:1-3:1) to give the title compound. NMR δ (ppm) (CDCl$_3$): 7.75 (d, 2H), 7.31 (d, 2H), 4.18 (s, 2H), 2.00 (s, 3H), 1.26 (s, 12H), 0.95 (m, 4H).

Intermediate 25

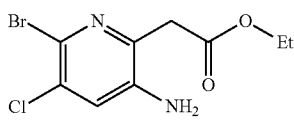 [SMILES: CCOC(=O)Cc1nc(Br)c(Cl)cc1N]

Ethyl 2-(3-amino-6-bromo-5-chloropyridin-2-yl)acetate

To a mixture of ethyl 2-(3-amino-5-chloropyridin-2-yl)acetate (30 g, 0.14 mol) in CH$_3$CN (500 mL) was added NBS (24.9 g, 0.14 mol) at 0° C. and the mixture was stirred for 1 h at 0° C. Then the reaction was diluted with CH$_3$CN, washed with brine, dried over anhydrous Na$_2$SO$_4$, filtered and concentrated under reduced pressure. The resulting residue was purified by silica gel column chromatography (PE:EtOAc=30:1~3:1) to afford the title compound. NMR δ (ppm) (CDCl$_3$): 7.20 (s, 1H), 4.15 (q, 2H), 3.69 (s, 2H), 1.24 (t, 3H).

TABLE 6

Compounds prepared according to the methods described in Intermediate 25.

| Example Number | Structure | HPLC-mass spectrum m/e |
|---|---|---|
| Intermediate 26 | 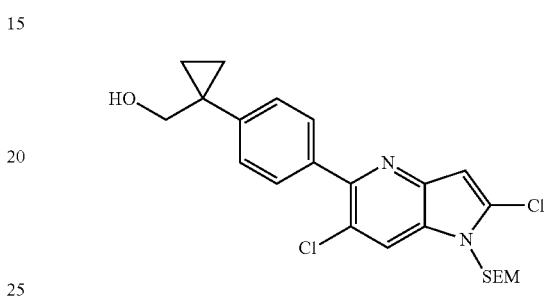 | 277.0/279.0 |

Intermediate 27

(1-(4-(2,6-dichloro-1-((2-(trimethylsilyl)ethoxy)methyl)-1H-pyrrolo[3,2-b]pyridin-5-yl)phenyl)cyclopropyl)methanol Step A: ethyl 2-(6-(4-(1-(acetoxymethyl)cyclopropyl)phenyl)-3-amino-5-chloropyridin-2-yl)acetate A mixture of ethyl 2-(3-amino-6-bromo-5-chloropyridin-2-yl)acetate (1.0 g, 3.4 mmol), (1-(4-(4,4,5,5-tetramethyl-1,3,2-dioxaborolan-2-yl)phenyl)cyclopropyl)-methyl acetate (1.3 g, 4.1 mmol), Pd(PPh$_3$)$_2$Cl$_2$ (239 mg, 0.34 mmol) and Na$_2$CO$_3$ (542 mg, 5.1 mmol) in MeCN (30 mL)/H$_2$O (3 mL) was heated to 100° C. under MW and stirred for 30 min. Then the mixture was extracted with EtOAc. The combined organic layers were washed with brine, dried over anhydrous Na$_2$SO$_4$, filtered and concentrated under reduced pressure. The resulting residue was purified by silica gel column chromatography (PE:EtOAc=10:1~2:1) to afford the title compound. NMR δ (ppm) (CDCl$_3$): 7.61 (d, 2H), 7.35 (d, 2H), 7.10 (s, 1H), 4.17 (m, 4H), 3.85 (s, 2H), 2.03 (s, 3H), 1.25 (t, 3H), 0.95 (m, 4H).

Step B: (1-(4-(6-chloro-2-oxo-2,3-dihydro-1H-pyrrolo[3,2-b]pyridin-5-yl)phenyl)-cyclopropyl)methyl acetate To a suspension of ethyl 2-(6-(4-(1-(acetoxymethyl)cyclo-propyl)phenyl)-3-amino-5-chloropyridin-2-yl)acetate (800 mg, 2.0 mmol) in toluene (20 mL) was added acetic acid (238 mg, 4.0 mmol), and the reaction was heated to reflux for 4 h. The reaction was cooled to rt and the solvents were removed under reduced pressure. The resulting residue was suspended in toluene (20 mL), filtered, washed with diethyl ether and dried to give the title compound. NMR δ (ppm) (CDCl$_3$): 8.19 (s, 1H), 7.60 (d, 2H), 7.39 (d, 2H), 7.26 (s, 1H), 4.20 (s, 2H), 3.70 (s, 2H), 2.03 (s, 3H), 0.98 (d, 4H).

Step C: (1-(4-(2,6-dichloro-1H-pyrrolo[3,2-b]pyridin-5-yl)phenyl)cyclopropyl)methyl acetate To a mixture of (1-(4-(6-chloro-2-oxo-2,3-dihydro-1H-pyrrolo[3,2-b]pyridin-5-yl)phenyl)cyclopropyl)methyl acetate (400 mg, 1.1 mmol) in phosphoryl trichloride (10 mL) was added N,N-dimethylaniline (272 mg, 2.2 mmol). The mixture was heated to reflux and stirred for 1 h, then evaporated under vacuum. The resulting residue was dissolved in water, and the resulting mixture was adjusted to pH=8 with saturated NaHCO$_3$, and extracted with ethyl acetate. The combined organic layers were washed with brine, dried over anhydrous Na$_2$SO$_4$, filtered and concentrated under reduced pressure. The resulting residue was purified by silica gel column chromatography (PE:EtOAc=20:1~3:1) to afford the title compound. NMR δ (ppm) (CDCl$_3$): 8.29 (s, 1H), 7.69 (s, 1H), 7.29 (d, 2H), 7.40 (d, 2H), 6.66 (s, 1H), 4.20 (s, 2H), 2.04 (s, 3H), 0.98 (q, 4H).

Step D (1-(4-(2,6-dichloro-1-((2-(trimethylsilyl)ethoxy)methyl)-1H-pyrrolo[3,2-b]pyridin-5-yl)phenyl)cyclopropyl)methanol Sodium hydride (13 mg, 0.32 mmol) was added to a solution of (1-(4-(2,6-dichloro-1H-pyrrolo[3,2-b]pyridin-5-yl)phenyl)cyclo-propyl)methyl acetate (100 mg, 0.27 mmol) in N,N-dimethylformamide (5 mL) at 0° C. and the mixture was stirred at 0° C. for 30 min. Then (2-(chloromethoxy)ethyl)trimethyl-silane (53 mg, 0.32 mmol) was added to the reaction. The reaction was warmed to room temperature for 1 h, then quenched with saturated NH$_4$Cl, and extracted with ethyl acetate. The combined organic layers were washed with brine, dried over anhydrous Na$_2$SO$_4$, filtered and concentrated under reduced pressure. The resulting residue was purified by silica gel column chromatography (PE:EtOAc=30:1~5:1) to afford the title compound. NMR δ (ppm) (CDCl$_3$): 7.85 (s, 1H), 7.66 (d, 2H), 7.46 (d, 2H), 6.70 (s, 1H), 5.56 (s, 2H), 3.72 (d, 2H), 3.57 (t, 2H), 0.93 (m, 6H), 0.00 (s, 9H). LC-MS: calculated for C$_{23}$H$_{28}$Cl$_2$N$_2$O$_2$Si 462.13, observed m/e: 463.2 (M+H)$^+$ (Rt 1.43/2 min).

TABLE 7

Compounds prepared according to the methods described in Intermediate 27.

| Example Number | Structure | HPLC-mass spectrum m/e |
|---|---|---|
| Intermediate 28 | 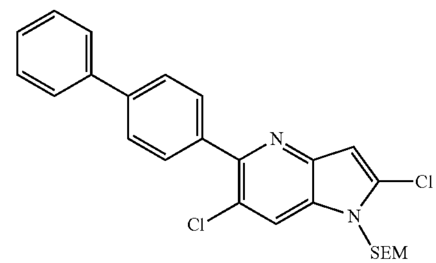 | 469.2 |
| Intermediate 29 | 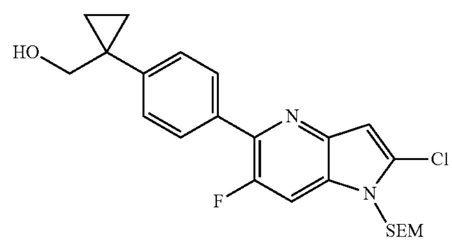 [SMILES: C[Si](C)(C)CCOCn1c(Cl)cc2nc(-c3ccc(C4(CO)CC4)cc3)c(Cl)cc21] | 447.1 |
| Intermediate 30 | 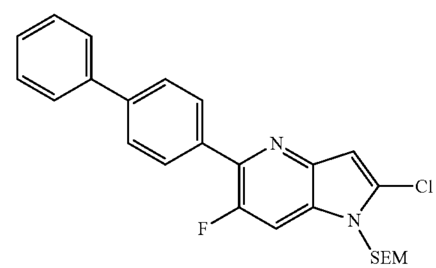 [SMILES: C[Si](C)(C)CCOCn1c(Cl)cc2nc(-c3ccc(-c4ccccc4)cc3)c(F)cc21] | 453.2 |
| Intermediate 31 | 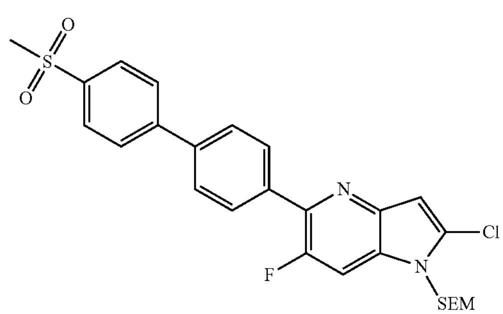 [SMILES: C[Si](C)(C)CCOCn1c(Cl)cc2nc(-c3ccc(-c4ccc(S(C)(=O)=O)cc4)cc3)c(F)cc21] | 531.1 |

TABLE 7-continued

Compounds prepared according to the methods described in Intermediate 27.

| Example Number | Structure | HPLC-mass spectrum m/e |
|---|---|---|
| Intermediate 32 | 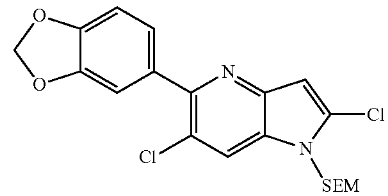 [SMILES: C[Si](C)(C)CCOCn1c(Cl)cc2nc(-c3ccc4c(c3)OCO4)c(Cl)cc21] | 437.1 |
| Intermediate 33 | 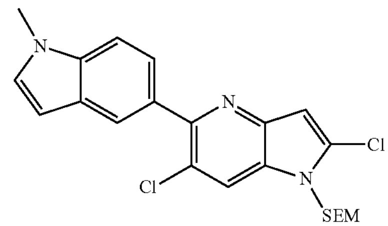 [SMILES: Cn1ccc2cc(-c3nc4cc(Cl)n(COCC[Si](C)(C)C)c4cc3Cl)ccc21] | 446.1 |
| Intermediate 34 | 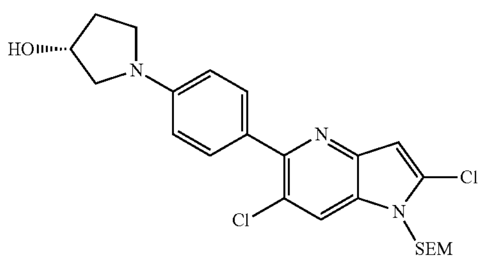 [SMILES: C[Si](C)(C)CCOCn1c(Cl)cc2nc(-c3ccc(N4CC[C@@H](O)C4)cc3)c(Cl)cc21] | 478.1 |

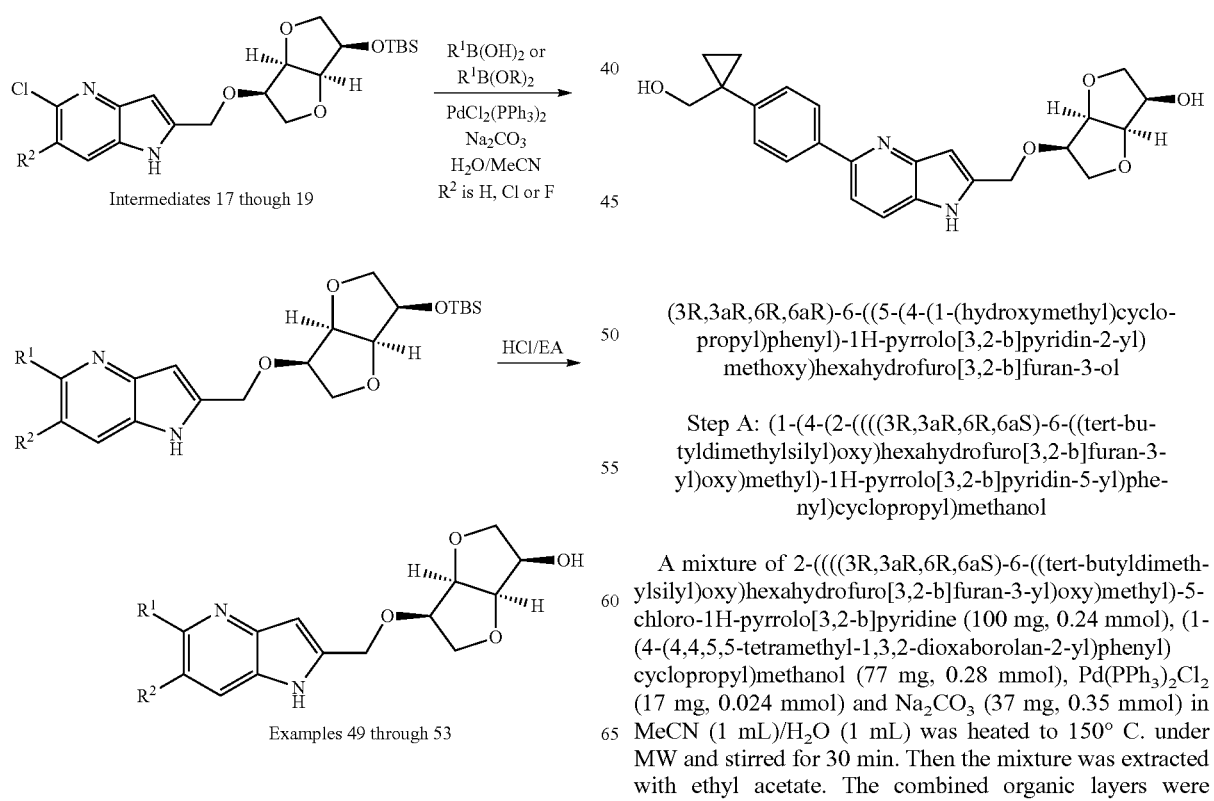

SCHEME 10

Intermediates 17 though 19

Examples 49 through 53

Example 49

(3R,3aR,6R,6aR)-6-((5-(4-(1-(hydroxymethyl)cyclopropyl)phenyl)-1H-pyrrolo[3,2-b]pyridin-2-yl)methoxy)hexahydrofuro[3,2-b]furan-3-ol Step A: (1-(4-(2-((((3R,3aR,6R,6aS)-6-((tert-butyldimethylsilyl)oxy)hexahydrofuro[3,2-b]furan-3-yl)oxy)methyl)-1H-pyrrolo[3,2-b]pyridin-5-yl)phenyl)cyclopropyl)methanol A mixture of 2-((((3R,3aR,6R,6aS)-6-((tert-butyldimethylsilyl)oxy)hexahydrofuro[3,2-b]furan-3-yl)oxy)methyl)-5-chloro-1H-pyrrolo[3,2-b]pyridine (100 mg, 0.24 mmol), (1-(4-(4,4,5,5-tetramethyl-1,3,2-dioxaborolan-2-yl)phenyl)cyclopropyl)methanol (77 mg, 0.28 mmol), Pd(PPh$_3$)$_2$Cl$_2$ (17 mg, 0.024 mmol) and Na$_2$CO$_3$ (37 mg, 0.35 mmol) in MeCN (1 mL)/H$_2$O (1 mL) was heated to 150° C. under MW and stirred for 30 min. Then the mixture was extracted with ethyl acetate. The combined organic layers were washed with brine, dried over anhydrous Na₂SO₄, filtered and concentrated to give the crude product, which was purified by silica gel column chromatography (PE: EtOAc=20:1~3:1) to afford the title compound. NMR δ (ppm) (CDCl₃): 9.09 (brs, 1H), 7.88 (d, 2H), 7.62 (d, 1H), 7.45 (d, 1H), 7.39 (d, 2H), 6.61 (s, 1H), 4.80 (m, 2H), 4.35 (m, 1H), 4.30 (m, 1H), 4.26 (m, 1H), 4.07 (m, 1H), 3.97 (m, 1H), 3.85 (m, 1H), 3.66 (m, 4H), 0.84 (m, 13H), 0.03 (d, 6H).

by prep. HPLC to afford the title compound. NMR δ (ppm) (CDCl₃): 8.50 (d, 1H), 7.88 (m, 3H), 7.66 (d, 2H), 6.85 (s, 1H), 5.08 (m, 1H), 4.71 (m, 1H), 4.49 (m, 1H), 4.31 (m, 2H), 4.08 (m, 1H), 3.98 (m, 1H), 3.80 (m, 1H), 3.75 (m, 2H), 3.65 (m, 1H), 0.98 (m, 4H). LC-MS: calculated for $C_{24}H_{26}N_2O_5$ 422.18, observed m/e: 423.2 (M+H)⁺ (Rt 2.22/4 min).

TABLE 8

Compounds prepared according to the methods described in Example 49.

| Example Number | Structure | PLC-mass spectrum m/e |
|---|---|---|
| 50 | 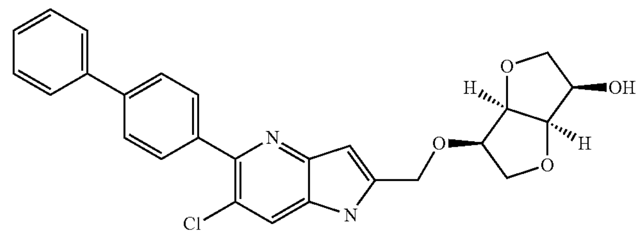 [SMILES: O[C@@H]1CO[C@H]2[C@@H]1OC[C@H]2OCc1cc2nc(-c3ccc(-c4ccccc4)cc3)c(Cl)cc2[nH]1] | 463.1 |
| 51 | 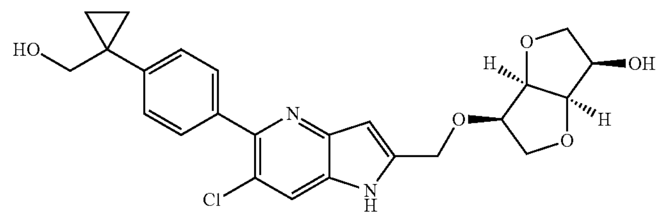 [SMILES: OCC1(c2ccc(-c3nc4cc(CO[C@@H]5CO[C@H]6[C@@H]5OC[C@H]6O)[nH]c4cc3Cl)cc2)CC1] | 457.1 |
| 52 | 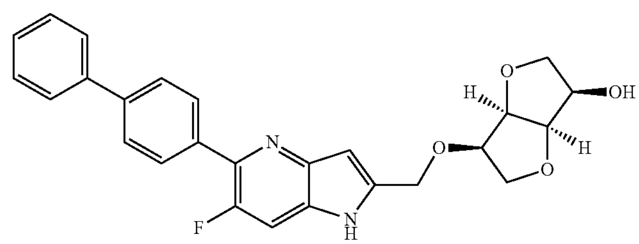 [SMILES: O[C@@H]1CO[C@H]2[C@@H]1OC[C@H]2OCc1cc2nc(-c3ccc(-c4ccccc4)cc3)c(F)cc2[nH]1] | 447.2 |
| 53 | 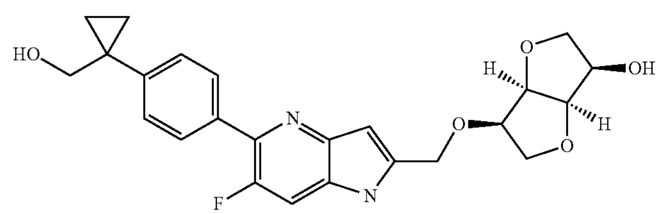 [SMILES: OCC1(c2ccc(-c3nc4cc(CO[C@@H]5CO[C@H]6[C@@H]5OC[C@H]6O)[nH]c4cc3F)cc2)CC1] | 441.2 |

Step B: (3R,3aR,6R,6aR)-6-((5-(4-(1-(hydroxymethyl)cyclopropyl)phenyl)-1H-pyrrolo[3,2-b]pyridin-2-yl)methoxy)hexahydrofuro[3,2-b]furan-3-ol 4 M HCl/EtOAc (1 mL) was added to a mixture of (1-(4-(2-(((((3R,3aR,6R,6aS)-6-((tert-butyldimethyl-silyl)oxy) hexa-hydrofuro[3,2-b]furan-3-yl)oxy)methyl)-1H-pyrrolo[3,2-b]pyridin-5-yl)phenyl)cyclo-propyl)methanol (70 mg, 0.13 mmol) in EtOAc (5 mL) at 0° C. The reaction mixture was stirred at 0° C. for 30 min, then concentrated under reduced pressure. The resulting residue was purified

SCHEME 11

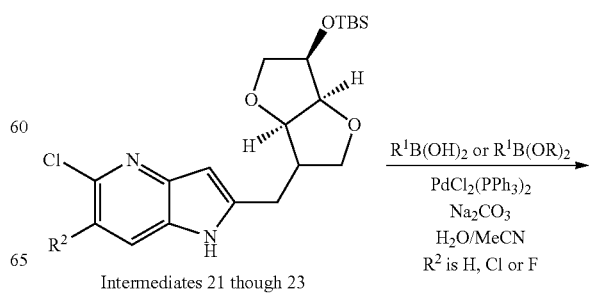

Intermediates 21 though 23

-continued

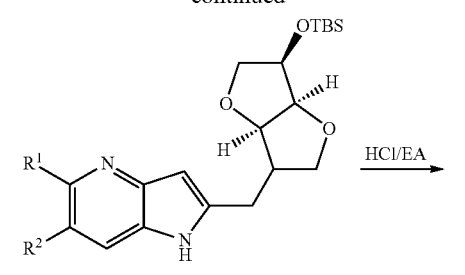

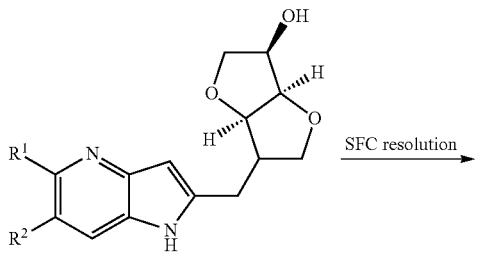

Examples 54 through 55

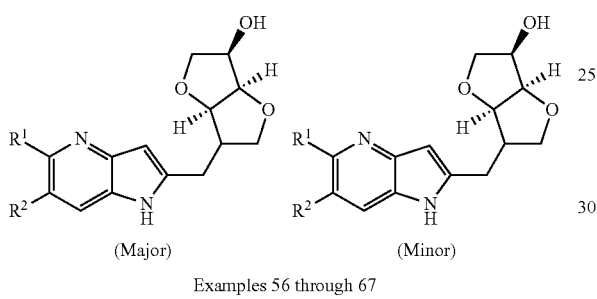

(Major)       (Minor)

Examples 56 through 67

Examples 54, 56, 57

Examples 54

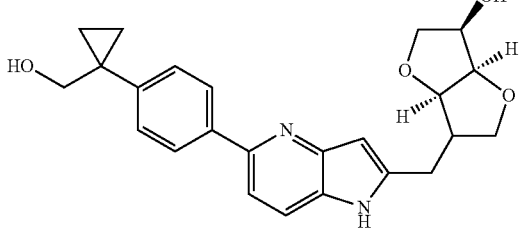

Examples 56

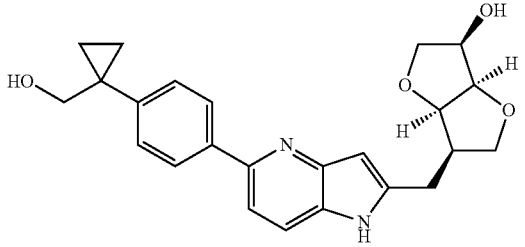

-continued

Examples 57

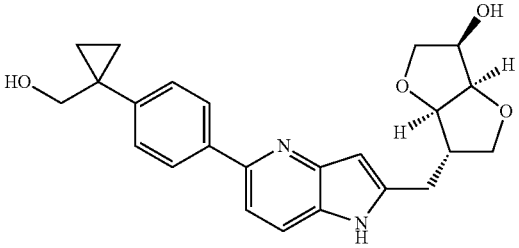

(3R,3aR,6aR)-6-((5-(4-(1-(hydroxymethyl)cyclopropyl)phenyl)-1H-pyrrolo[3,2-b]pyridin-2-yl)methyl)hexahydrofuro[3,2-b]furan-3-ol; (3R,3aR,6R,6aR)-6-((5-(4-(1-(hydroxymethyl)-cyclopropyl)phenyl)-1H-pyrrolo[3,2-b]pyridin-2-yl)methyl)hexahydrofuro[3,2-b]furan-3-ol; and (3R,3aR,6S,6aR)-6-((5-(4-(1-(hydroxymethyl)cyclopropyl)-phenyl)-1H-pyrrolo[3,2-b]pyridin-2-yl)methyl)hexahydrofuro[3,2-b]furan-3-ol Step A: (1-(4-(2-(((3aR,6R,6aS)-6-((tert-butyldimethylsilyl)oxy)hexahydrofuro[3,2-b]furan-3-yl)methyl)-1H-pyrrolo[3,2-b]pyridin-5-yl)phenyl)cyclopropyl)methanol A mixture of 2-(((3aR,6R,6aS)-6-((tert-butyldimethylsilyl)oxy)hexahydrofuro[3,2-b]furan-3-yl)methyl)-5-chloro-1H-pyrrolo[3,2-b]pyridine (200 mg, 0.49 mmol), (1-(4-(4,4,5,5-tetramethyl-1,3,2-dioxaborolan-2-yl)phenyl)cyclopropyl)methanol (161 mg, 0.59 mmol), Pd(PPh$_3$)$_2$Cl$_2$ (34 mg, 0.049 mmol) and Na$_2$CO$_3$ (78 mg, 0.73 mmol) in MeCN (2 mL)-H$_2$O (2 mL) was heated to 150° C. under MW and stirred for 30 min. Then the mixture was extracted with ethyl acetate.

The combined organic layers were washed with brine, dried over anhydrous Na$_2$SO$_4$, filtered and evaporated. The resulting residue was purified by silica gel column chromatography (PE:EtOAc=20:1~3:1) to afford the title compound. LC-MS: calculated for C$_{30}$H$_{40}$N$_2$O$_4$Si 520.28, observed m/e: 521.4 (M+H)$^+$ (Rt 1.11/2 min).

Step B: (3R,3aR,6aR)-6-((5-(4-(1-(hydroxymethyl)cyclopropyl)phenyl)-1H-pyrrolo[3,2-b]pyridin-2-yl)methyl)hexahydrofuro[3,2-b]furan-3-ol 4 M HCl/EtOAc (1 mL) was added to a mixture of (1-(4-(2-(((3aR,6R,6aS)-6-((tert-butyldimethylsilyl)oxy)hexa-hydrofuro[3,2-b]furan-3-yl)methyl)-1H-pyrrolo[3,2-b]pyridin-5-yl)phenyl)cyclopropyl)-methanol (110 mg, 0.21 mmol) in EtOAc (5 mL) at 0° C. and the reaction mixture was stirred at 0° C. for 30 min. Then the mixture was concentrated under reduced pressure and the resulting residue was purified by prep-HPLC to give the title compound. NMR δ (ppm) (CDCl$_3$): 8.40 (d, 1H), 7.81 (m, 3H), 7.62 (d, 2H), 6.73 (s, 1H), 4.52 (m, 1H), 4.47 (m, 1H), 4.29 (m, 1H), 4.08 (m, 1H), 3.89 (m, 1H), 3.72 (m, 2H), 3.60 (m, 2H), 3.22 (m, 1H), 3.10 (m, 1H), 2.75 (br, 1H), 0.96 (m, 4H).

Step C: (3R,3aR,6R,6aR)-6-((5-(4-(1-(hydroxymethyl)cyclopropyl)phenyl)-1H-pyrrolo[3,2-b]pyridin-2-yl)methyl)hexahydrofuro[3,2-b]furan-3-ol; and (3R,3aR,6S,6aR)-6-((5-(4-(1-(hydroxymethyl)cyclopropyl)phenyl)-1H-pyrrolo[3,2-b]pyridin-2-yl)methyl)hexahydrofuro[3,2-b]furan-3-ol The mixture of stereoisomers of (3R,3aR,6aR)-6-((5-(4-(1-(hydroxymethyl)cyclopropyl)-phenyl)-1H-pyrrolo[3,2-b]pyridin-2-yl)methyl)hexahydrofuro[3,2-b]furan-3-ol was separated via SFC to afford the title compounds. NMR δ (ppm) (CDCl₃): 7.81 (d, 2H), 7.76 (d, 1H), 7.48 (m, 3H), 6.46 (s, 1H), 4.52 (m, 1H), 4.43 (m, 1H), 4.22 (m, 1H), 4.01 (m, 1H), 3.78 (m, 2H), 3.61 (m, 2H), 2.88 (m, 2H), 2.74 (br, 1H), 0.89 (d, 4H). LC-MS: calculated for C24H26N2O4 406.19, observed m/e: 407.2 (M+H)⁺ (Rt 2.262/4.5 min).

NMR δ (ppm) (CDCl₃): 7.87 (d, 1H), 7.81 (d, 2H), 7.51 (m, 3H), 6.50 (s, 1H), 4.49 (m, 2H), 4.28 (m, 1H), 4.06 (m, 1H), 3.89 (m, 1H), 3.63 (m, 2H), 3.14 (m, 1H), 2.98 (m, 1H), 2.74 (br, 1H), 0.90 (d, 4H). LC-MS: calculated for C24H26N2O4 406.19, observed m/e: 407.2 (M+H)⁺ (Rt 2.258/4.5 min).

TABLE 9

Compounds prepared according to the methods described in Examples 54, 56, 57.

| Example Number | Structure | HPLC-mass spectrum m/e |
|---|---|---|
| 55 | 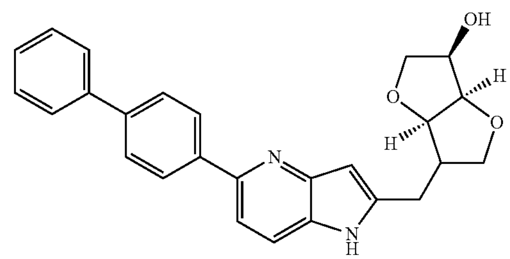 [SMILES: O[C@@H]1CO[C@@H]2C(Cc3cc4nc(-c5ccc(-c6ccccc6)cc5)ccc4[nH]3)CO[C@H]12] | 413.2 |
| 58 | 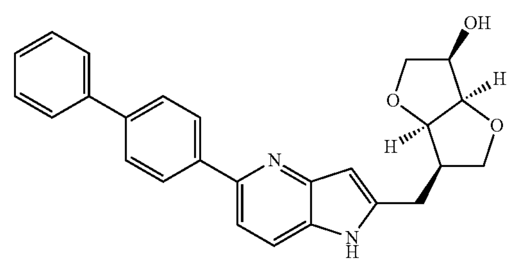 [SMILES: O[C@@H]1CO[C@@H]2[C@H](Cc3cc4nc(-c5ccc(-c6ccccc6)cc5)ccc4[nH]3)CO[C@@H]21] | 413.1 |
| 59 | 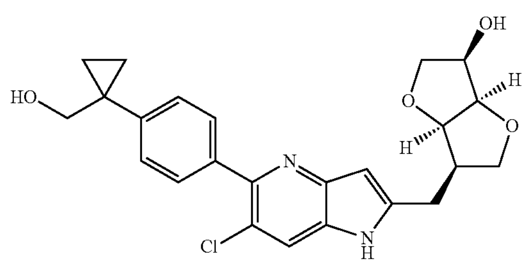 [SMILES: OCC1(c2ccc(-c3nc4cc(C[C@@H]5CO[C@H]6[C@@H]5OC[C@H]6O)[nH]c4cc3Cl)cc2)CC1] | 441.1 |
| 60 | 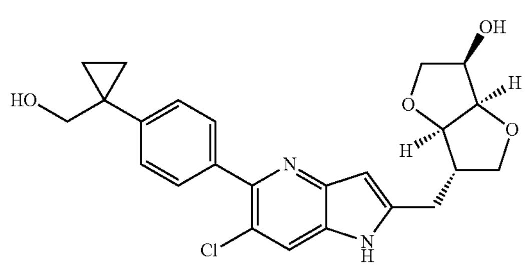 [SMILES: OCC1(c2ccc(-c3nc4cc(C[C@H]5CO[C@H]6[C@@H]5OC[C@H]6O)[nH]c4cc3Cl)cc2)CC1] | 441.1 |
| 61 | 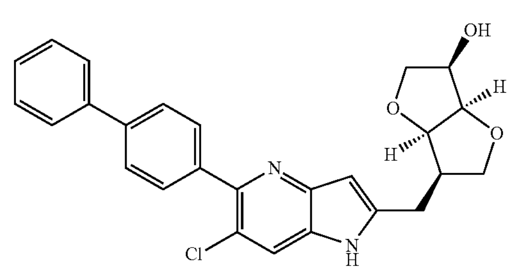 [SMILES: O[C@@H]1CO[C@@H]2[C@H](Cc3cc4nc(-c5ccc(-c6ccccc6)cc5)c(Cl)cc4[nH]3)CO[C@@H]21] | 447.1 |

TABLE 9-continued

Compounds prepared according to the methods described in Examples 54, 56, 57.

| Example Number | Structure | HPLC-mass spectrum m/e |
|---|---|---|
| 62 | 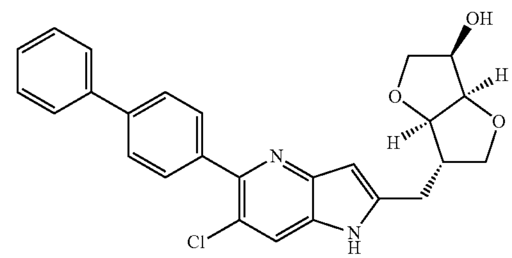 [SMILES: O[C@@H]1CO[C@@H]2[C@@H](Cc3cc4nc(-c5ccc(-c6ccccc6)cc5)c(Cl)cc4[nH]3)CO[C@@H]21] | 447.1 |
| 63 | 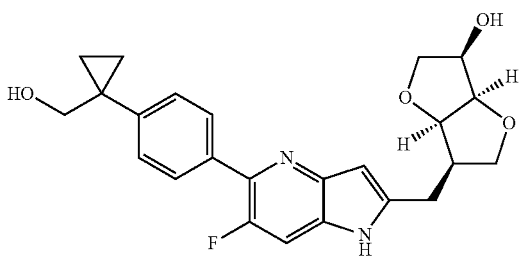 [SMILES: OCC1(c2ccc(-c3nc4cc(C[C@@H]5CO[C@H]6[C@@H]5OC[C@H]6O)[nH]c4cc3F)cc2)CC1] | 425.2 |
| 64 | 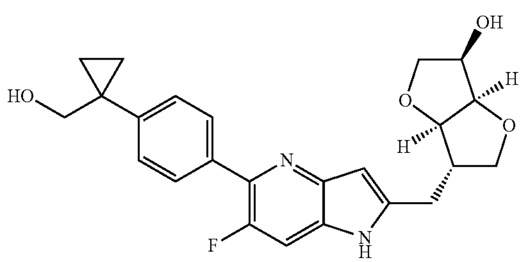 [SMILES: OCC1(c2ccc(-c3nc4cc(C[C@H]5CO[C@H]6[C@@H]5OC[C@H]6O)[nH]c4cc3F)cc2)CC1] | 425.1 |
| 65 | 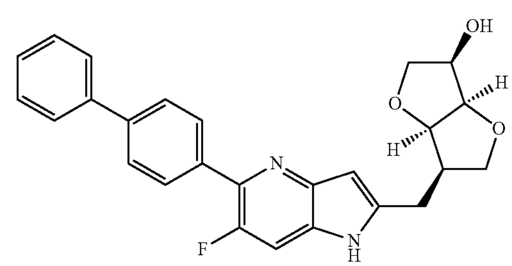 [SMILES: O[C@@H]1CO[C@@H]2[C@H](Cc3cc4nc(-c5ccc(-c6ccccc6)cc5)c(F)cc4[nH]3)CO[C@@H]21] | 431.1 |
| 66 | 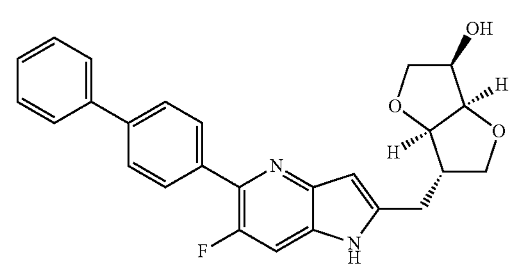 [SMILES: O[C@@H]1CO[C@@H]2[C@@H](Cc3cc4nc(-c5ccc(-c6ccccc6)cc5)c(F)cc4[nH]3)CO[C@@H]21] | 431.1 |

TABLE 9-continued

Compounds prepared according to the methods described in Examples 54, 56, 57.

| Example Number | Structure | HPLC-mass spectrum m/e |
|---|---|---|
| 67 | 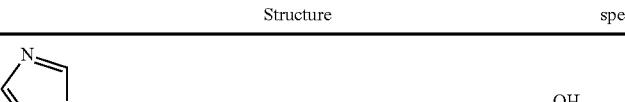 | 480.2 |

SCHEME 12

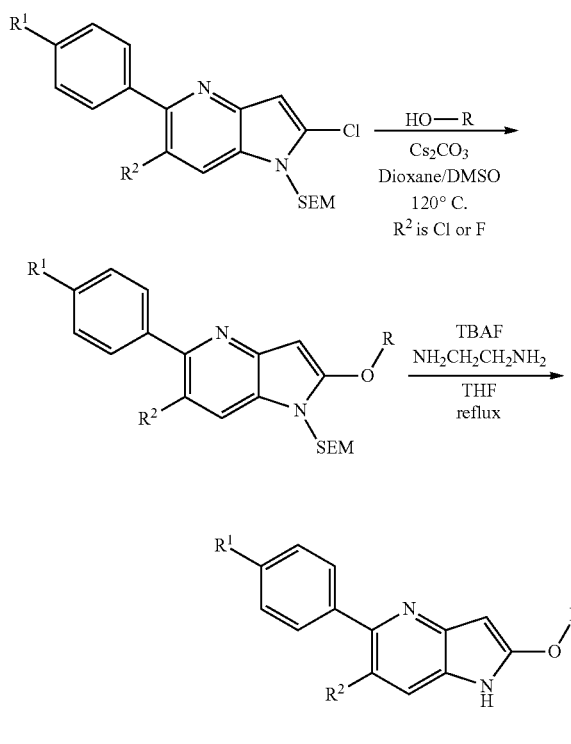

Example 68

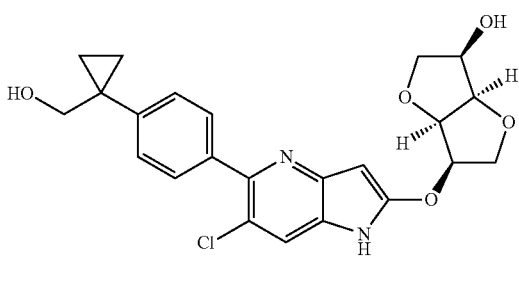 [SMILES: OCC1(c2ccc(-c3nc4cc(O[C@@H]5CO[C@H]6[C@@H]5OC[C@H]6O)[nH]c4cc3Cl)cc2)CC1]

20  (3R,3aR,6R,6aR)-6-((6-chloro-5-(4-(1-(hydroxymethyl)cyclopropyl)phenyl)-1H-pyrrolo-[3,2-b]pyridin-2-yl)oxy)hexahydrofuro[3,2-b]furan-3-ol 25  Step A: (3R,3aR,6R,6aR)-6-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)hexahydro-furo[3,2-b]furan-3-ol To a mixture of (1-(4-(2,6-dichloro-1-((2-(trimethylsilyl)ethoxy)methyl)-1H-pyrrolo[3,2-b]pyridin-5-yl)phenyl)cyclopropyl)-methanol (50 mg, 0.11 mmol) in DMSO (3 mL)/dioxane (3 mL) were added (3R,3aR,6R,6aR)-hexahydrofuro[3,2-b]furan-3,6-diol (160 mg, 1.1 mmol) and cesium carbonate (108 mg, 0.33 mmol). The reaction was heated at 120° C. overnight. Then the reaction mixture was diluted with ethyl acetate, washed with brine, dried over anhydrous $Na_2SO_4$, filtered and concentrated under reduced pressure. The resulting residue was purified by pre-TLC (PE:EtOAc=2:1) to afford the title compound. LC-MS: calculated for $C_{29}H_{37}ClN_2O_6Si$ 572.21, observed m/e: 573.2 $(M+H)^+$ (Rt 1.17/2 min).

Step B: (3R,3aR,6R,6aR)-6-((6-chloro-5-(4-(1-(hydroxymethyl)cyclopropyl)phenyl)-1H-pyrrolo[3,2-b]pyridin-2-yl)oxy)hexahydrofuro[3,2-b]furan-3-ol To a solution of (3R,3aR,6R,6aR)-6-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)hexahydrofuro[3,2-b]furan-3-ol (50 mg, 0.087 mmol) in THF (10 mL) were added tetrabutylammonium fluoride (46 mg, 0.17 mmol) and ethane-1,2-diamine (10 mg, 0.17 mmol). The mixture was heated to reflux and stirred for 18 h. Then the mixture was evaporated on a water bath under reduced pressure, the resulting crude product was purified by prep. HPLC (MeCN/$H_2O$ as eluent, 0.05% TFA) to afford the title compound. NMR δ (ppm) (CDCl$_3$): 8.22 (s, 1H), 7.60 (s, 4H), 6.17 (s, 1H), 5.22 (m, 1H), 4.96 (m, 1H), 4.46 (m, 1H), 4.28 (m, 1H), 4.17 (m, 1H), 4.12 (m, 1H), 3.88 (m, 1H), 3.72 (s, 2H), 3.66 (m, 1H), 0.96 (m, 4H). LC-MS: calculated for $C_{23}H_{23}ClN_2O_5$ 442.13, observed m/e: 443.1 $(M+H)^+$ (Rt 2.34/4.5 min).

TABLE 10

Compounds prepared according to the methods described in Example 68.

| Example Number | Structure | HPLC-mass spectrum m/e |
|---|---|---|
| 69 | 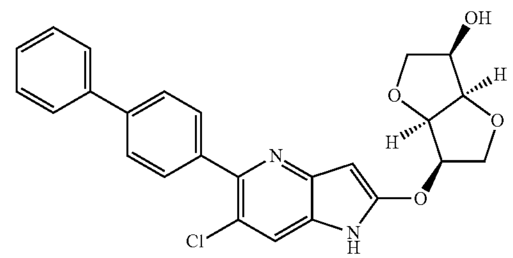 [SMILES: O[C@@H]1CO[C@H]2[C@@H]1OC[C@H]2Oc1cc2nc(-c3ccc(-c4ccccc4)cc3)c(Cl)cc2[nH]1] | 449.1 |
| 70 | 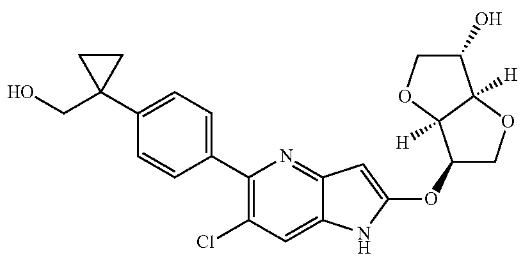 [SMILES: OCC1(c2ccc(-c3nc4cc(O[C@@H]5CO[C@H]6[C@@H]5OC[C@@H]6O)[nH]c4cc3Cl)cc2)CC1] | 443.1 |
| 71 | 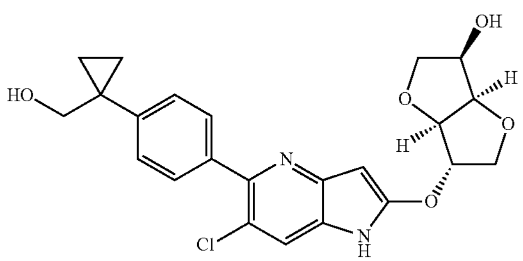 | 443.1 |
| 72 | 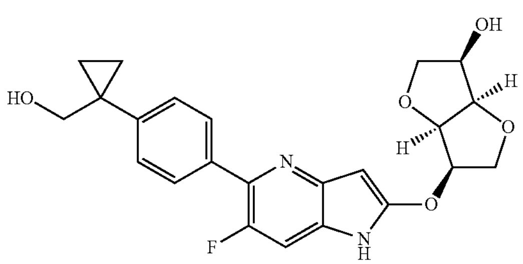 [SMILES: OCC1(c2ccc(-c3nc4cc(O[C@@H]5CO[C@H]6[C@@H]5OC[C@H]6O)[nH]c4cc3F)cc2)CC1] | 427.1 |
| 73 | 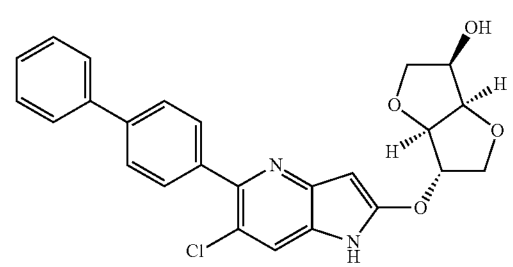 | 449.1 |

TABLE 10-continued

Compounds prepared according to the methods described in Example 68.

| Example Number | Structure | HPLC-mass spectrum m/e |
|---|---|---|
| 74 | 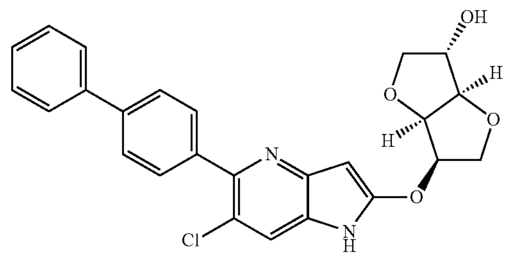 [SMILES: O[C@H]1CO[C@H]2[C@@H]1OC[C@H]2Oc1cc2nc(-c3ccc(-c4ccccc4)cc3)c(Cl)cc2[nH]1] | 449.1 |
| 75 | 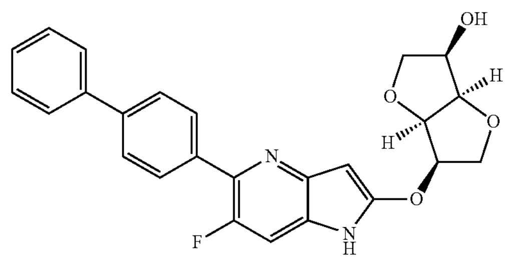 | 433.1 |
| 76 | 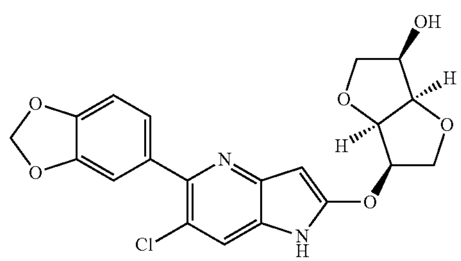 [SMILES: O[C@@H]1CO[C@H]2[C@@H]1OC[C@H]2Oc1cc2nc(-c3ccc4c(c3)OCO4)c(Cl)cc2[nH]1] | 417.0 |
| 77 | 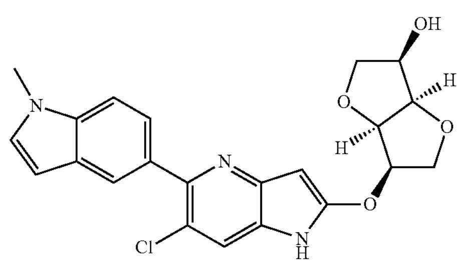 [SMILES: Cn1ccc2cc(-c3nc4cc(O[C@@H]5CO[C@H]6[C@@H]5OC[C@H]6O)[nH]c4cc3Cl)ccc21] | 426.2 |
| 78 | 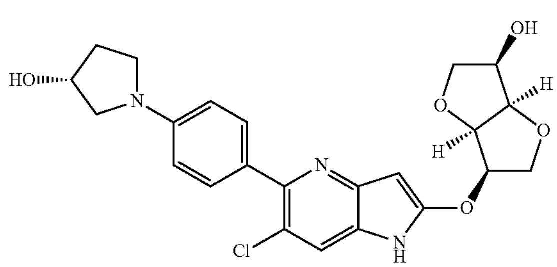 [SMILES: O[C@@H]1CCN(c2ccc(-c3nc4cc(O[C@@H]5CO[C@H]6[C@@H]5OC[C@H]6O)[nH]c4cc3Cl)cc2)C1] | 458.3 |

TABLE 10-continued
Compounds prepared according to the methods described in Example 68.
| Example Number | Structure | HPLC-mass spectrum m/e |
|---|---|---|
| 79 | 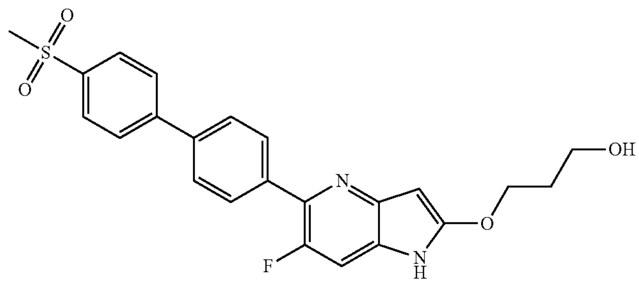 [SMILES: CS(=O)(=O)c1ccc(-c2ccc(-c3nc4cc(OCCCO)[nH]c4cc3F)cc2)cc1] | 441.1 |
| 80 | 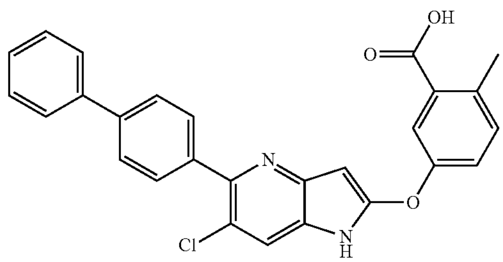 | 455.1 |
| 81 | 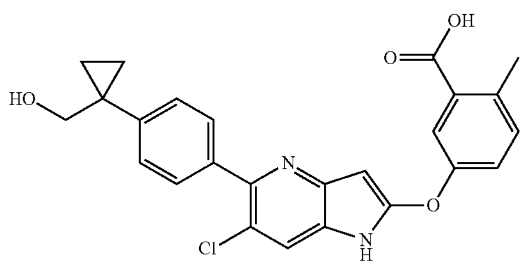 [SMILES: Cc1ccc(Oc2cc3nc(-c4ccc(C5(CO)CC5)cc4)c(Cl)cc3[nH]2)cc1C(=O)O] | 449.3 |
| 82 | 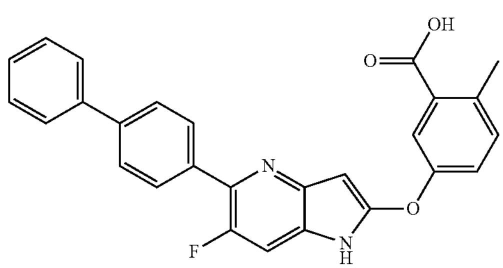 [SMILES: Cc1ccc(Oc2cc3nc(-c4ccc(-c5ccccc5)cc4)c(F)cc3[nH]2)cc1C(=O)O] | 439.1 |
SCHEME 13
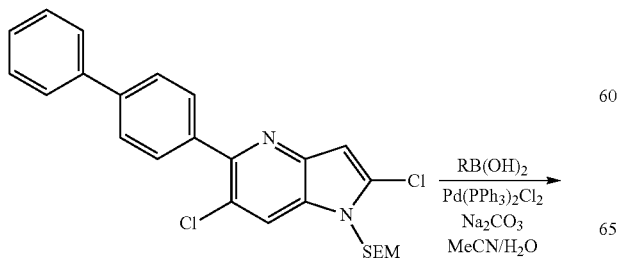

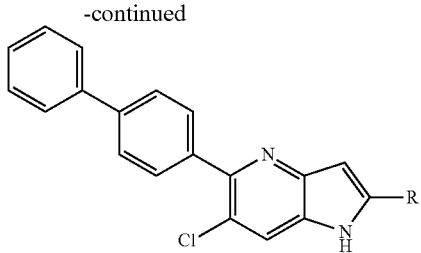

Example 83

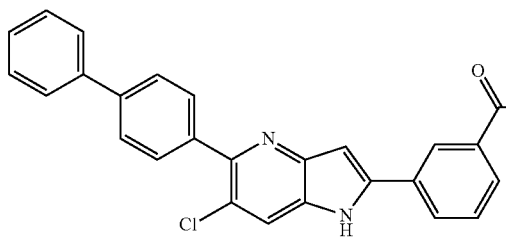

3-(5-([1,1'-biphenyl]-4-yl)-6-chloro-1H-pyrrolo[3,2-b]pyridin-2-yl)benzoic acid

Step A: 3-(5-([1,1'-biphenyl]-4-yl)-6-chloro-1-((2-(trimethylsilyl)ethoxy)methyl)-1H-pyrrolo[3,2-b]pyridin-2-yl)benzoic acid To a mixture of 5-([1,1'-biphenyl]-4-yl)-2,6-dichloro-1-((2-(trimethylsilyl)ethoxy)methyl)- 1H-pyrrolo[3,2-b]pyridine (20 mg, 0.043 mmol) and 3-boronobenzoic acid (9 mg, 0.055 mmol) in acetonitrile (1.5 mL)/H$_2$O (0.5 mL) were added Pd(PPh$_3$)$_2$Cl$_2$ (3 mg, 0.0043 mmol) and Na$_2$CO$_3$ (14 mg, 0.13 mmol). The mixture was stirred at reflux for 5 h under N$_2$. Then the reaction mixture was cooled to room temperature, diluted with water (5 mL) and extracted with ethyl acetate (3×5 mL). The organic layers were combined, dried over anhydrous magnesium sulfate, filtered and concentrated in vacuo. The resulting oil was purified by prep. TLC (PE:EtOAc=1:1) to give the title compound. LC-MS: calculated for C$_{32}$H$_{31}$ClN$_2$O$_3$Si 554.18, observed m/e: 555.2 (M+H)$^+$ (Rt 1.52/2 min).

Step B: 3-(5-([1,1'-biphenyl]-4-yl)-6-chloro-1H-pyrrolo[3,2-b]pyridin-2-yl)benzoic acid To a mixture of 3-(5-([1,1'-biphenyl]-4-yl)-6-chloro-1-((2-(trimethylsilyl)ethoxy)methyl)-1H-pyrrolo[3,2-b]pyridin-2-yl)benzoic acid (13 mg, 0.023 mmol) in THF (2 mL) were added TBAF (13 mg, 0.047 mmol) and ethane-1,2-diamine (3 mg, 0.047 mmol). The mixture was stirred at reflux for 8 h. Then the reaction mixture was cooled to room temperature, diluted with water (5 mL) and extracted with ethyl acetate (3×5 mL). The organic layers were combined, dried over anhydrous magnesium sulfate, filtered and concentrated in vacuo. The resulting oil was purified by prep. HPLC to give the title compound. NMR δ (ppm) (CDCl$_3$): 8.59 (s, 1H), 8.36 (s, 1H), 8.15 (m, 2H), 7.65 (m, 10H), 7.19 (s, 1H). LC-MS: calculated for C$_{26}$H$_{17}$ClN$_2$O$_2$ 424.10, observed m/e: 425.1 (M+H)$^+$ (Rt 2.023/4.5 min).

TABLE 11

Compounds prepared according to the methods described in Example 83.

| Example Number | Structure | HPLC-mass spectrum m/e |
|---|---|---|
| 84 | 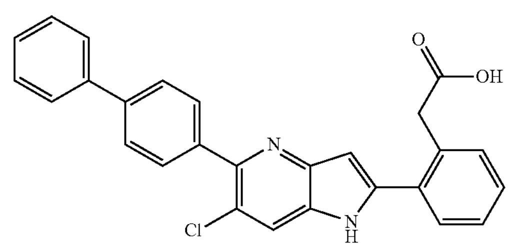 [SMILES: O=C(O)Cc1ccccc1-c1cc2nc(-c3ccc(-c4ccccc4)cc3)c(Cl)cc2[nH]1] | 439.0 |
| 85 | 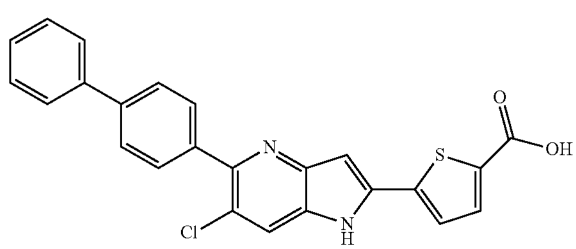 [SMILES: O=C(O)c1ccc(-c2cc3nc(-c4ccc(-c5ccccc5)cc4)c(Cl)cc3[nH]2)s1] | 431.0 |

Example 86

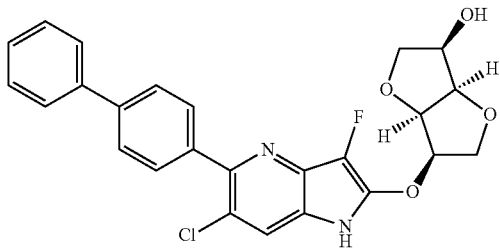 [SMILES: O[C@@H]1CO[C@H]2[C@@H]1OC[C@H]2Oc1[nH]c2cc(Cl)c(-c3ccc(-c4ccccc4)cc3)nc2c1F]

(3R,3aR,6R,6aR)-6-((5-([1,1'-biphenyl]-4-yl)-6-chloro-3-fluoro-1H-pyrrolo[3,2-b]pyridin-2-yl)oxy)hexahydrofuro[3,2-b]furan-3-ol Step A: (3R,3aR,6R,6aR)-6-((5-([1,1'-biphenyl]-4-yl)-6-chloro-1-((2-(trimethylsilyl)-ethoxy)methyl)-1H-pyrrolo[3,2-b]pyridin-2-yl)oxy)hexahydrofuro[3,2-b]furan-3-ol To a mixture of 5-([1,1'-biphenyl]-4-yl)-2,6-dichloro-1-((2-(trimethylsilyl)ethoxy)methyl)-1H-pyrrolo[3,2-b]pyridine (500 mg, 1.1 mmol) in (methylsulfinyl)methane (10 mL)/dioxane (10 mL) were added (3R,3aR,6R,6aR)-hexahydrofuro[3,2-b]furan-3,6-diol (311 mg, 2.1 mmol) and cesium carbonate (694 mg, 2.14 mmol). The mixture was heated to 120° C. and stirred for 4 h. Then the mixture was diluted with ethyl acetate, washed with brine, dried over anhydrous $Na_2SO_4$, filtered and concentrated under reduced pressure. The resulting residue was purified by silica gel column chromatography (PE:EtOAc=10:1~2:1) to afford the title compound. LC-MS: calculated for $C_{31}H_{35}ClN_2O_5Si$ 578.20, observed m/e: 579.2 $(M+H)^+$ (Rt 1.28/2 min).

Step B: (3R,3aR,6R,6aR)-6-((5-([1,1'-biphenyl]-4-yl)-6-chloro-3-fluoro-1-((2-(trimethylsilyl)ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydrofuro-[3,2-b]furan-3-ol (50 mg, 0.086 mmol) in acetonitrile (20 mL) were added Select-Fluor (28 mg, 0.10 mmol) and $NaHCO_3$ (15 mg, 0.17 mmol) at 0° C. The mixture was stirred at 0° C. for 1 h. Then the mixture was quenched with saturated $NH_4Cl$, extracted with ethyl acetate, washed with brine, dried over anhydrous $Na_2SO_4$, filtered and concentrated under reduced pressure. The resulting residue was purified by silica gel column chromatography (PE:EtOAc=10:1~2:1) to afford the title compound. LC-MS: calculated for $C_{31}H_{34}ClFN_2O_5Si$ 596.19, observed m/e: 597.2 $(M+H)^+$ (Rt 1.58/2 min).

Step C: (3R,3aR,6R,6aR)-6-((5-([1,1'-biphenyl]-4-yl)-6-chloro-1-((2-(trimethylsilyl)-ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-3-fluoro-1-((2-(tri-methylsilyl)ethoxy)methyl)-1H-pyrrolo[3,2-b]pyridin-2-yl)oxy)hexa-hydrofuro[3,2-b]furan-3-ol (20 mg, 0.033 mmol) in tetrahydrofuran (10 mL) were added tetrabutylammonium fluoride (18 mg, 0.067 mmol) and ethane-1,2-diamine (4 mg, 0.067 mmol), and the mixture was heated to reflux for 4 h. Then the mixture was diluted with ethyl acetate, washed with brine, dried over anhydrous $Na_2SO_4$, filtered and concentrated under reduced pressure. The resulting residue was purified by prep. HPLC to afford the title compound. NMR δ (ppm) ($CDCl_3$): 7.71 (m, 5H), 7.45 (m, 3H), 7.36 (m, 2H), 4.65 (m, 2H), 4.55 (m, 1H), 4.31 (m, 1H), 4.15 (m, 1H), 3.92 (m, 1H), 3.80 (m, 1H), 3.63 (m, 1H), 3.49 (m, 1H). LC-MS: calculated for $C_{25}H_{20}ClFN_2O_4$ 466.11, observed m/e: 467.1 $(M+H)^+$ (Rt 2.78/4.5 min).

Example 87

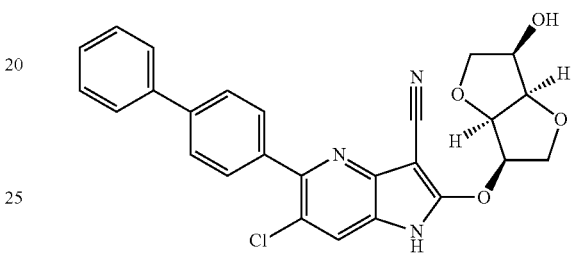

5-([1,1'-biphenyl]-4-yl)-6-chloro-2-(((3R,3aR,6R,6aR)-6-hydroxyhexahydrofuro[3,2-b]furan-3-yl)oxy)-1H-pyrrolo[3,2-b]pyridine-3-carbonitrile Step A: (3R,3aR,6R,6aR)-6-((5-([1,1'-biphenyl]-4-yl)-3-bromo-6-chloro-1-((2-(trimethylsilyl)-ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydrofuro-[3,2-b]furan-3-ol (200 mg, 0.35 mmol) in dichloromethane (10 mL) was added NBS (68 mg, 0.38 mmol) at 0° C. The mixture was stirred at 0° C. for 1 h. Then the mixture was diluted with dichloromethane, washed with brine, dried over anhydrous $Na_2SO_4$, filtered and concentrated under reduced pressure. The resulting residue was purified by silica gel column chromatography (PE:EtOAc=20:1~2:1) to afford the title compound. NMR δ (ppm) ($CDCl_3$): 7.84 (d, 2H), 7.79 (s, 1H), 7.65 (m, 4H), 7.45 (m, 1H), 5.61 (m, 2H), 5.43 (d, 1H), 4.68 (m, 1H), 4.62 (m, 1H), 4.37 (m, 2H), 4.05 (m, 2H), 3.75 (m, 1H), 3.56 (m, 2H), 2.68 (d, 1H), 0.94 (m, 2H), 0.00 (s, 9H).

Step B: 5-([1,1'-biphenyl]-4-yl)-6-chloro-2-(((3R,3aR,6R,6aR)-6-hydroxyhexahydrofuro-[3,2-b]furan-3-yl)oxy)-1-((2-(trimethylsilyl)ethoxy)methyl)-1H-pyrrolo[3,2-b]pyridine-3-carbonitrile To a mixture of 3R,3aR,6R,6aR)-6-((5-([1,1'-biphenyl]-4-yl)-3-bromo-6-chloro-1-((2-(trimethylsilyl)ethoxy)methyl)-1H-pyrrolo[3,2-b]pyridin-2-yl)oxy)-hexahydrofuro[3,2-b]furan-3-ol (60 mg, 0.091 mmol) in 1-methylpyrrolidin-2-one (3 mL) were added cyanosodium (9 mg, 0.18 mmol) and nickel(II) bromide (20 mg, 0.091 mmol), and the mixture was heated to 150° C. under MW for 1 h. Then the mixture was diluted with ethyl acetate, washed with brine, dried over anhydrous Na₂SO₄, filtered and concentrated under reduced pressure. The resulting residue was purified by silica gel column chromatography (PE:EtOAc=15:1~2:1) to afford the title compound. LC-MS: calculated for C₃₂H₃₄ClN₃O₅Si 603.20, observed m/e: 604.2/606.2 (M+H)⁺ (Rt 1.49/2 min).

Step C: 5-([1,1'-biphenyl]-4-yl)-6-chloro-2-(((3R,3aR,6R,6aR)-6-hydroxyhexahydrofuro[3,2-b]furan-3-yl)oxy)-1H-pyrrolo[3,2-b]pyridine-3-carbonitrile To a mixture of 5-([1,1'-biphenyl]-4-yl)-6-chloro-2-(((3R,3aR,6R,6aR)-6-hydroxyhexahydrofuro[3,2-b]furan-3-yl)oxy)-1-((2-(trimethylsilyl)ethoxy)methyl)-1H-pyrrolo[3,2-b]pyridine-3-carbonitrile (20 mg, 0.033 mmol) in tetrahydrofuran (10 mL) were added tetrabutylammonium fluoride (26 mg, 0.099 mmol) and ethane-1,2-diamine (6 mg, 0.099 mmol). The reaction mixture was heated to reflux and stirred overnight. Then the mixture was concentrated under reduced pressure and the resulting residue was purified by prep. HPLC to afford the title compound. NMR δ (ppm) (CDCl₃): 7.80 (s, 1H), 7.71 (m, 6H), 7.45 (m, 2H), 7.34 (m, 1H), 5.50 (m, 1H), 5.03 (m, 1H), 4.44 (m, 1H), 4.29 (m, 2H), 4.08 (m, 1H), 3.89 (m, 1H), 3.60 (m, 1H). LC-MS: calculated for C₂₆H₂₀ClN₃O₄ 473.11, observed m/e: 474.1 (M+H)⁺ (Rt 2.83/4.5 min).

Examples 88, 89, 90

Example 88

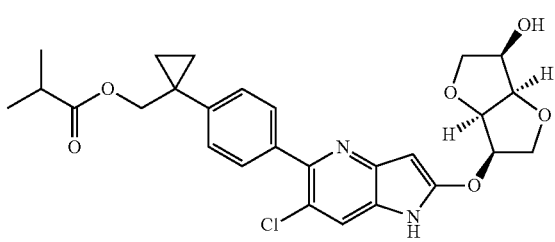

Examle 89

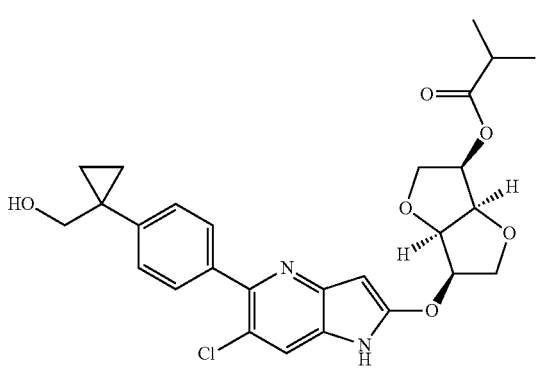

Example 90

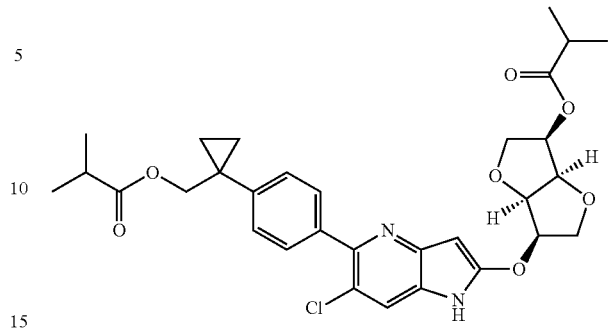

(1-(4-(6-chloro-2-(((3R,3aR,6R,6aR)-6-hydroxyhexahydrofuro[3,2-b]furan-3-yl)oxy)-1H-pyrrolo[3,2-b]pyridin-5-yl)phenyl)cyclopropyl)methyl isobutyrate; (3R,3aR,6R,6aR)-6-((6-chloro-5-(4-(1-(hydroxymethyl)cyclopropyl)phenyl)-1H-pyrrolo[3,2-b]pyridin-2-yl)oxy)-hexahydrofuro[3,2-b]furan-3-yl isobutyrate; and (1-(4-(6-chloro-2-(((3R,3aR,6R,6aR)-6-(isobutyryloxy)hexahydrofuro[3,2-b]furan-3-yl)oxy)-1H-pyrrolo[3,2-b]pyridin-5-yl)phenyl)cyclopropyl)methyl isobutyrate Step A: (1-(4-(6-chloro-2-(((3R,3aR,6R,6aR)-6-(isobutyryloxy)hexahydrofuro[3,2-b]furan-3-yl)oxy)-1-((2-(trimethylsilyl)ethoxy)methyl)-1H-pyrrolo[3,2-b]pyridin-5-yl)phenyl)cyclopropyl)methyl isobutyrate Isobutyric anhydride (81 mg, 0.51 mmol), triethylamine (34 mg, 0.34 mmol) and 4-(N,N-dimethylamino)pyridine (4 mg, 0.026 mmol) were added to a stirred solution of (3R,3aR,6R,6aR)-6-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)hexahydrofuro[3,2-b]furan-3-ol (100 mg, 0.17 mmol) in CH₂Cl₂ (2 mL). The reaction was stirred at room temperature overnight, then cooled to 0° C. and quenched with saturated aqueous NaHCO₃ (2 mL). The resulting mixture was stirred for 15 min and the aqueous layer was extracted with DCM (3×2 mL). The combined organic layers were dried over MgSO₄ and concentrated under vacuum to give the crude product, which was purified by pre-TLC (PE:EA=2:1) to afford the title compound. LC-MS: calculated for C₃₇H₄₉ClN₂O₈Si 712.29, observed m/e: 713.2 (M+H)⁺ (Rt 1.42/2 min).

Step B: (1-(4-(6-chloro-2-(((3R,3aR,6R,6aR)-6-hydroxyhexahydrofuro[3,2-b]furan-3-yl)oxy)-1H-pyrrolo[3,2-b]pyridin-5-yl)phenyl)cyclopropyl) methyl isobutyrate; (3R,3aR,6R,6aR)-6-((6-chloro-5-(4-(1-(hydroxymethyl)cyclopropyl)phenyl)-1H-pyrrolo[3,2-b]pyridin-2-yl)oxy)hexahydrofuro[3,2-b]furan-3-yl isobutyrate; and (1-(4-(6-chloro-2-(((3R,3aR,6R,6aR)-6-(isobutyryloxy)hexahydrofuro[3,2-b]furan-3-yl)oxy)-1H-pyrrolo[3,2-b]pyridin-5-yl)phenyl)cyclopropyl)methyl isobutyrate To a mixture of (1-(4-(6-chloro-2-(((3R,3aR,6R,6aR)-6-(isobutyryloxy)hexahydrofuro[3,2-b]furan-3-yl)oxy)-1-((2-(trimethylsilyl)ethoxy)methyl)-1H-pyrrolo[3,2-b]pyridin-5-yl)phenyl)cyclopropyl)methyl isobutyrate (100 mg, 0.14 mmol) in tetrahydrofuran (10 mL) were added tetrabutyl ammonium fluoride (102 mg, 0.42 mmol) and ethane-1,2-diamine (25 mg, 0.42 mmol). The mixture was heated to reflux and stirred for 18 h. Then the mixture was diluted with ethyl acetate, washed with brine, dried over anhydrous Na$_2$SO$_4$, filtered and concentrated under reduced pressure. The resulting residue was purified by prep-HPLC to afford the three title compounds.

Example 88

NMR δ (ppm) (CDCl$_3$): 8.04 (s, 1H), 7.59 (d, 2H), 7.54 (d, 2H), 6.07 (s, 1H), 5.17 (m, 1H), 4.96 (m, 1H), 4.74 (m, 1H), 4.47 (m, 1H), 4.27 (s, 2H), 4.14 (m, 2H), 3.89 (m, 1H), 3.59 (m, 1H), 2.51 (m, 1H), 1.09 (d, 6H), 1.02 (d, 4H). LC-MS: calculated for C$_{27}$H$_{29}$ClN$_2$O$_6$ 512.17, observed m/e: 513.3 (M+H)$^+$ (Rt 2.32/4.5 min).

Example 89

NMR δ (ppm) (CDCl$_3$): 7.23 (m, 1H), 7.55 (d, 2H), 7.33 (d, 2H), 6.04 (s, 1H), 5.35 (m, 1H), 5.13 (m, 1H), 4.17 (m, 1H), 4.04 (m, 1H), 3.88 (m, 1H), 3.71 (m, 1H), 3.70 (m, 2H), 3.56 (m, 1H), 3.50 (m, 1H), 2.20 (m, 1H), 1.04 (d, 6H), 0.91 (d, 4H). LC-MS: calculated for C$_{27}$H$_{29}$ClN$_2$O$_6$ 512.17, observed m/e: 513.3 (M+H)$^+$ (Rt 2.21/4.5 min).

Example 90

NMR δ (ppm) (CDCl$_3$): 8.14 (s, 1H), 7.58 (m, 4H), 6.15 (s, 1H), 5.18 (m, 1H), 5.09 (m, 1H), 4.99 (m, 1H), 4.78 (m, 1H), 4.27 (s, 2H), 4.17 (m, 1H), 4.01 (m, 2H), 3.83 (m, 1H), 2.54 (m, 1H), 2.52 (m, 1H), 1.19 (m, 6H), 1.10 (d, 6H), 1.04 (d, 4H). LC-MS: calculated for C$_{31}$H$_{35}$ClN$_2$O$_7$, observed m/e: 583.1 (M+H)$^+$ (Rt 2.37/4.5 min).

Example 91

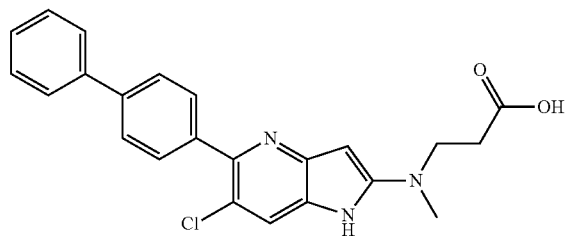 [SMILES: CN(CCC(=O)O)c1cc2nc(-c3ccc(-c4ccccc4)cc3)c(Cl)cc2[nH]1]

3-((5-([1,1'-biphenyl]-4-yl)-6-chloro-1H-pyrrolo[3,2-b]pyridin-2-yl)(methyl)amino)-propanoic acid To a mixture of 5-([1,1'-biphenyl]-4-yl)-2,6-dichloro-1H-pyrrolo[3,2-b]pyridine (50 mg, 0.15 mmol) in propan-2-ol (2 mL) were added 3-(methylamino)-propanoic acid (61 mg, 0.59 mmol) and potassium carbonate (81 mg, 0.59 mmol). The mixture was heated to 120° C. under MW and stirred for 1 h. Then the mixture was diluted with ethyl acetate (20 mL), washed with brine, dried over anhydrous Na$_2$SO$_4$, filtered and concentrated under reduced pressure. The resulting residue was purified by prep. TLC (PE:EtOAc=1:1) to afford the title compound. NMR δ (ppm) (CDCl$_3$): 7.85 (d, 2H), 7.72 (m, 5H), 7.49 (m, 2H), 7.40 (m, 1H), 3.83 (t, 2H), 3.24 (s, 3H), 2.75 (t, 2H).

SCHEME 14

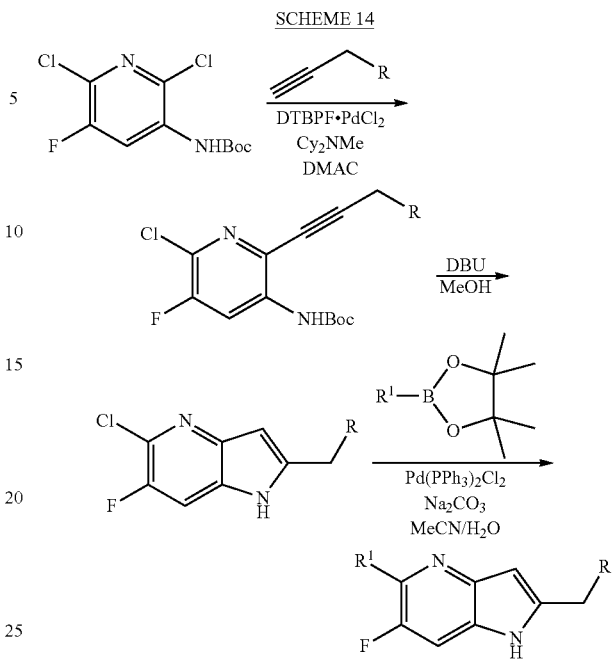

Examples 92 through 100

Example 92

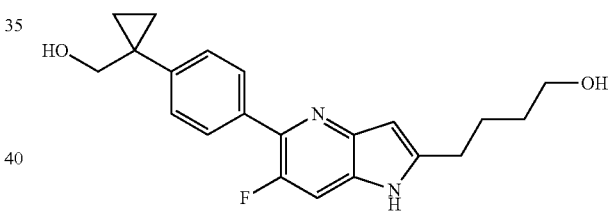

4-(6-fluoro-5-(4-(1-(hydroxymethyl)cyclopropyl)phenyl)-1H-pyrrolo[3,2-b]pyridin-2-yl)butan-1-ol Step A: tert-butyl (6-chloro-5-fluoro-2-(6-hydroxy-hex-1-yn-1-yl)pyridin-3-yl)carbamate To a solution of tert-butyl (2,6-dichloro-5-fluoropyridin-3-yl)carbamate (500 mg, 1.8 mmol) in N,N-dimethylacetamide (10 mL) were added hex-5-yn-1-ol (175 mg, 1.8 mmol), DTBPF.PdCl$_2$ (121 mg, 0.18 mmol) and N-cyclohexyl-N-methylcyclo-hexanamine (521 mg, 2.7 mmol). The mixture was heated to 80° C. under MW and stirred for 30 min. Then the mixture was filtered and concentrated under reduced pressure, and the resulting residue was purified by silica gel column chromatography (PE:EtOAc=10:1~3:1) to afford the title compound. LC-MS: calculated for C$_{16}$H$_{20}$ClFN$_2$O$_3$ 342.11, observed m/e: 343.2 (M+H)$^+$ (Rt 1.33/2 min).

Step B: 4-(5-chloro-6-fluoro-1H-pyrrolo[3,2-b]pyridin-2-yl)butan-1-ol

A mixture of tert-butyl (6-chloro-5-fluoro-2-(6-hydroxy-hex-1-yn-1-yl)pyridin-3-yl)carbamate (200 mg, 0.58 mmol)

and DBU (178 mg, 1.2 mmol) in methanol (10 mL) was heated to 90° C. under MW and stirred for 30 min. Then the mixture was concentrated under reduced pressure and the resulting residue was purified by silica gel column chromatography (PE:EtOAc=10:1~1:1) to afford the title compound. NMR δ (ppm) (CDCl₃): 8.64 (br, 1H), 7.33 (s, 1H), 6.29 (s, 1H), 3.67 (t, 2H), 2.78 (m, 2H), 1.79 (m, 4H).

Step C: 4-(6-fluoro-5-(4-(1-(hydroxymethyl)cyclopropyl)phenyl)-1H-pyrrolo[3,2-b]pyridin-2-yl)butan-1-ol A mixture of 4-(5-chloro-6-fluoro-1H-pyrrolo[3,2-b]pyridin-2-yl)butan-1-ol (100 mg, 0.42 mmol), (1-(4-(4,4,5,5-tetramethyl-1,3,2-dioxaborolan-2-yl)phenyl)cyclopropyl)methanol (136 mg, 0.50 mmol), Pd(PPh₃)₄ (28 mg, 0.042 mmol) and Na₂CO₃ (66 mg, 0.61 mmol) in MeCN (2 mL)/H₂O (2 mL) was heated to 120° C. under MW and stirred for 30 min. Then the mixture was extracted with ethyl acetate. The combined organic layers were washed with brine, dried over anhydrous Na₂SO₄, filtered and evaporated. The resulting residue was purified by prep. HPLC to afford the title compound. NMR δ (ppm) (CDCl₃): 8.28 (d, 1H), 7.73 (d, 2H), 7.61 (d, 2H), 6.61 (s, 1H), 3.73 (s, 2H), 3.62 (t, 2H), 2.98 (t, 2H), 1.88 (m, 2H), 1.64 (m, 2H), 0.96 (m, 4H). LC-MS: calculated for $C_{21}H_{23}FN_2O_2$ 354.17, observed m/e: 355.1 (M+H)⁺ (Rt 2.35/4.5 min).

TABLE 12

Compounds prepared according to the methods described in Example 92.

| Example Number | Structure | HPLC-mass spectrum m/e |
|---|---|---|
| 93 | 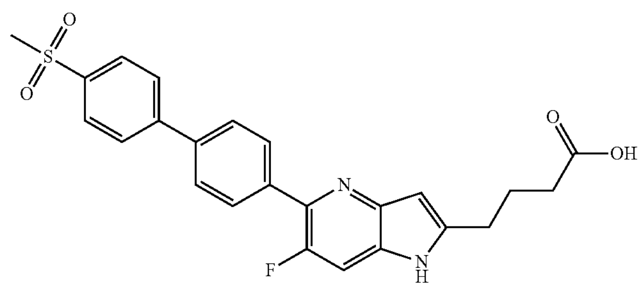 [SMILES: CS(=O)(=O)c1ccc(-c2ccc(-c3nc4cc(CCCC(=O)O)[nH]c4cc3F)cc2)cc1] | 453.1 |
| 94 | 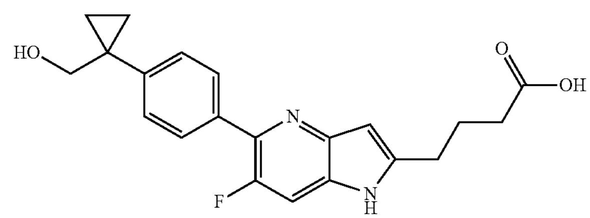 [SMILES: O=C(O)CCCc1cc2nc(-c3ccc(C4(CO)CC4)cc3)c(F)cc2[nH]1] | 369.1 |
| 95 | 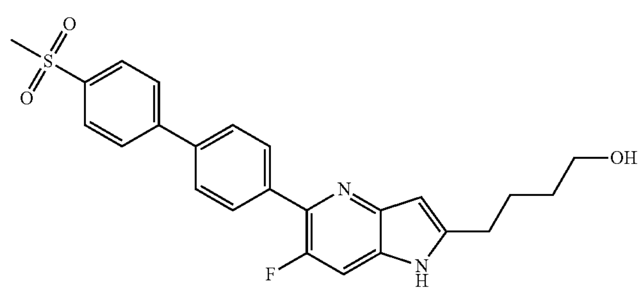 [SMILES: CS(=O)(=O)c1ccc(-c2ccc(-c3nc4cc(CCCCO)[nH]c4cc3F)cc2)cc1] | 441.1 |
| 96 | 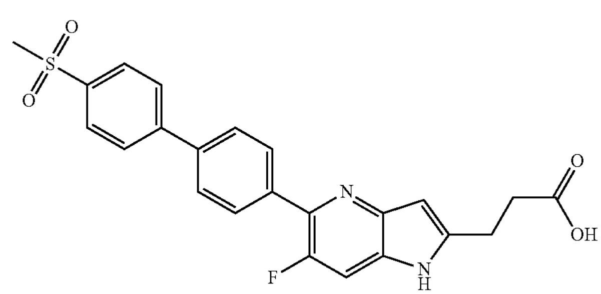 [SMILES: CS(=O)(=O)c1ccc(-c2ccc(-c3nc4cc(CCC(=O)O)[nH]c4cc3F)cc2)cc1] | 439.1 |

TABLE 12-continued

Compounds prepared according to the methods described in Example 92.

| Example Number | Structure | HPLC-mass spectrum m/e |
|---|---|---|
| 97 | 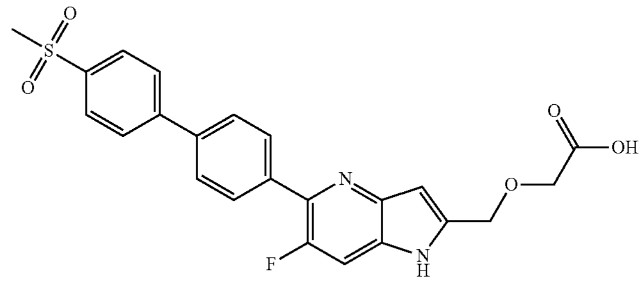 [SMILES: CS(=O)(=O)c1ccc(-c2ccc(-c3nc4cc(COCC(=O)O)[nH]c4cc3F)cc2)cc1] | 455.1 |
| 98 | 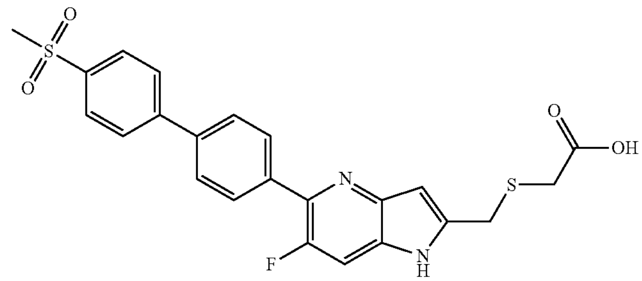 [SMILES: CS(=O)(=O)c1ccc(-c2ccc(-c3nc4cc(CSCC(=O)O)[nH]c4cc3F)cc2)cc1] | 471.2 |
| 99 | 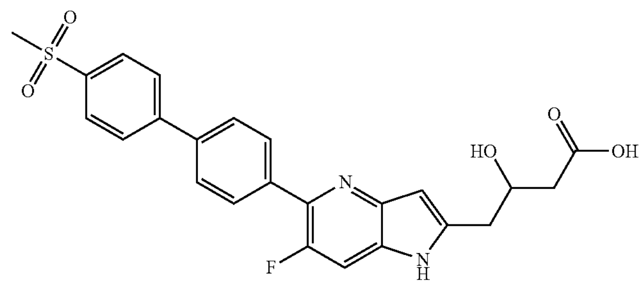 [SMILES: CS(=O)(=O)c1ccc(-c2ccc(-c3nc4cc(CC(O)CC(=O)O)[nH]c4cc3F)cc2)cc1] | 469.2 |
| 100 | 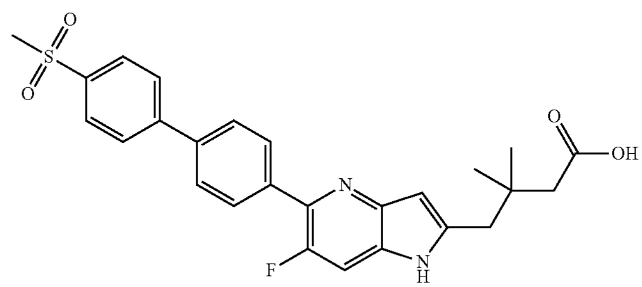 [SMILES: CC(C)(CC(=O)O)Cc1cc2nc(-c3ccc(-c4ccc(S(C)(=O)=O)cc4)cc3)c(F)cc2[nH]1] | 481.3 |

Intermediate 36

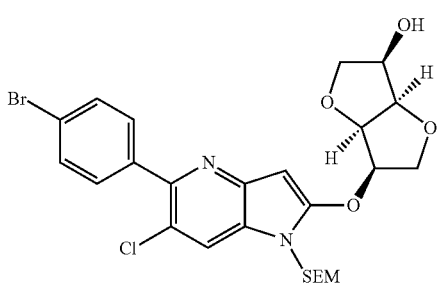 [SMILES: C[Si](C)(C)CCOCn1c(O[C@@H]2CO[C@H]3[C@@H]2OC[C@H]3O)cc2nc(-c3ccc(Br)cc3)c(Cl)cc21]

(3R,3aR,6R,6aR)-6-((5-(4-bromophenyl)-6-chloro-1-((2-(trimethylsilyl)ethoxy)methyl)-1H-pyrrolo[3,2-b]pyridin-2-yl)pyridin-2-yl)oxy)hexahydrofuro[3,2-b]furan-3-ol Step A: ethyl 2-(3-amino-6-(4-bromophenyl)-5-chloropyridin-2-yl)acetate To a solution of ethyl 2-(3-amino-6-bromo-5-chloropyridin-2-yl)acetate (5.0 g, 17.0 mmol, Intermediate 25) in toluene (150 mL), ethanol (45 mL) and water (12.5 mL) were added (4-bromophenyl)boronic acid (3.4 g, 17.0 mmol) and sodium carbonate (1.8 g, 17.0 mmol). The mixture was bubbled with nitrogen for 30 seconds. Then Pd(PPh$_3$)$_4$ (1.8 g, 1.7 mmol) was added under nitrogen, and the mixture was stirred at 90° C. for 7 hours. Then the mixture was concentrated under reduced pressure, and the resulting crude product was purified by flash chromatography (petroleum ether:ethyl acetate=50:1 to 3:1) to give the title compound. LC-MS: calculated for $C_{15}H_{14}BrClN_2O_2$ 367.99, observed m/e: 371.0 (M+H)$^+$ (Rt 1.33/2 min).

Step B: 5-(4-bromophenyl)-6-chloro-1H-pyrrolo[3,2-b]pyridin-2(3H)-one

To a solution of ethyl 2-(3-amino-6-(4-bromophenyl)-5-chloropyridin-2-yl)acetate (6.0 g, 16.3 mmol) in toluene (90 mL) was added acetic acid (5.9 g, 97.8 mmol). The mixture was stirred at reflux overnight. Then the mixture was concentrated under reduced pressure, and the crude product was purified by flash chromatography (petroleum ether:ethyl acetate=15:1 to 1:1) to give the title compound. LC-MS: calculated for $C_{13}H_8BrClN_2O$ 321.95, observed m/e: 325.0 (M+H)$^+$ (Rt 1.14/2 min).

Step C: 5-(4-bromophenyl)-2,6-dichloro-1H-pyrrolo[3,2-b]pyridine

To a mixture of 5-(4-bromophenyl)-6-chloro-1H-pyrrolo[3,2-b]pyridin-2(3H)-one (4.0 g, 12.4 mmol) in phosphoryl trichloride (140 mL) was added N,N-dimethylaniline (3.1 g, 24.8 mmol). The mixture stirred at reflux for 1 hour, then cooled to room temperature. Then the mixture was poured into water (150 mL) slowly, and filtered. The filtrate was diluted with water (100 mL), basified by sodium bicarbonate to pH=7-8, and extracted with ethyl acetate (4×500 mL) and dichloromethane (2×500 mL). The separated organic layers were combined, dried over Na$_2$SO$_4$, and concentrated under reduced pressure. The resulting crude product was purified by flash chromatography (petroleum ether:ethyl acetate=15:1 to 4:1) to give the title compound. LC-MS: calculated for $C_{13}H_7BrCl_2N_2$ 339.92, observed m/e: 343.0 (M+H)$^+$ (Rt 1.22/2 min).

Step D: 5-(4-bromophenyl)-2,6-dichloro-1-((2-(trimethylsilyl)ethoxy)methyl)-1H-pyrrolo[3,2-b]pyridine To a solution of 5-(4-bromophenyl)-2,6-dichloro-1H-pyrrolo[3,2-b]pyridine (2.0 g, 5.8 mmol) in N,N-dimethylformamide (20 mL) was added sodium hydride (580 mg, 14.5 mmol) under 0° C. The mixture was stirred at 0° C. for 30 min, then (2-(chloromethoxy)ethyl)trimethylsilane (1.2 g, 7.0 mmol) was added slowly under 0° C. The mixture was warmed to room temperature and stirred for 1.5 hours. Then the reaction mixture was quenched with saturated ammonium chloride, and extracted with ethyl acetate. The combined organic layers were washed with brine, dried over anhydrous Na$_2$SO$_4$, filtered and concentrated to give the crude product, which was purified by flash column chromatography (petroleum ether:ethyl acetate=50:1 to 15:1) to give the title compound. NMR δ (ppm) (CDCl$_3$): 7.85 (s, 1H), 7.59 (s, 4H), 6.71 (s, 1H), 5.55 (s, 2H), 3.56 (m, 2H), 0.92 (m, 3H), 0.00 (s, 9H). LC-MS: calculated for $C_{19}H_{21}BrCl_2N_2OSi$ 470.00, observed m/e: 472.9 (M+H)$^+$ (Rt 1.59/2 min).

Step E: (3R,3aR,6R,6aR)-6-((5-(4-bromophenyl)-6-chloro-1-((2-(trimethylsilyl)ethoxy)methyl)-1H-pyrrolo[3,2-b]pyridin-2-yl)oxy)hexahydrofuro[3,2-b]furan-3-ol To a solution of 5-(4-bromophenyl)-2,6-dichloro-1-((2-(trimethylsilyl)ethoxy)methyl)-1H- pyrrolo[3,2-b]pyridine (2.5 g, 5.3 mmol) in (methylsulfinyl)methane (25 mL) and dioxane (25 mL) was added (3R,3aR,6R,6aR)-hexahydrofuro[3,2-b]furan-3,6-diol (3.9 g, 26.5 mmol) and cesium carbonate (5.2 g, 15.6 mmol). The mixture stirred at 120° C. overnight, then cooled to room temperature. Then the mixture was diluted with ethyl acetate, washed with brine, dried over anhydrous Na$_2$SO$_4$, filtered and concentrated under reduced pressure to give the crude product, which was purified by flash column chromatography (petroleum ether:ethyl acetate=20:1 to 1:1) to give the title compound. NMR δ (ppm) (CDCl$_3$): 7.69 (s, 1H), 7.58 (s, 4H), 5.85 (s, 1H), 5.44 (m, 2H), 4.97 (q, 1H), 4.84 (t, 1H), 4.61 (t, 1H), 4.36 (br, 1H), 4.28 (dd, 1H), 4.06 (dd, 1H), 4.00 (dd, 1H), 3.68 (dd, 1H), 3.55 (t, 2H), 3.48 (s, 1H), 0.92 (m, 2H), 0.00 (s, 9H). LC-MS: calculated for $C_{25}H_{30}BrClN_2O_5Si$ 580.08, observed m/e: 583.1 (M+H)$^+$ (Rt 1.18/2 min).

Example 101

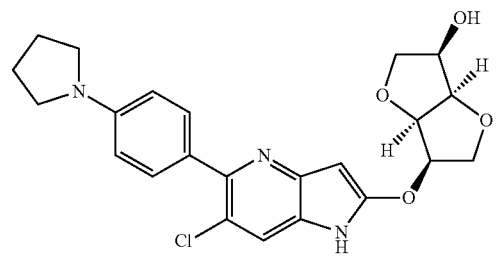 [SMILES: O[C@@H]1CO[C@H]2[C@@H]1OC[C@H]2Oc1cc2nc(-c3ccc(N4CCCC4)cc3)c(Cl)cc2[nH]1]

(3R,3aR,6R,6aR)-6-((6-chloro-5-(4-(pyrrolidin-1-yl)phenyl)-1H-pyrrolo[3,2-b]pyridin-2-yl)oxy)hexahydrofuro[3,2-b]furan-3-ol Step A: (3R,3aR,6R,6aR)-6-((6-chloro-5-(4-(pyrrolidin-1-yl)phenyl)-1-((2-(trimethylsilyl)ethoxy)methyl)-1H-pyrrolo[3,2-b]pyridin-2-yl)oxy)hexahydrofuro[3,2-b]furan-3-ol To a solution of (3R,3aR,6R,6aR)-6-((5-(4-bromophenyl)-6-chloro-1-((2-(trimethylsilyl)ethoxy)methyl)-1H-pyrrolo[3,2-b]pyridin-2-yl)oxy)hexahydrofuro[3,2-b]furan-3-ol (70 mg, 0.12 mmol) in (methylsulfinyl)methane (2 mL) were added pyrrolidine (9.4 mg, 0.13 mmol), cuprous iodide (66 mg, 0.35 mmol), cesium carbonate (78 mg, 0.24 mmol) and L-proline (15 mg, 0.13 mmol) under nitrogen. The mixture was stirred at 105° C. under microwave irradiation for 1 h. Then the mixture was purified by prep. HPLC (MeCN/H$_2$O as eluent, 0.05% TFA) to give the title compound. LC-MS: calculated for $C_{29}H_{38}ClN_3O_5Si$ 571.23, observed m/e: 572.3 (M+H)$^+$ (Rt 1.22/2 min).

Step B: (3R,3aR,6R,6aR)-6-((6-chloro-1-(hydroxymethyl)-5-(4-(pyrrolidin-1-yl)phenyl)-1H-pyrrolo[3,2-b]pyridin-2-yl)oxy)hexahydrofuro[3,2-b]furan-3-ol To a solution of (3R,3aR,6R,6aR)-6-((6-chloro-5-(4-(pyrrolidin-1-yl)phenyl)-1-((2-(trimethylsilyl)ethoxy)methyl)-1H-pyrrolo[3,2-b]pyridin-2-yl)oxy)hexahydrofuro[3,2-b]furan-3-ol (57 mg, 0.12 mmol) in tetrahydrofuran (1 mL) was added concentrated hydrochloric acid (1 mL, 12 M) at 0° C. The mixture was warmed slowly to room temperature and stirred overnight. Then the mixture was concentrated under reduced pressure at room temperature to give the title compound, which was used for next step directly. LC-MS: calculated for $C_{24}H_{26}ClN_3O_5$ 471.16, observed m/e: 472.2 (M+H)$^+$ (Rt 0.91/2 min).

Step C: (3R,3aR,6R,6aR)-6-((6-chloro-5-(4-(pyrrolidin-1-yl)phenyl)-1H-pyrrolo[3,2-b]pyridin-2-yl)oxy)hexahydrofuro[3,2-b]furan-3-ol To a solution of (3R,3aR,6R,6aR)-6-((6-chloro-1-(hydroxymethyl)-5-(4-(pyrrolidin-1- yl)phenyl)-1H-pyrrolo[3,2-b]pyridin-2-yl)oxy)hexahydrofuro[3,2-b]furan-3-ol (100 mg, 0.12 mmol, crude) in dimethyl formamide (1 mL) was added ethane-1,2-diamine (28 mg, 0.42 mmol) at 0° C. The mixture was stirred at 0° C. for 5 mins, then directly purified by prep. HPLC (MeCN/H$_2$O as eluent, 0.05% TFA) to give the title compound. NMR δ (ppm) (CD$_3$OD): 8.17 (s, 1H), 7.53 (d, 2H), 6.74 (d, 3H), 6.13 (s, 1H), 5.22 (m, 1H), 4.96 (t, 1H), 4.47 (t, 1H), 4.28 (m, 1H), 4.14 (m, 2H), 3.89 (t, 1H), 3.58 (t, 1H), 3.38 (m, 4H), 2.08 (m, 4H). LC-MS: calculated for $C_{23}H_{24}ClN_3O_4$ 441.15, observed m/e: 442.2 (M+H)$^+$ (Rt 1.00/2 min).

TABLE 13

Compounds prepared according to the methods described in Example 101.

| Example Number | Structure | HPLC-mass spectrum m/e |
|---|---|---|
| 102 | 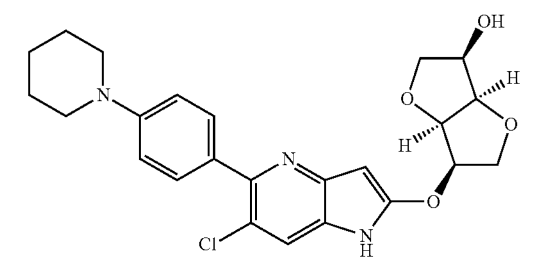 [SMILES: O[C@@H]1CO[C@H]2[C@@H]1OC[C@H]2Oc1cc2nc(-c3ccc(N4CCCCC4)cc3)c(Cl)cc2[nH]1] | 456.1 |
| 103 | 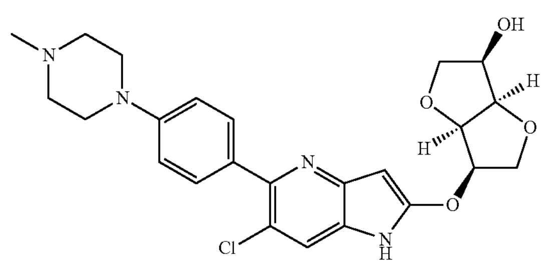 [SMILES: CN1CCN(c2ccc(-c3nc4cc(O[C@@H]5CO[C@H]6[C@@H]5OC[C@H]6O)[nH]c4cc3Cl)cc2)CC1] | 471.1 |
| 104 | 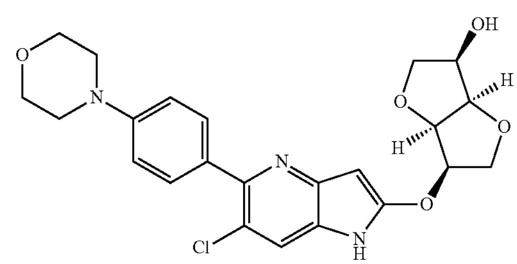 [SMILES: O[C@@H]1CO[C@H]2[C@@H]1OC[C@H]2Oc1cc2nc(-c3ccc(N4CCOCC4)cc3)c(Cl)cc2[nH]1] | 458.2 |
| 105 | 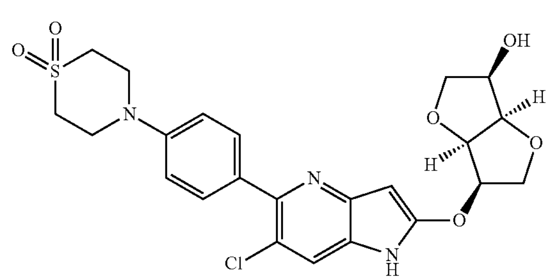 [SMILES: O=S1(=O)CCN(c2ccc(-c3nc4cc(O[C@@H]5CO[C@H]6[C@@H]5OC[C@H]6O)[nH]c4cc3Cl)cc2)CC1] | 506.0 |

TABLE 13-continued

Compounds prepared according to the methods described in Example 101.

| Example Number | Structure | HPLC-mass spectrum m/e |
|---|---|---|
| 106 | 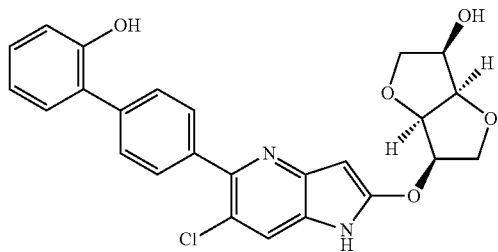 [SMILES: Oc1ccccc1-c1ccc(-c2nc3cc(O[C@@H]4CO[C@H]5[C@@H]4OC[C@H]5O)[nH]c3cc2Cl)cc1] | 428.1 |

Example 107

(3R,3aR,6R,6aR)-6-((6-chloro-5-(2'-hydroxy-[1,1'-biphenyl]-4-yl)-1H-pyrrolo[3,2-b]pyridin-2-yl)oxy)hexahydrofuro[3,2-b]furan-3-ol Step A: (3R,3aR,6R,6aR)-6-((6-chloro-5-(2'-hydroxy-[1,1'-biphenyl]-4-yl)-1-((2-(trimethylsilyl)ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-(4-bromophenyl)-6-chloro-1-((2-(trimethylsilyl)ethoxy)methyl)-1H-pyrrolo[3,2-b]pyridin-2-yl)oxy)hexahydrofuro[3,2-b]furan-3-ol (50 mg, 0.086 mmol) and (2-hydroxyphenyl)boronic acid (18 mg, 0.13 mmol) in acetonitrile (1.5 mL) and H$_2$O (0.5 mL) was added Pd(dppf)Cl$_2$ (6 mg, 0.0086 mmol) and Na$_2$CO$_3$ (22 mg, 0.26 mmol). The resulting mixture was stirred at reflux temperature for 3 hours. Then the reaction was cooled to room temperature, diluted with water (5 mL) and extracted with ethyl acetate (3×5 mL). The organic layers were combined, dried over anhydrous magnesium sulfate, filtered and concentrated under vacuum. The resulting crude product was purified by prep. TLC (petroleum ether:ethyl acetate=50:1 5:1) to afford the title compound. LC-MS: calculated for C$_{31}$H$_{35}$ClN$_2$O$_6$Si 594.20, observed m/e: 595.3 (M+H)$^+$ (Rt 1.20/2 min).

Step B: (3R,3aR,6R,6aR)-6-((6-chloro-5-(2'-hydroxy-[1,1'-biphenyl]-4-yl)-1-hydroxymethyl)-1H-pyrrolo[3,2-b]pyridin-2-yl)oxy)hexahydrofuro[3,2-b]furan-3-ol To a solution of (3R,3aR,6R,6aR)-6-((6-chloro-5-(2'-hydroxy-[1,1'-biphenyl]-4-yl)-1-((2-(trimethylsilyl)ethoxy)methyl)-1H-pyrrolo[3,2-b]pyridin-2-yl)oxy)hexahydrofuro[3,2-b]furan-3-ol (46 mg, 0.071 mmol) in THF (1 mL) was added dropwise conc. HCl (1 mL). Then the mixture was warmed slowly to room temperature and stirred overnight. The resulting mixture was concentrated under reduced pressure at room temperature to give the title compound, which was used directly in the next step without purification. LC-MS: calculated for C$_{26}$H$_{23}$ClN$_2$O$_6$ 494.12, observed m/e: 495.1 (M+H)$^+$ (Rt 0.88/2 min).

Step C: (3R,3aR,6R,6aR)-6-((6-chloro-5-(2'-hydroxy-[1,1'-biphenyl]-4-yl)-1H-pyrrolo[3,2-b]pyridin-2-yl)oxy)hexahydrofuro[3,2-b]furan-3-ol To a mixture of (3R,3aR,6R,6aR)-6-((6-chloro-5-(2'-hydroxy-[1,1'-biphenyl]-4-yl)-1-(hydroxymethyl)-1H-pyrrolo[3,2-b]pyridin-2-yl)oxy)hexahydrofuro[3,2-b]furan-3-ol (Crude 40 mg) in DMF (2 mL) was added ethane-1,2-diamine (6 mg, 0.10 mmol) at 0° C. The reaction mixture was stirred at 0° C. for 10 minutes. Then the resulting mixture was directly purified by prep. HPLC (MeCN/H$_2$O as eluent, 0.05% TFA) to afford the title compound. NMR δ (ppm) (CD$_3$OD): 8.24 (s, 1H), 7.83 (d, 2H), 7.73 (d, 2H), 7.35 (d, 1H), 7.21 (q, 1H), 6.95 (t, 2H), 6.19 (s, 1H), 5.24 (t, 1H), 4.89 (d, 1H), 4.47 (t, 1H), 4.18 (d, 1H), 4.14 (d, 2H), 3.89 (t, 1H), 3.59 (t, 1H). LC-MS: calculated for C$_{25}$H$_{21}$ClN$_2$O$_5$ 464.11, observed m/e: 465.0 (M+H)$^+$ (Rt 2.29/4.5 min).

TABLE 14

Compounds prepared according to the methods described in Example 107.

| Example Number | Structure | HPLC-mass spectrum m/e |
|---|---|---|
| 108 | 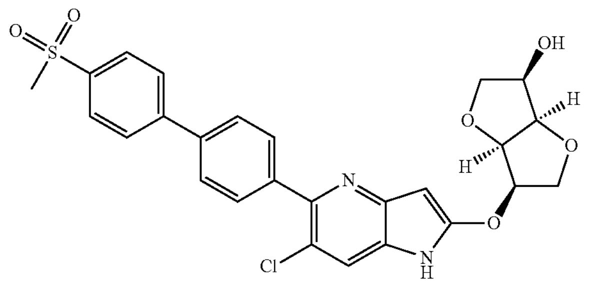 [SMILES: CS(=O)(=O)c1ccc(-c2ccc(-c3nc4cc(O[C@@H]5CO[C@H]6[C@@H]5OC[C@H]6O)[nH]c4cc3Cl)cc2)cc1] | 527.0 |
| 109 | 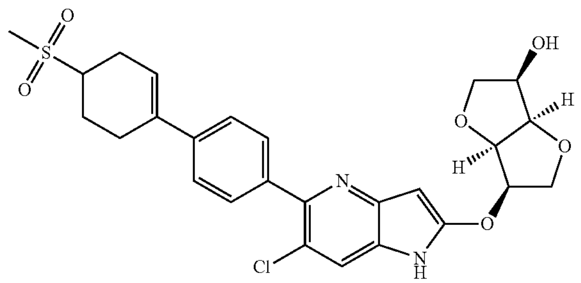 [SMILES: CS(=O)(=O)C1CC=C(c2ccc(-c3nc4cc(O[C@@H]5CO[C@H]6[C@@H]5OC[C@H]6O)[nH]c4cc3Cl)cc2)CC1] | 531.0 |
| 110 | 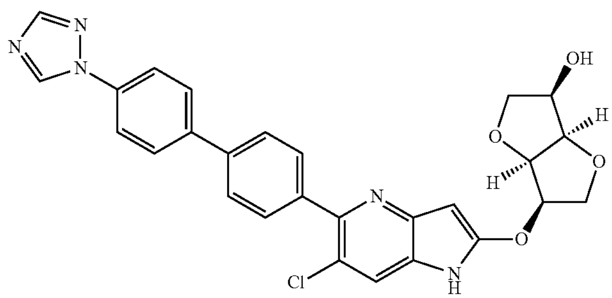 [SMILES: O[C@@H]1CO[C@H]2[C@@H]1OC[C@H]2Oc1cc2nc(-c3ccc(-c4ccc(-n5cncn5)cc4)cc3)c(Cl)cc2[nH]1] | 515.9 |
| 111 | 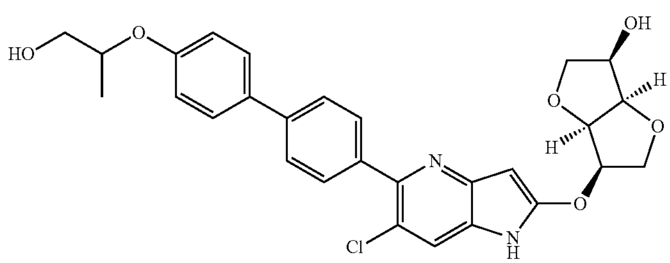 [SMILES: CC(CO)Oc1ccc(-c2ccc(-c3nc4cc(O[C@@H]5CO[C@H]6[C@@H]5OC[C@H]6O)[nH]c4cc3Cl)cc2)cc1] | 523.1 |

Intermediate 37

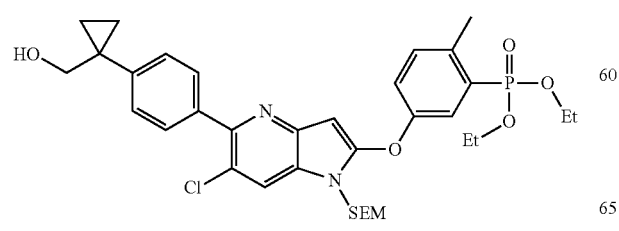

Diethyl (5-(((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)-2-methylphenyl)phosphonate Step A: (1-(4-(6-chloro-2-(3-iodo-4-methylphenoxy)-1-((2-(trimethylsilyl)ethoxy)methyl)-1H-pyrrolo[3,2-b]pyridin-5-yl)phenyl)cyclopropyl)methanol To a mixture of (1-(4-(2,6-dichloro-1-((2-(trimethylsilyl)ethoxy)methyl)-1H-pyrrolo[3,2-b]pyridin-5-yl)phenyl)cyclopropyl)methanol (200 mg, 0.43 mmol) and 3-iodo-4-methylphenol (50 mg, 2.16 mmol) in DMSO (5 mL) and dioxane (5 mL) was added Cs$_2$CO$_3$ (0.70 g, 2.16 mmol). The reaction mixture was heated under microwave irradiation at 150° C. for 40 minutes. Then the reaction mixture was cooled to room temperature, diluted with water (15 mL) and extracted with ethyl acetate (3×10 mL). The organic layers were combined, dried over anhydrous magnesium sulfate, filtered and concentrated under vacuum to give crude product, which was purified by flash column chromatography on silica gel (petroleum ether:ethyl acetate=10:1 to 3:1) to give the title compound. LC-MS: calculated for $C_{34}H_{44}ClN_2O_6PSi$ 660.11, observed m/e: 661.1 $(M+H)^+$ (Rt 1.45/2 min).

Step B: diethyl (5-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)-2-methylphenyl)phosphonate To a mixture of (1-(4-(6-chloro-2-(3-iodo-4-methyl-phenoxy)-1-((2-(trimethylsilyl)ethoxy)methyl)-1H-pyrrolo[3,2-b]pyridin-5-yl)phenyl)-cyclopropyl)methanol (0.15 g, 0.23 mmol) and $P(OEt)_3$ (57 mg, 0.34 mmol) in $CH_3CN$ (3 mL) was added $Pd(OAc)_2$ (5 mg, 0.023 mmol). The reaction mixture was heated under microwave irradiation at 80° C. for 45 minutes. Then the reaction mixture was cooled to room temperature, diluted with water (5 mL) and extracted with ethyl acetate (3×5 mL). The organic layers were separated, combined, dried over anhydrous magnesium sulfate, filtered and concentrated under vacuum to give the crude product, which was purified by flash column chromatography on silica gel (petroleum ether:ethyl acetate=10:1 to 1:2) to give the title compound. NMR δ (ppm) (CDCl3): 7.81 (m, 2H), 7.65 (d, 2H), 7.44 (d, 2H), 7.31 (br, 2H), 5.73 (s, 1H), 5.52 (s, 2H), 4.14 (m, 4H), 3.71 (s, 2H), 3.62 (t, 2H), 2.17 (s, 3H), 1.3 (m, 6H), 0.92 (m, 6H), 0.00 (s, 9H). LC-MS: calculated for $C_{34}H_{44}ClN_2O_6PSi$ 670.24, observed m/e: 671.3 $(M+H)^+$ (Rt 1.32/2 min).

Example 112

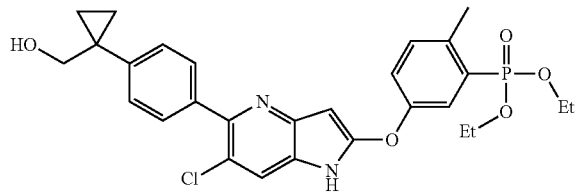 [SMILES: CCOP(=O)(OCC)c1cc(Oc2cc3nc(-c4ccc(C5(CO)CC5)cc4)c(Cl)cc3[nH]2)ccc1C]

Diethyl (5-((6-chloro-5-(4-(1-(hydroxymethyl)cyclopropyl)phenyl)-1H-pyrrolo[3,2-b]pyridin-2-yl)oxy)-2-methylphenyl)phosphonate To a solution of diethyl (5-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)-2-methylphenyl)phosphonate (20 mg, 0.03 mmol, Intermediate 37) in THF (2 mL) was added TBAF (16 mg, 0.06 mmol) and ethane-1,2-diamine (4 mg, 0.06 mmol). The reaction mixture was stirred at reflux for 5 hours. Then the reaction mixture was cooled to room temperature, and concentrated under vacuum to give the crude product, which was purified by prep. HPLC (MeCN/$H_2O$ as eluent, 0.05% TFA) to afford the title compound. NMR δ (ppm) (CD$_3$OD): 7.78 (s, 1H), 7.70 (d, 1H), 7.48 (m, 6H), 5.66 (s, 1H), 4.13 (m, 4H), 3.69 (s, 2H), 2.58 (s, 3H), 1.31 (m, 6H), 0.89 (d, 4H). LC-MS: calculated for $C_{28}H_{30}ClN_2O_5P$ 540.16, observed m/e: 541.1 $(M+H)^+$ (Rt 1.79/4.5 min).

Example 113

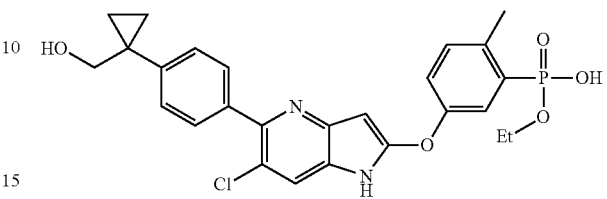

Ethyl hydrogen (5-((6-chloro-5-(4-(1-(hydroxymethyl)cyclopropyl)phenyl)-1H-pyrrolo[3,2-b]pyridin-2-yl)oxy)-2-methylphenyl)phosphonate Step A: ethyl hydrogen (5-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)-2-methylphenyl)-phosphonate To a mixture of diethyl (5-((6-chloro-5-(4-(1-(hydroxymethyl)cyclopropyl)-phenyl)-1-((2-(trimethylsilyl)ethoxy)methyl)-1H-pyrrolo[3,2-b]pyridin-2-yl)oxy)-2-methyl-phenyl)phosphonate (80 mg, 0.12 mmol, Intermediate 37) in EtOH (3 mL) was added NaOH (48 mg, 1.2 mmol). The reaction mixture was stirred at reflux for 3 hours. Then the reaction mixture was cooled to room temperature, and concentrated under vacuum to give the crude product, which was further purified by prep. HPLC (MeCN/$H_2O$ as eluent, 0.05% TFA) to afford the title compound. LC-MS: calculated for $C_{32}H_{40}ClN_2O_6PSi$ 642.21, observed m/e: 643.2 $(M+H)^+$ (Rt 1.26/2 min).

Step B: ethyl hydrogen(5-((6-chloro-1-(hydroxymethyl)-5-(4-(1-(hydroxymethyl)-cyclopropyl)phenyl)-1H-pyrrolo[3,2-b]pyridin-2-yl)oxy)-2-methylphenyl)phosphonate To a solution of ethyl hydrogen (5-((6-chloro-5-(4-(1-(hydroxymethyl)cyclopropyl)-phenyl)-1-((2-(trimethylsilyl)ethoxy)methyl)-1H-pyrrolo[3,2-b]pyridin-2-yl)oxy)-2-methylphenyl)-phosphonate (46 mg, 0.071 mmol) in THF (2 mL) at 0° C. was added dropwise conc. HCl (2 mL). The reaction was warmed slowly to room temperature and stirred overnight. Then the reaction mixture was concentrated under vacuum to afford the title compound, which was used directly in the next step without purification. LC-MS: calculated for $C_{27}H_{28}ClN_2O_6P$ 542.14, observed m/e: 543.1 $(M+H)^+$ (Rt 0.90/2 min).

Step C: ethyl hydrogen(5-((6-chloro-5-(4-(1-(hydroxymethyl)cyclopropyl)phenyl)-1H-pyrrolo[3,2-b]pyridin-2-yl)oxy)-2-methylphenyl)phosphonate To a solution of ethyl hydrogen (5-((6-chloro-1-(hydroxymethyl)-5-(4-(1-(hydroxymethyl)cyclopropyl)phenyl)-1H-pyrrolo[3,2-b]pyridin-2-yl)oxy)-2-methylphenyl) phosphonate (crude 40 mg) in DMF (2 mL) was added ethane-1,2-diamine (6 mg, 0.103 mmol) at 0° C. The reaction mixture was stirred at 0° C. for 10 minutes. Then the reaction mixture was concentrated under vacuum to give the crude product, which was purified by prep. HPLC (MeCN/H₂O as eluent, 0.05% TFA) to afford the title compound. NMR δ (ppm) (CD₃OD): 8.29 (s, 1H), 7.82 (d, 1H), 7.61 (s, 4H), 7.37 (m, 2H), 5.77 (s, 1H), 3.86 (q, 2H), 3.74 (s, 2H), 2.67 (s, 3H), 1.23 (t, 3H), 1.06 (m, 4H). LC-MS: calculated for $C_{26}H_{26}ClN_2O_5P$ 512.13, observed m/e: 513.1 (M+H)⁺ (Rt 1.43/2 min).

Example 114

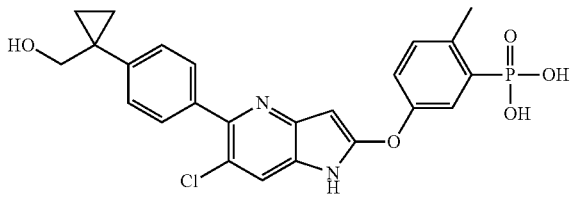 [SMILES: Cc1ccc(Oc2cc3nc(-c4ccc(C5(CO)CC5)cc4)c(Cl)cc3[nH]2)cc1P(=O)(O)O]

(5-((6-chloro-1-(hydroxymethyl)-5-(4-(1-(hydroxymethyl)cyclopropyl)phenyl)-1H-pyrrolo[3,2-b]pyridin-2-yl)oxy)-2-methylphenyl)phosphonic acid Step A: (5-((6-chloro-5-(4-(1-(hydroxymethyl)cyclopropyl)phenyl)-1-((2-(trimethylsilyl)ethoxy)methyl)-1H-pyrrolo[3,2-b]pyridin-2-yl)oxy)-2-methylphenyl)-phosphonic acid To a solution of diethyl (5-((6-chloro-5-(4-(1-(hydroxymethyl)-cyclopropyl)phenyl)-1-((2-(trimethylsilyl)ethoxy)methyl)-1H-pyrrolo[3,2-b]pyridin-2-yl)oxy)-2-methylphenyl)phosphonate (25 mg, 0.0373 mmol, Intermediate 37) in dichloromethane (4 mL) were added hexamethyldisilazane (30 mg, 0.187 mmol) and bromotrimethylsilane (46 mg, 0.298 mmol) at 0° C. The mixture was stirred at 0° C. for 2 hours. Then additional hexamethyldisilazane (30 mg, 0.187 mmol) and bromotrimethylsilane (46 mg, 0.298 mmol) were added. The reaction was stirred at 0° C. for 2 hours, then quenched with MeOH. The reaction mixture was concentrated. The resulting crude product was purified by prep. HPLC (MeCN/H₂O as eluent, 0.05% TFA) to give the title compound. LC-MS: calculated for $C_{30}H_{36}ClN_2O_6PSi$ 614.18, observed m/e: 615.2 (M+H)⁺ (Rt 1.13/2 min).

Step B: (5-((6-chloro-1-(hydroxymethyl)-5-(4-(1-(hydroxymethyl)cyclopropyl)phenyl)-1H-pyrrolo[3,2-b]pyridin-2-yl)oxy)-2-methylphenyl)phosphonic acid To a solution of (5-((6-chloro-5-(4-(1-(hydroxymethyl)cyclopropyl)phenyl)-1-((2-(trimethylsilyl)-ethoxy)methyl)-1H-pyrrolo[3,2-b]pyridin-2-yl)oxy)-2-methylphenyl)phosphonic acid (10 mg, 0.0163 mmol) in THF (1.5 mL) at 0° C. was added concentrated HCl (1.5 mL). The reaction was stirred for 15 minutes, then concentrated in vacuum at room temperature via oil pump to afford the title compound, which was used directly in the next step without purification. LC-MS: calculated for $C_{25}H_{24}ClN_2O_6P$ 514.11, observed m/e: 515.1 (M+H)⁺ (Rt 0.91/2 min).

Step C: (5-((6-chloro-5-(4-(1-(hydroxymethyl)cyclopropyl)phenyl)-1H-pyrrolo[3,2-b]pyridin-2-yl)oxy)-2-methylphenyl)phosphonic acid To a solution of (5-((6-chloro-1-(hydroxy-methyl)-5-(4-(1-(hydroxymethyl)cyclopropyl)phenyl)-1H-pyrrolo[3,2-b]pyridin-2-yl)oxy)-2-methylphenyl)phosphonic acid (crude 10 mg) in DMF (2 mL) was added ethane-1,2-diamine (2.62 mg, 0.0437 mmol) at 0° C. The reaction was stirred for 15 minutes, then concentrated. The resulting crude product was purified by prep. HPLC (MeCN/H₂O as eluent, 0.05% TFA) to give the title compound. NMR δ (ppm) (CD₃OD): 8.27 (s, 1H), 7.79 (s, 2H), 7.58 (s, 4H), 7.40 (d, 2H), 5.75 (s, 1H), 3.71 (s, 2H), 2.67 (s, 3H), 0.94 (d, 4H). LC-MS: calculated for $C_{24}H_{22}ClN_2O_5P$ 484.10, observed m/e: 485.1 (M+H)⁺ (Rt 0.94/2 min).

Example 115

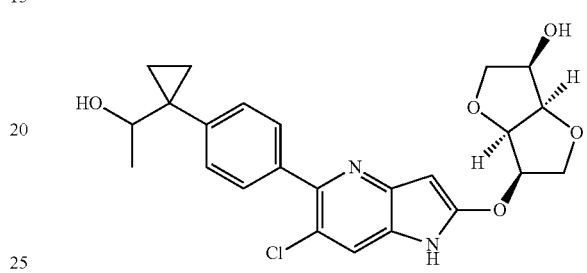

(3R,3aR,6R,6aR)-6-((6-chloro-5-(4-(1-(1-hydroxyethyl)cyclopropyl)phenyl)-1H-pyrrolo[3,2-b]pyridin-2-yl)oxy)hexahydrofuro[3,2-b]furan-3-ol Step A: 1-(4-(2,6-dichloro-1-((2-(trimethylsilyl)ethoxy)methyl)-1H-pyrrolo[3,2-b]pyridin-5-yl)phenyl)cyclopropanecarbaldehyde To a solution of (1-(4-(2,6-dichloro-1-((2-(trimethylsilyl)ethoxy)methyl)-1H-pyrrolo[3,2-b]pyridin-5-yl)phenyl)cyclopropyl)-methanol (100 mg, 0.2 mmol, Intermediate 27) in DCM (10 mL) was added DMP (169 mg, 0.4 mmol) at 0° C. The reaction was warmed slowly to room temperature and stirred for 2 hours. Then the reaction was quenched with an aqueous solution of Na₂SO₃. The separated organic layer was washed with brine twice, dried over Na₂SO₄, and concentrated under reduced pressure to give the crude product, which was purified by flash column chromatography (petroleum ether:ethyl acetate=50:1 to 10:1) to give the title compound. LC-MS: calculated for $C_{23}H_{26}Cl_2N_2O_2Si$ 460.11, observed m/e: 461.1 (M+H)⁺ (Rt 1.51/2 min).

Step B: 1-(1-(4-(2,6-dichloro-1-((2-(trimethylsilyl)ethoxy)methyl)-1H-pyrrolo[3,2-b]pyridin-5-yl)phenyl)cyclopropyl)ethanol To a solution of 1-(4-(2,6-dichloro-1-((2-(trimethylsilyl)ethoxy)methyl)-1H-pyrrolo[3,2-b]pyridin-5-yl)phenyl)cyclopropanecarbaldehyde (40 mg, 0.08 mmol) in THF (5 mL) was added CH₃MgBr (1 ml, 3.0 mmol, 3M) dropwise (under N₂) at 0° C. The reaction was stirred at 0° C. for 2 hours, then quenched with an aqueous NH₄Cl solution and extracted with EtOAc (2×20 mL). The combined organic layers were washed with brine, dried over Na₂SO₄ and concentrated under reduced pressure to give the crude product, which was purified by prep TLC (petroleum ether: ethyl acetate=5:1) to give the title compound. LC-MS: calculated for $C_{24}H_{30}Cl_2N_2O_2Si$ 476.15, observed m/e: 477.0 (M+H)⁺ (Rt 1.39/2 min).

Step C: (3R,3aR,6R,6aR)-6-((6-chloro-5-(4-(1-(1-hydroxyethyl)cyclopropyl)phenyl)-1-((2-(trimethylsilyl)ethoxy)methyl)-1H-pyrrolo[3,2-b]pyridin-2-yl)oxy)hexahydro-furo[3,2-b]furan-3-ol To a solution of 1-(1-(4-(2,6-dichloro-1-((2-(trimethylsilyl)-ethoxy)methyl)-1H-pyrrolo[3,2-b]pyridin-5-yl)phenyl)cyclopropyl)ethanol (24 mg, 0.05 mmol) in DMSO (2 mL) and dioxane (2 mL) was added $Cs_2CO_3$ (81 mg, 0.25 mmol) and (3S,3aS,6S,6aS)-hexahydrofuro[3,2-b]furan-3,6-diol (73 mg, 0.5 mmol). The mixture was stirred at 120° C. for 18 hours, then EtOAc (20 mL) and water (8 mL) were added. The combined organic layers were washed with water (2×8 mL) and brine (8 mL), then dried over $Na_2SO_4$ and concentrated under reduced pressure to give the crude product, which was purified by flash column chromatography (petroleum ether:ethyl acetate=10:1 to 3:1) to give the title compound. LC-MS: calculated for $C_{30}H_{39}ClN_2O_6Si$ 586.23, observed m/e: 587.1 $(M+H)^+$ (Rt 0.89/2 min).

Step D: (3R,3aR,6R,6aR)-6-((6-chloro-5-(4-(1-(1-hydroxyethyl)cyclopropyl)phenyl)-1H-pyrrolo[3,2-b]pyridin-2-yl)oxy)hexahydrofuro[3,2-b]furan-3-ol To a solution of (3R,3aR,6R,6aR)-6-((6-chloro-5-(4-(1-(1-hydroxyethyl)cyclopropyl)phenyl)-1-((2-(trimethylsilyl)ethoxy)methyl)-1H-pyrrolo[3,2-b]pyridin-2-yl)oxy)hexahydrofuro[3,2-b]furan-3-ol (20 mg, 0.03 mmol) in THF (2 mL) was added ethane-1,2-diamine (6 mg, 0.1 mmol) and TBAF (0.09 mL (1 M in THF, 0.09 mmol). The reaction was heated to reflux overnight, then cooled to room temperature, and concentrated under vacuum. The resulting crude product was purified by prep. HPLC ($MeCN/H_2O$ as eluent, 0.05% TFA) to afford the title compound. NMR δ (ppm) ($CD_3OD$): 7.61 (s, 1H), 7.45 (t, 4H), 7.11 (t, 1H), 5.04 (d, 1H), 5.01 (d, 1H), 4.46 (d, 1H), 4.15 (t, 1H), 4.02 (d, 1H), 3.90 (t, 2H), 3.60 (1H), 3.43 (1H), 2.81 (1H), 1.10 (d, 3H), 0.81 (t, 4H). LC-MS: calculated for $C_{24}H_{25}ClN_2O_5$ 456.15, observed m/e: 457.2 $(M+H)^+$ (Rt 0.95/2 min).

Examples 116A and 116B

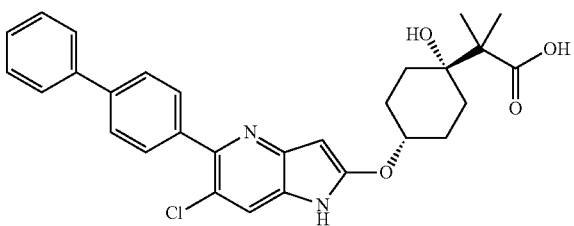

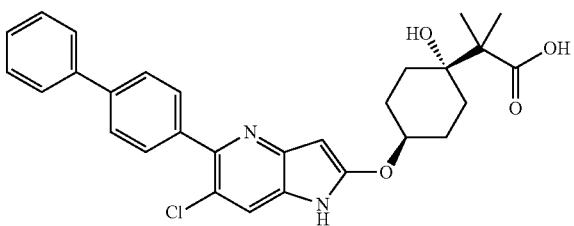

2-((1S,4S)-4-((5-([1,1'-biphenyl]-4-yl)-6-chloro-1H-pyrrolo[3,2-b]pyridin-2-yl)oxy)-1-hydroxycyclohexyl)-2-methylpropanoic acid; 2-((1R,4R)-4-((5-([1,1'-biphenyl]-4-yl)-6-chloro-1H-pyrrolo[3,2-b]pyridin-2-yl)oxy)-1-hydroxycyclohexyl)-2-methylpropanoic acid Step A: 2-(1,4-dioxaspiro[4.5]decan-8-yloxy)-5-([1,1'-biphenyl]-4-yl)-6-chloro-1H-pyrrolo[3,2-b]pyridine To a mixture of 1,4-dioxaspiro[4.5]decan-8-ol (500 mg, 1.1 mmol) in 1-methylpyrrolidin-2-one (20 mL) was added sodium hydride (170 mg, 4.3 mmol, 60% in oil) at 0° C. The mixture was stirred at 0° C. for 30 min, then 5-([1,1'-biphenyl]-4-yl)-2,6-dichloro-1-((2-(trimethylsilyl)ethoxy)methyl)-1H-pyrrolo[3,2-b]pyridine (674 mg, 4.3 mmol, Intermediate 28) was added, and the mixture was heated to 120° C. by MW and stirred for 1 hour. Then the mixture was quenched with saturated aqueous ammonium chloride, and extracted with ethyl acetate. The combined organic layers were washed with brine, dried over anhydrous $Na_2SO_4$, filtered and concentrated under reduced pressure to give crude product, which was purified by silica gel column chromatography (PE:EtOAc=20:1~2:1) to afford the title compound. NMR δ (ppm) ($CD_3CD$): 8.18 (s, 1H), 7.90 (d, 2H), 7.70 (m, 4H), 7.51 (m, 2H), 7.41 (s, 1H), 6.15 (s, 1H), 4.60 (d, 1H), 2.07 (m, 4H), 1.85 (m, 4H), 1.26 (s, 6H). LC-MS: calculated for $C_{27}H_{25}ClN_2O_3$ 460.16, observed m/e: 461.1 $(M+H)^+$ (Rt 2.13/4.5 min).

Step B: 4-((5-([1,1'-biphenyl]-4-yl)-6-chloro-1H-pyrrolo[3,2-b]pyridin-2-yl)oxy)cyclohexanone To a mixture of 2-(1,4-dioxaspiro[4.5]decan-8-yloxy)-5-([1,1'-biphenyl]-4-yl)-6-chloro-1H-pyrrolo[3,2-b]pyridine (100 mg, 0.22 mmol) in tetrahydrofuran (10 mL) was added aq. HCl (5 mL, 1M). The mixture was heated to reflux and stirred for 4 hours, then concentrated under reduced pressure to afford the title compound, which was used directly in the next step without purification. NMR δ (ppm) ($CD_3CD$): 8.20 (s, 1H), 7.90 (d, 2H), 7.76 (m, 4H), 7.52 (m, 2H), 7.41 (s, 1H), 6.11 (s, 1H), 4.95 (s, 1H), 2.06 (m, 6H), 1.66 (d, 2H), 1.27 (s, 6H). LC-MS: calculated for $C_{25}H_{21}ClN_2O_2$ 416.13, observed m/e: 417.1 $(M+H)^+$ (Rt 1.94/4.5 min).

Step C: tert-butyl 5-([1,1'-biphenyl]-4-yl)-6-chloro-2-((4-oxocyclohexyl)oxy)-1H-pyrrolo[3,2-b]pyridine-1-carboxylate To a mixture of 4-((5-([1,1'-biphenyl]-4-yl)-6-chloro-1H-pyrrolo[3,2-b]pyridin-2-yl)oxy)cyclohexanone (80 mg, 0.19 mmol) in tetrahydrofuran (5 mL) were added di-tert-butyl dicarbonate (46 mg, 0.21 mmol), triethylamine (23 mg, 0.23 mmol) and N,N-dimethylpyridin-4-amine (2 mg, 0.019 mmol). The mixture was stirred at room temperature for 4 hours, then concentrated under reduced pressure to give crude product, which was purified by silica gel column chromatography (PE:EtOAc=30:1~4:1) to afford the title compound. LC-MS: calculated for $C_{30}H_{29}ClN_2O_4$ 516.18, observed m/e: 517.2 $(M+H)^+$ (Rt 1.38/4.5 min).

Step D: tert-butyl 5-([1,1'-biphenyl]-4-yl)-2-(((1S,4S)-4-(1-(tert-butoxy)-2-methyl-1-oxopropan-2-yl)-4-hydroxycyclohexyl)oxy)-6-chloro-1H-pyrrolo[3,2-b]pyridine-1-carboxylate; tert-butyl 5-([1,1'-biphenyl]-4-yl)-2-(((1R,4R)-4-(1-(tert-butoxy)-2-methyl-1-oxopropan-2-yl)-4-hydroxycyclohexyl)oxy)-6-chloro-1H-pyrrolo[3,2-b]pyridine-1-carboxylate To a mixture of tert-butyl isobutyrate (27 mg, 0.19 mmol) in dry tetrahydrofuran (10 mL) at −78° C. was added lithium diisopropylamide (0.19 ml, 0.19 mmol). The mixture stirred at −78° C. for 1 hour, then tert-butyl 5-([1,1'-biphenyl]-4-yl)-6-chloro-2-((4-oxocyclohexyl)oxy)-1H-pyrrolo[3,2-b]pyridine-1-carboxylate (80 mg, 0.15 mmol) was added, and the reaction mixture was stirred at −78° C. for 1 hour. Then the reaction was quenched with saturated aqueous ammonium chloride and extracted with EtOAc. The combined organic layers were washed with brine, dried over anhydrous Na$_2$SO$_4$, filtered and concentrated under reduced pressure to give crude product, which was purified by prep. TLC (PE:EtOAc=3:1) to afford the title compounds. [Upper spot in TLC, LC-MS: calculated for C$_{38}$H$_{45}$ClN$_2$O$_6$ 660.30, observed m/e: 661.2 (M+H)$^+$ (Rt 1.55/2 min); lower spot in TLC, LC-MS: calculated for C$_{38}$H$_{45}$ClN$_2$O$_6$ 660.30, observed m/e: 661.2 (M+H)$^+$ (Rt 1.57/2 min)]

Step E: 2-((1S,4S)-4-((5-([1,1'-biphenyl]-4-yl)-6-chloro-1H-pyrrolo[3,2-b]pyridin-2-yl)oxy)-1-hydroxycyclohexyl)-2-methylpropanoic acid To a solution of tert-butyl 5-([1,1'-biphenyl]-4-yl)-2-(((1S,4S)-4-(1-(tert-butoxy)-2-methyl-1-oxopropan-2-yl)-4-hydroxycyclohexyl)oxy)-6-chloro-1H-pyrrolo[3,2-b]pyridine-1-carboxylate (20 mg, 0.030 mmol) in ethyl acetate (2 mL) was added hydrogen chloride in ethyl acetate (2 mL, 4 M) at 0° C. The reaction mixture was stirred at 0° C. for 4 hours, then concentrated under reduced pressure to give the crude product, which was directly purified by prep HPLC (MeCN/H$_2$O as eluent, 0.05% TFA) to afford the title compound. NMR δ (ppm) (CD$_3$OD): 8.18 (s, 1H), 7.90 (d, 2H), 7.76 (m, 4H), 7.52 (t, 2H), 7.41 (s, 1H), 6.15 (s, 1H), 4.60 (d, 1H), 2.07 (m, 4H), 1.85 (m, 4H), 1.26 (s, 6H). LC-MS: calculated for C$_{29}$H$_{29}$ClN$_2$O$_4$ 504.18, observed m/e: 505.1 (M+H)$^+$ (Rt 2.03/4.5 min).

2-((1R,4R)-4-((5-([1,1'-biphenyl]-4-yl)-6-chloro-1H-pyrrolo[3,2-b]pyridin-2-yl)oxy)-1-hydroxycyclohexyl)-2-methylpropanoic acid To a solution of tert-butyl 5-([1,1'-biphenyl]-4-yl)-2-(((1R,4R)-4-(1-(tert-butoxy)-2-methyl-1-oxopropan-2-yl)-4-hydroxycyclohexyl)oxy)-6-chloro-1H-pyrrolo[3,2-b]pyridine-1-carboxylate (20 mg, 0.030 mmol) in ethyl acetate (2 mL) was added hydrogen chloride in ethyl acetate (2 mL, 4 M) at 0° C. The reaction mixture was stirred at 0° C. for 4 hours, then concentrated under reduced pressure to give the crude product, which was directly purified by prep. HPLC (MeCN/H$_2$O as eluent, 0.05% TFA) to afford the title compound. NMR δ (ppm) (CD$_3$OD): 8.20 (s, 1H), 7.90 (d, 2H), 7.76 (dd, 4H), 7.52 (t, 2H), 7.41 (s, 1H), 6.11 (s, 1H), 4.95 (s, 1H), 2.06 (m, 6H), 1.66 (d, 2H), 1.27 (s, 6H). LC-MS: calculated for C$_{29}$H$_{29}$ClN$_2$O$_4$ 504.18, observed m/e: 505.1 (M+H)$^+$ (Rt 2.02/4.5 min).

TABLE 15

Compounds prepared according to the methods described in Example 115.

| Example Number | Structure | HPLC-mass spectrum m/e |
|---|---|---|
| 117 | (structure) | 533.2 |
| 118 | (structure) | 533.2 |

TABLE 15-continued

Compounds prepared according to the methods described in Example 115.

| Example Number | Structure | HPLC-mass spectrum m/e |
|---|---|---|
| 119 | 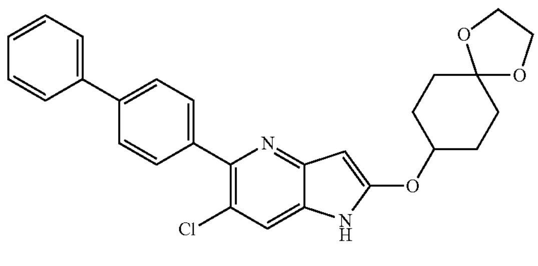 [SMILES: Clc1cc2[nH]c(OC3CCC4(CC3)OCCO4)cc2nc1-c1ccc(-c2ccccc2)cc1] | 461.2 |
| 120 | 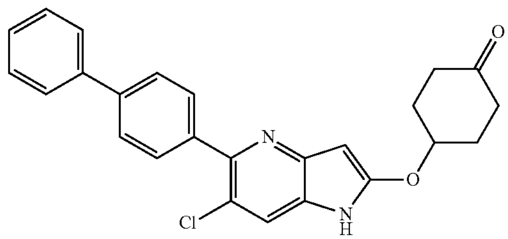 [SMILES: O=C1CCC(Oc2cc3nc(-c4ccc(-c5ccccc5)cc4)c(Cl)cc3[nH]2)CC1] | 417.2 |

Example 121

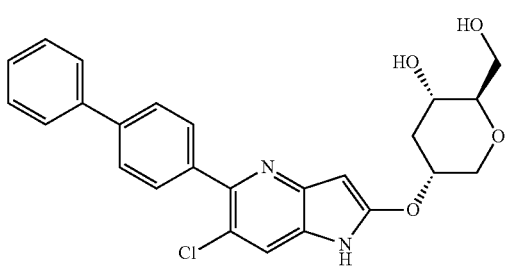 [SMILES: OC[C@H]1OC[C@H](Oc2cc3nc(-c4ccc(-c5ccccc5)cc4)c(Cl)cc3[nH]2)C[C@@H]1O]

(2R,3S,5R)-5-((5-([1,1'-biphenyl]-4-yl)-6-chloro-1H-pyrrolo[3,2-b]pyridin-2-yl)oxy)-2-(hydroxymethyl)tetrahydro-2H-pyran-3-ol Step A: 5-([1,1'-biphenyl]-4-yl)-6-chloro-2-(((4aR,7R,8aS)-2-phenylhexahydropyrano[3,2-d][1,3]dioxin-7-yl)oxy)-1-((2-(trimethylsilyl)ethoxy)methyl)-1H-pyrrolo[3,2-b]pyridine To a mixture of 5-([1,1'-biphenyl]-4-yl)-2,6-dichloro-1-((2-(trimethylsilyl)-ethoxy)methyl)-1H-pyrrolo[3,2-b]pyridine (100 mg, 0.21 mmol, Intermediate 28) in (methylsulfinyl)methane (5 mL) and dioxane (5 mL) were added (4aR,7R,8aS)-2-phenylhexahydropyrano[3,2-d][1,3]dioxin-7-ol (101 mg, 0.43 mmol) and cesium carbonate (139 mg, 0.43 mmol). The mixture was heated to 120° C. by MW and stirred for 1 hour. Then the mixture was diluted with ethyl acetate, washed with brine, dried over anhydrous Na$_2$SO$_4$, filtered and concentrated under reduced pressure. The resulting crude product was purified by silica gel column chromatography (PE:EtOAc=10:1~2:1) to afford the title compound. LC-MS: calculated for C$_{38}$H$_{41}$ClN$_2$O$_5$Si 668.25, observed m/e: 669.3 (M+H)$^+$ (Rt 1.53/2 min).

Step B: (2R,3S,5R)-5-((5-([1,1'-biphenyl]-4-yl)-6-chloro-1-(hydroxymethyl)-1H-pyrrolo[3,2-b]pyridin-2-yl)oxy)-2-(hydroxymethyl)tetrahydro-2H-pyran-3-ol To a solution of 5-([1,1'-biphenyl]-4-yl)-6-chloro-2-(((4aR,7R,8aS)-2-phenylhexahydro-pyrano[3,2-d][1,3]dioxin-7-yl)oxy)-1-((2-(trimethylsilyl)ethoxy)methyl)-1H-pyrrolo[3,2-b]pyridine (40 mg, 0.060 mmol) in THF (2 mL) at 0° C. was added conc. HCl (2 mL). The reaction mixture was stirred at room temperature for 18 hours, then concentrated under reduced pressure to afford the title compound, which was used directly in next step without purification. LC-MS: calculated for C$_{26}$H$_{25}$ClN$_2$O$_5$ 480.15, observed m/e: 481.2 (M+H)$^+$ (Rt 1.04/2 min).

Step C: (2R,3S,5R)-5-((5-([1,1'-biphenyl]-4-yl)-6-chloro-1H-pyrrolo[3,2-b]pyridin-2-yl)oxy)-2-(hydroxymethyl)tetrahydro-2H-pyran-3-ol To a solution of (2R,3S,5R)-5-((5-([1,1'-biphenyl]-4-yl)-6-chloro-1-(hydroxymethyl)-1H-pyrrolo[3,2-b]pyridin-2-yl)oxy)-2-(hydroxymethyl)tetrahydro-2H-pyran-3-ol (20 mg, 0.042 mmol) in DMF (2 mL) was added ethane-1,2-diamine (7.1 mg, 0.12 mmol) at 0° C. The reaction mixture was stirred at 0° C. for 10 minutes and then directly purified by prep. HPLC (MeCN/H$_2$O as eluent, 0.05% TFA) to afford the title compound. NMR δ (ppm) (CD$_3$OD): 8.21 (s, 1H), 7.87 (d, 2H), 7.76 (d, 3H), 7.71 (t, 2H), 7.49 (d, 1H), 6.13 (s, 1H), 4.53 (d, 1H), 4.16 (s, 1H), 4.05 (t, 1H), 3.86 (d, 1H), 3.58 (t, 1H), 3.46 (t, 1H), 1.81 (t, 1H), 1.70 (t, 1H). LC-MS: calculated for C$_{25}$H$_{23}$ClN$_2$O$_4$ 450.13, observed m/e: 451.1 (M+H)$^+$ (Rt 2.27/4.5 min).

TABLE 16

Compounds prepared according to the methods described in Example 121.

| Example Number | Structure | HPLC-mass spectrum m/e |
|---|---|---|
| 122 | 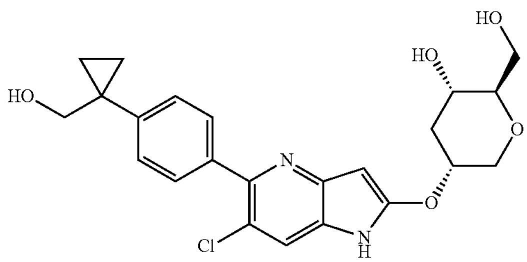 [SMILES: OC[C@H]1OC[C@H](Oc2cc3nc(-c4ccc(C5(CO)CC5)cc4)c(Cl)cc3[nH]2)C[C@@H]1O] | 445.0 |
| 123 | 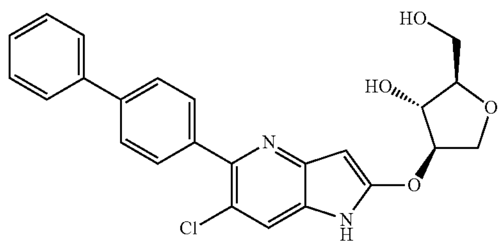 [SMILES: OC[C@H]1OC[C@@H](Oc2cc3nc(-c4ccc(-c5ccccc5)cc4)c(Cl)cc3[nH]2)[C@@H]1O] | 437.1 |
| 124 | 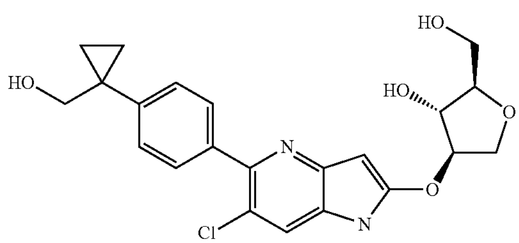 [SMILES: OC[C@H]1OC[C@@H](Oc2cc3nc(-c4ccc(C5(CO)CC5)cc4)c(Cl)cc3[nH]2)[C@@H]1O] | 431.0 |
| 125 | 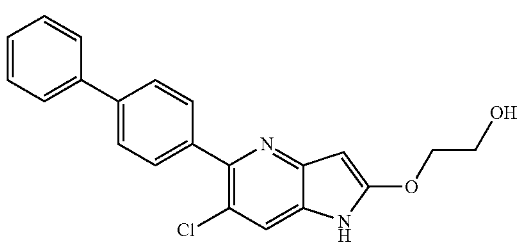 [SMILES: OCCOc1cc2nc(-c3ccc(-c4ccccc4)cc3)c(Cl)cc2[nH]1] | 365.1 |
| 126 | 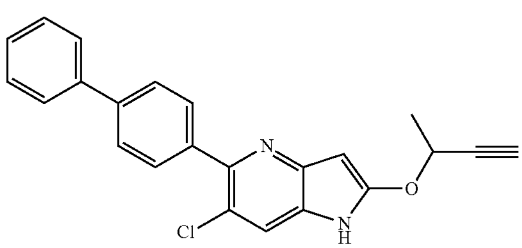 [SMILES: C#CC(C)Oc1cc2nc(-c3ccc(-c4ccccc4)cc3)c(Cl)cc2[nH]1] | 373.1 |

Example 127

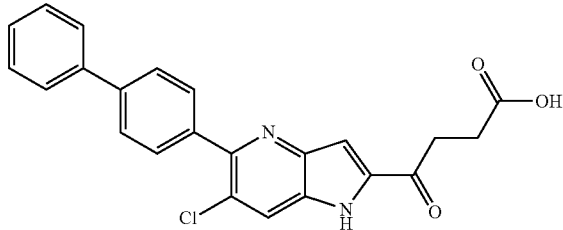 [SMILES: O=C(O)CCC(=O)c1cc2nc(-c3ccc(-c4ccccc4)cc3)c(Cl)cc2[nH]1]

(2R,3S,5R)-5-((5-([1,1'-biphenyl]-4-yl)-6-chloro-1H-pyrrolo[3,2-b]pyridin-2-yl)oxy)-2-(hydroxymethyl)tetrahydro-2H-pyran-3-ol

Step A: methyl 4-(5-([1,1'-biphenyl]-4-yl)-6-chloro-1-((2-(trimethylsilyl)ethoxy)methyl)-1H-pyrrolo[3,2-b]pyridin-2-yl)-4-oxobutanoate To a mixture of 5-([1,1'-biphenyl]-4-yl)-2,6-dichloro-1-((2-(trimethylsilyl)ethoxy)methyl)-1H-pyrrolo[3,2-b]pyridine (300 mg, 0.64 mmol, Intermediate 28) in dry tetrahydrofuran (50 mL) at −78° C. was added dropwise a solution of tert-BuLi in THF (1.4 mL, 1.4 mmol, 1M). The mixture was stirred at −78° C. for 1 hour, then methyl 4-(methoxy(methyl)amino)-4-oxobutanoate (134 mg, 0.77 mmol) was added, and the reaction mixture was stirred at −78° C. for 1 additional hour. The reaction was then quenched with saturated aqueous ammonium chloride, and extracted with EtOAc. The combined organic layers were washed with brine, dried over anhydrous $Na_2SO_4$, filtered and concentrated under reduced pressure to give crude product, which was purified by silica gel column chromatography (PE:EtOAc=30:1~5:1) to afford the title compound. LC-MS: calculated for $C_{30}H_{33}ClN_2O_4Si$ 548.19, observed m/e: 549.2 $(M+H)^+$ (Rt 1.63/2 min).

Step B: 4-(5-([1,1'-biphenyl]-4-yl)-6-chloro-1-((2-(trimethylsilyl)ethoxy)methyl)-1H-pyrrolo[3,2-b]pyridin-2-yl)-4-oxobutanoic acid To a solution of methyl 4-(5-([1,1'-biphenyl]-4-yl)-6-chloro-1-((2-(trimethylsilyl)ethoxy)methyl)-1H-pyrrolo[3,2-b]pyridin-2-yl)-4-oxobutanoate (70 mg, 0.13 mmol) in methanol (3 mL) and water (3 mL) at 0° C. was added $LiOH \cdot H_2O$ (16 mg, 0.38 mmol). The mixture was warmed to room temperature and stirred for 1 hour. Then the reaction mixture was adjusted to pH=4 with aqueous HCl solution (1M), and extracted with dichloromethane. The combined organic layers were washed with brine, dried over anhydrous $Na_2SO_4$, filtered and concentrated to afford the title compound. LC-MS: calculated for $C_{29}H_{31}ClN_2O_4Si$ 534.17, observed m/e: 535.2 $(M+H)^+$ (Rt 1.54/2 min).

Step C: 4-(5-([1,1'-biphenyl]-4-yl)-6-chloro-1H-pyrrolo[3,2-b]pyridin-2-yl)-4-oxobutanoic acid To a mixture of 4-(5-([1,1'-biphenyl]-4-yl)-6-chloro-1-((2-(trimethylsilyl)ethoxy)methyl)-1H-pyrrolo[3,2-b]pyridin-2-yl)-4-oxobutanoic acid (30 mg, 0.69 mmol) in DMF (3 mL) was added ethane-1,2-diamine (12 mg, 0.21 mmol) at 0° C. The reaction mixture was stirred at 0° C. for 10 minutes and then directly purified by prep. HPLC (MeCN/$H_2O$ as eluent, 0.05% TFA) to afford the title compound. NMR δ (ppm) ($CD_3OD$): 8.15 (d, 3H), 8.06 (d, 1H), 7.84 (s, 2H), 7.82 (s, 2H), 7.72 (d, 2H), 7.49 (d, 2H), 7.41 (s, 1H), 3.67 (t, 2H), 2.83 (t, 2H). LC-MS: calculated for $C_{23}H_{17}ClN_2O_3$ 404.09, observed m/e: 405.2 $(M+H)^+$ (Rt 2.53/4.5 min).

Example 128

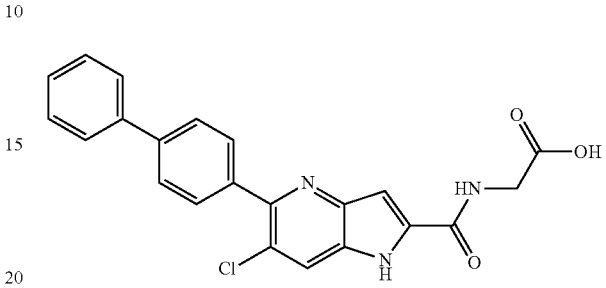

2-(5-([1,1'-biphenyl]-4-yl)-6-chloro-1H-pyrrolo[3,2-b]pyridine-2-carboxamido)acetic acid

Step A: methyl 5-([1,1'-biphenyl]-4-yl)-6-chloro-1-((2-(trimethylsilyl)ethoxy)methyl)-1H-pyrrolo[3,2-b]pyridine-2-carboxylate To a mixture of 5-([1,1'-biphenyl]-4-yl)-2,6-dichloro-1-((2-(trimethylsilyl)ethoxy)methyl)-1H-pyrrolo[3,2-b]pyridine (50 mg, 0.11 mmol, Intermediate 28) in MeOH (10 mL) were added TEA (22 mg, 0.21 mmol) and $Pd(dppf)Cl_2$ (8.1 mg, 0.011 mmol). The reaction mixture saturated with CO and stirred under 1 MPa of CO atmosphere at 100° C. for 16 hours. The reaction mixture was cooled to room temperature, and concentrated under reduced pressure to give the crude product, which was purified by prep TLC (PE:EtOAc=5:1) to afford the title compound. LC-MS: calculated $C_{27}H_{29}ClN_2O_3Si$ 492.16, observed m/e: 493.2 $(M+H)^+$ (Rt 1.69/2 min).

Step B: 5-([1,1'-biphenyl]-4-yl)-6-chloro-1-((2-(trimethylsilyl)ethoxy)methyl)-1H-pyrrolo[3,2-b]pyridine-2-carboxylic acid To a mixture of methyl 5-([1,1'-biphenyl]-4-yl)-6-chloro-1-((2-(trimethylsilyl)ethoxy)methyl)-1H-pyrrolo[3,2-b]pyridine-2-carboxylate (30 mg, 0.061 mmol) in MeOH (1 mL) and $H_2O$ (0.5 mL) was added LiOH (6 mg, 0.24 mmol) at 0° C. The reaction mixture was stirred at room temperature for 18 hours. Then the reaction mixture was concentrated under reduced pressure to give the title compound, which was directly used in the next step without further purification. LC-MS: calculated $C_{26}H_{27}ClN_2O_3Si$ 478.15, observed m/e: 479.2 $(M+H)^+$ (Rt 1.53/2 min).

Step C: 5-([1,1'-biphenyl]-4-yl)-6-chloro-1-(hydroxymethyl)-1H-pyrrolo[3,2-b]pyridine-2-carboxylic acid To a mixture of 5-([1,1'-biphenyl]-4-yl)-6-chloro-1-((2-(trimethyl-silyl)ethoxy)methyl)-1H-pyrrolo[3,2-b]pyridine-2-carboxylic acid (35 mg, 0.073 mmol) in THF (2 mL) was added dropwisely concentrated HCl (2 mL) at 0° C. The reaction mixture was stirred at room temperature for 18 hours. Then the reaction mixture was concentrated under reduced pressure to give the title compound, which was directly used in the next step without further purification. LC-MS: calculated $C_{21}H_{15}ClN_2O_3$ 378.08, observed m/e: 379.1 $(M+H)^+$ (Rt 1.22/2 min).

Step D: 5-([1,1'-biphenyl]-4-yl)-6-chloro-1H-pyrrolo[3,2-b]pyridine-2-carboxylic acid To a mixture of 5-([1,1'-biphenyl]-4-yl)-6-chloro-1-(hydroxymethyl)-1H-pyrrolo[3,2-b]pyridine-2-carboxylic acid (20 mg, 0.053 mmol) in DMF (2.4 mL) was added ethane-1,2-diamine (6.1 mg, 0.11 mmol) at 0° C. The reaction mixture was stirred at 0° C. for 10 min. Then the reaction mixture was directly purified by pre-HPLC (MeCN/$H_2O$ as eluent, 0.05% TFA) to give the title compound. NMR δ (ppm) ($CD_3CD$): 8.22 (s, 1H), 7.75 (m, 6H), 7.48 (m, 2H), 7.39 (d, 1H), 7.28 (s, 1H). LC-MS: calculated for $C_{20}H_{13}ClN_2O_2$ 348.07, observed m/e: 349.0 $(M+H)^+$ (Rt 2.71/4.5 min).

Step E: 2-(5-([1,1'-biphenyl]-4-yl)-6-chloro-1H-pyrrolo[3,2-b]pyridine-2-carboxamido)acetate To a mixture of tert-butyl 2-aminoacetate (4.1 mg, 0.028 mmol) and 5-([1,1'-biphenyl]-4-yl)-6-chloro-1H-pyrrolo[3,2-b]pyridine-2-carboxylic acid (5.1 mg, 0.014 mmol) in DMF (1 mL) were added HATU (8.1 mg, 0.022 mmol) and N-ethyl-N-isopropylpropan-2-amine (4.1 mg, 0.028 mmol). The reaction mixture was stirred at room temperature for 18 hours, then diluted with ethyl acetate and washed with water. The organic layer was separated, dried over $Na_2SO_4$ and concentrated under reduced pressure to give the crude product, which was purified by pre-TLC (PE:EtOAc=3:1) to afford the title compound. LC-MS: calculated for $C_{26}H_{24}ClN_3O_3$ 461.15, observed m/e: 462.2 $(M+H)^+$ (Rt 1.30/2 min).

Step F: 2-(5-([1,1'-biphenyl]-4-yl)-6-chloro-1H-pyrrolo[3,2-b]pyridine-2-carboxamido)acetic acid To a mixture of tert-butyl 2-(5-([1,1'-biphenyl]-4-yl)-6-chloro-1H-pyrrolo[3,2-b]pyridine-2-carboxamido)acetate (5.1 mg, 0.011 mmol) in 1,4-dioxane (1 mL) was added 4M HCl in 1,4-dioxane (1 mL) at 0° C. The reaction mixture was stirred at room temperature for 1.5 hours. Then the reaction mixture was purified by prep HPLC (MeCN/$H_2O$ as eluent, 0.05% TFA) to give the title compound. NMR δ (ppm) ($CD_3OD$): 8.09 (s, 1H), 7.74 (d, 6H), 7.46 (d, 2H), 7.37 (s, 1H), 7.26 (s, 1H), 3.72 (s, 2H). LC-MS: calculated for $C_{22}H_{16}ClN_3O_3$ 405.09, observed m/e: 406.1 $(M+H)^+$ (Rt 2.57/4.5 min).

Example 129

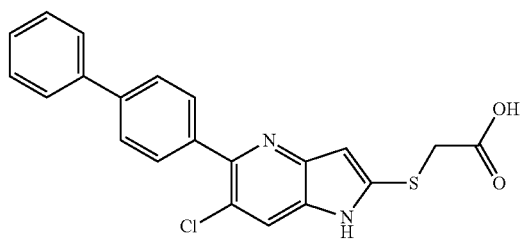 [SMILES: O=C(O)CSc1cc2nc(-c3ccc(-c4ccccc4)cc3)c(Cl)cc2[nH]1]

2-((5-([1,1'-biphenyl]-4-yl)-6-chloro-1H-pyrrolo[3,2-b]pyridin-2-yl)thio)acetic acid Step A: methyl ethyl 2-((5-([1,1'-biphenyl]-4-yl)-6-chloro-1-((2-(trimethylsilyl)-ethoxy)methyl)-1H-pyrrolo[3,2-b]pyridin-2-yl)thio)acetate To a mixture of 5-([1,1'-biphenyl]-4-yl)-2,6-dichloro-1-((2-(trimethylsilyl)ethoxy)methyl)-1H-pyrrolo[3,2-b]pyridine (500 mg, 1.1 mmol, Intermediate 28) in N,N-dimethylformamide (20 mL) were added ethyl 2-mercaptoacetate (512 mg, 4.3 mmol) and potassium carbonate (589 mg, 4.3 mmol). The mixture was heated to 60° C. and stirred for 4 hours. Then the mixture was diluted with ethyl acetate, washed with brine, dried over anhydrous $Na_2SO_4$, filtered and concentrated under reduced pressure. The resulting crude product was purified by silica gel column chromatography (PE:EtOAc=30:1~4:1) to afford the title compound. LC-MS: calculated for $C_{29}H_{33}ClN_2O_3SSi$ 552.17, observed m/e: 553.2 $(M+H)^+$ (Rt 1.59/2 min).

Step B: 2-((5-([1,1'-biphenyl]-4-yl)-6-chloro-1-((2-(trimethylsilyl)ethoxy)methyl)-1H-pyrrolo[3,2-b]pyridin-2-yl)thio)acetic acid To a solution of methyl ethyl 2-((5-([1,1'-biphenyl]-4-yl)-6-chloro-1-((2-(trimethylsilyl)ethoxy)methyl)-1H-pyrrolo[3,2-b]pyridin-2-yl)thio)acetate (100 mg, 0.18 mmol) in ethanol (5 mL) and water (5 mL) at 0° C. was added $LiOH.H_2O$ (23 mg, 0.54 mmol). The mixture was warmed to room temperature and stirred for 1 hour. Then the reaction mixture was adjusted to pH=4 with aqueous HCl solution (1M), and extracted with dichloromethane. The combined organic layers were washed with brine, dried over anhydrous $Na_2SO_4$, filtered and concentrated to afford the title compound. LC-MS: calculated for $C_{27}H_{29}ClN_2O_3SSi$ 524.14, observed m/e: 525.2 $(M+H)^+$ (Rt 1.53/2 min).

Step C: 2-((5-([1,1'-biphenyl]-4-yl)-6-chloro-1-(hydroxymethyl)-1H-pyrrolo[3,2-b]pyridin-2-yl)thio) acetic acid To a solution of 2-((5-([1,1'-biphenyl]-4-yl)-6-chloro-1-((2-(trimethylsilyl)ethoxy)methyl)-1H-pyrrolo[3,2-b]pyridin-2-yl)thio)acetic acid (50 mg, 0.095 mmol) in THF (2 mL) at 0° C. was added conc. HCl (2 mL). The reaction mixture was stirred at room temperature for 18 hours. Then the reaction mixture was concentrated under reduced pressure to afford the title compound, which was used directly in next step without purification. LC-MS: calculated for $C_{22}H_{17}ClN_2O_3S$ 424.06, observed m/e: 425.1 $(M+H)^+$ (Rt 1.12/2 min).

Step D: 2-((5-([1,1'-biphenyl]-4-yl)-6-chloro-1H-pyrrolo[3,2-b]pyridin-2-yl)thio)acetic acid To a solution of 2-((5-([1,1'-biphenyl]-4-yl)-6-chloro-1-(hydroxymethyl)-1H-pyrrolo[3,2-b]pyridin-2-yl)thio)acetic acid (20 mg, 0.047 mmol) in DMF (2 mL) was added ethane-1,2-diamine (8 mg, 0.14 mmol) at 0° C. The reaction mixture was stirred at 0° C. for 10 minutes and then directly purified by prep. HPLC (MeCN/$H_2O$ as eluent, 0.05% TFA) to give the title compound. NMR δ (ppm) ($CD_3OD$): 8.21 (s, 1H), 7.89 (d, 2H), 7.78 (d, 4H), 7.73 (d, 2H), 7.50 (d, 1H), 7.42 (s, 1H), 6.14 (s, 1H), 4.00 (s, 1H), 2.09 (m, 4H), 2.00

(d, 2H), 1.75 (t, 2H). LC-MS: calculated for C$_{21}$H$_{15}$ClN$_2$O$_2$S 394.05, observed m/e: 395.1 (M+H)$^+$ (Rt 1.99/4.5 min).

Example 130

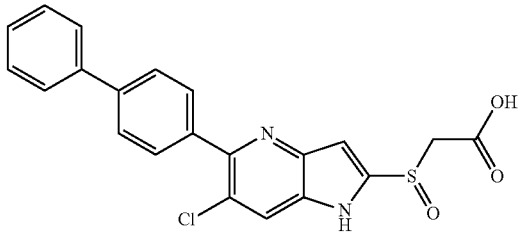 [SMILES: O=C(O)CS(=O)c1cc2nc(-c3ccc(-c4ccccc4)cc3)c(Cl)cc2[nH]1]

2-((5-([1,1'-biphenyl]-4-yl)-6-chloro-1H-pyrrolo[3,2-b]pyridin-2-yl)sulfinyl)acetic acid A mixture of 2-((5-([1,1'-biphenyl]-4-yl)-6-chloro-1H-pyrrolo[3,2-b]pyridin-2-yl)thio)acetic acid (50 mg, 0.13 mmol, Example 129) and NaIO$_4$ (30 mg, 0.14 mmol) in MeOH (2 mL) and H$_2$O (2 mL) was stirred at room temperature for 18 hours, and then concentrated. The resulting residue was extracted with EtOAc, washed with brine, concentrated and purified by prep. HPLC (MeCN/H$_2$O as eluent, 0.05% TFA) to give the title compound. NMR δ (ppm) (CD$_3$OD): 12.63 (s, 1H), 8.16 (s, 1H), 7.80 (m, 7H), 7.54 (t, 2H), 7.45 (d, 1H), 7.21 (s, 1H), 4.35 (s, 2H). LC-MS: calculated for C$_{21}$H$_{15}$ClN$_2$O$_3$S 410.05, observed m/e: 411.1 (M+H)$^+$ (Rt 1.11/2 min).

Example 131

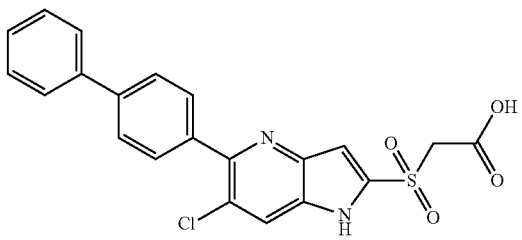 [SMILES: O=C(O)CS(=O)(=O)c1cc2nc(-c3ccc(-c4ccccc4)cc3)c(Cl)cc2[nH]1]

2-((5-([1,1'-biphenyl]-4-yl)-6-chloro-1H-pyrrolo[3,2-b]pyridin-2-yl)sulfonyl)acetic acid To a solution of 2-((5-([1,1'-biphenyl]-4-yl)-6-chloro-1H-pyrrolo[3,2-b]pyridin-2-yl)thio)acetic acid (30 mg, 0.07 mmol, Example 129) in DCM (3 mL) was added m-CPBA (35 mg, 0.21 mmol) at 0° C. The mixture was stirred at room temperature for 20 min. Then the reaction was quenched with aq. Na$_2$S$_2$O$_3$, and extracted with DCM. The combined organic layers were concentrated and purified by prep. HPLC (MeCN/H$_2$O as eluent, 0.05% TFA) to give the title compound. NMR δ (ppm) (CD$_3$OD): 12.80 (s, 1H), 8.14 (s, 1H), 7.76 (m, 6H), 7.49 (t, 2H), 7.39 (s, 1H), 5.73 (s, 1H), 4.67 (s, 2H). LC-MS: calculated for C$_{21}$H$_{15}$ClN$_2$O$_4$S 426.04, observed m/e: 427.0 (M+H)$^+$ (Rt 1.24/2 min).

Example 132

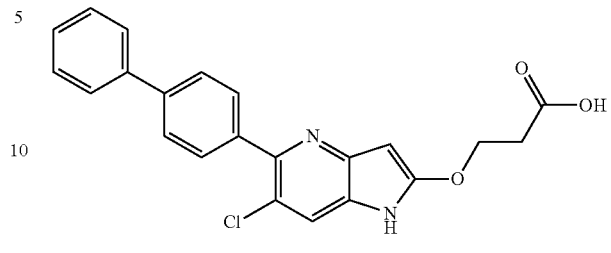

3-((5-([1,1'-biphenyl]-4-yl)-6-chloro-1H-pyrrolo[3,2-b]pyridin-2-yl)oxy)propanoic acid Step A: 3-((5-([1,1'-biphenyl]-4-yl)-6-chloro-1-((2-(trimethylsilyl)ethoxy)methyl)-1H-pyrrolo[3,2-b]pyridin-2-yl)oxy)propan-1-ol To a mixture of 5-([1,1'-biphenyl]-4-yl)-2,6-dichloro-1-((2-(trimethylsilyl)ethoxy)methyl)-1H-pyrrolo[3,2-b]pyridine (200 mg, 0.43 mmol, Intermediate 28) in (methylsulfinyl)methane (20 mL) were added propane-1,3-diol (130 mg, 1.7 mmol) and cesium carbonate (555 mg, 1.7 mmol). The mixture was stirred at 80° C. for 4 hours. Then the mixture was diluted with ethyl acetate, washed with brine, dried over anhydrous Na$_2$SO$_4$, filtered and concentrated under reduced pressure to give crude product, which was purified by silica gel column chromatography (PE:EtOAc=20:1~4:1) to afford the title compound. LC-MS: calculated for C$_{28}$H$_{33}$ClN$_2$O$_3$Si 508.19, observed m/e: 509.2 (M+H)$^+$ (Rt 1.30/2 min).

Step B: 3-((5-([1,1'-biphenyl]-4-yl)-6-chloro-1-((2-(trimethylsilyl)ethoxy)methyl)-1H-pyrrolo[3,2-b]pyridin-2-yl)oxy)propanal To a solution of compound 3-((5-([1,1'-biphenyl]-4-yl)-6-chloro-1-((2-(trimethylsilyl)ethoxy)methyl)-1H-pyrrolo[3,2-b]pyridin-2-yl)oxy)propan-1-ol (24 mg, 0.05 mmol) in DCM (3 mL) was added Dess-Martin Periodinane (63 mg, 0.15 mmol) at 0° C. The mixture was stirred at 0° C. for 5 min, then the ice-bath was removed and the mixture was stirred for 2 hours. Then the reaction was quenched with Na$_2$SO$_3$ solution and washed with brine twice. The organic layer was concentrated to give crude product, which was purified with silica gel to the title compound. LC-MS: calculated for C$_{28}$H$_{31}$ClN$_2$O$_3$Si 506.18, observed m/e: 507.2 (M+H)$^+$ (Rt 1.30/2 min).

Step C: 3-((5-([1,1'-biphenyl]-4-yl)-6-chloro-1-((2-(trimethylsilyl)ethoxy)methyl)-1H-pyrrolo[3,2-b]pyridin-2-yl)oxy)propanoic acid To a solution of 3-((5-([1,1'-biphenyl]-4-yl)-6-chloro-1-((2-(trimethylsilyl)ethoxy)methyl)-1H-pyrrolo[3,2-b]pyridin-2-yl)oxy)propanal (5.1 mg, 0.01 mmol) in t-BuOH (1 mL) were added dropwise a mixture of 2-methylbut-2-ene (0.7 mL) in MeCN (2 mL), and a mixture of NaClO$_2$ (10 mg, 0.1 mmol) and NaH$_2$PO$_4$ (10 mg, 0.1 mmol) in H$_2$O (1 mL). The resulting two-phase mixture was stirred for 18 hours at room temperature. The organic components were evaporated and the remaining aqueous phase was extracted three times with EtOAc. The combined organic layers were washed with brine, dried over Na$_2$SO$_4$, and purified by prep TLC (PE:EtOAc=2:1) to give the title compound. NMR δ (ppm) (CD$_3$OD): 8.27 (s, 1H), 7.81 (m, 7H), 7.56 (t, 2H), 7.46 (s, 1H), 5.60 (s, 2H), 4.94 (t, 2H), 3.64 (t, 2H), 2.72 (t, 2H), 0.91 (d, 2H). LC-MS: calculated for C$_{28}$H$_{31}$ClN$_2$O$_4$Si 522.17, observed m/e: 505.2 (M+H—H$_2$O)$^+$ (Rt 1.12/2 min).

Step D: 3-((5-([1,1'-biphenyl]-4-yl)-6-chloro-1H-pyrrolo[3,2-b]pyridin-2-yl)oxy)propanoic acid To a solution of 3-((5-([1,1'-biphenyl]-4-yl)-6-chloro-1-((2-(trimethylsilyl)ethoxy)methyl)-1H-pyrrolo[3,2-b]pyridin-2-yl)oxy)propanoic acid (20 mg, 0.03 mmol) in THF (2 mL) was added concentrated aqueous HCl (2 mL). The mixture was stirred at 0° C. for 18 hours, then concentrated to give the crude product. To a solution of the crude product (12 mg, 0.03 mmol) in DMF (2 mL) was added ethane-1,2-diamine (3.6 mg, 0.06 mmol) at 0° C. The mixture was stirred for 5 min, then directly purified by prep HPLC (MeCN/H$_2$O as eluent, 0.05% TFA) to afford the title compound. NMR δ (ppm) (CD$_3$OD): 7.78 (m, 8H), 7.48 (d, 2H), 7.39 (s, 1H), 4.95 (s, 2H), 2.81 (t, 2H). LC-MS: calculated for C$_{22}$H$_{17}$ClN$_2$O$_3$ 392.09, observed m/e: 375.0 (M+H—H$_2$O)$^+$ (Rt 1.10/2 min).

Example 133

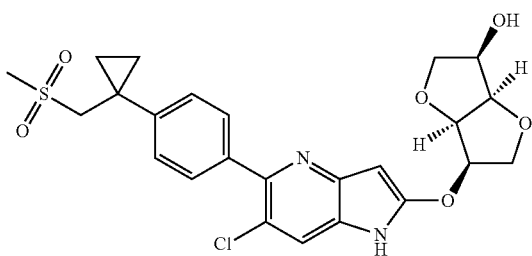 [SMILES: CS(=O)(=O)CC1(c2ccc(-c3nc4cc(O[C@@H]5CO[C@H]6[C@@H]5OC[C@H]6O)[nH]c4cc3Cl)cc2)CC1]

2,6-dichloro-5-(4-(1-(iodomethyl)cyclopropyl)phenyl)-1-((2-(trimethylsilyl)ethoxy)methyl)-1H-pyrrolo[3,2-b]pyridine Step A: 2,6-dichloro-5-(4-(1-(iodomethyl)cyclopropyl)phenyl)-1-((2-(trimethylsilyl)ethoxy)methyl)-1H-pyrrolo[3,2-b]pyridine (1-(4-(2,6-dichloro-1-((2-(trimethylsilyl)ethoxy)methyl)-1H-pyrrolo[3,2-b]pyridin-5-yl)phenyl)cyclopropyl)methanol (100 mg, 0.22 mmol, Intermediate 27) was dissolved in tetrahydrofuran (3.5 mL), then triphenyl phosphine (67.93 mg, 0.26 mmol), imidazole (22.06 mg, 0.32 mmol) and iodine (65.78 mg, 0.26 mmol) were added sequentially. The resulting mixture was stirred at about 20-35° C. under a nitrogen atmosphere for 18 hours. Then the reaction was quenched with saturated aqueous ammonium chloride and diluted with dichloromethane. The organic layer was washed with 10% sodium thiosulfate (1×), water (1×), and brine (1×). The organic layer was dried over sodium sulfate, filtered, and concentrated by rotary evaporation. The resulting residue was purified by prep-TLC (petroleum ether:ethyl acetate=7:1) to give the title compound. NMR δ (ppm) (CD$_3$OD): 7.86 (s, 1H), 7.67 (d, 2H), 7.45 (d, 2H), 6.71 (s, 1H), 5.56 (s, 2H), 3.58 (d, 2H), 3.54 (d, 2H), 0.92 (t, 6H), 0.02 (s, 9H). LC-MS: calculated for C$_{23}$H$_{27}$Cl$_2$IN$_2$OSi 572.03, observed m/e: 573.0 (M+H)$^+$ (Rt 1.57/2 min).

Step B: 2,6-dichloro-5-(4-(1-((methylsulfonyl)methyl)cyclopropyl)phenyl)-1-((2-(trimethylsilyl)ethoxy)methyl)-1H-pyrrolo[3,2-b]pyridine To a solution of 2,6-dichloro-5-(4-(1-(iodomethyl)cyclopropyl)phenyl)-1-((2-(trimethylsilyl)ethoxy)methyl)-1H-pyrrolo[3,2-b]pyridine (20 mg, 0.035 mmol) in ethanol (2 mL) was added methanesulfinic acid sodium salt (17.8 mg, 0.17 mmol). The reaction was stirred and heated at 70° C. for 18 hours. Then the reaction mixture was filtered and the filtrate was concentrated to give the title compound. LC-MS: calculated for C$_{24}$H$_{30}$Cl$_2$N$_2$O$_3$SSi 524.11, observed m/e: 525.1 (M+H)$^+$ (Rt 1.32/2 min).

Step C: (3R,3aR,6R,6aR)-6-((6-chloro-5-(4-(1-((methylsulfonyl)methyl)cyclopropyl)phenyl)-1-((2-(trimethylsilyl)ethoxy)methyl)-1H-pyrrolo[3,2-b]pyridin-2-yl)oxy)hexahydrofuro[3,2-b]furan-3-ol To a mixture of 2,6-dichloro-5-(4-(1-((methylsulfonyl)methyl)cyclopropyl)phenyl)-1-((2-(trimethylsilyl)ethoxy)methyl)-1H-pyrrolo[3,2-b]pyridine (22.4 mg, 0.039 mmol) in (methylsulfinyl)methane (2 mL) were added (3R,3aR,6R,6aR)-hexahydrofuro[3,2-b]furan-3,6-diol (28.5 mg, 0.195 mmol) and cesium carbonate (38.2 mg, 0.12 mmol). The mixture was stirred and heated to 120° C. for 18 hours. After cooling, the mixture was concentrated under reduced pressure, diluted with water, and extracted with ethyl acetate. The combined organic layers were washed with brine, dried over anhydrous Na$_2$SO$_4$, filtered and concentrated under reduced pressure to give the crude product, which was purified by prep-TLC (petroleum ether:ethyl acetate=3:1) to afford the title compound. LC-MS: calculated for C$_{30}$H$_{39}$ClN$_2$O$_7$SSi 634.19, observed m/e: 635.2 (M+H)$^+$ (Rt 1.04/2 min).

Step D: (3R,3aR,6R,6aR)-6-((6-chloro-1-(hydroxymethyl)-5-(4-(1-((methylsulfonyl)methyl)cyclopropyl)phenyl)-1H-pyrrolo[3,2-b]pyridin-2-yl)oxy)hexahydrofuro[3,2-b]furan-3-ol To a solution of (3R,3aR,6R,6aR)-6-((6-chloro-5-(4-(1-((methylsulfonyl)-methyl)cyclopropyl)phenyl)-1-((2-(trimethylsilyl)ethoxy)methyl)-1H-pyrrolo[3,2-b]pyridin-2-yl)oxy)hexahydrofuro[3,2-b]furan-3-ol (15 mg, 0.024 mmol) in tetrahydrofuran (1 mL) was added concentrated aqueous hydrochloride (1 mL) at 0° C. The mixture was stirred at 0° C., then allowed to warm up to room temperature slowly and stirred at room temperature for 18 hours. Then the reaction mixture was concentrated under vacuum at room temperature to afford the title compound, which was used in next step without purification. LC-MS: calculated for C$_{25}$H$_{27}$ClN$_2$O$_7$S 534.12, observed m/e: 535.1 (M+H)$^+$ (Rt 0.68/2 min).

Step E: (3R,3aR,6R,6aR)-6-((6-chloro-5-(4-(1-((methylsulfonyl)methyl)cyclopropyl)phenyl)-1H-pyrrolo[3,2-b]pyridin-2-yl)oxy)hexahydrofuro[3,2-b]furan-3-ol To a stirred solution of (3R,3aR,6R,6aR)-6-((6-chloro-1-(hydroxymethyl)-5-(4-(1-((methylsulfonyl)methyl)cyclopropyl)phenyl)-1H-pyrrolo[3,2-b]pyridin-2-yl)oxy)hexahydrofuro[3,2-b]furan-3-ol (14 mg, 0.026 mmol) in N,N- dimethylformamide (1.5 mL) was slowly added ethane-1,2-diamine (3.15 mg, 0.052 mmol) at 0° C. The mixture was stirred at room temperature for 5 minutes, then purified by prep-HPLC (MeCN/H₂O as eluent, 0.05% TFA) to give the title compound. NMR δ (ppm) (CD₃OD): 8.24 (s, 1H), 7.73 (d, 2H), 7.65 (t, 2H), 6.20 (s, 1H), 5.25 (d, 1H), 4.99 (t, 1H), 4.48 (d, 1H), 4.20 (d, 1H), 3.91 (d, 1H), 3.65 (s), 3.60 (m, 3H), 2.76 (s, 3H), 1.25 (t, 2H), 1.18 (t, 2H). LC-MS: calculated for C₂₄H₂₅ClN₂O₆S 504.11, observed m/e: 505.0 (M+H)⁺ (Rt 0.68/2 min).

Example 134

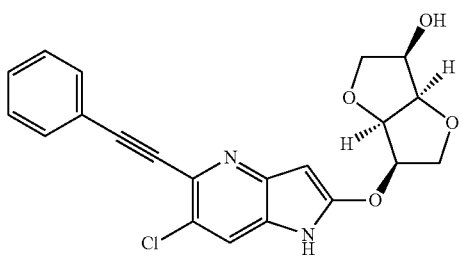 [SMILES: O[C@@H]1CO[C@H]2[C@@H]1OC[C@H]2Oc1cc2nc(C#Cc3ccccc3)c(Cl)cc2[nH]1]

(3R,3aR,6R,6aR)-6-((6-chloro-5-(phenylethynyl)-1H-pyrrolo[3,2-b]pyridin-2-yl)oxy)hexahydrofuro[3,2-b]furan-3-ol Step A: 6-chloro-5-(phenylethynyl)-1H-pyrrolo[3,2-b]pyridin-2(3H)-one To a mixture of ethyl 2-(3-amino-6-bromo-5-chloropyridin-2-yl)acetate (1 g, 3.42 mmol, Intermediate 25), Pd(PPh₃)₂Cl₂ (66 mg, 0.1 mmol) and CuI (40 g, 0.2 mmol) in TEA (15 mL) was add ethynylbenzene (385 g, 3.76 mmol). The mixture was heated to 100° C. in a silicone bath for 2 hours. Then the mixture was allowed to cool to room temperature, and ethyl acetate and water were added. The organic layer was separated, dried over Na₂SO₄, and filtered. The filtrate was concentrated under reduced pressure to give the crude product, which was purified by column chromatography (PE:EtOAc=10:1 to 3:1) to give the title compound. NMR δ (ppm) (CD₃OD): 7.54 (d, 2H), 7.37 (d, 3H), 7.17 (s, 1H), 4.15 (m, 2H), 3.74 (d, 2H), 1.26 (t, 3H). LC-MS: calculated for C₁₇H₁₅ClN₂O₂ 314.08, observed m/e: 315.0 (M+H)⁺ (Rt 1.19/2 min).

Step B: 6-chloro-5-(phenylethynyl)-1H-pyrrolo[3,2-b]pyridin-2(3H)-one

To a suspension of 6-chloro-5-(phenylethynyl)-1H-pyrrolo[3,2-b]pyridin-2(3H)-one (700 mg, 2.23 mmol) in toluene (15 mL) was added acetic acid (3 mL). The mixture was heated to reflux for 18 hours. The mixture was then cooled to room temperature, and the solvents were removed under reduced pressure. The resulting residue was suspended in toluene (15 mL), filtered, washed with diethyl ether and dried to give the title compound. LC-MS: calculated for C₁₅H₉ClN₂O 268.04, observed m/e: 269.0 (M+H)⁺ (Rt 1.07/2 min).

Step C: 2,6-dichloro-5-(phenylethynyl)-1H-pyrrolo[3,2-b]pyridine

To a mixture of 6-chloro-5-(phenylethynyl)-1H-pyrrolo[3,2-b]pyridin-2(3H)-one (440 mg, 1.64 mmol) in phosphoryl trichloride (15 mL) was added N,N-dimethylaniline (397 mg, 3.28 mmol). The mixture was heated to reflux and stirred for 1 hour, then evaporated under vacuum. The resulting residue was dissolved in water, then the mixture was adjusted to pH=8 with saturated aqueous NaHCO₃, and extracted with ethyl acetate. The combined organic layers were washed with brine, dried over anhydrous Na₂SO₄, filtered and concentrated under reduced pressure to give the crude product, which was purified by silica gel column chromatography (PE:EtOAc=5:1 to 1:1) to afford the title compound. LC-MS: calculated for C₁₅H₈Cl₂N₂ 286.01, observed m/e: 287.1 (M+H)⁺ (Rt 1.20/2 min).

Step D: 2,6-dichloro-5-(phenylethynyl)-1-((2-(trimethylsilyl)ethoxy)methyl)-1H-pyrrolo[3,2-b]pyridine To a solution of 2,6-dichloro-5-(phenylethynyl)-1H-pyrrolo[3,2-b]pyridine (450 mg, 1.57 mmol) in N,N-dimethylformamide (10 mL) at 0° C. was added sodium hydride (57 mg, 2.36 mmol). The mixture was stirred at 0° C. for 30 min, then (2-(chloromethoxy)ethyl)trimethylsilane (394 mg, 2.36 mmol) was added. The mixture was warmed to room temperature for 1 hour. Then the reaction mixture was quenched with saturated aqueous NH₄Cl, and extracted with ethyl acetate. The combined organic layers were washed with brine, dried over anhydrous Na₂SO₄, filtered and concentrated to give the crude product, which was purified by silica gel column chromatography (PE:EtOAc=30:1 to 3:1) to afford the title compound. LC-MS: calculated for C₂₁H₂₂Cl₂N₂OSi 416.09, observed m/e: 417.1 (M+H)⁺ (Rt 1.63/2 min).

Step E: (3R,3aR,6R,6aR)-6-((6-chloro-5-(phenylethynyl)-1-((2-(trimethylsilyl)ethoxy)methyl)-1H-pyrrolo[3,2-b]pyridin-2-yl)oxy)hexahydrofuro[3,2-b]furan-3-ol To a mixture of 2,6-dichloro-5-(phenylethynyl)-1-((2-(trimethylsilyl)ethoxy)methyl)-1H-pyrrolo[3,2-b]pyridine (200 mg, 0.48 mmol) in 1,4-dioxane (4 mL) and DMSO (4 mL) were added (3R,3aR,6R,6aR)-hexahydrofuro[3,2-b]furan-3,6-diol (701 mg, 4.8 mmol) and cesium carbonate (784 mg, 2.4 mmol). The mixture was heated to 120° C. and stirred for 18 hours. Then the mixture was diluted with ethyl acetate, washed with brine, dried over anhydrous Na₂SO₄, filtered and concentrated under reduced pressure to give the crude product, which was purified by silica gel column chromatography (PE:EtOAc=5:1~1:1) to afford the title compound. NMR δ (ppm) (CD₃OD): 7.92 (s, 1H), 7.66 (s, 2H), 7.47 (m, 3H), 5.97 (s, 1H), 5.55 (d, 2H), 5.18 (q, 1H), 4.98 (t, 1H), 4.56 (t, 1H), 4.36 (m, 2H), 4.26 (dd, 1H), 4.12 (dd, 1H), 3.98 (t, 1H), 3.66 (q, 3H), 0.94 (t, 2H), 0.00 (s, 9H). LC-MS: calculated for C₂₇H₃₁ClN₂O₅Si 526.17, observed m/e: 527.1 (M+H)⁺ (Rt 1.32/2 min).

Step F: (3R,3aR,6R,6aR)-6-((6-chloro-1-(hydroxymethyl)-5-(phenylethynyl)-1H-pyrrolo[3,2-b]pyridin-2-yl)oxy)hexahydrofuro[3,2-b]furan-3-ol To a mixture of (3R,3aR,6R,6aR)-6-((6-chloro-5-(phenylethynyl)-1-((2-(trimethylsilyl)ethoxy)methyl)-1H-pyrrolo[3,2-b]pyridin-2-yl)oxy)hexahydrofuro[3,2-b]furan-3-ol (100 mg, 0.19 mmol) in THF (4 mL) was added conc. HCl (4 mL, 12 M). The mixture was stirred at 0° C. to room temperature for 18 hours. Then the mixture was concentrated under reduced pressure at room temperature to give the title compound, which was used in next step without further purification. LC-MS: calculated for $C_{22}H_{19}ClN_2O_5$ 426.10, observed m/e: 427.1 $(M+H)^+$ (Rt 0.99/2 min).

Step G: (3R,3aR,6R,6aR)-6-((6-chloro-5-(phenylethynyl)-1H-pyrrolo[3,2-b]pyridin-2-yl)oxy)hexahydrofuro[3,2-b]furan-3-ol To a mixture of (3R,3aR,6R,6aR)-6-((6-chloro-1-(hydroxymethyl)-5-(phenylethynyl)-1H-pyrrolo[3,2-b]pyridin-2-yl)oxy)hexahydrofuro[3,2-b]furan-3-ol (60 mg, 0.14 mmol, crude) in DMF (4 mL) was added ethane-1,2-diamine (17 mg, 0.28 mmol). The mixture was stirred at 0° C. for 15 minutes. Then the mixture was directly purified by pre-HPLC (MeCN/H$_2$O as eluent, 0.05% TFA) to give the title compound. NMR δ (ppm) (CD$_3$OD): 7.63 (m, 3H), 7.43 (s, 3H), 5.86 (s, 1H), 5.09 (m, 1H), 4.61 (s, 1H), 4.51 (t, 1H), 4.31 (dd, 1H), 4.19 (dd, 1H), 4.06 (dd, 1H), 3.94 (t, 1H), 3.63 (t, 1H). LC-MS: calculated for $C_{21}H_{17}ClN_2O_4$ 396.09, observed m/e: 397.1 $(M+H)^+$ (Rt 2.14/4.5 min).

Example 135

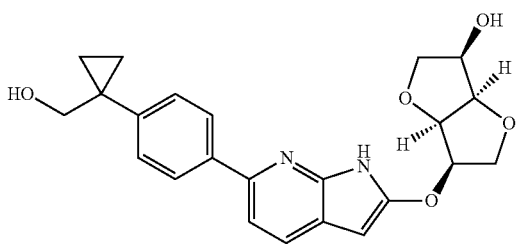 [SMILES: OCC1(c2ccc(-c3ccc4cc(O[C@@H]5CO[C@H]6[C@@H]5OC[C@H]6O)[nH]c4n3)cc2)CC1]

(3R,3aR,6R,6aR)-6-((6-(4-(1-(hydroxymethyl)cyclopropyl)phenyl)-1H-pyrrolo[2,3-b]pyridin-2-yl)oxy)hexahydrofuro[3,2-b]furan-3-ol Step A: (1-(4-(2-oxo-2,3-dihydro-1H-pyrrolo[2,3-b]pyridin-6-yl)phenyl)cyclopropyl)methyl acetate A mixture of 6-chloro-1H-pyrrolo[2,3-b]pyridin-2(3H)-one (0.3 g, 1.78 mmol), (1-(4-(4,4,5,5-tetramethyl-1,3,2-dioxaborolan-2-yl)phenyl)cyclopropyl)methyl acetate (0.676 g, 2.14 mmol, Intermediate 24), Pd(PPh$_3$)$_2$Cl$_2$ (0.131 g, 0.178 mmol) and Na$_2$CO$_3$ (0.377 g, 3.56 mmol) in MeCN (1 mL) and H$_2$O (2 mL) was heated to 130° C. by MW and stirred for 30 min. Then the mixture was extracted with ethyl acetate. The combined organic layers were washed with brine, dried over anhydrous Na$_2$SO$_4$, filtered and concentrated to give the crude product, which was purified by silica gel column chromatography (PE:EtOAc=10:1~2:1) to afford the title compound. NMR δ (ppm) (CD$_3$OD): 8.24 (s, 1H), 7.30 (d, 2H), 7.51 (d, 1H), 7.36 (m, 3H), 4.18 (s, 2H), 3.59 (s, 2H), 2.00 (s, 3H), 0.95 (s, 4H). LC-MS: calculated for $C_{19}H_{18}N_2O_3$ 322.13, observed m/e: 323.2 $(M+H)^+$ (Rt 1.14/2 min).

Step B: (1-(4-(2-chloro-1H-pyrrolo[2,3-b]pyridin-6-yl)phenyl)cyclopropyl)methyl acetate To a mixture of (1-(4-(2-oxo-2,3-dihydro-1H-pyrrolo[2,3-b]pyridin-6-yl)phenyl)cyclo-propyl)methyl acetate (150 mg, 0.47 mmol) in phosphoryl trichloride (10 mL) was added N,N-dimethylaniline (57 mg, 0.47 mmol). The mixture was heated to reflux and stirred for 1 hour, then evaporated under vacuum. The resulting residue was dissolved in water, then the mixture was adjusted to pH=~8 with saturated aqueous Na$_2$CO$_3$, and extracted with ethyl acetate. The combined organic layers were washed with brine, dried over anhydrous Na$_2$SO$_4$, filtered and concentrated under reduced pressure to give the crude product, which was purified by silica gel column chromatography (PE:EtOAc=30:1~5:1) to afford the title compound. NMR δ (ppm) (CD$_3$OD): 8.20 (d, 2H), 7.97 (s, 2H), 7.69 (m, 2H), 7.44 (m, 3H), 7.26 (s, 3H), 5.30 (s, 2H), 2.84 (d, 2H). LC-MS: calculated for $C_{19}H_{17}ClN_2O_2$ 340.10, observed m/e: 341.1 $(M+H)^+$ (Rt 1.17/2 min).

Step C: (1-(4-(2-chloro-1H-pyrrolo[2,3-b]pyridin-6-yl)phenyl)cyclopropyl)methanol To a solution of (1-(4-(2-chloro-1H-pyrrolo[2,3-b]pyridin-6-yl)phenyl)cyclopropyl) methyl acetate (100 mg, 0.29 mmol) in N,N-dimethylformamide (10 mL) at 0° C. was added sodium hydride (18 mg, 0.35 mmol, 60% in mineral oil). The mixture was stirred at 0° C. for 30 min, then (2-(chloromethoxy)ethyl)trimethylsilane (59 mg, 0.35 mmol) was added. The mixture was warmed to room temperature and stirred for 1 hour. Then the reaction was quenched with saturated aqueous NH$_4$Cl, and extracted with ethyl acetate. The combined organic layers were washed with brine, dried over anhydrous Na$_2$SO$_4$, filtered and concentrated to give the crude product, which was purified by silica gel column chromatography (PE:EtOAc=10:1~3:1) to afford the title compound. LC-MS: calculated for $C_{23}H_{29}ClN_2O_2Si$ 428.17, observed m/e: 429.1 $(M+H)^+$ (Rt 1.44/2 min).

Step D: (3R,3aR,6R,6aR)-6-((6-(4-(1-(hydroxymethyl)cyclopropyl)phenyl)-1-((2-(trimethylsilyl)ethoxy)methyl)-1H-pyrrolo[2,3-b]pyridin-2-yl)oxy)hexahydrofuro[3,2-b]furan-3-ol To a mixture of (1-(4-(2-chloro-1H-pyrrolo[2,3-b]pyridin-6-yl)phenyl)-cyclopropyl)methanol (100 mg, 0.23 mmol) in (methylsulfinyl)methane (20 mL) were added (3R,3aR,6R,6aR)-hexahydrofuro[3,2-b]furan-3,6-diol (336 mg, 2.3 mmol) and cesium carbonate (373 mg, 1.15 mmol). The mixture was heated to 120° C. and stirred for 48 hours. Then the mixture was diluted with ethyl acetate, washed with brine, dried over anhydrous Na$_2$SO$_4$, filtered and concentrated under reduced pressure to give the crude product, which was purified by silica gel column chromatography (PE:EtOAc=10:1~3:1) to afford the title compound. LC-MS: calculated for $C_{29}H_{38}N_2O_6Si$ 538.25, observed m/e: 539.3 $(M+H)^+$ (Rt 1.32/2 min).

Step E: (3R,3aR,6R,6aR)-6-((6-(4-(1-(hydroxymethyl)cyclopropyl)phenyl)-1H-pyrrolo[2,3-b]pyridin-2-yl)oxy)hexahydrofuro[3,2-b]furan-3-ol To a mixture of (3R,3aR,6R,6aR)-6-((6-(4-(1-(hydroxymethyl)cyclopropyl)phenyl)-1-((2-(trimethylsilyl)ethoxy)methyl)-1H-pyrrolo[2,3-b]pyridin-2-yl)oxy)hexahydrofuro[3,2-b]furan-3-ol (20 mg, 0.037 mmol) in tetrahydrofuran (10 mL) was added tetrabutylammonium fluoride (97 mg, 0.37 mmol). The mixture was heated to reflux and stirred for 15 hours. Then the mixture was diluted with ethyl acetate, washed with brine, dried over anhydrous Na$_2$SO$_4$, filtered and concentrated under reduced pressure to give the crude product, which was purified by prep. HPLC (MeCN/H$_2$O as eluent, 0.05% TFA) to afford the title compound. NMR δ

(ppm) (CD$_3$OD): 7.96 (d, 1H), 7.84 (d, 2H), 7.67 (d, 1H), 7.59 (d, 1H), 7.40 (d, 4H), 5.62 (d, 1H), 4.89 (s, 1H), 4.82 (s, 1H), 4.77 (d, 1H), 4.52 (m, 2H), 4.30 (d, 2H), 4.21 (s, 1H), 3.94 (m, 2H). LC-MS: calculated for C$_{23}$H$_{24}$N$_2$O$_5$ 408.17, observed m/e: 409.1 (M+H)$^+$ (Rt 2.24/4.5 min).

Example 136

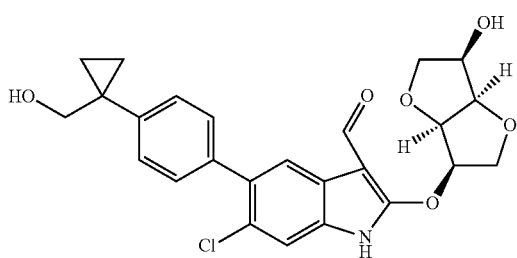 [SMILES: O=Cc1c(O[C@@H]2CO[C@H]3[C@@H]2OC[C@H]3O)[nH]c2cc(Cl)c(-c3ccc(C4(CO)CC4)cc3)cc12]

6-chloro-2-(((3R,3aR,6R,6aR)-6-hydroxyhexahydro-furo[3,2-b]furan-3-yl)oxy)-5-(4-(1-(hydroxymethyl)cyclopropyl)phenyl)-1H-indole-3-carbaldehyde Step A: (1-(4-(6-chloro-2-oxoindolin-5-yl)phenyl)cyclopropyl)methyl acetate The mixture of 5-bromo-6-chloroindolin-2-one (4.0 g, 15.8 mmol), intermediate 24 (9.0 g, 31.6 mmol), Pd(PPh$_3$)$_2$Cl$_2$ (950 mg, 2.37 mmol) and sodium carbonate (5.0 g, 47.4 mmol) in acetonitrile (150 mL) and water (50 mL) was stirred at 90° C. for under nitrogen for 2 hours. Then the mixture was filtered, and extracted with ethyl acetate (3×100 mL). The combined organic layers were washed with brine, dried over anhydrous sodium sulfate, filtered and concentrated to give the crude product, which was purified by silica gel column chromatography (hexane/ethyl acetate=10:1~2:1) to afford the title compound. NMR δ (ppm) (CD$_3$OD): 10.54 (s, 1H), 7.32 (m, 4H), 7.21 (s, 1H), 6.92 (s, 1H), 4.20 (s, 2H), 3.50 (s, 2H), 2.00 (s, 3H), 0.97 (m, 4H).

Step B: (1-(4-(2,6-dichloro-1H-indol-5-yl)phenyl)cyclopropyl)methyl acetate

To a mixture of (1-(4-(6-chloro-2-oxoindolin-5-yl)phenyl)cyclopropyl)methyl acetate (2.1 g, 5.9 mmol) in 1,2-dichloroethane (40 mL) was slowly added phosphoryl trichloride (1.8 g, 11.8 mmol) at 0° C. The mixture was heated to reflux and stirred for 30 min, then imidazole (482 mg, 7.1 mmol) was added. The mixture was then evaporated under vacuum, and the residue was dissolved in water. The mixture was adjusted to pH=~8 with saturated aqueous sodium bicarbonate, and extracted with ethyl acetate (3×50 mL). The combined organic layers were washed with brine, dried over anhydrous sodium sulfate, filtered and concentrated under reduced pressure to give the crude product, which was purified by silica gel column chromatography (hexane/ethyl acetate=30:1~5:1) to afford the title compound. LC-MS: calculated for C$_{20}$H$_{17}$Cl$_2$NO$_2$ 373.06, observed m/e: 396.1 (M+Na)$^+$ (Rt 1.37/2 min).

Step C: (1-(4-(2,6-dichloro-1-((2-(trimethylsilyl)ethoxy)methyl)-1H-indol-5-yl)phenyl)cyclopropyl)methyl acetate To a solution of (1-(4-(2,6-dichloro-1H-indol-5-yl)phenyl)cyclopropyl)methyl acetate (800 mg, 2.29 mmol) in N,N-dimethylformamide (10 mL) was added sodium hydride (77 mg, 3.2 mmol, 60% in mineral oil) at 0° C. The mixture was stirred at 0° C. for 30 min, then (2-(chloromethoxy)ethyl)trimethylsilane (531 mg, 3.2 mmol) was added, and the mixture was warmed to room temperature for 1 hour. Then the reaction mixture was quenched with saturated ammonium chloride aqueous solution, and extracted with ethyl acetate (3×30 mL). The combined organic layers were washed with brine, dried over anhydrous sodium sulfate, filtered and concentrated to give the crude product, which was purified by silica gel column chromatography (hexane/ethyl acetate=10:1~3:1) to afford the title compound. LC-MS: calculated for C$_{26}$H$_{31}$Cl$_2$NO$_3$Si 503.15, observed m/e: 504.2 (M+H)$^+$ (Rt 1.92/2 min).

Step D: (1-(4-(2,6-dichloro-1-((2-(trimethylsilyl)ethoxy)methyl)-1H-indol-5-yl)phenyl)cyclopropyl)methanol To a solution of (1-(4-(2,6-dichloro-1-((2-(trimethyl-silyl)ethoxy)methyl)-1H-indol-5-yl)phenyl)cyclopropyl)methyl acetate (980 mg, 1.9 mmol) in tetrahydrofuran (10 mL) was added lithium hydrate (233 mg in 1 mL of water, 9.7 mmol). The mixture was stirred at room temperature for 6 hours, then extracted with ethyl acetate (3×20 mL). The combined organic layers were washed with brine, dried over anhydrous sodium sulfate, filtered, concentrated. The resulting crude product was purified by silica gel column chromatography (hexane/ethyl acetate=10:1~3:1) to afford the title compound. LC-MS: calculated for C$_{24}$H$_{29}$Cl$_2$NO$_2$Si 461.13, observed m/e: 462.1 (M+H)$^+$ (Rt 1.61/2 min).

Step E: (3R,3aR,6R,6aR)-6-((6-chloro-5-(4-(1-(hydroxymethyl)cyclopropyl)phenyl)-1-((2-(trimethylsilyl)ethoxy)methyl)-1H-indol-2-yl)oxy)hexahydro-furo[3,2-b]furan-3-ol To a mixture of (1-(4-(2,6-dichloro-1-((2-(trimethylsilyl)ethoxy)methyl)-1H-indol-5-yl)phenyl)cyclopropyl)methanol (200 mg, 0.38 mmol) in dimethylsulfoxide (5 mL) and dioxane (5 ml) were added (3R,3aR,6R,6aR)-hexahydrofuro[3,2-b]furan-3,6-diol (555 mg, 3.8 mmol) and cesium carbonate (1.2 g, 3.8 mmol). The mixture was heated to 120° C. and stirred for 24 hours. Then the mixture was diluted with water (20 mL), extracted with ethyl acetate (20 mL), washed with brine, dried over anhydrous sodium sulfate and concentrated under reduced pressure to give the crude product, which was purified b by prep-TLC (hexane/ethyl acetate=1:1) to afford the title compound. NMR δ (ppm) (CD$_3$OD): 7.38 (m, 7H), 5.78 (s, 1H), 5.49 (d, 2H), 5.03 (q, 1H), 4.62 (s, 1H), 4.52 (t, 1H), 4.33 (m, 1H), 4.23 (dd, 1H), 3.99 (m, 2H), 3.71 (s, 2H), 3.61 (m, 2H), 0.90 (m, 6H). LC-MS: calculated for C$_{30}$H$_{38}$ClNO$_6$Si 571.22, observed m/e: 572.4 (M+H)$^+$ (Rt 3.05/4.5 min).

Step F: 5-([1,1'-biphenyl]-4-yl)-6-chloro-2-(((3R,3aR,6R,6aR)-6-hydroxyhexahydro-furo[3,2-b]furan-3-yl)oxy)-1-((2-(trimethylsilyl)ethoxy)methyl)-1H-pyrrolo[3,2-b]pyridine-3-carbonitrile To a mixture of (3R,3aR,6R,6aR)-6-((6-chloro-5-(4-(1-(hydroxymethyl)cyclopropyl)phenyl)-1-((2-(trimethylsilyl)ethoxy)methyl)-1H-indol-2-yl)oxy)hexahydrofuro[3,2-b]furan-3-ol (25 mg, 0.044 mmol) in DMF (5 mL) were added BnCN (5 mg, 0.048 mmol) and CuI (4 mg, 0.022 mmol). The mixture was heated to 90° C. and stirred for 5 hours, then heated to 120° C. and stirred for 12 hours. Then the mixture was diluted with ethyl acetate, washed with brine, dried over anhydrous Na₂SO₄, filtered and concentrated under reduced pressure to give the crude product, which was purified by pre-HPLC (MeCN/H₂O as eluent, 0.05% TFA) to afford the title compound. NMR δ (ppm) (CD₃CD): 8.08 (s, 1H), 7.63 (s, 1H), 7.46 (d, 2H), 7.39 (d, 2H), 5.65 (m, 1H), 5.56 (m, 2H), 4.51 (m, 1H), 4.24 (m, 1H), 4.20 (m, 2H), 4.00 (s, 1H), 3.68 (m, 4H), 1.33 (s, 2H), 0.95 (d, 4H), 0.01 (d, 9H). LC-MS: calculated for $C_{31}H_{38}ClNO_7Si$ 599.21, observed m/e: 600.2 (M+H)⁺ (Rt 1.25/2 min).

Step G: 6-chloro-2-(((3R,3aR,6R,6aR)-6-hydroxy-hexahydrofuro[3,2-b]furan-3-yl)oxy)-5-(4-(1-(hydroxymethyl)cyclopropyl)phenyl)-1H-indole-3-carbaldehyde To a mixture of 5-([1,1'-biphenyl]-4-yl)-6-chloro-2-(((3R,3aR,6R,6aR)-6-hydroxyhexahydrofuro[3,2-b]furan-3-yl)oxy)-1-((2-(trimethylsilyl)ethoxy)methyl)-1H-pyrrolo[3,2-b]pyridine-3-carbonitrile (20 mg, 0.033 mmol) in THF (2 mL) was added concentrated aqueous HCl (2 mL, 12 M). The mixture was stirred at 0° C. to room temperature for 18 hours, then concentrated under reduced pressure at room temperature. The resulting crude product was purified by pre-HPLC (MeCN/H₂O as eluent, 0.05% TFA) to afford the title compound. NMR δ (ppm) (CD₃OD): 9.86 (s, 1H), 7.93 (s, 1H), 7.44 (m, 2H), 7.37 (m, 3H), 5.36 (s, 1H), 5.24 (s, 1H), 5.00 (t, 1H), 4.46 (t, 1H), 4.29 (m, 2H), 4.08 (dd, 1H), 3.90 (m, 1H), 3.71 (s, 2H), 0.91 (s, 4H). LC-MS: calculated for $C_{25}H_{24}ClNO_6$ 469.13, observed m/e: 470.1 (M+H)⁺ (Rt 2.56/4.5 min).

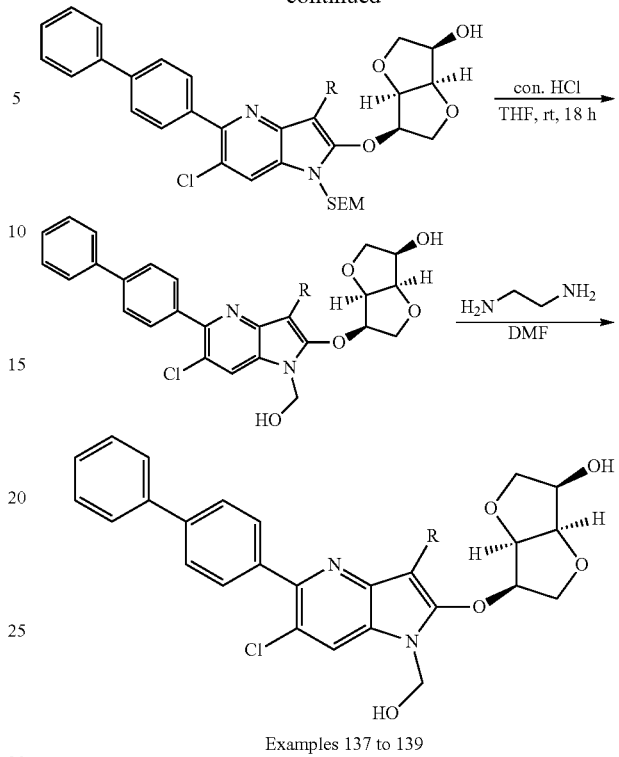

Examples 137 to 139

Intermediate 38

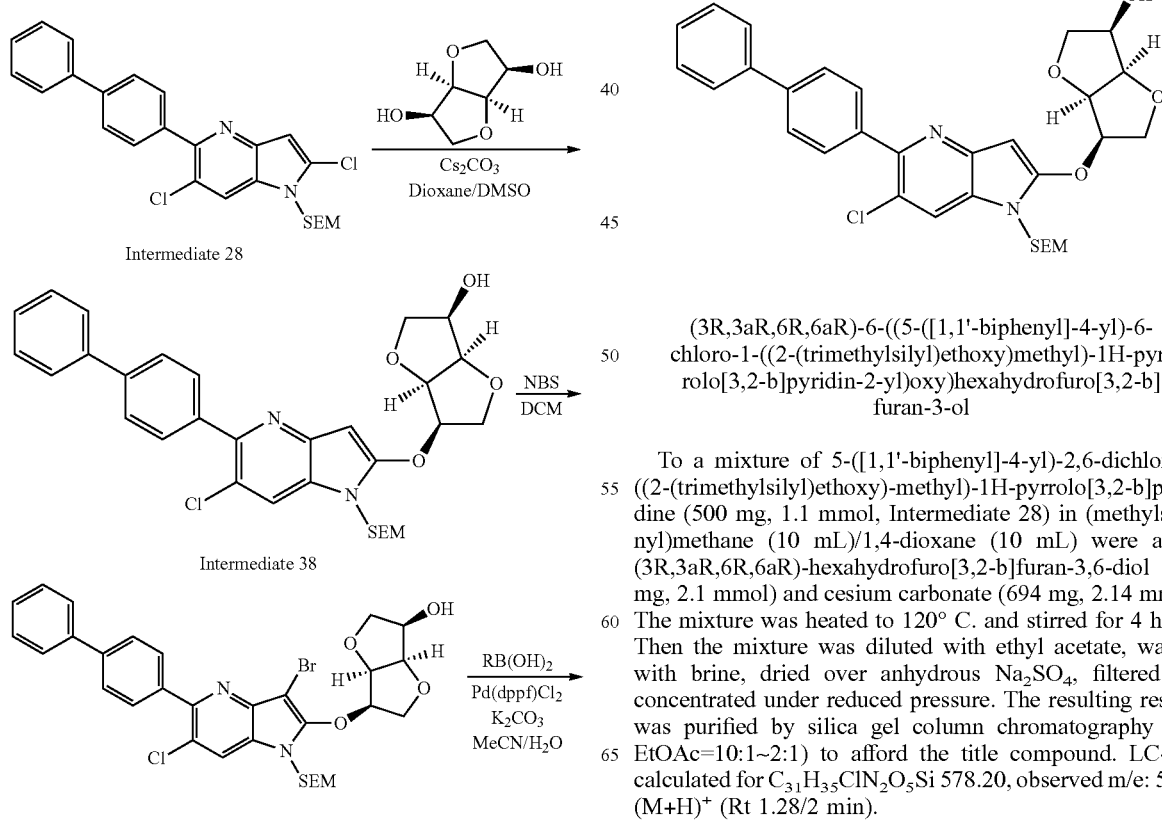

(3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydrofuro[3,2-b]furan-3-ol To a mixture of 5-([1,1'-biphenyl]-4-yl)-2,6-dichloro-1-((2-(trimethylsilyl)ethoxy)-methyl)-1H-pyrrolo[3,2-b]pyridine (500 mg, 1.1 mmol, Intermediate 28) in (methylsulfinyl)methane (10 mL)/1,4-dioxane (10 mL) were added (3R,3aR,6R,6aR)-hexahydrofuro[3,2-b]furan-3,6-diol (311 mg, 2.1 mmol) and cesium carbonate (694 mg, 2.14 mmol). The mixture was heated to 120° C. and stirred for 4 hours. Then the mixture was diluted with ethyl acetate, washed with brine, dried over anhydrous Na₂SO₄, filtered and concentrated under reduced pressure. The resulting residue was purified by silica gel column chromatography (PE:EtOAc=10:1~2:1) to afford the title compound. LC-MS: calculated for $C_{31}H_{35}ClN_2O_5Si$ 578.20, observed m/e: 579.2 (M+H)⁺ (Rt 1.28/2 min).

Example 137

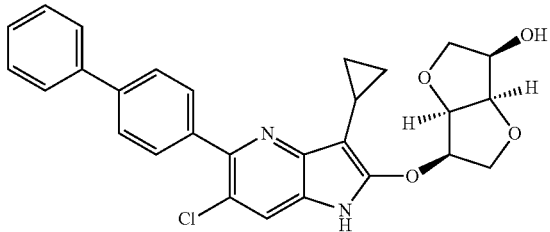 [SMILES: O[C@@H]1CO[C@H]2[C@@H]1OC[C@H]2Oc1[nH]c2cc(Cl)c(-c3ccc(-c4ccccc4)cc3)nc2c1C1CC1]

6-chloro-2-(((3R,3aR,6R,6aR)-6-hydroxyhexahydrofuro[3,2-b]furan-3-yl)oxy)-5-(4-(1-(hydroxymethyl)cyclopropyl)phenyl)-1H-indole-3-carbaldehyde Step A: (3R,3aR,6R,6aR)-6-((5-([1,1'-biphenyl]-4-yl)-3-bromo-6-chloro-1-((2-(trimethylsilyl)ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydrofuro[3,2-b]furan-3-ol (200 mg, 0.35 mmol, Intermediate 38) in dichloromethane (10 mL) was added NBS (68 mg, 0.38 mmol) at 0° C. The mixture was stirred at 0° C. for 1 hour. Then the mixture was diluted with dichloromethane, washed with brine, dried over anhydrous $Na_2SO_4$, filtered and concentrated under reduced pressure. The resulting residue was purified by silica gel column chromatography (PE: EtOAc=20:1~2:1) to afford the title compound. NMR δ (ppm) (CDCl$_3$): 7.84 (d, 2H), 7.79 (s, 1H), 7.65 (m, 4H), 7.45 (m, 1H), 5.61 (m, 2H), 5.43 (d, 1H), 4.68 (m, 1H), 4.62 (m, 1H), 4.37 (m, 2H), 4.05 (m, 2H), 3.75 (m, 1H), 3.56 (m, 2H), 2.68 (d, 1H), 0.94 (m, 2H), 0.00 (s, 9H). LC-MS: calculated for $C_{31}H_{34}BrClN_2O_5Si$ 656.11, observed m/e: 657.0/659.0 (M+H)$^+$ (Rt 1.61/2 min).

Step B: (3R,3aR,6R,6aR)-6-((5-([1,1'-biphenyl]-4-yl)-6-chloro-3-cyclopropyl-1-((2-(trimethylsilyl)ethoxy)methyl)-1H-pyrrolo[3,2-b]pyridin-2-yl)oxy)hexahydrofuro[3,2-b]furan-3-ol A mixture of (3R,3aR,6R,6aR)-6-((5-([1,1'-biphenyl]-4-yl)-3-bromo-6-chloro-1-((2-(trimethylsilyl)ethoxy)methyl)-1H-pyrrolo[3,2-b]pyridin-2-yl)oxy)hexahydrofuro[3,2-b]furan-3-ol (130 mg, 0.2 mmol), cyclopropylboronic acid (34 mg, 0.4 mmol), Pd(dppf)Cl$_2$ (15 mg, 0.02 mmol) and $Na_2CO_3$ (83 mg, 0.6 mmol) in MeCN (3 mL) and $H_2O$ (0.3 mL) was heated to 110° C. by MW and stirred for 60 min. Then the mixture was extracted with ethyl acetate. The combined organic layers were washed with brine, dried over anhydrous $Na_2SO_4$, filtered and concentrated to give the crude product, which was purified by preparative-TLC (PE: EtOAc=2:1) to afford the title compound. LC-MS: calculated for $C_{34}H_{39}ClN_2O_5Si$ 618.23, observed m/e: 619.2 (M+H)$^+$ (Rt 1.46/2 min).

Step C: (3R,3aR,6R,6aR)-6-((5-([1,1'-biphenyl]-4-yl)-6-chloro-3-cyclopropyl-1-(hydroxymethyl)-1H-pyrrolo[3,2-b]pyridin-2-yl)oxy)hexahydrofuro[3,2-b]furan-3-ol To a solution of (3R,3aR,6R,6aR)-6-((5-([1,1'-biphenyl]-4-yl)-6-chloro-3-cyclopropyl-1-((2-(trimethylsilyl)ethoxy)methyl)-1H-pyrrolo[3,2-b]pyridin-2-yl)oxy)hexahydrofuro[3,2-b]furan-3-ol (20 mg, 0.032 mmol) in THF (1.5 mL) was added concentrated aqueous HCl (1.5 mL, 12 M) at 0° C. The mixture was stirred to room temperature for 18 hours, then concentrated under reduced pressure to give the title compound, which was used in next step without further purification. LC-MS: calculated for $C_{29}H_{27}ClN_2O_5$ 518.16, observed m/e: 519.2 (M+H)$^+$ (Rt 1.16/2 min).

Step D: (3R,3aR,6R,6aR)-6-((5-([1,1'-biphenyl]-4-yl)-6-chloro-3-cyclopropyl-1H-pyrrolo[3,2-b]pyridin-2-yl)oxy)hexahydrofuro[3,2-b]furan-3-ol To a stirred solution of (3R,3aR,6R,6aR)-6-((5-([1,1'-biphenyl]-4-yl)-6-chloro-3-cyclopropyl-1-(hydroxymethyl)-1H-pyrrolo[3,2-b]pyridin-2-yl)oxy)hexahydrofuro[3,2-b]furan-3-ol (17 mg, 0.033 mmol, crude) in DMF (2 mL) was added ethane-1,2-diamine (4 mg, 0.066 mmol) at 0° C. The mixture was stirred at 0° C. for 5 min, then directly purified by pre-HPLC (MeCN/$H_2O$ as eluent, 0.05% TFA) to give the title compound. NMR δ (ppm) (CD$_3$OD): 8.10 (s, 1H), 7.87 (d, 2H), 7.74 (t, 4H), 7.50 (d, 2H), 7.43 (d, 1H), 5.37 (d, 1H), 5.31 (s, 1H), 4.57 (d, 1H), 4.25 (d, 2H), 4.11 (s, 1H), 3.75 (d, 1H), 3.60 (s, 1H), 1.39 (s, 1H), 0.95 (d, 2H), 0.91 (d, 2H). LC-MS: calculated for $C_{28}H_{25}ClN_2O_4$ 488.15, observed m/e: 489.1 (M+H)$^+$ (Rt 2.58/4.5 min).

TABLE 17

Compounds prepared according to the methods described in Example 137.

| Example Number | Structure | HPLC-mass spectrum m/e |
|---|---|---|
| 138 | 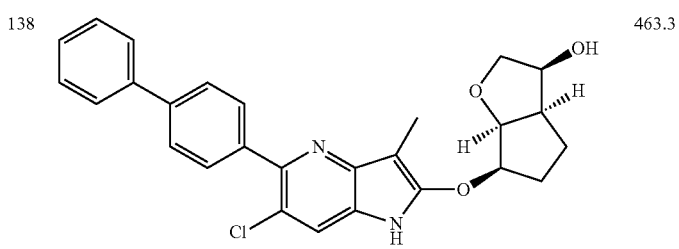 | 463.3 |

TABLE 17-continued

Compounds prepared according to the methods described in Example 137.

| Example Number | Structure | HPLC-mass spectrum m/e |
|---|---|---|
| 139 | 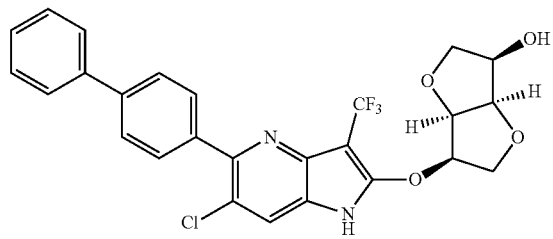 [SMILES: O[C@@H]1CO[C@H]2[C@@H]1OC[C@H]2Oc1[nH]c2cc(Cl)c(-c3ccc(-c4ccccc4)cc3)nc2c1C(F)(F)F] | 525.1 |

Example 140

(3R,3aR,6R,6aR)-6-((5-([1,1'-biphenyl]-4-yl)-6-chloro-3-(trifluoromethyl)-1H-pyrrolo[3,2-b]pyridin-2-yl)oxy)hexahydrofuro[3,2-b]furan-3-ol Step A: (3R,3aR,6R,6aR)-6-((5-([1,1'-biphenyl]-4-yl)-6-chloro-3-(trifluoromethyl)-1-((2-(trimethylsilyl)ethoxy)methyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydrofuro[3,2-b]furan-3-ol (20 mg, 0.035 mmol, Intermediate 38) in MeCN (3 mL) were added 5-(trifluoromethyl)-5H-dibenzo[b,d]thiophen-5-ium tetrafluoroborate (18 mg, 0.052 mmol) and $K_2CO_3$ (10 mg, 0.07 mmol). The mixture was heated to 70° C. for 18 hours, and then extracted with ethyl acetate. The combined organic layers were washed with brine, dried over anhydrous $Na_2SO_4$, filtered and concentrated to give the crude product, which was purified by prep HPLC (MeCN/$H_2O$ as eluent, 0.05% TFA) to afford the title compound. LC-MS: calculated for $C_{32}H_{34}ClF_3N_2O_5Si$ 646.19, observed m/e: 647.2 (M+H)$^+$ (Rt 1.58/2 min).

Step B: (3R,3aR,6R,6aR)-6-((5-([1,1'-biphenyl]-4-yl)-6-chloro-1-(hydroxymethyl)-3-(trifluoromethyl)-1H-pyrrolo[3,2-b]pyridin-2-yl)oxy)hexahydrofuro[3,2-b]furan-3-ol To a mixture of (3R,3aR,6R,6aR)-6-((5-([1,1'-biphenyl]-4-yl)-6-chloro-3-(trifluoromethyl)-1-((2-(trimethylsilyl)ethoxy)methyl)-1H-pyrrolo[3,2-b]pyridin-2-yl)oxy)hexahydrofuro[3,2-b]furan-3-ol (5.1 mg, 0.0077 mmol) in THF (1.5 mL) was added concentrated aqueous HCl (1.5 mL, 12 M) at 0° C. The mixture was warmed slowly to room temperature and stirred for 18 hours. Then the mixture was concentrated under reduced pressure at room temperature to give the title compound, which was directly used in next step without further purification. LC-MS: calculated for $C_{27}H_{22}ClF_3N_2O_5$ 546.12, observed m/e: 547.1 (M+H)$^+$ (Rt 1.22/2 min).

Step C: (3R,3aR,6R,6aR)-6-((5-([1,1'-biphenyl]-4-yl)-6-chloro-3-(trifluoromethyl)-1H-pyrrolo[3,2-b]pyridin-2-yl)oxy)hexahydrofuro[3,2-b]furan-3-ol To a stirred mixture of (3R,3aR,6R,6aR)-6-((5-([1,1'-biphenyl]-4-yl)-6-chloro-1-(hydroxymethyl)-3-(trifluoromethyl)-1H-pyrrolo[3,2-b]pyridin-2-yl)oxy)hexahydrofuro[3,2-b]furan-3-ol (5 mg, 0.0092 mmol, crude) in DMF (2 mL) was added ethane-1,2-diamine (2 mg, 0.0184 mmol) at 0° C. The mixture was stirred at 0° C. for 5 minutes, then directly purified by prep HPLC (MeCN/$H_2O$ as eluent, 0.05% TFA) to give the title compound. NMR δ (ppm) (CD$_3$OD): 7.99 (d, 3H), 7.73 (d, 3H), 7.52 (s, 4H), 5.33 (m, 2H), 4.35 (s, 2H), 4.17 (d, 1H), 3.63 (s, 1H), 3.48 (s, 1H). LC-MS: calculated for $C_{26}H_{20}ClF_3N_2O_4$ 516.11, observed m/e: 517.0 (M+H)$^+$ (Rt 2.05/4.5 min).

Intermediate 39

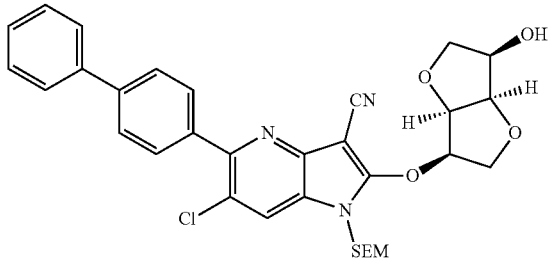 [SMILES: C[Si](C)(C)CCOCn1c(O[C@@H]2CO[C@H]3[C@@H]2OC[C@H]3O)c(C#N)c2nc(-c3ccc(-c4ccccc4)cc3)c(Cl)cc21]

5-([1,1'-biphenyl]-4-yl)-6-chloro-2-(((3R,3aR,6R,6aR)-6-hydroxyhexahydrofuro[3,2-b]furan-3-yl)oxy)-1-((2-(trimethylsilyl)ethoxy)methyl)-1H-pyrrolo[3,2-b]pyridine-3-carbonitrile To a solution of (3R,3aR,6R,6aR)-6-((5-([1,1'-biphenyl]-4-yl)-6-chloro-1-((2-(trimethylsilyl)ethoxy)methyl)-1H-pyrrolo[3,2-b]pyridin-2-yl)oxy)hexahydro-furo[3,2-b]furan-3-ol (400 mg, 0.68 mmol, Intermediate 38) in DMF (5 mL) were added BnCN (90 mg, 0.76 mmol) and CuI (66 mg, 0.35 mmol). The mixture was heated to 130° C. and stirred for 24 hours. Then the mixture was diluted with ethyl acetate, washed with brine, dried over anhydrous $Na_2SO_4$, filtered and concentrated under reduced pressure to give crude product, which was purified by column chromatography (PE:EtOAc=10:1~2:1) to afford the title compound. NMR δ (ppm) ($CD_3CD$): 8.06 (s, 1H), 7.98 (s, 1H), 7.74 (m, 3H), 7.46 (d, 2H), 7.71 (m, 2H), 7.37 (s, 1H), 5.68 (m, 1H), 5.59 (s, 2H), 5.34 (s, 1H), 5.06 (m, 1H), 4.58 (s, 3H), 4.49 (m, 1H), 4.29 (m, 2H), 4.17 (m, 1H), 3.92 (m, 1H), 3.61 (s, 1H), 0.91 (d, 2H), 0.03 (m, 9H). LC-MS: calculated for $C_{32}H_{34}ClN_3O_5Si$ 603.20, observed m/e: 604.2 $(M+H)^+$ (Rt 1.45/2 min).

Example 141

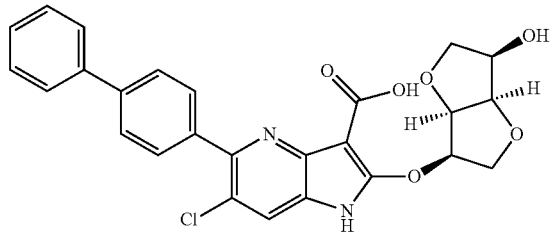 [SMILES: O=C(O)c1c(O[C@@H]2CO[C@H]3[C@@H]2OC[C@H]3O)[nH]c2cc(Cl)c(-c3ccc(-c4ccccc4)cc3)nc12]

5-([1,1'-biphenyl]-4-yl)-6-chloro-2-(((3R,3aR,6R,6aR)-6-hydroxhexahydrofuro[3,2-b]furan-3-yl)oxy)-1H-pyrrolo[3,2-b]pyridine-3-carboxylic acid A mixture of 5-([1,1'-biphenyl]-4-yl)-6-chloro-2-(((3R,3aR,6R,6aR)-6-hydroxyhexahydrofuro[3,2-b]furan-3-yl)oxy)-1-((2-(trimethylsilyl)ethoxy)methyl)-1H-pyrrolo[3,2-b]pyridine-3-carbonitrile (10 mg, 0.017 mmol, Intermediate 39) in 4 M HCl in MeOH (6 mL) was stirred at 80° C. for 18 hours. Then the mixture was concentrated under reduced pressure, and the resulting residue was purified by pre-HPLC (MeCN/$H_2O$ as eluent, 0.05% TFA) to give the title compound. NMR δ (ppm) ($CD_3OD$): 7.86 (s, 1H), 7.77 (m, 6H), 7.48 (m, 2H), 7.38 (s, 1H), 5.47 (d, 1H), 5.04 (s, 1H), 4.47 (t, 1H), 4.17 (d, 1H), 4.26 (d, 1H), 4.12 (d, 1H), 3.91 (d, 1H), 4.69 (d, 1H). LC-MS: calculated for $C_{26}H_{21}ClN_2O_6$ 492.11, observed m/e: 493.0 $(M+H)^+$ (Rt 0.78/2 min).

Example 142

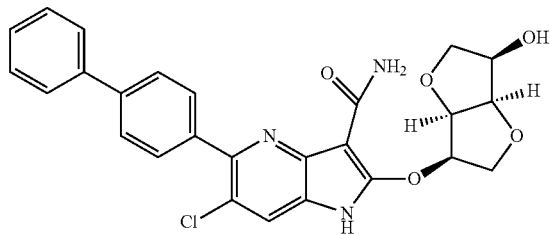 [SMILES: NC(=O)c1c(O[C@@H]2CO[C@H]3[C@@H]2OC[C@H]3O)[nH]c2cc(Cl)c(-c3ccc(-c4ccccc4)cc3)nc12]

5-([1,1'-biphenyl]-4-yl)-6-chloro-2-(((3R,3aR,6R,6aR)-6-hydroxyhexahydrofuro[3,2-b]furan-3-yl)oxy)-1H-pyrrolo[3,2-b]pyridine-3-carboxamide A mixture of 5-([1,1'-biphenyl]-4-yl)-6-chloro-2-(((3R,3aR,6R,6aR)-6-hydroxyhexa-hydrofuro[3,2-b]furan-3-yl)oxy)-1-((2-(trimethylsilyl)ethoxy)methyl)-1H-pyrrolo[3,2-b]pyridine-3-carbonitrile (10 mg, 0.017 mmol, Intermediate 39) in concentrated HCl solution (2 mL, 12 M) was stirred at 70° C., then at room temperature for 18 hours. Then the mixture was concentrated under reduced pressure, and the resulting residue was directly purified by pre-HPLC (MeCN/$H_2O$ as eluent, 0.05% TFA) to give the title compound. NMR δ (ppm) ($CD_3OD$): 8.05 (s, 1H), 7.83 (s, 4H), 7.74 (d, 2H), 7.51 (t, 2H), 7.42 (d, 1H), 5.48 (d, 1H), 4.99 (d, 1H), 4.52 (t, 1H), 4.38 (s, 1H), 4.27 (t, 1H), 4.16 (t, 1H), 3.91 (d, 1H), 3.70 (s, 1H). LC-MS: calculated for $C_{26}H_{22}ClN_3O_5$ 491.12, observed m/e: 492.3 $(M+H)^+$ (Rt 2.54/4.5 min).

Biological Example 1

AMPKSAMSF (In Vitro AMPK Activation Assay)

The recombinant human AMPK complex 1 (containing α1β1γ1) and complex 7 (containing α2β1γ1) were obtained from baculovirus expression system. Recombinant viruses were generated by cotransfection of AMPK/pBacPak9 clones with Baculogold baculovirus DNA (Pharmingen) in spodoptera frugiperda 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900 II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, $1×10^6$ cells/ml, at a multiplicity of infection of ~5. Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM $ZnCl_2$, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, J. Clin. Invest. 108, 1167-1174, 2001).

The in vitro AMPK activation assay is performed in a volume of 30 μl in a 384-well plate. Enzyme reactions were assembled in the microtiter plate by adding 15 μl of 2× enzyme in assay buffer (20 mM HEPES, pH 7.3, 5 mM $MgCl_2$, 3 mM DTT, 0.01% Brij 35 and CamK Kinase, to activate AMPK) to wells which contained either DMSO or compound. The reaction was initiated with the addition of 15 μl 2× substrate mixture containing 200 μM ATP, and 3.0 μM fluorescently labeled SAMS (5-FAM-HMRSAMSGL-HLVKRR—COOH) in assay buffer. After 45-minute incubation at 25° C., the reaction was stopped by the addition of 70 μl stop buffer (100 mM HEPES, pH 7.3, 40 mM EDTA, 0.015% Brij 35). Phosphorylated 5-FAM SAMS product is assessed using a Caliper EZ Reader LabChip microfluidics reader. Product conversion is determined by calculating the peak heights of the substrate and product and reporting the product/(product+substrate) peak ratio. The 10-point titration data were expressed as % maximum AMP activation. The results were plotted using 4 parameter fit and the inflection point reflecting 50% of the maximum activation was reported as the $EC_{50}$. The % maximum AMP activation for selected compounds is provided in Table 1 and Table 2 below.

The compounds of present invention, including the compounds of Examples 1-142, were tested in the in vitro AMPK activation assay using recombinant human AMPK complex 1 (containing α1β1γ1) or AMPK complex 7 (containing α2β1γ1) and found to have increased activation of human AMPK complex 1 or complex 7 at concentrations of less than 50 μM. Preferred compounds of the present invention were found to have $EC_{50}$ values of less than 1 μM in the in vitro AMPK activation assay using recombinant human AMPK complex 1 or complex 7.

TABLE 1

Maximum AMP Activation for Selected Compounds

| Example No. | % Maximum AMP Activation of human AMPK Complex 1 | $EC_{50}$ (nM) |
|---|---|---|
| 1 | 581% | 37 |
| 3 | 680% | 13 |
| 6 | 601% | 10 |
| 8 | 265% | 493 |
| 15 | 370% | 24 |
| 18 | 573% | 4 |
| 21 | 590% | 2 |
| 22 | 416% | 8 |
| 23 | 575% | 1 |
| 24 | 256% | 14 |
| 30 | 583% | 15 |

TABLE 2

Maximum AMP Activation for Selected Compounds

| Example No. | % Maximum AMP activation of human AMPK complex 7 | $EC_{50}$ (nM) |
|---|---|---|
| 69 | 354% | 5 |
| 80 | 230% | <3 |
| 72 | 530% | <3 |
| 82 | 239% | 6 |
| 77 | 472% | <3 |
| 76 | 446% | <3 |
| 138 | 486% | 56 |
| 107 | 492% | <1 |
| 105 | 495% | 8 |
| 110 | 412% | <1 |
| 123 | 295% | 12 |
| 121 | 213% | 71 |
| 124 | 305% | 15 |
| 122 | 384% | 4 |
| 114 | 333% | <3 |

Biological Example 2

Phosphorylation of Acetyl CoA Carboxylase by AMPK Activators in db/+ Mice

To assess the potential for AMPK activators to increase the phosphorylation of Acetyl COA Carboxylase (ACC) in liver and skeletal muscle, db/+ mice were dosed with AMPK activators at either 2 or 7 h prior to evaluation where phosphorylated ACC (p-ACC)/total ACC levels were compared in the tissues of vehicle and compound treated mice. Briefly, mice were anesthetized using gas anesthesia with 1-4% isoflurane administered to effect via nose cone. Once anesthetized, samples of liver and skeletal muscle (gastrocnemius) are removed, snap frozen in liquid nitrogen, and homogenized. Homogenates are analyzed for protein concentration and equal amounts of protein are assayed for total and phosphorylated ACC (p-ACC) levels using Meso Scale Discovery's Multi-array assay kit. MSD assay plates contain an electrode surface that is coated with streptavidin. Protein sample binds to streptavidin. The primary ACC or p-ACC specific antibody binds to protein and a secondary antibody labeled with MSD SULFO-TAG then binds to the primary antibody. The electrode surface of the MSD plate responds to an electrical stimulus and causes the SULFO-TAG labels bound to ACC and p-ACC to emit a light signal in proportion to the amount of p-ACC or total ACC present. The ratio of p-ACC/total ACC levels are determined for each sample and the ratio of p-ACC/total ACC levels for mice treated with AMPK activators is significantly elevated compared to the ratio of those treated with the vehicle control (significant elevations are described as differences where $p<0.05$).

Biological Example 3

Inhibition of Fatty Acid Synthesis (FAS) by AMPK Activators in db/+ Mice

To determine the effect of AMPK activators on Fatty Acid Synthesis (FAS) in the liver, the effect of oral pre-dosing of compounds on the amount of $^3H$ incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3H$ water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH<2 with 10 M $H_2SO_4$. The fatty acids of liver are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3H$ incorporated into hepatic triglyceride. The amount of $^3H$ radiolabelled fatty acids synthesized in mice with treated with an AMPK activator is significantly less than the amount of $^3H$ radiolabelled fatty acids synthesized in the control mice.

Biological Example 4

In Vivo Study for Therapy with an AMPK Activator in Mice (Glucose Tolerance Test)

DIO mice are treated simultaneously with an effective dose of an AMPK-activated protein kinase activator.

Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

Biological Example 5

Acute Food Intake Studies in Diet Induced Obese (DIO) Mice: General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

Biological Example 6

Chronic Weight Reduction Studies in Diet Induced Obese (DIO) Mice: General Procedure Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 7

Assay for Triglycerides

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 8

Assay for Low HDL and/or High LDL

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 9

Assay for Sarcopenia

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various changes, modifications and substitutions can be made therein without departing from the scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention.

What is claimed is:

1. A compound of structural formula I:

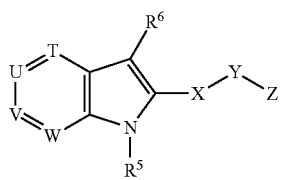

(I)

or a pharmaceutically acceptable salt thereof, wherein:
T is selected from the group consisting of: $CR^3$, N and N-oxide;
U is selected from the group consisting of: $CR^1$, N and N-oxide;
V is selected from the group consisting of: $CR^2$, N and N-oxide;
W is selected from the group consisting of: $CR^4$, N and N-oxide;
X is selected from:
  (1) —$CH_2$—,
  (2) —CHF—,
  (3) —$CF_2$—,
  (4) —S—,
  (5) —S(O)—,
  (6) —$S(O)_2$—,
  (7) —O—,
  (8) —O—$CH_2$—,
  (9) —$CH_2$—O—,
  (10) —$CH_2$—S—,
  (11) —NH—,
  (12) —C(O)—,
  (13) —NHC(O)—,
  (14) —C(O)NH—,
  (15) —$NHSO_2$—,
  (16) —$SO_2NH$—, and
  (17) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$ alkyl, $COC_{1-6}$alkyl, phenyl and —$CH_2$phenyl;
Y is selected from:
  (1) —$C_{1-6}$ alkyl,
  (2) —$C_{2-6}$ alkynyl,
  (3) $C_{3-10}$cycloalkyl,
  (4) $C_{2-10}$cycloheteroalkyl,
  (5) aryl,
  (6) heteroaryl, and (7)

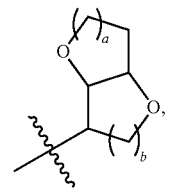

wherein Y is unsubstituted or substituted with 1, 2, 3 or 4 substituents selected from $R^b$;
Z is selected from:
  (1) hydrogen,
  (2) oxo,
  (3) —$(CH_2)_n CO_2H$,
  (4) —$(CH_2)_n CO_2R^i$,
  (5) —$(CH_2)_n OCOR^i$,
  (6) —$(CH_2)_n OH$, and
  (7) —$(CH_2)_n P(O)(OR^j)_2$,
wherein each $CH_2$ is unsubstituted or substituted with 1 or 2 substituents selected from $C_{1-6}$alkyl, —OH and —$NH_2$;
each $R^1$ and $R^2$ is independently selected from:
  (2) halogen,
  (3) aryl,
  (4) -aryl-$C_{3-7}$cycloalkyl,
  (5) -aryl-$C_{3-7}$cycloalkenyl,
  (6) -aryl-$C_{2-10}$cycloheteroalkyl,
  (7) aryl-aryl,
  (8) -aryl-heteroaryl,
  (9) heteroaryl, and
  (10) —$C_{2-6}$alkynyl-aryl,
wherein each alkynyl, cycloalkyl, cycloalkenyl, cycloheteroalkyl, aryl and heteroaryl is unsubstituted or substituted with 1, 2, 3 or 4 substituents independently selected from $R^a$, provided that at least one of and only one of $R^1$ and $R^2$ is selected from the group consisting of: halogen;
$R^3$ is hydrogen or absent;
$R^4$ is hydrogen or absent;
$R^5$ is hydrogen;
$R^6$ is selected from:
  (1) hydrogen,
  (2) —$C_{1-6}$alkyl,
  (3) —$(CH_2)_m OC_{1-6}$alkyl,
  (4) halogen,
  (5) —$(CH_2)_m CN$,
  (6) —$(CH_2)_m CF_3$,
  (7) —$(CH_2)_m OCF_3$,
  (8) —$(CH_2)_m CHF_2$,
  (9) —$(CH_2)_m CH_2F$,
  (10) —$(CH_2)_m SO_2C_{1-6}$ alkyl,
  (11) —$(CH_2)_m CO_2H$,
  (12) —$(CH_2)_m CO_2C_{1-6}$ alkyl,

(13) —$(CH_2)_mC(O)H$,
(14) —$(CH_2)_mC(O)NH_2$,
(15) —$(CH_2)_mC_{3-6}$cycloalkyl,
(16) —$(CH_2)_mC_{2-7}$cycloheteroalkyl,
(17) —$(CH_2)_m$aryl, and
(18) —$(CH_2)_m$heteroaryl, wherein each $CH_2$ is unsubstituted or substituted with 1 or 2 substituents selected from: oxo, —$(CH_2)_{0-3}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloheteroalkyl, aryl and heteroaryl are unsubstituted or substituted with 1, 2, 3 or 4 substituents selected from: oxo, —$(CH_2)_{0-5}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$SO_2C_{1-6}$alkyl, —$C_{3-7}$cycloalkyl, phenyl, $CH_2$phenyl, heteroaryl and $CH_2$heteroaryl;

each $R^a$ is independently selected from the group consisting of:
(1) —$(CH_2)_m$-halogen,
(2) oxo,
(3) —$(CH_2)_m$OH,
(4) —$(CH_2)_mN(R^j)_2$,
(5) —$(CH_2)_mNO_2$,
(6) —$(CH_2)_mCN$,
(7) —$C_{1-6}$ alkyl,
(8) —$(CH_2)_m CF_3$,
(9) —$(CH_2)_mOCF_3$,
(10) —O—$(CH_2)_m$—$OC_{1-6}$ alkyl,
(11) —$(CH_2)_mC(O)N(R^j)_2$,
(12) —$(CH_2)_m C(=N-OH)N(R^j)_2$,
(13) —$(CH_2)_m OC_{1-6}$alkyl,
(14) —$(CH_2)_mO$—$(CH_2)_m$—$C_{3-7}$cycloalkyl,
(15) —$(CH_2)_mO$—$(CH_2)_m$—$C_{2-7}$cycloheteroalkyl,
(16) —$(CH_2)_m O$—$(CH_2)_m$-aryl,
(17) —$(CH_2)_m O$—$(CH_2)_m$-heteroaryl,
(18) —$(CH_2)_m SC_{1-6}$alkyl,
(19) —$(CH_2)_m S(O)C_{1-6}$alkyl,
(20) —$(CH_2)_m SO_2C_{1-6}$alkyl,
(21) —$(CH_2)_m SO_2C_{3-7}$cycloalkyl,
(22) —$(CH_2)_m SO_2C_{2-7}$cycloheteroalkyl,
(23) —$(CH_2)_m SO_2$-aryl,
(24) —$(CH_2)_m SO_2$-heteroaryl,
(25) —$(CH_2)_m SO_2NHC_{1-6}$ alkyl,
(26) —$(CH_2)_m SO_2N(C_{1-6}alkyl)_2$,
(27) —$(CH_2)_m SO_2NHC_{3-7}$cycloalkyl,
(28) —$(CH_2)_m SO_2NHC_{2-7}$cycloheteroalkyl,
(29) —$(CH_2)_m SO_2NH$-aryl,
(30) —$(CH_2)_m SO_2NH$-heteroaryl,
(31) —$(CH_2)_mNHSO_2$—$C_{1-6}$alkyl,
(32) —$(CH_2)_mNHSO_2$—$C_{3-7}$cycloalkyl,
(33) —$(CH_2)_mNHSO_2$—$C_{2-7}$cycloheteroalkyl,
(34) —$(CH_2)_mNHSO_2$-aryl,
(35) —$(CH_2)_mNHSO_2NH$-heteroaryl,
(36) —$(CH_2)_mN(R^j)$—$C_{1-6}$alkyl,
(37) —$(CH_2)_mN(R^j)$—$C_{3-7}$cycloalkyl,
(38) —$(CH_2)_mN(R^j)$—$C_{2-7}$cycloheteroalkyl,
(39) —$(CH_2)_mN(R^j)$—$C_{2-7}$cycloheteroalkenyl,
(40) —$(CH_2)_mN(R^j)$-aryl,
(41) —$(CH_2)_mN(R^j)$-heteroaryl,
(42) —$(CH_2)_mC(O)R^f$,
(43) —$(CH_2)_mC(O)N(R^j)_2$,
(44) —$(CH_2)_mN(R^j)C(O)N(R^j)_2$,
(45) —$(CH_2)_mCO_2H$,
(46) —$(CH_2)_mOCOH$,
(47) —$(CH_2)_mCO_2R^f$,
(48) —$(CH_2)_mOCOR^f$,
(49) —$(CH_2)_mC_{3-7}$cycloalkyl,
(50) —$(CH_2)_mC_{3-7}$cycloalkenyl,
(51) —$(CH_2)_mC_{2-6}$cycloheteroalkyl,
(52) —$(CH_2)_mC_{2-6}$cycloheteroalkenyl,
(53) —$(CH_2)_m$aryl, and
(54) —$(CH_2)_m$heteroaryl, wherein each $CH_2$ is unsubstituted or substituted with 1 or 2 substituents selected from: oxo, —$(CH_2)_{0-3}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$ alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-5}$OH, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$ alkyl, —$SO_2C_{1-6}$alkyl, —$C_{3-7}$cycloalkyl, phenyl, $CH_2$phenyl, heteroaryl and $CH_2$heteroaryl;

each $R^b$ is independently selected from:
(1) hydrogen,
(2) —$C_{1-6}$ alkyl,
(3) —$C_{3-6}$cycloalkyl,
(4) —$C_{3-6}$cycloalkenyl,
(5) —$C_{2-6}$cycloheteroalkyl,
(6) —$C_{2-6}$cycloheteroalkenyl,
(7) aryl,
(8) heteroaryl,
(9) —$(CH_2)$t-halogen,
(10) —$(CH_2)$s-OH,
(11) —$(CH_2)sNO_2$,
(12) —$(CH_2)sNH_2$,
(13) —$(CH_2)sNH(C_{1-6}alkyl)$,
(14) —$(CH_2)sN(C_{1-6}alkyl)_2$,
(15) —$(CH_2)sOC_{1-6}$alkyl,
(16) —$(CH_2)qCO_2H$,
(17) —$(CH_2)qCO_2C_{1-6}$alkyl,
(18) —$(CH_2)sCF_3$,
(19) —$(CH_2)sOCF_3$,
(20) —$(CH_2)sCHF_2$,
(21) —$(CH_2)sCH_2F$,
(22) —$(CH_2)sCN$,
(23) —$(CH_2)sSO_2C_{1-6}$alkyl, and
(24) —$(CH_2)sCON(R^e)_2$, wherein each $CH_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens, and wherein two $R^b$ substituents together with the atom to which they are attached may form a $C_{3-6}$cycloalkyl ring or a $C_{2-6}$cycloheteroalkyl ring;

each $R^c$ is independently selected from:
(1) halogen,
(2) oxo,
(3) —$(CH_2)_r$OH,
(4) —$(CH_2)_rN(R^e)_2$,
(5) —$(CH_2)_rCN$,
(6) —$C_{1-6}$alkyl,
(7) —$CF_3$,
(8) —$C_{1-6}$alkyl-OH,
(9) —$OCH_2OC_{1-6}$alkyl,

219

(10) —(CH$_2$)$_r$OC$_{1-6}$alkyl,
(11) —OCH$_2$aryl,
(12) —(CH$_2$)$_r$SC$_{1-6}$ alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;
each R$^e$, R$^g$ and R$^h$ is independently selected from:
 (1) hydrogen,
 (2) —C$_{1-6}$alkyl, and
 (3) —O—C$_{1-6}$alkyl,
wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^j$ is independently selected from:
 (1) hydrogen,
 (2) C$_{1-6}$alkyl,
 (3) C$_{3-6}$ cycloalkyl,
 (4) —C(O)R$^i$, and
 (5) —SO$_2$R$^i$,
wherein each alkyl and cycloalkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
 (1) C$_{1-6}$alkyl,
 (2) C$_{4-7}$cycloalkyl,
 (3) C$_{4-7}$cycloalkenyl,
 (4) C$_{3-7}$ cycloheteroalkyl,
 (5) C$_{3-7}$ cycloheteroalkenyl,
 (6) aryl, and
 (7) heteroaryl,
wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$ alkyl, —C$_{3-7}$cycloakyl, and heteroaryl;
each a independently selected from 0, 1 or 2;
each b independently selected from 0, 1 or 2;
each n independently selected from 0, 1, 2, 3 or 4;
each m independently selected from 0, 1, 2, 3 or 4;
each p independently selected from 0, 1, 2, or 3;
each q independently selected from 0, 1, 2, 3 or 4;
each r independently selected from 0, 1 or 2;
each s independently selected from 0, 1, 2, 3 or 4; and
each t independently selected from 0, 1, 2, 3 or 4.

2. The compound of structural formula I according to claim 1

220

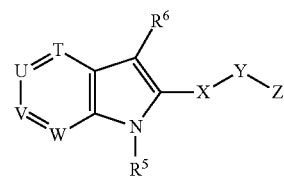

(I)

or a pharmaceutically acceptable salt thereof, wherein:
T is selected from the group consisting of: CR$^3$, N and N-oxide;
U is selected from the group consisting of: CR$^1$, N and N-oxide;
V is selected from the group consisting of: CR$^2$, N and N-oxide;
W is selected from the group consisting of: CR$^4$, N and N-oxide;
X is selected from:
 (1) —CH$_2$—,
 (2) —CHF—,
 (3) —CF$_2$—,
 (4) —S—,
 (5) —O—,
 (6) —O—CH$_2$—,
 (7) —CH$_2$—O—,
 (8) —NH—,
 (9) —C(O)—,
 (10) —NHC(O)—,
 (11) —C(O)NH—,
 (12) —NHSO$_2$—,
 (13) —SO$_2$NH—, and
 (14) —CO$_2$—,
wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl;
Y is selected from:
 (1) —C$_{1-6}$alkyl,
 (2) —C$_{1-6}$alkynyl,
 (3) C$_{3-10}$cycloalkyl,
 (4) C$_{2-10}$cycloheteroalkyl,
 (5) aryl,
 (6) heteroaryl, and
 (7)

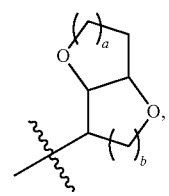

wherein Y is unsubstituted or substituted with 1, 2, 3 or 4 substituents selected from R$^b$;
Z is selected from:
 (1) hydrogen,
 (2) oxo,
 (3) —(CH$_2$)$_n$CO$_2$H,
 (4) —(CH$_2$)$_n$CO$_2$R$^i$,
 (5) —(CH$_2$)$_n$OCOR$^i$, (6) —(CH$_2$)$_n$OH, and
(7) —(CH$_2$)$_n$P(O)(OR$^j$)$_2$,
wherein each CH$_2$ is unsubstituted or substituted with 1 or 2 substituents selected from C$_{1-6}$alkyl, —OH and —NH$_2$;
each R$^1$ and R$^2$ is independently selected from:
(2) halogen,
(3) aryl,
(4) -aryl-C$_{3-7}$cycloalkyl,
(5) -aryl-C$_{3-7}$cycloalkenyl,
(6) -aryl-C$_{2-10}$cycloheteroalkyl,
(7) aryl-aryl,
(8) -aryl-heteroaryl,
(9) heteroaryl, and
(10) —C$_{2-6}$ alkynyl-aryl,
wherein each alkynyl, cycloalkyl, cycloalkenyl, cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of: halogen;
R$^3$ is hydrogen or absent;
R$^4$ is hydrogen or absent;
R$^5$ is hydrogen;
R$^6$ is selected from:
(1) hydrogen,
(2) —C$_{1-6}$ alkyl,
(3) —(CH$_2$)$_m$OC$_{1-6}$alkyl,
(4) halogen,
(5) —(CH$_2$)$_m$CN,
(6) —(CH$_2$)$_m$CF$_3$,
(7) —(CH$_2$)$_m$OCF$_3$,
(8) —(CH$_2$)$_m$CHF$_2$,
(9) —(CH$_2$)$_m$CH$_2$F,
(10) —(CH$_2$)$_m$SO$_2$C$_{1-6}$ alkyl,
(11) —(CH$_2$)$_m$C$_{3-6}$cycloalkyl,
(12) —(CH$_2$)$_m$C$_{2-7}$cycloheteroalkyl,
(13) —(CH$_2$)$_m$aryl, and
(14) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$ alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$ cycloalkyl, phenyl, CH$_2$phenyl, heteroaryl and CH$_2$heteroaryl, and wherein alkyl, cycloalkyl, cycloheteroalkyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;
each R$^a$ is independently selected from the group consisting of:
(1) —(CH$_2$)$_m$-halogen,
(2) oxo,
(3) —(CH$_2$)$_m$OH,
(4) —(CH$_2$)$_m$N(R$^j$)$_2$,
(5) —(CH$_2$)$_m$NO$_2$,
(6) —(CH$_2$)$_m$CN,
(7) —C$_{1-6}$ alkyl,
(8) —(CH$_2$)$_m$ CF$_3$,
(9) —(CH$_2$)$_m$OCF$_3$,
(10) —O—(CH$_2$)$_m$—OC$_{1-6}$ alkyl,
(11) —(CH$_2$)$_m$C(O)N(R$^j$)$_2$,
(12) —(CH$_2$)$_m$ C(=N—OH)N(R$^j$)$_2$,
(13) —(CH$_2$)$_m$ OC$_{1-6}$alkyl,
(14) —(CH$_2$)$_m$O—(CH$_2$)$_m$—C$_{3-7}$cycloalkyl,
(15) —(CH$_2$)$_m$O—(CH$_2$)$_m$—C$_{2-7}$cycloheteroalkyl,
(16) —(CH$_2$)$_m$ O—(CH$_2$)$_m$-aryl,
(17) —(CH$_2$)$_m$ O—(CH$_2$)$_m$-heteroaryl,
(18) —(CH$_2$)$_m$ SC$_{1-6}$alkyl,
(19) —(CH$_2$)$_m$ S(O)C$_{1-6}$alkyl,
(20) —(CH$_2$)$_m$ SO$_2$C$_{1-6}$alkyl,
(21) —(CH$_2$)$_m$ SO$_2$C$_{3-7}$cycloalkyl,
(22) —(CH$_2$)$_m$ SO$_2$C$_{2-7}$cycloheteroalkyl,
(23) —(CH$_2$)$_m$ SO$_2$-aryl,
(24) —(CH$_2$)$_m$ SO$_2$-heteroaryl,
(25) —(CH$_2$)$_m$ SO$_2$NHC$_{1-6}$ alkyl,
(26) —(CH$_2$)$_m$ SO$_2$N(C$_{1-6}$alkyl)$_2$,
(27) —(CH$_2$)$_m$ SO$_2$NHC$_{3-7}$cycloalkyl,
(28) —(CH$_2$)$_m$ SO$_2$NHC$_{2-7}$cycloheteroalkyl,
(29) —(CH$_2$)$_m$ SO$_2$NH-aryl,
(30) —(CH$_2$)$_m$ SO$_2$NH-heteroaryl,
(31) —(CH$_2$)$_m$NHSO$_2$—C$_{1-6}$alkyl,
(32) —(CH$_2$)$_m$NHSO$_2$—C$_{3-7}$cycloalkyl,
(33) —(CH$_2$)$_m$NHSO$_2$—C$_{2-7}$cycloheteroalkyl,
(34) —(CH$_2$)$_m$NHSO$_2$-aryl,
(35) —(CH$_2$)$_m$NHSO$_2$NH-heteroaryl,
(36) —(CH$_2$)$_m$N(R$^j$)—C$_{1-6}$alkyl,
(37) —(CH$_2$)$_m$N(R$^j$)—C$_{3-7}$cycloalkyl,
(38) —(CH$_2$)$_m$N(R$^j$)—C$_{2-7}$cycloheteroalkyl,
(39) —(CH$_2$)$_m$N(R$^j$)—C$_{2-7}$cycloheteroalkenyl,
(40) —(CH$_2$)$_m$N(R$^j$)-aryl,
(41) —(CH$_2$)$_m$N(R$^j$)-heteroaryl,
(42) —(CH$_2$)$_m$C(O)R$^f$,
(43) —(CH$_2$)$_m$C(O)N(R$^j$)$_2$,
(44) —(CH$_2$)$_m$N(R$^j$)C(O)N(R$^j$)$_2$,
(45) —(CH$_2$)$_m$CO$_2$H,
(46) —(CH$_2$)$_m$OCOH,
(47) —(CH$_2$)$_m$CO$_2$R$^f$,
(48) —(CH$_2$)$_m$OCOR$^f$,
(49) —(CH$_2$)$_m$C$_{3-7}$cycloalkyl,
(50) —(CH$_2$)$_m$C$_{3-7}$cycloalkenyl,
(51) —(CH$_2$)$_m$C$_{2-6}$cycloheteroalkyl,
(52) —(CH$_2$)$_m$C$_{2-6}$cycloheteroalkenyl,
(53) —(CH$_2$)$_m$aryl, and
(54) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$ alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$ cycloalkyl, phenyl, CH$_2$phenyl, heteroaryl and CH$_2$heteroaryl, and wherein alkyl, cycloalkyl cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-5}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;
each R$^b$ is independently selected from:
(1) hydrogen,
(2) —C$_{1-6}$alkyl,
(3) —C$_{3-6}$cycloalkyl,
(4) —C$_{3-6}$cycloalkenyl,
(5) —C$_{2-6}$cycloheteroalkyl,
(6) —C$_{2-6}$cycloheteroalkenyl,
(7) aryl,
(8) heteroaryl,
(9) —(CH$_2$)t-halogen,

(10) —(CH$_2$)s-OH,
(11) —(CH$_2$)sNO$_2$,
(12) —(CH$_2$)sNH$_2$,
(13) —(CH$_2$)sNH(C$_{1-6}$alkyl),
(14) —(CH$_2$)sN(C$_{1-6}$alkyl)$_2$,
(15) —(CH$_2$)sOC$_{1-6}$ alkyl,
(16) —(CH$_2$)qCO$_2$H,
(17) —(CH$_2$)qCO$_2$C$_{1-6}$alkyl,
(18) —(CH$_2$)sCF$_3$,
(19) —(CH$_2$)sOCF$_3$,
(20) —(CH$_2$)sCHF$_2$,
(21) —(CH$_2$)sCH$_2$F,
(22) —(CH$_2$)sCN,
(23) —(CH$_2$)sSO$_2$C$_{1-6}$alkyl, and
(24) —(CH$_2$)sCON(R$^e$)$_2$,
wherein each CH$_2$ is unsubstituted or substituted with 1 or 2 halogens, and wherein each alkyl, cycloalkyl, cycloalkenyl, cycloheteroalkyl, cycloheteroalkenyl, aryl and heteroaryl is unsubstituted or substituted with 1, 2 or 3 halogens;
each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$ alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;
each R$^e$, R$^g$ and R$^h$ is independently selected from:
(1) hydrogen,
(2) —C$_{1-6}$alkyl, and
(3) —O—C$_{1-6}$alkyl,
wherein each alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^j$ is independently selected from:
(1) hydrogen,
(2) C$_{1-6}$alkyl,
(3) C$_{3-6}$ cycloalkyl,
(4) —C(O)R$^i$, and
(5) —SO$_2$R$^i$,
wherein each alkyl and cycloalkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
(1) C$_{1-6}$alkyl,
(2) C$_{4-7}$ cycloalkyl,
(3) C$_{4-7}$ cycloalkenyl,
(4) C$_{3-7}$cycloheteroalkyl,
(5) C$_{3-7}$cycloheteroalkenyl,
(6) aryl, and
(7) heteroaryl,
wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$ cycloalkyl, and heteroaryl;
a is 0, 1 or 2;
b is 0, 1 or 2;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4; and
t is 0, 1, 2, 3 or 4.

3. The compound according to claim 1, wherein
T is selected from —CR$^3$— and N;
U is —CR$^1$—;
V is —CR$^2$—; and
W is selected from —CR$^4$— and N,
provided that one of T and W is N, and further provided that if W is N, then R$^1$ is selected from hydrogen, halogen, —CN, —CF$_3$, —C$_{1-6}$alkyl, —C$_{2-6}$alkenyl and —C$_{2-6}$alkynyl, and if T is N then R$^2$ is selected from hydrogen, halogen, —CN, —CF$_3$, —C$_{1-6}$alkyl, —C$_{2-6}$alkenyl and —C$_{2-6}$alkynyl;
or a pharmaceutically acceptable salt thereof.

4. The compound according to claim 1, wherein T is —CR$^3$— or N; U is —CR$^1$—; V is —CR$^2$—; and W is —CR$^4$—; or a pharmaceutically acceptable salt thereof.

5. The compound according to claim 1, wherein X is selected from:
(1) —CH$_2$—,
(2) —S—,
(3) —S(O)—,
(4) —S(O)$_2$—,
(5) —O—,
(6) —O—CH$_2$—,
(7) —CH$_2$—O—,
(8) —CH$_2$—S—,
(9) —NH—,
(10) —C(O)—, and
(11) —C(O)NH—,
wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, and COC$_{1-6}$alkyl, and wherein each NH is unsubstituted or substituted with 1 substituent selected from: C$_{1-6}$alkyl, CO$_2$H, CO$_2$C$_{1-6}$alkyl, and COC$_{1-6}$alkyl;
or a pharmaceutically acceptable salt thereof.

6. The compound according to claim 4, wherein X is —CH$_2$—; or a pharmaceutically acceptable salt thereof.

7. The compound according to claim 6, wherein Y is selected from:

(1) $C_{1-6}$ alkyl,
(2) $C_{3-10}$cycloalkyl, and
(3) aryl,
wherein Y is unsubstituted or substituted with 1, 2, 3 or 4 substituents selected from $R^b$; or a pharmaceutically acceptable salt thereof.

8. The compound according to claim 7, wherein Z is selected from:
(1) —$(CH_2)_nCO_2H$, and
(2) —$(CH_2)_nOH$,
wherein each $CH_2$ is unsubstituted or substituted with 1 or 2 substituents selected from $C_{1-6}$alkyl, —OH and —$NH_2$; or a pharmaceutically acceptable salt thereof.

9. The compound according to claim 1, wherein each $R^1$ and $R^2$ is independently selected from:
(1) halogen,
(2) aryl,
(3) aryl-$C_{3-7}$ cycloalkyl,
(4) aryl-$C_{2-10}$cycloheteroalkyl,
(5) aryl-aryl,
(6) aryl-heteroaryl, and
(7) heteroaryl,
wherein each cycloalkyl, cycloheteroalkyl, aryl and heteroaryl is unsubstituted or substituted with 1, 2, 3 or 4 substituents independently selected from $R^a$, provided that at least one of and only one of $R^1$ and $R^2$ is halogen; or a pharmaceutically acceptable salt thereof.

10. The compound according to claim 1, wherein $R^1$ is independently selected from:
(1) aryl,
(2) -aryl-$C_{3-7}$ cycloalkyl,
(3) -aryl-$C_{2-10}$cycloheteroalkyl,
(4) aryl-aryl, and
(5) -aryl-heteroaryl,
wherein each cycloalkyl, cycloheteroalkyl, aryl and heteroaryl is unsubstituted or substituted with 1, 2, 3 or 4 substituents independently selected from $R^a$, and $R^2$ is halogen; or a pharmaceutically acceptable salt thereof.

11. The compound according to claim 10, wherein $R^1$ is independently selected from:
(1) phenyl,
(2) -phenyl-cyclopropyl,
(3) -phenyl-pyrrolidine,
(4) biphenyl, and
(5) -phenyl-pyridine,
wherein each cycloalkyl, cycloheteroalkyl, aryl and heteroaryl is unsubstituted or substituted with 1, 2, 3 or 4 substituents independently selected from $R^a$; and $R^2$ is halogen; or a pharmaceutically acceptable salt thereof.

12. The compound according to claim 1 wherein $R^6$ is selected from:
(1) hydrogen,
(2) —$C_{1-6}$alkyl,
(3) halogen,
(4) CN,
(5) $CF_3$,
(6) —$CO_2H$,
(7) —C(O)H,
(8) —$C(O)NH_2$,
(9) —$C_{3-6}$ cycloalkyl, and
(10) aryl,
wherein alkyl, cycloalkyl, and aryl are unsubstituted or substituted with 1, 2, 3 or 4 substituents selected from: oxo, —$(CH_2)_{0-5}$OH, —CN, —$NH_2$, —$NH(C_{1-6}$alkyl), —$N(C_{1-6}$alkyl$)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and —$SO_2C_{1-6}$alkyl;
or a pharmaceutically acceptable salt thereof.

13. The compound according to claim 1, wherein $R^3$ is hydrogen or absent; $R^4$ is hydrogen; $R^5$ is hydrogen, and $R^6$ is hydrogen; or a pharmaceutically acceptable salt thereof.

14. The compound according to claim 1 wherein:
T is selected from —$CR^3$— and N;
U is —$CR^1$—;
V is —$CR^2$—; and
W is selected from —$CR^4$— and N,
provided that one of T and W is N, and further provided that if W is N, then $R^1$ is selected from hydrogen, halogen, —CN, —$CF_3$, —$C_{1-6}$alkyl, —$C_{2-6}$alkenyl and —$C_{2-6}$alkynyl, and if T is N then $R^2$ is selected from hydrogen, halogen, —CN, —$CF_3$, —$C_{1-6}$alkyl, —$C_{2-6}$alkenyl and —$C_{2-6}$alkynyl;
X is selected from:
(1) —$CH_2$—,
(2) —S—,
(3) —S(O)—,
(4) —$S(O)_2$—,
(5) —O—,
(6) —O—$CH_2$—,
(7) —$CH_2$—O—,
(8) —$CH_2$—S—,
(9) —NH—,
(10) —C(O)—, and
(11) —C(O)NH—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$ alkyl, and $COC_{1-6}$alkyl, and wherein each NH is unsubstituted or substituted with 1 substituent selected from: $C_{1-6}$alkyl, $CO_2H$, $CO_2C_{1-6}$alkyl, and $COC_{1-6}$alkyl;
Y is selected from:
(1) —$C_{1-6}$alkyl,
(2) —$C_{2-6}$ alkynyl,
(3) $C_{3-10}$cycloalkyl,
(4) $C_{2-10}$cycloheteroalkyl,
(5) aryl,
(6) heteroaryl, and
(7) 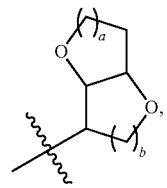

wherein Y is unsubstituted or substituted with 1, 2, 3 or 4 substituents selected from $R^b$;
Z is selected from:
(1) hydrogen,
(2) oxo,
(3) —$(CH_2)_nCO_2H$,
(4) —$(CH_2)_nCO_2R^i$,
(5) —$(CH_2)_nOCOR^i$,
(6) —$(CH_2)_nOH$, and
(7) —$(CH_2)_nP(O)(OR^j)_2$,
wherein each $CH_2$ is unsubstituted or substituted with 1 or 2 substituents selected from $C_{1-6}$alkyl, —OH and —$NH_2$;

$R^1$ and $R^2$ are independently selected from:
(2) halogen,
(3) aryl,
(4) -aryl-$C_{3-7}$cycloalkyl,
(5) -aryl-$C_{3-7}$cycloalkenyl,
(6) -aryl-$C_{2-10}$cycloheteroalkyl,
(7) aryl-aryl,
(8) -aryl-heteroaryl,
(9) heteroaryl, and
(10) —$C_{2-6}$alkynyl-aryl,
wherein each alkynyl, cycloalkyl, cycloalkenyl, cycloheteroalkyl, aryl and heteroaryl is unsubstituted or substituted with 1, 2, 3 or 4 substituents independently selected from $R^a$, provided that at least one of and only one of $R^1$ and $R^2$ is selected from the group consisting of: halogen;
$R^3$ is hydrogen or absent;
$R^4$ is hydrogen or absent;
$R^5$ is hydrogen, and
$R^6$ is selected from:
(1) hydrogen,
(2) —$C_{1-6}$alkyl,
(3) halogen,
(4) CN,
(5) $CF_3$,
(6) —$CO_2H$,
(7) —C(O)H,
(8) —C(O)$NH_2$,
(9) —$C_{3-6}$ cycloalkyl, and
(10) aryl,
wherein alkyl, cycloalkyl, and aryl are unsubstituted or substituted with 1, 2, 3 or 4 substituents selected from: oxo, —$(CH_2)_{0-5}OH$, —CN, —$NH_2$, —NH($C_{1-6}$alkyl), —N($C_{1-6}$alkyl)$_2$, —$C_{1-6}$alkyl, —O$C_{1-6}$alkyl, halogen, —$CH_2F$, —$CHF_2$, —$CF_3$, —$CO_2H$, —$CO_2C_{1-6}$alkyl, and —$SO_2C_{1-6}$alkyl;
or a pharmaceutically acceptable salt thereof.
15. The compound according to claim 1 wherein:
T is —$CR^3$— or N;
U is —$CR^1$—;
V is —$CR^2$—;
W is —$CR^4$—;
X is —$CH_2$—;
Y is selected from:
(1) $C_{1-6}$ alkyl,
(2) $C_{3-10}$cycloalkyl, and
(3) aryl,
wherein Y is unsubstituted or substituted with 1, 2, 3 or 4 substituents selected from $R^b$;
Z is selected from:
(1) —$(CH_2)_nCO_2H$, and
(2) —$(CH_2)_nOH$,
wherein each $CH_2$ is unsubstituted or substituted with 1 or 2 substituents selected from $C_{1-6}$alkyl, —OH and —$NH_2$;
$R^1$ is independently selected from:
(1) phenyl,
(2) -phenyl-cyclopropyl,
(3) -phenyl-pyrrolidine,
(4) biphenyl, and
(5) -phenyl-pyridine,
wherein each cycloalkyl, cycloheteroalkyl, aryl and heteroaryl is unsubstituted or substituted with 1, 2, 3 or 4 substituents independently selected from $R^a$;
$R^2$ is halogen;
$R^3$ is hydrogen or absent;
$R^4$ is hydrogen;

$R^5$ is hydrogen, and
$R^6$ is hydrogen;
or a pharmaceutically acceptable salt thereof.
16. The compound according to claim 15, selected from:

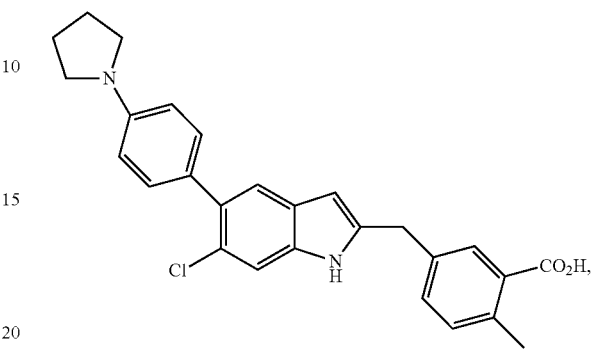

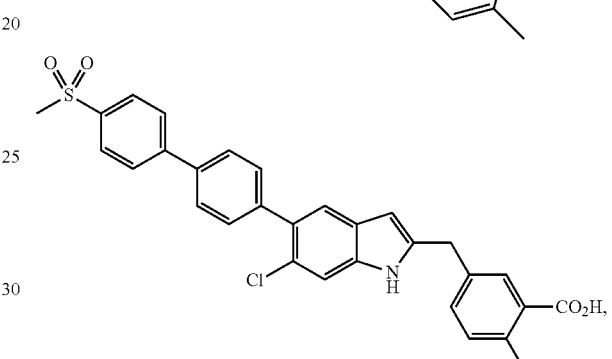

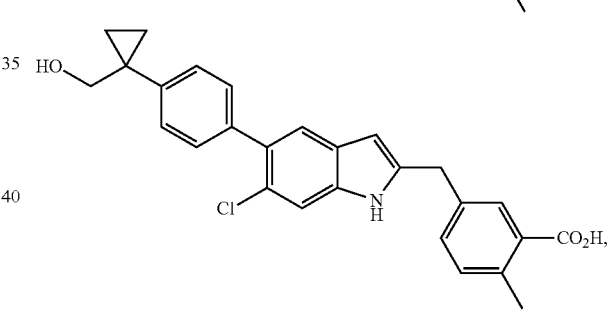

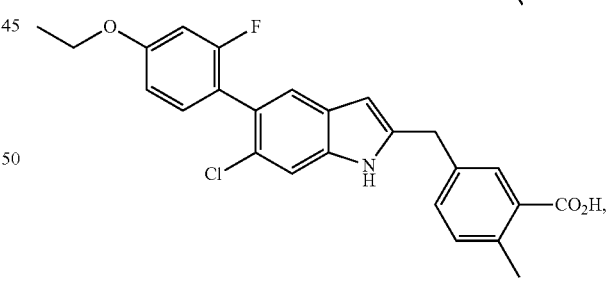

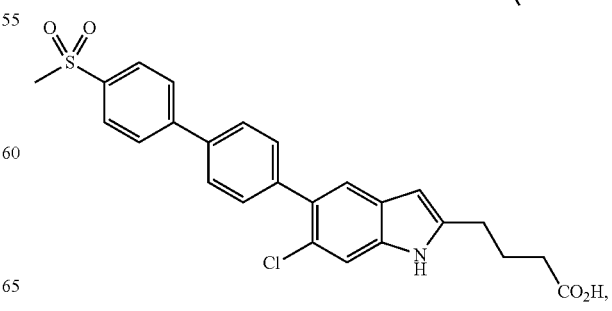

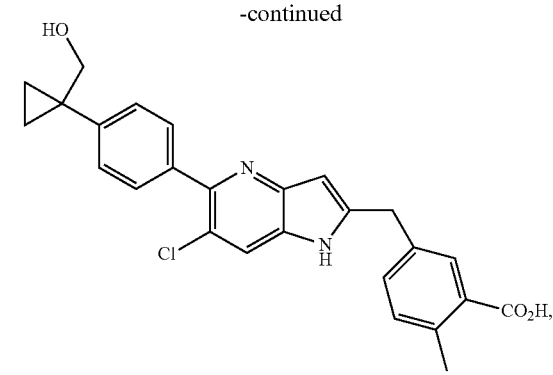

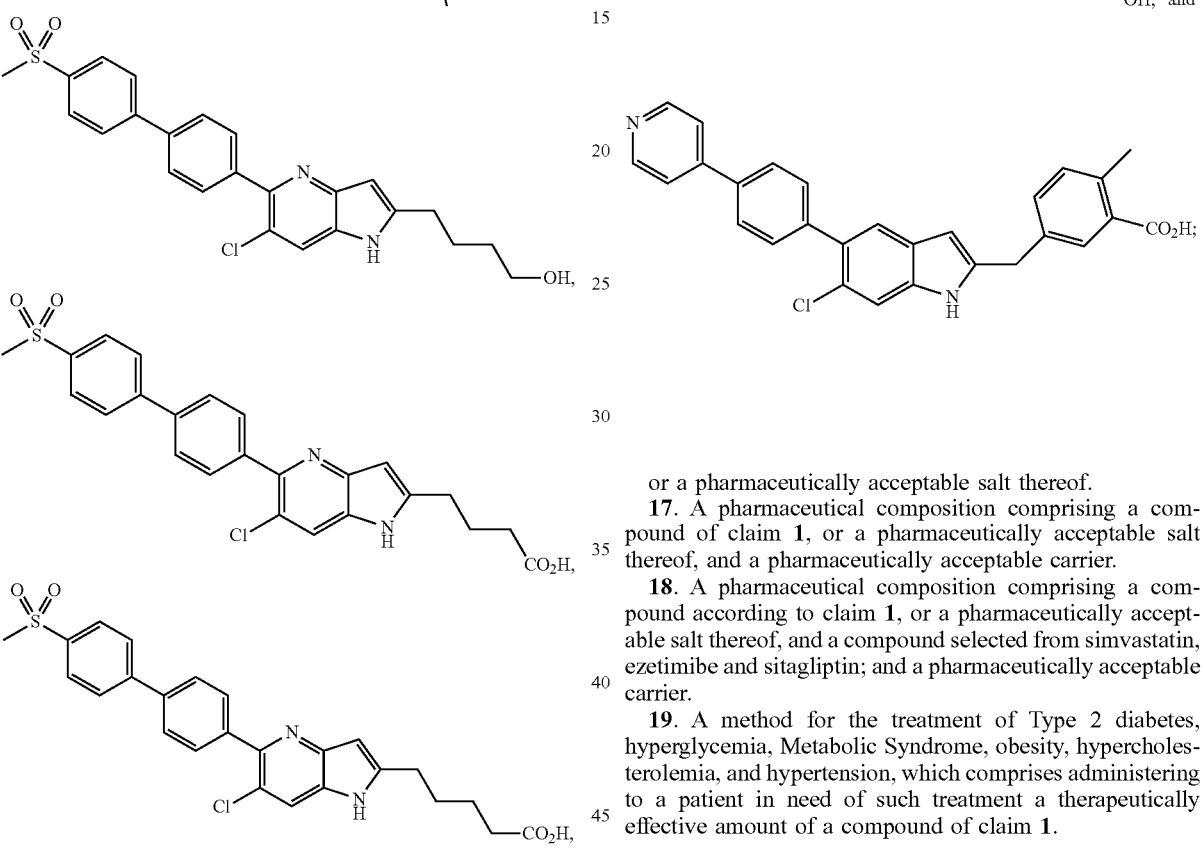

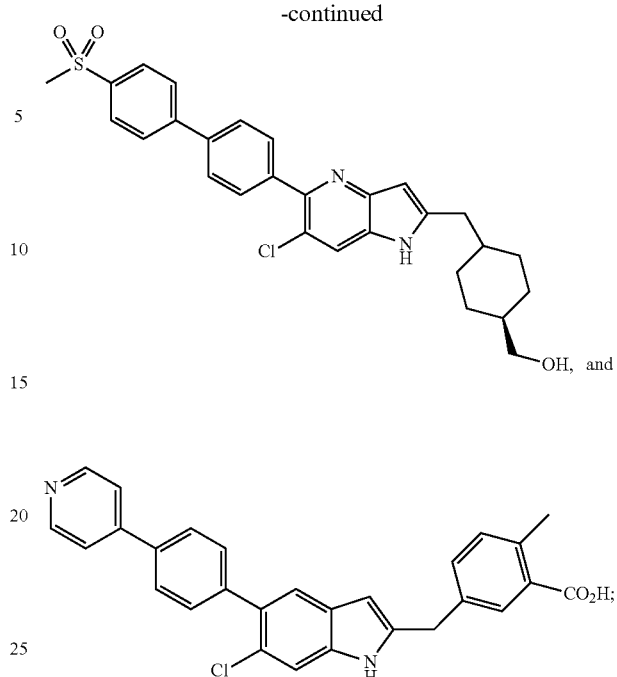

or a pharmaceutically acceptable salt thereof.

17. A pharmaceutical composition comprising a compound of claim 1, or a pharmaceutically acceptable salt thereof, and a pharmaceutically acceptable carrier.

18. A pharmaceutical composition comprising a compound according to claim 1, or a pharmaceutically acceptable salt thereof, and a compound selected from simvastatin, ezetimibe and sitagliptin; and a pharmaceutically acceptable carrier.

19. A method for the treatment of Type 2 diabetes, hyperglycemia, Metabolic Syndrome, obesity, hypercholesterolemia, and hypertension, which comprises administering to a patient in need of such treatment a therapeutically effective amount of a compound of claim 1.

\* \* \* \* \*